US012599403B2

(12) United States Patent
Frederick et al.

(10) Patent No.: US 12,599,403 B2
(45) Date of Patent: Apr. 14, 2026

(54) METHODS, SYSTEMS, AND DEVICES FOR SURGICAL ACCESS AND INSERTION

(71) Applicant: Board of Regents of the University of Nebraska, Lincoln, NE (US)

(72) Inventors: Thomas Frederick, Gretna, NE (US); Shane Farritor, Lincoln, NE (US); Jack Mondry, Edina, MN (US); Eric Markvicka, Lincoln, NE (US); Dmitry Oleynikov, Omaha, NE (US); Jacob Greenburg, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 154 days.

(21) Appl. No.: 18/403,328

(22) Filed: Jan. 3, 2024

(65) Prior Publication Data

US 2024/0407804 A1     Dec. 12, 2024

Related U.S. Application Data

(63) Continuation of application No. 16/999,407, filed on Aug. 21, 2020, now Pat. No. 11,883,065, which is a
(Continued)

(51) Int. Cl.
*A61B 17/02* (2006.01)
*A61B 17/34* (2006.01)
(Continued)

(52) U.S. Cl.
CPC ...... *A61B 17/3423* (2013.01); *A61B 17/0218* (2013.01); *A61B 90/40* (2016.02); *A61B 2017/00283* (2013.01); *A61B 2017/3441*

(2013.01); *A61B 2017/3447* (2013.01); *A61B 2017/3464* (2013.01); *A61B 2017/3466* (2013.01); *A61B 17/3498* (2013.01); *A61B 2034/302* (2016.02); *A61B 2090/062* (2016.02); *A61B 90/50* (2016.02)

(58) Field of Classification Search
CPC ...................................... A61B 17/02–17/0293
See application file for complete search history.

(56) References Cited

U.S. PATENT DOCUMENTS

| | | | |
|---|---|---|---|
| 3,870,264 | A | 3/1975 | Robinson |
| 3,989,952 | A | 11/1976 | Hohmann |

(Continued)

FOREIGN PATENT DOCUMENTS

| | | |
|---|---|---|
| CA | 2690808 C | 9/2016 |
| CN | 102821918 A | 12/2012 |

(Continued)

OTHER PUBLICATIONS

Begos et al., "Laparoscopic Cholecystectomy: From Gimmick to Gold Standard," J Clin Gastroenterol, 1994; 19(4): 325-330.
(Continued)

*Primary Examiner* — Zade Coley
(74) *Attorney, Agent, or Firm* — Fredrikson & Byron, P.A.

(57) ABSTRACT

The various embodiments herein relate to systems, devices, and/or methods relating to surgical procedures, and more specifically for accessing an insufflated cavity of a patient and/or positioning surgical systems or devices into the cavity.

20 Claims, 101 Drawing Sheets

Related U.S. Application Data continuation of application No. 15/890,860, filed on Feb. 7, 2018, now abandoned, which is a continuation of application No. 14/661,465, filed on Mar. 18, 2015, now abandoned, which is a continuation of application No. 13/738,706, filed on Jan. 10, 2013, now abandoned.

(60) Provisional application No. 61/683,483, filed on Aug. 15, 2012, provisional application No. 61/584,947, filed on Jan. 10, 2012.

(51) Int. Cl.

| | |
|---|---|
| *A61B 90/40* | (2016.01) |
| *A61B 17/00* | (2006.01) |
| *A61B 34/30* | (2016.01) |
| *A61B 90/00* | (2016.01) |
| *A61B 90/50* | (2016.01) |

(56) References Cited

U.S. PATENT DOCUMENTS

| | | | |
|---|---|---|---|
| 4,246,661 A | 1/1981 | Pinson | |
| 4,258,716 A | 3/1981 | Sutherland | |
| 4,278,077 A | 7/1981 | Mizumoto | |
| 4,538,594 A | 9/1985 | Boebel et al. | |
| 4,568,311 A | 2/1986 | Miyake | |
| 4,579,476 A | 4/1986 | Post | |
| 4,623,183 A | 11/1986 | Aomori | |
| 4,736,645 A | 4/1988 | Zimmer | |
| 4,771,652 A | 9/1988 | Zimmer | |
| 4,852,391 A | 8/1989 | Ruch et al. | |
| 4,896,015 A | 1/1990 | Taboada et al. | |
| 4,897,014 A | 1/1990 | Tietze | |
| 4,922,755 A | 5/1990 | Oshiro et al. | |
| 4,922,782 A | 5/1990 | Kawai | |
| 4,990,050 A | 2/1991 | Tsuge et al. | |
| 5,000,745 A * | 3/1991 | Guest ................ A61M 39/0606 | |
| | | | 604/167.04 |
| 5,019,968 A | 5/1991 | Wang et al. | |
| 5,108,140 A | 4/1992 | Bartholet | |
| 5,172,639 A | 12/1992 | Wiesman et al. | |
| 5,176,649 A | 1/1993 | Wakabayashi | |
| 5,178,032 A | 1/1993 | Zona et al. | |
| 5,187,032 A | 2/1993 | Sasaki et al. | |
| 5,187,796 A | 2/1993 | Wang et al. | |
| 5,195,388 A | 3/1993 | Zona et al. | |
| 5,201,325 A | 4/1993 | Mcewen et al. | |
| 5,217,003 A | 6/1993 | Wilk | |
| 5,263,382 A | 11/1993 | Brooks et al. | |
| 5,271,384 A | 12/1993 | Mcewen et al. | |
| 5,284,096 A | 2/1994 | Pelrine et al. | |
| 5,297,443 A | 3/1994 | Wentz | |
| 5,297,536 A | 3/1994 | Wilk | |
| 5,304,899 A | 4/1994 | Sasaki et al. | |
| 5,307,447 A | 4/1994 | Asano et al. | |
| 5,353,807 A | 10/1994 | Demarco | |
| 5,363,935 A | 11/1994 | Schempf et al. | |
| 5,382,885 A | 1/1995 | Salcudean et al. | |
| 5,388,528 A | 2/1995 | Pelrine et al. | |
| 5,436,542 A | 7/1995 | Petelin et al. | |
| 5,441,494 A | 8/1995 | Ortiz | |
| 5,458,131 A | 10/1995 | Wilk | |
| 5,458,583 A | 10/1995 | Mcneely et al. | |
| 5,458,598 A | 10/1995 | Feinberg et al. | |
| 5,471,515 A | 11/1995 | Fossum et al. | |
| 5,515,478 A | 5/1996 | Wang | |
| 5,522,669 A | 6/1996 | Recker | |
| 5,524,180 A | 6/1996 | Wang et al. | |
| 5,553,198 A | 9/1996 | Wang et al. | |
| 5,562,448 A | 10/1996 | Mushabac | |
| 5,588,442 A | 12/1996 | Scovil et al. | |
| 5,620,417 A | 4/1997 | Jang et al. | |
| 5,623,582 A | 4/1997 | Rosenberg | |

| | | | |
|---|---|---|---|
| 5,624,380 A | 4/1997 | Kaneko et al. | |
| 5,624,398 A | 4/1997 | Smith et al. | |
| 5,632,761 A | 5/1997 | Smith et al. | |
| 5,645,520 A | 7/1997 | Nakamura et al. | |
| 5,657,429 A | 8/1997 | Wang et al. | |
| 5,657,584 A | 8/1997 | Hamlin | |
| 5,667,479 A * | 9/1997 | Kieturakis ......... A61B 17/3417 | |
| | | | 600/207 |
| 5,672,168 A * | 9/1997 | de la Torre ........ A61B 17/3423 | |
| | | | 606/1 |
| 5,674,030 A | 10/1997 | Sigel | |
| 5,728,599 A | 3/1998 | Rostoker et al. | |
| 5,736,821 A | 4/1998 | Suyama | |
| 5,754,741 A | 5/1998 | Wang et al. | |
| 5,762,458 A | 6/1998 | Wang et al. | |
| 5,769,640 A | 6/1998 | Jacobus et al. | |
| 5,791,231 A | 8/1998 | Cohn et al. | |
| 5,792,135 A | 8/1998 | Madhani et al. | |
| 5,797,538 A | 8/1998 | Heaton et al. | |
| 5,797,900 A | 8/1998 | Madhani et al. | |
| 5,807,377 A | 9/1998 | Madhani et al. | |
| 5,808,665 A | 9/1998 | Green | |
| 5,815,640 A | 9/1998 | Wang et al. | |
| 5,825,982 A | 10/1998 | Wright et al. | |
| 5,841,950 A | 11/1998 | Wang et al. | |
| 5,845,646 A | 12/1998 | Lemelson | |
| 5,853,395 A * | 12/1998 | Crook .................... A61B 90/40 | |
| | | | 604/338 |
| 5,855,583 A | 1/1999 | Wang et al. | |
| 5,876,325 A | 3/1999 | Mizuno et al. | |
| 5,878,193 A | 3/1999 | Wang et al. | |
| 5,878,783 A | 3/1999 | Smart | |
| 5,895,417 A | 4/1999 | Pomeranz et al. | |
| 5,906,577 A * | 5/1999 | Beane ................ A61B 17/0293 | |
| | | | 600/206 |
| 5,906,591 A | 5/1999 | Dario et al. | |
| 5,907,664 A | 5/1999 | Wang et al. | |
| 5,910,129 A | 6/1999 | Koblish et al. | |
| 5,911,036 A | 6/1999 | Wright et al. | |
| 5,913,874 A | 6/1999 | Berns et al. | |
| 5,971,976 A | 10/1999 | Wang et al. | |
| 5,993,467 A | 11/1999 | Yoon | |
| 6,001,108 A | 12/1999 | Wang et al. | |
| 6,007,550 A | 12/1999 | Wang et al. | |
| 6,030,365 A | 2/2000 | Laufer | |
| 6,031,371 A | 2/2000 | Smart | |
| 6,058,323 A | 5/2000 | Lemelson | |
| 6,063,095 A | 5/2000 | Wang et al. | |
| 6,066,090 A | 5/2000 | Yoon | |
| 6,086,529 A | 7/2000 | Arndt | |
| 6,102,850 A | 8/2000 | Wang et al. | |
| 6,107,795 A | 8/2000 | Smart | |
| 6,132,368 A | 10/2000 | Cooper | |
| 6,132,441 A | 10/2000 | Grace | |
| 6,139,563 A | 10/2000 | Cosgrove, III et al. | |
| 6,142,936 A * | 11/2000 | Beane .................... A61B 42/10 | |
| | | | 600/206 |
| 6,156,006 A | 12/2000 | Brosens et al. | |
| 6,159,146 A | 12/2000 | El Gazayerli | |
| 6,162,171 A | 12/2000 | Ng et al. | |
| D438,617 S | 3/2001 | Cooper et al. | |
| 6,206,903 B1 | 3/2001 | Ramans | |
| D441,076 S | 4/2001 | Cooper et al. | |
| 6,223,100 B1 | 4/2001 | Green | |
| D441,862 S | 5/2001 | Cooper et al. | |
| 6,238,415 B1 | 5/2001 | Sepetka et al. | |
| 6,240,312 B1 | 5/2001 | Alfano et al. | |
| 6,241,730 B1 | 6/2001 | Alby | |
| 6,244,809 B1 | 6/2001 | Wang et al. | |
| 6,246,200 B1 | 6/2001 | Blumenkranz et al. | |
| D444,555 S | 7/2001 | Cooper et al. | |
| 6,286,514 B1 | 9/2001 | Lemelson | |
| 6,292,678 B1 | 9/2001 | Hall et al. | |
| 6,293,282 B1 | 9/2001 | Lemelson | |
| 6,296,635 B1 | 10/2001 | Smith et al. | |
| 6,309,397 B1 | 10/2001 | Julian et al. | |
| 6,309,403 B1 | 10/2001 | Minor et al. | |
| 6,312,435 B1 | 11/2001 | Wallace et al. | |
| 6,321,106 B1 | 11/2001 | Lemelson | |

(56)  References Cited

U.S. PATENT DOCUMENTS

| | | | |
|---|---|---|---|
| 6,327,492 | B1 | 12/2001 | Lemelson |
| 6,331,181 | B1 | 12/2001 | Tierney et al. |
| 6,346,072 | B1 | 2/2002 | Cooper |
| 6,352,503 | B1 | 3/2002 | Matsui et al. |
| 6,364,888 | B1 | 4/2002 | Niemeyer et al. |
| 6,371,952 | B1 | 4/2002 | Madhani et al. |
| 6,394,998 | B1 | 5/2002 | Wallace et al. |
| 6,398,726 | B1 | 6/2002 | Ramans et al. |
| 6,400,980 | B1 | 6/2002 | Lemelson |
| 6,408,224 | B1 | 6/2002 | Okamoto et al. |
| 6,424,885 | B1 | 7/2002 | Niemeyer et al. |
| 6,432,112 | B2 | 8/2002 | Brock et al. |
| 6,436,107 | B1 | 8/2002 | Wang et al. |
| 6,441,577 | B2 | 8/2002 | Blumenkranz et al. |
| 6,450,104 | B1 | 9/2002 | Grant et al. |
| 6,451,027 | B1 | 9/2002 | Cooper et al. |
| 6,454,758 | B1 | 9/2002 | Thompson et al. |
| 6,459,926 | B1 | 10/2002 | Nowlin et al. |
| 6,463,361 | B1 | 10/2002 | Wang et al. |
| 6,468,203 | B2 | 10/2002 | Belson |
| 6,468,265 | B1 | 10/2002 | Evans et al. |
| 6,470,236 | B2 | 10/2002 | Ohtsuki |
| 6,478,681 | B1 | 11/2002 | Overaker et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,496,099 | B2 | 12/2002 | Wang et al. |
| 6,497,651 | B1 | 12/2002 | Kan et al. |
| 6,508,413 | B2 | 1/2003 | Bauer et al. |
| 6,512,345 | B2 | 1/2003 | Borenstein et al. |
| 6,522,906 | B1 | 2/2003 | Salisbury et al. |
| 6,544,276 | B1 | 4/2003 | Azizi |
| 6,548,982 | B1 | 4/2003 | Papanikolopoulos et al. |
| 6,551,282 | B1 * | 4/2003 | Exline ............... A61B 17/3462<br>604/167.01 |
| 6,554,790 | B1 | 4/2003 | Moll |
| 6,565,554 | B1 | 5/2003 | Niemeyer |
| 6,574,355 | B2 | 6/2003 | Green |
| 6,587,750 | B2 | 7/2003 | Gerbi et al. |
| 6,589,167 | B1 * | 7/2003 | Shimomura ....... A61B 17/3462<br>128/897 |
| 6,591,239 | B1 | 7/2003 | Mccall et al. |
| 6,594,552 | B1 | 7/2003 | Nowlin et al. |
| 6,610,007 | B2 | 8/2003 | Belson et al. |
| 6,620,173 | B2 | 9/2003 | Gerbi et al. |
| 6,642,836 | B1 | 11/2003 | Wang et al. |
| 6,645,196 | B1 | 11/2003 | Nixon et al. |
| 6,646,541 | B1 | 11/2003 | Wang et al. |
| 6,648,814 | B2 | 11/2003 | Kim et al. |
| 6,659,939 | B2 | 12/2003 | Moll et al. |
| 6,661,571 | B1 | 12/2003 | Shioda et al. |
| 6,671,581 | B2 | 12/2003 | Niemeyer et al. |
| 6,676,684 | B1 | 1/2004 | Morley et al. |
| 6,684,129 | B2 | 1/2004 | Salisbury et al. |
| 6,685,648 | B2 | 2/2004 | Flaherty et al. |
| 6,685,698 | B2 | 2/2004 | Morley et al. |
| 6,687,571 | B1 | 2/2004 | Byrne et al. |
| 6,692,485 | B1 | 2/2004 | Brock et al. |
| 6,699,177 | B1 | 3/2004 | Wang et al. |
| 6,699,235 | B2 | 3/2004 | Wallace et al. |
| 6,702,734 | B2 | 3/2004 | Kim et al. |
| 6,702,805 | B1 | 3/2004 | Stuart |
| 6,714,839 | B2 | 3/2004 | Salisbury et al. |
| 6,714,841 | B1 | 3/2004 | Wright et al. |
| 6,719,684 | B2 | 4/2004 | Kim et al. |
| 6,720,988 | B1 | 4/2004 | Gere et al. |
| 6,726,699 | B1 | 4/2004 | Wright et al. |
| 6,728,599 | B2 | 4/2004 | Wang et al. |
| 6,730,021 | B2 | 5/2004 | Vassiliades et al. |
| 6,731,988 | B1 | 5/2004 | Green |
| 6,746,443 | B1 | 6/2004 | Morley et al. |
| 6,764,441 | B2 | 7/2004 | Chiel et al. |
| 6,764,445 | B2 | 7/2004 | Ramans et al. |
| 6,766,204 | B2 | 7/2004 | Niemeyer et al. |
| 6,770,081 | B1 | 8/2004 | Cooper et al. |
| 6,774,597 | B1 | 8/2004 | Borenstein |
| 6,776,165 | B2 | 8/2004 | Jin |
| 6,780,184 | B2 | 8/2004 | Tanrisever |
| 6,783,524 | B2 | 8/2004 | Anderson et al. |
| 6,785,593 | B2 | 8/2004 | Wang et al. |
| 6,788,018 | B1 | 9/2004 | Blumenkranz |
| 6,792,663 | B2 | 9/2004 | Krzyzanowski |
| 6,793,653 | B2 | 9/2004 | Sanchez et al. |
| 6,799,065 | B1 | 9/2004 | Niemeyer |
| 6,799,088 | B2 | 9/2004 | Wang et al. |
| 6,801,325 | B2 | 10/2004 | Farr et al. |
| 6,804,581 | B2 | 10/2004 | Wang et al. |
| 6,810,281 | B2 | 10/2004 | Brock et al. |
| 6,817,972 | B2 | 11/2004 | Snow |
| 6,817,974 | B2 | 11/2004 | Cooper et al. |
| 6,817,975 | B1 | 11/2004 | Farr et al. |
| 6,820,653 | B1 | 11/2004 | Schempf et al. |
| 6,824,508 | B2 | 11/2004 | Kim et al. |
| 6,824,510 | B2 | 11/2004 | Kim et al. |
| 6,832,988 | B2 | 12/2004 | Sproul |
| 6,832,996 | B2 | 12/2004 | Woloszko et al. |
| 6,836,703 | B2 | 12/2004 | Wang et al. |
| 6,837,846 | B2 | 1/2005 | Jaffe et al. |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,852,107 | B2 | 2/2005 | Wang et al. |
| 6,858,003 | B2 | 2/2005 | Evans et al. |
| 6,860,346 | B2 | 3/2005 | Burt et al. |
| 6,860,877 | B1 | 3/2005 | Sanchez et al. |
| 6,866,671 | B2 | 3/2005 | Tierney et al. |
| 6,870,343 | B2 | 3/2005 | Borenstein et al. |
| 6,871,117 | B2 | 3/2005 | Wang et al. |
| 6,871,563 | B2 | 3/2005 | Choset et al. |
| 6,879,880 | B2 | 4/2005 | Nowlin et al. |
| 6,892,112 | B2 | 5/2005 | Wang et al. |
| 6,899,705 | B2 | 5/2005 | Niemeyer |
| 6,902,560 | B1 | 6/2005 | Morley et al. |
| 6,905,460 | B2 | 6/2005 | Wang et al. |
| 6,905,491 | B1 | 6/2005 | Wang et al. |
| 6,911,916 | B1 | 6/2005 | Wang et al. |
| 6,917,176 | B2 | 7/2005 | Schempf et al. |
| 6,933,695 | B2 | 8/2005 | Blumenkranz |
| 6,936,001 | B1 | 8/2005 | Snow |
| 6,936,003 | B2 | 8/2005 | Iddan |
| 6,936,042 | B2 | 8/2005 | Wallace et al. |
| 6,943,663 | B2 | 9/2005 | Wang et al. |
| 6,949,096 | B2 | 9/2005 | Davison et al. |
| 6,951,535 | B2 | 10/2005 | Ghodoussi et al. |
| 6,965,812 | B2 | 11/2005 | Wang et al. |
| 6,974,411 | B2 | 12/2005 | Belson |
| 6,974,449 | B2 | 12/2005 | Niemeyer |
| 6,979,423 | B2 | 12/2005 | Moll |
| 6,984,203 | B2 | 1/2006 | Tartaglia et al. |
| 6,984,205 | B2 | 1/2006 | Gazdzinski |
| 6,991,627 | B2 | 1/2006 | Madhani et al. |
| 6,993,413 | B2 | 1/2006 | Sunaoshi |
| 6,994,703 | B2 | 2/2006 | Wang et al. |
| 6,994,708 | B2 | 2/2006 | Manzo |
| 6,997,908 | B2 | 2/2006 | Carrillo, Jr. et al. |
| 7,008,377 | B2 * | 3/2006 | Beane ............... A61B 17/3423<br>600/206 |
| 7,025,064 | B2 | 4/2006 | Wang et al. |
| 7,027,892 | B2 | 4/2006 | Wang et al. |
| 7,033,344 | B2 | 4/2006 | Imran |
| 7,036,509 | B2 * | 5/2006 | Rapacki ............ A61M 16/0463<br>128/207.14 |
| 7,039,453 | B2 | 5/2006 | Mullick et al. |
| 7,042,184 | B2 | 5/2006 | Oleynikov et al. |
| 7,048,745 | B2 | 5/2006 | Tierney et al. |
| 7,053,752 | B2 | 5/2006 | Wang et al. |
| 7,063,682 | B1 | 6/2006 | Whayne et al. |
| 7,066,879 | B2 | 6/2006 | Fowler et al. |
| 7,066,926 | B2 | 6/2006 | Wallace et al. |
| 7,074,179 | B2 | 7/2006 | Wang et al. |
| 7,077,446 | B2 | 7/2006 | Kameda et al. |
| 7,083,571 | B2 | 8/2006 | Wang et al. |
| 7,083,615 | B2 | 8/2006 | Peterson et al. |
| 7,087,049 | B2 | 8/2006 | Nowlin et al. |

(56) References Cited

U.S. PATENT DOCUMENTS

| | | | |
|---|---|---|---|
| 7,090,683 B2 | 8/2006 | Brock et al. | |
| 7,097,640 B2 | 8/2006 | Wang et al. | |
| 7,105,000 B2 | 9/2006 | Mcbrayer | |
| 7,107,090 B2 | 9/2006 | Salisbury, Jr. et al. | |
| 7,109,678 B2 | 9/2006 | Kraus et al. | |
| 7,118,582 B1 | 10/2006 | Wang et al. | |
| 7,121,781 B2 | 10/2006 | Sanchez | |
| 7,125,403 B2 | 10/2006 | Julian et al. | |
| 7,126,303 B2 | 10/2006 | Farritor et al. | |
| 7,147,650 B2 | 12/2006 | Lee | |
| 7,155,315 B2 | 12/2006 | Niemeyer et al. | |
| 7,169,141 B2 | 1/2007 | Brock et al. | |
| 7,182,025 B2 | 2/2007 | Ghorbel et al. | |
| 7,182,089 B2 | 2/2007 | Ries | |
| 7,199,545 B2 | 4/2007 | Oleynikov et al. | |
| 7,206,626 B2 | 4/2007 | Quaid, III | |
| 7,206,627 B2 | 4/2007 | Abovitz et al. | |
| 7,210,364 B2 | 5/2007 | Ghorbel et al. | |
| 7,214,230 B2 | 5/2007 | Brock et al. | |
| 7,217,240 B2 | 5/2007 | Snow | |
| 7,239,940 B2 | 7/2007 | Wang et al. | |
| 7,250,028 B2 | 7/2007 | Julian et al. | |
| 7,259,652 B2 | 8/2007 | Wang et al. | |
| 7,273,488 B2 | 9/2007 | Nakamura et al. | |
| 7,311,107 B2 | 12/2007 | Harel et al. | |
| 7,339,341 B2 | 3/2008 | Oleynikov et al. | |
| 7,372,229 B2 | 5/2008 | Farritor et al. | |
| 7,377,898 B2* | 5/2008 | Ewers | A61B 17/3423 |
| | | | 600/208 |
| 7,447,537 B1 | 11/2008 | Funda et al. | |
| 7,492,116 B2 | 2/2009 | Oleynikov et al. | |
| 7,566,300 B2 | 7/2009 | Devierre et al. | |
| 7,574,250 B2 | 8/2009 | Niemeyer | |
| 7,637,905 B2 | 12/2009 | Saadat et al. | |
| 7,645,230 B2 | 1/2010 | Mikkaichi et al. | |
| 7,655,004 B2 | 2/2010 | Long | |
| 7,670,329 B2 | 3/2010 | Flaherty et al. | |
| 7,731,727 B2 | 6/2010 | Sauer | |
| 7,762,825 B2 | 7/2010 | Burbank et al. | |
| 7,772,796 B2 | 8/2010 | Farritor et al. | |
| 7,785,251 B2 | 8/2010 | Wilk | |
| 7,785,333 B2 | 8/2010 | Miyamoto et al. | |
| 7,789,825 B2 | 9/2010 | Nobis et al. | |
| 7,794,494 B2 | 9/2010 | Sahatjian et al. | |
| 7,865,266 B2 | 1/2011 | Moll et al. | |
| 7,960,935 B2 | 6/2011 | Farritor et al. | |
| 8,021,358 B2 | 9/2011 | Doyle et al. | |
| 8,179,073 B2 | 5/2012 | Farritor et al. | |
| 8,231,610 B2 | 7/2012 | Jo et al. | |
| 8,317,691 B2* | 11/2012 | Bonadio | A61B 17/3423 |
| | | | 600/208 |
| 8,343,171 B2 | 1/2013 | Farritor et al. | |
| 8,353,897 B2 | 1/2013 | Doyle et al. | |
| 8,679,096 B2 | 3/2014 | Farritor et al. | |
| 8,828,024 B2 | 9/2014 | Farritor et al. | |
| 8,834,488 B2 | 9/2014 | Farritor et al. | |
| 8,876,708 B1* | 11/2014 | Piskun | A61B 1/32 |
| | | | 600/204 |
| 8,894,633 B2 | 11/2014 | Farritor et al. | |
| 8,968,267 B2 | 3/2015 | Nelson et al. | |
| 8,968,332 B2 | 3/2015 | Farritor et al. | |
| 8,974,440 B2 | 3/2015 | Farritor et al. | |
| 9,010,214 B2 | 4/2015 | Markvicka et al. | |
| 9,060,781 B2 | 6/2015 | Farritor et al. | |
| 9,089,353 B2 | 7/2015 | Farritor et al. | |
| 9,179,981 B2 | 11/2015 | Farritor et al. | |
| 9,498,292 B2 | 11/2016 | Mondry et al. | |
| 9,579,088 B2 | 2/2017 | Farritor et al. | |
| 9,649,020 B2 | 5/2017 | Finlay | |
| 9,743,987 B2 | 8/2017 | Farritor et al. | |
| 9,757,187 B2 | 9/2017 | Farritor et al. | |
| 9,770,305 B2 | 9/2017 | Farritor et al. | |
| 9,883,911 B2 | 2/2018 | Farritor et al. | |
| 9,888,966 B2 | 2/2018 | Farritor et al. | |
| 9,956,073 B2 | 5/2018 | Haddock et al. | |
| 10,111,711 B2 | 10/2018 | Farritor et al. | |
| 10,219,870 B2 | 3/2019 | Mondry et al. | |
| 10,307,199 B2 | 6/2019 | Farritor et al. | |
| 10,335,024 B2 | 7/2019 | Rentschler et al. | |
| 10,342,561 B2 | 7/2019 | Farritor et al. | |
| 10,376,322 B2 | 8/2019 | Frederick et al. | |
| 10,470,828 B2 | 11/2019 | Markvicka et al. | |
| 10,582,973 B2 | 3/2020 | Wilson et al. | |
| 10,667,883 B2 | 6/2020 | Farritor et al. | |
| 10,751,136 B2 | 8/2020 | Farritor et al. | |
| 10,806,538 B2 | 10/2020 | Farritor et al. | |
| 10,966,700 B2 | 4/2021 | Farritor et al. | |
| 11,065,050 B2 | 7/2021 | Farritor et al. | |
| 2001/0018591 A1 | 8/2001 | Brock et al. | |
| 2001/0049497 A1 | 12/2001 | Kalloo et al. | |
| 2002/0003173 A1 | 1/2002 | Bauer et al. | |
| 2002/0013601 A1 | 1/2002 | Nobles et al. | |
| 2002/0026186 A1 | 2/2002 | Woloszko et al. | |
| 2002/0038077 A1* | 3/2002 | de la Torre | A61B 46/10 |
| | | | 600/203 |
| 2002/0065507 A1 | 5/2002 | Zadno-Azizi | |
| 2002/0091374 A1 | 7/2002 | Cooper | |
| 2002/0103417 A1 | 8/2002 | Gazdzinski | |
| 2002/0111535 A1 | 8/2002 | Kim et al. | |
| 2002/0120254 A1 | 8/2002 | Julian et al. | |
| 2002/0128552 A1 | 9/2002 | Nowlin et al. | |
| 2002/0140392 A1 | 10/2002 | Borenstein et al. | |
| 2002/0147487 A1 | 10/2002 | Sundquist et al. | |
| 2002/0151906 A1 | 10/2002 | Demarais et al. | |
| 2002/0156347 A1 | 10/2002 | Kim et al. | |
| 2002/0171385 A1 | 11/2002 | Kim et al. | |
| 2002/0173700 A1 | 11/2002 | Kim et al. | |
| 2002/0190682 A1 | 12/2002 | Schempf et al. | |
| 2003/0020810 A1 | 1/2003 | Takizawa et al. | |
| 2003/0045888 A1 | 3/2003 | Brock et al. | |
| 2003/0065250 A1 | 4/2003 | Chiel et al. | |
| 2003/0089267 A1 | 5/2003 | Ghorbel et al. | |
| 2003/0092964 A1 | 5/2003 | Kim et al. | |
| 2003/0097129 A1 | 5/2003 | Davison et al. | |
| 2003/0100817 A1 | 5/2003 | Wang et al. | |
| 2003/0114731 A1 | 6/2003 | Cadeddu et al. | |
| 2003/0135203 A1 | 7/2003 | Wang et al. | |
| 2003/0139742 A1 | 7/2003 | Wampler et al. | |
| 2003/0144656 A1 | 7/2003 | Ocel et al. | |
| 2003/0159535 A1 | 8/2003 | Grover et al. | |
| 2003/0167000 A1 | 9/2003 | Mullick et al. | |
| 2003/0172871 A1 | 9/2003 | Scherer | |
| 2003/0179308 A1 | 9/2003 | Zamorano et al. | |
| 2003/0181788 A1 | 9/2003 | Yokoi et al. | |
| 2003/0229268 A1 | 12/2003 | Uchiyama et al. | |
| 2003/0229338 A1 | 12/2003 | Irion et al. | |
| 2003/0230372 A1 | 12/2003 | Schmidt | |
| 2004/0024311 A1 | 2/2004 | Quaid, III | |
| 2004/0034282 A1 | 2/2004 | Quaid, III | |
| 2004/0034283 A1 | 2/2004 | Quaid, III | |
| 2004/0034302 A1 | 2/2004 | Abovitz et al. | |
| 2004/0050394 A1 | 3/2004 | Jin | |
| 2004/0070822 A1 | 4/2004 | Takayama et al. | |
| 2004/0099175 A1 | 5/2004 | Perrot et al. | |
| 2004/0102772 A1 | 5/2004 | Baxter et al. | |
| 2004/0106916 A1 | 6/2004 | Quaid et al. | |
| 2004/0111113 A1 | 6/2004 | Nakamura et al. | |
| 2004/0117032 A1 | 6/2004 | Roth | |
| 2004/0138525 A1 | 7/2004 | Saadat et al. | |
| 2004/0138552 A1 | 7/2004 | Harel et al. | |
| 2004/0140786 A1 | 7/2004 | Borenstein | |
| 2004/0153057 A1 | 8/2004 | Davison | |
| 2004/0173116 A1 | 9/2004 | Ghorbel et al. | |
| 2004/0176664 A1 | 9/2004 | Iddan | |
| 2004/0215331 A1 | 10/2004 | Chew et al. | |
| 2004/0225229 A1 | 11/2004 | Viola | |
| 2004/0254680 A1 | 12/2004 | Sunaoshi | |
| 2004/0267254 A1 | 12/2004 | Manzo et al. | |
| 2004/0267326 A1 | 12/2004 | Ocel et al. | |
| 2005/0014994 A1 | 1/2005 | Fowler et al. | |
| 2005/0021069 A1 | 1/2005 | Feuer et al. | |
| 2005/0029978 A1 | 2/2005 | Oleynikov et al. | |
| 2005/0043583 A1 | 2/2005 | Killmann et al. | |
| 2005/0049462 A1 | 3/2005 | Kanazawa | |

(56)                References Cited

U.S. PATENT DOCUMENTS

| | | |
|---|---|---|
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0090717 A1* | 4/2005 | Bonadio ............ A61B 17/0293 |
| | | 600/208 |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0192483 A1* | 9/2005 | Bonadio ............ A61B 17/3462 |
| | | 600/208 |
| 2005/0222582 A1* | 10/2005 | Wenchell ........... A61B 17/3462 |
| | | 606/108 |
| 2005/0234435 A1 | 10/2005 | Layer |
| 2005/0239311 A1 | 10/2005 | Yokoigawa et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0135803 A1 | 6/2007 | Belson |
| 2007/0142725 A1 | 6/2007 | Hardin et al. |
| 2007/0156019 A1 | 7/2007 | Larkin et al. |
| 2007/0156211 A1 | 7/2007 | Wood et al. |
| 2007/0167955 A1 | 7/2007 | Arnault De La Menardiere et al. |
| 2007/0225633 A1 | 9/2007 | Wood et al. |
| 2007/0225634 A1 | 9/2007 | Wood et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | De La Pena |
| 2008/0111513 A1 | 5/2008 | Farritor et al. |
| 2008/0119870 A1 | 5/2008 | Williams |
| 2008/0132890 A1 | 6/2008 | Woloszko et al. |
| 2008/0161804 A1 | 7/2008 | Rioux et al. |
| 2008/0164079 A1 | 7/2008 | Jacobsen |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0012433 A1* | 1/2009 | Fernstrom ............ A61B 5/0022 |
| | | 600/593 |
| 2009/0012532 A1 | 1/2009 | Blackwell et al. |
| 2009/0020724 A1 | 1/2009 | Paffrath |
| 2009/0024142 A1 | 1/2009 | Ruiz Morales |

| | | |
|---|---|---|
| 2009/0036745 A1* | 2/2009 | Bonadio ............ A61B 17/3498 |
| | | 600/208 |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | de la Pena |
| 2009/0163929 A1 | 6/2009 | Yeung et al. |
| 2009/0171373 A1 | 7/2009 | Farritor et al. |
| 2009/0227843 A1* | 9/2009 | Smith ................ A61B 17/3423 |
| | | 600/201 |
| 2009/0234369 A1 | 9/2009 | Bax et al. |
| 2009/0236400 A1 | 9/2009 | Cole et al. |
| 2009/0240246 A1 | 9/2009 | Deville et al. |
| 2009/0247821 A1 | 10/2009 | Rogers |
| 2009/0248038 A1 | 10/2009 | Blumenkranz et al. |
| 2009/0281377 A1 | 11/2009 | Acosta et al. |
| 2009/0287043 A1 | 11/2009 | Naito et al. |
| 2009/0305210 A1 | 12/2009 | Guru et al. |
| 2010/0010294 A1 | 1/2010 | Conlon et al. |
| 2010/0016659 A1 | 1/2010 | Weitzner |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0063362 A1* | 3/2010 | Bonadio ............ A61B 17/3439 |
| | | 600/203 |
| 2010/0063364 A1* | 3/2010 | Bonadio ............ A61B 17/3423 |
| | | 600/208 |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0081880 A1* | 4/2010 | Widenhouse ...... A61B 17/0218 |
| | | 600/206 |
| 2010/0139436 A1 | 6/2010 | Kawashima et al. |
| 2010/0145340 A1 | 6/2010 | Phan et al. |
| 2010/0185212 A1 | 7/2010 | Sholev |
| 2010/0198231 A1 | 8/2010 | Scott |
| 2010/0204713 A1 | 8/2010 | Ruiz Morales |
| 2010/0217087 A1* | 8/2010 | Bonadio ............ A61B 17/3498 |
| | | 600/208 |
| 2010/0245549 A1 | 9/2010 | Allen et al. |
| 2010/0250000 A1 | 9/2010 | Blumenkranz et al. |
| 2010/0262080 A1 | 10/2010 | Shelton, IV et al. |
| 2010/0262162 A1 | 10/2010 | Omori |
| 2010/0268035 A1* | 10/2010 | Oberlander ........ A61B 17/3462 |
| | | 600/204 |
| 2010/0286480 A1 | 11/2010 | Peine et al. |
| 2010/0292691 A1 | 11/2010 | Brogna |
| 2010/0312067 A1 | 12/2010 | Jensen et al. |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0098529 A1 | 4/2011 | Ostrovsky et al. |
| 2011/0132960 A1 | 6/2011 | Whitman et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0245619 A1 | 10/2011 | Holcomb |
| 2011/0264078 A1 | 10/2011 | Lipow et al. |
| 2011/0270443 A1 | 11/2011 | Kamiya et al. |
| 2011/0276046 A1 | 11/2011 | Heimbecher et al. |
| 2011/0282157 A1* | 11/2011 | Hart .................. A61B 17/0293 |
| | | 600/208 |
| 2012/0029727 A1 | 2/2012 | Malik |
| 2012/0035582 A1 | 2/2012 | Nelson et al. |
| 2012/0078058 A1* | 3/2012 | Richard ............. A61B 17/3423 |
| | | 600/208 |
| 2012/0109150 A1 | 5/2012 | Blackwell et al. |
| 2012/0116362 A1 | 5/2012 | Kieturakis |
| 2012/0179168 A1 | 7/2012 | Farritor et al. |
| 2012/0253515 A1 | 10/2012 | Coste-Maniere et al. |
| 2013/0041360 A1 | 2/2013 | Farritor et al. |

(56) References Cited

U.S. PATENT DOCUMENTS

| | | | |
|---|---|---|---|
| 2013/0066156 A1* | 3/2013 | Seo | A61B 17/3423 |
| | | | 600/204 |
| 2013/0131695 A1 | 5/2013 | Scarfogliero et al. | |
| 2013/0345717 A1 | 12/2013 | Markvicka et al. | |
| 2014/0001234 A1 | 1/2014 | Shelton, IV et al. | |
| 2014/0039515 A1 | 2/2014 | Mondry et al. | |
| 2014/0046340 A1 | 2/2014 | Wilson et al. | |
| 2014/0058205 A1 | 2/2014 | Frederick et al. | |
| 2014/0107425 A1 | 4/2014 | Bonadio et al. | |
| 2014/0249474 A1 | 9/2014 | Suon et al. | |
| 2014/0303434 A1 | 10/2014 | Farritor et al. | |
| 2014/0373652 A1 | 12/2014 | Zergiebel et al. | |
| 2015/0051446 A1 | 2/2015 | Farritor et al. | |
| 2015/0190170 A1 | 7/2015 | Frederick et al. | |
| 2016/0143688 A1 | 5/2016 | Orban III et al. | |
| 2016/0291915 A1 | 10/2016 | Panchapakesan et al. | |
| 2021/0128134 A1 | 5/2021 | Farritor et al. | |
| 2021/0244439 A1 | 8/2021 | Frederick et al. | |

FOREIGN PATENT DOCUMENTS

| | | | | | |
|---|---|---|---|---|---|
| CN | 104224258 | A | 12/2014 | | |
| DE | 102010040405 | A1 | 3/2012 | | |
| EP | 105656 | A2 | 4/1984 | | |
| EP | 279591 | A1 | 8/1988 | | |
| EP | 1354670 | A1 | 10/2003 | | |
| EP | 2286756 | A1 | 2/2011 | | |
| EP | 2329787 | A2 | 6/2011 | | |
| EP | 2563261 | A1 | 3/2013 | | |
| EP | 2647339 | A1 | 10/2013 | | |
| EP | 2684528 | A1 | 1/2014 | | |
| EP | 2123225 | B1 | 12/2014 | | |
| EP | 2815705 | A1 | 12/2014 | | |
| EP | 2881046 | A2 | 6/2015 | | |
| EP | 2937047 | A1 | 10/2015 | | |
| JP | H04144533 | A | 5/1992 | | |
| JP | H05115425 | A | 5/1993 | | |
| JP | H05184535 | A | 7/1993 | | |
| JP | H06507809 | A | 9/1994 | | |
| JP | H06508049 | A | 9/1994 | | |
| JP | H07016235 | A | 1/1995 | | |
| JP | H07136173 | A | 5/1995 | | |
| JP | H07306155 | A | 11/1995 | | |
| JP | H08224248 | A | 9/1996 | | |
| JP | 2001500510 | A | 1/2001 | | |
| JP | 2001505810 | A | 5/2001 | | |
| JP | 2002000524 | A | 1/2002 | | |
| JP | 2003220065 | A | 8/2003 | | |
| JP | 2004180781 | A | 7/2004 | | |
| JP | 2004180858 | A | 7/2004 | | |
| JP | 2004322310 | A | 11/2004 | | |
| JP | 2004329292 | A | 11/2004 | | |
| JP | 2009106606 | A | 5/2009 | | |
| JP | 2010533045 | A | 10/2010 | | |
| JP | 2010536436 | A | 12/2010 | | |
| JP | 2011504794 | A | 2/2011 | | |
| JP | 2011045500 | A | 3/2011 | | |
| JP | 2011115591 | A | 6/2011 | | |
| JP | 2017527392 | A | 9/2017 | | |
| KR | 1020100029087 | A | 3/2010 | | |
| WO | 9221291 | A2 | 12/1992 | | |
| WO | 9610957 | A1 | 4/1996 | | |
| WO | 9639944 | A1 | 12/1996 | | |
| WO | 0189405 | A1 | 11/2001 | | |
| WO | 02082979 | A2 | 10/2002 | | |
| WO | 02100256 | A2 | 12/2002 | | |
| WO | 2005009211 | A2 | 2/2005 | | |
| WO | 2005044095 | A1 | 5/2005 | | |
| WO | 2006005075 | A2 | 1/2006 | | |
| WO | 2006052927 | A2 | 5/2006 | | |
| WO | 2006079108 | A1 | 7/2006 | | |
| WO | 2007011654 | A1 | 1/2007 | | |
| WO | 2007111571 | A1 | 10/2007 | | |
| WO | 2007146987 | A2 | 12/2007 | | |
| WO | 2007149559 | A2 | 12/2007 | | |
| WO | 2009014917 | A2 | 1/2009 | | |
| WO | 2009023851 | A1 | 2/2009 | | |
| WO | 2009144729 | A1 | 12/2009 | | |
| WO | 2010042611 | A1 | 4/2010 | | |
| WO | 2010046823 | A1 | 4/2010 | | |
| WO | 2010050771 | A2 | 5/2010 | | |
| WO | 2011060311 | A2 | 5/2011 | | |
| WO | 2011075693 | A1 | 6/2011 | | |
| WO | 2011118646 | A1 | 9/2011 | | |
| WO | WO-2011135503 | A1 * | 11/2011 | | A61B 17/00 |
| WO | 2013009887 | A1 | 1/2013 | | |
| WO | 2014011238 | A2 | 1/2014 | | |
| WO | 2015088655 | A1 | 6/2015 | | |

OTHER PUBLICATIONS

Fukuda et al., "Mechanism and Swimming Experiment of Micro Mobile Robot in Water," Proceedings of the 1994 IEEE International Conference on Robotics and Automation, 1994: 814-819.

Fukuda et al., "Micro Active Catheter System with Multi Degrees of Freedom," Proceedings of the IEEE International Conference on Robotics and Automation, May 1994, pp. 2290-2295.

Hanly et al., "Robotic Abdominal Surgery," The American Journal of Surgery 188 (Suppl. to Oct. 1994): 19S-26S, 2004.

Bailey et al., "Complications of Laparoscopic Surgery," Quality Medical Publishers, Inc., 1995, 25 pp.

Green, "Telepresence Surgery", Jan. 1, 1995, Publisher: IEEE Engineering in Medicine and Biology.

Franklin et al., "Prospective Comparison of Open vs. Laparoscopic Colon Surgery for Carcinoma: Five-Year Results," Dis Colon Rectum, 1996; 39: S35-S46.

Allendorf et al., "Postoperative Immune Function Varies Inversely with the Degree of Surgical Trauma in a Murine Model," Surgical Endoscopy 1997; 11:427-430.

Calafiore et al., Multiple Arterial Conduits Without Cardiopulmonary Bypass: Early Angiographic Results,: Ann Thorac Surg, 1999; 67: 450-456.

Cuschieri, "Technology for Minimal Access Surgery," BMJ, 1999, 319: 1-6.

Faraz et al., "Engineering Approaches to Mechanical and Robotic Design for Minimaly Invasive Surgery (MIS)," Kluwer Academic Publishers (Boston), 2000, 13 pp.

Fearing et al., "Wing Transmission for a Micromechanical Flying Insect," Proceedings of the 2000 IEEE International Conference to Robotics & Automation, Apr. 2000; 1509-1516.

Gong et al., "Wireless endoscopy," Gastrointestinal Endoscopy 2000; 51(6): 725-729.

Heikkinen et al., "Comparison of laparoscopic and open Nissen fundoplication two years after operation: A prospective randomized trial," Surgical Endoscopy, 2000; 14: 1019-1023.

Abbou et al., "Laparoscopic Radical Prostatectomy with a Remote Controlled Robot," The Journal of Urology, Jun. 2001, 165: 1964-1966.

Bauer et al., "Case Report: Remote Percutaneous Renal Percutaneous Renal Access Using a New Automated Telesurgical Robotic System," Telemedicine Journal and e-Health 2001; (4): 341-347.

Breda et al., "Future developments and perspectives in laparoscopy," Eur. Urology 2001; 40(1): 84-91.

Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.

Horgan et al., "Technical Report: Robots in Laparoscopic Surgery," Journal of Laparoendoscopic & Advanced Surgical Techniques, 2001; 11(6): 415-419.

Ballantyne, "Robotic Surgery, Telerobotic Surgery, Telepresence, and Telementoring," Surgical Endoscopy, 2002; 16: 1389-1402.

Cleary et al., "State of the Art in Surgical Robotics: Clinical Applications and Technology Challenges", "Computer Aided Surgery" , Jan. 1, 2002, pp. 312-328, vol. 6.

Fraulob et al., "Miniature assistance module for robot-assisted heart surgery," Biomed. Tech. 2002, 47 Suppl. 1, Pt. 1: 12-15.

(56) References Cited

OTHER PUBLICATIONS

Guber et al., "Miniaturized Instrument Systems for Minimally Invasive Diagnosis and Therapy," Biomedizinishe Technic. 2002, Band 47, Erganmngsband 1.

Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.

Chanthasopeephan et al., (2003), "Measuring Forces in Liver Cutting: New Equipment and Experimenal Results," Annals of Biomedical Engineering 31: 1372-1382.

Dakin et al., "Comparison of laparoscopic skills performance between standard instruments and two surgical robotic systems," Surg Endosc., 2003; 17: 574-579.

Falcone et al., "Robotic Surgery," Clin. Obstel. Gynecol. 2003, 46(1): 37-43.

Fireman et al., "Diagnosing small bowel Crohn's desease with wireless capsule endoscopy," Gut 2003; 52: 390-392.

Franzino, "The Laprotek Surgical System and the Next Generation of Robotics," Surg Clin North Am, 2003 83(6), pp. 1317-1320.

Ang, "Active Tremor Compensation in Handheld Instrument for Microsurgery," Doctoral Dissertation, tech report CMU-RI-TR-04-28, Robotics Institute, Carnegie Mellon University, May 2004, 167 pp.

Albers et al., Design and development process of a humanoid robot upper body through experimentation, 2004, IEEE, p. 77-92 (Year: 2004).

Breedveld et al., "Design of Steerable Endoscopes to Improve the Visual Perception of Depth During Laparoscopic Surgery," ASME, Jan. 2004; vol. 126, pp. 1-5.

Breedveld et al., "Locomotion through the Intestine by means of Rolling Stents," Proceedings of the ASME Design Engineering Technical Conferences, 2004, pp. 1-7.

Camarillo et al., "Robotic Technology in Surgery: Past, Present and Future," The American Journal of Surgery, 2004; 188: 2S-15.

Glukhovsky et al., "The development and application of wireless capsule endoscopy," Int. J. Med. Robot. Comput. Assisi. Surgery, 2004; I (1): 114-123.

Hanly et al., "Value of the SAGES Learning Center in introducing new technology," Surgical Endoscopy, 2004; 19 (4): 477-483.

Hissink, "Olympus Medical develops capsule camera technology," Dec. 2004, accessed Aug. 29, 2007, http://www.letsgodigital.org , 3 pp.

Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4 pp.

Dumpert et al., "Improving in Vivo Robot Visioin Quality," from the Proceedings of Medicine Meets Virtual Reality, Long Beach, CA, Jan. 26-29, 2005. 1 pg.

Atmel 80C5X2 Core, http://www.atmel.com, 2006, 186 pp.

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.

Berg et al., "Surgery with Cooperative Robots," Medicine Meets Virtual Reality, Feb. 2007, 1 pg.

Dumpert et al., "Stereoscopic In Vivo Surgical Robots," IEEE Sensors Special Issue on In Vivo Sensors for Medicine, Jan. 2007, 10 pp.

Grady, "Doctors Try New Surgery for Gallbladder Removal," The New York Times, Apr. 20, 2007, 3 pp.

Tomorrow's Surgery: micromotors and microbots for minimally invasive procedures, "Minimally Invasive Surgery & Allied Technologies."

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committee," U.S. Food and Drug Adminstration, available at http://www.fdaJ.:?; ov, Finalized: Nov. 7, 2003; Updated: Jun. 24, 2005, 11 pp.

Gopura et al., "Mechanical designs of active upper-limb exoskeleton robots: State-of-the-art and design difficulties",2009, IEEE, p. 178-187 (Year: 2009).

Mack et al., "Present Role of Thoracoscopy in the Diagnosis and Treatment of Diseases of the Chest," Ann Thorac Surgery, 1992; 54: 403-409.

Peters, "Minimally Invasive Colectomy: Are the Potential Benefits Realized?" Dis Colon Rectum 1993; 36: 751-756.

Liem et al., "Comparison of Conventional Anterior Surgery and Laparoscopic Surgery for Inguinal-hernia Repair," New England Journal of Medicine, 1997; 336 (22): 1541-1547.

Kazemier et al. (1998), "Vascular Injuries During Laparoscopy," J. Am. Coli. Surg. 186(5): 604-5.

Palm, William, "Rapid Prototyping Primer" May 1998 (revised Jul. 30, 2002) (http://www.me.psu.edu/lamancusa/rapidpro/primer/chapter2.htm).

MacFarlane et al., "Force-Feedback Grasper Helps Restore the Sense of Touch in Minimally Invasive Surgery," Journal of Gastrointestinal Surgery, 1999; 3: 278-285.

Ishiyama et al., "Spiral-type Micro-machine for Medical Applications," 2000 International Symposium on Micromechatronics and Human Science, 2000: 65-69.

Li et al. (2000), "Microvascular Anastomoses Performed in Rats Using a Microsurgical Telemanipulator," Comp. Aid. Surg. 5: 326-332.

Meron, "The development of the swallowable video capsule (M2A)," Gastrointestinal Endoscopy 2000; 52 6: 817-819.

Kang et al., "Robotic Assistants Aid Surgeons During Minimally Invasive Procedures," IEEE Engineering in Medicine and Biology, Jan.-Feb. 2001; pp. 94-104.

Lafullarde et al., "Laparoscopic Nissen Fundoplication: Five-year Results and Beyond," Arch/Surg, Feb. 2001; 136:180-184.

Mack, "Minimally Invasive and Robotic Surgery," JAMA, Feb. 2001; 285(5): 568-572.

Phee et al., "Development of Microrobotic Devices for Locomotion in the Human Gastrointestinal Tract," International Conference on Computational Intelligence, Robotics and Autonomous Systems (CIRAS 2001), Nov. 28-30, 2001, Singapore.

Melvin et al., "Computer-Enhanced vs. Standard Laparoscopic Antireflux Surgery," J Gastrointest Surg 2002; 6: 11-16.

Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.

Leggett et al. (2002), "Aortic injury during laparoscopic fundoplication," Surg. Endoscopy 16(2): 362.

Mei et al., "Wireless Drive and Control of a Swimming Microrobot," Proceedings of the 2002 IEEE International Conference on Robotics & Automation, May 2002: 1131-1136.

Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.

Munro (2002), "Laparoscopic access: complications, technologies, and techniques," Curro Opin. Obstel. Gynecol., 14(4): 365-74.

Nio et al., "Efficiency of manual vs robotical (Zeus) assisted laparoscopic surgery in the performance of standardized tasks," Surg Endosc, 2002; 16: 412-415.

Phee et al., "Analysis and Development of Locomotion Devices for the Gastrointestinal Tract," IEEE Transaction on Biomedical Engineering, vol. 49, No. 6, Jun. 2002, pp. 613-616.

Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.

Kalloo et al., "Flexible transgastric peritoneoscopy: a novel approach to diagnostic and therapeutic interventions in the peritoneal cavity," Gastrointestinal Endoscopy, 2004; 60(1): 114-117.

Oleynikov et al., "In Vivo Camera Robots Provide Improved Vision for Laparoscopic Surgery," Computer Assisted Radiology and Surgery (CARS), Chicago, IL, Jun. 23-26, 2004.

(56)        References Cited

OTHER PUBLICATIONS

Patronik et al., "Crawling on the Heart: A Mobile Robotic Device for Minimally Invasive Cardiac Interventions," MICCAI, 2004, pp. 9-16.

Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.

Jagannath et al., "Peroral transgastric endoscopic ligation of fallopian tubes with long-term survival in a porcine model," Gastrointestinal Endoscopy, 2005; 61(3): 449-453.

Kantsevoy et al., "Endoscopic gastrojejunostomy with survival in a porcine model," Gastrointestinal Endoscopy, 2005; 62(2): 287-292.

Menciassi et al., "Shape memory alloy clamping devices of a capsule for monitoring tasks in the gastrointestinal tract," J. Micromech. Microeng, 2005, 15: 2045-2055.

Oleynikov et al., "In Vivo Robotic Laparoscopy," Surgical Innovation, Jun. 2005, 12(2): 177-181.

Oleynikov et al., "Miniature Robots Can Assist in Laparoscopic Cholecystectomy," Journal of Surgical Endoscopy, 19-4: 473-476, 2005.

Patronik et al., "Preliminary evaluation of a mobile robotic device for navigation and intervention on the beating heart," Computer Aided Surgery, 10(4): 225-232, Jul. 2005.

Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, FL. Lauderdale, FL, Apr. 13-16, 2005, 1 pg.

Park et al., "Experimental studies of transgastric gallbladder surgery: cholecystectomy and cholecystogastric anastomosis (videos)," Gastrointestinal Endoscopy, 2005; 61(4): 601-606.

O'Neill, "Surgeon takes new route to gallbladder," The Oregonian, Jun. 2007, 2 pp.

Park et al., "Trocar-less Instrumentation for Laparoscopy: Magnetic Positioning of Intra-abdominal Camera and Retractor," Ann Surg, Mar. 2007; 245(3): 379-384.

Rentschler et al., "An In Vivo Mobile Robot for Surgical Vision and Task Assistance," Journal of Medical Devices, Mar. 2007, vol. 1: 23-29.

Rentschler et al., "In vivo Robotics during the NEEMO 9 Mission," Medicine Meets Virtual Reality, Feb. 2007, 1 pg.

Midday Jeff et al., "Material Handling System for Robotic natural Orifice Surgery", Proceedings of the 2011 Design of medical Devices Conference, Apr. 12-14, 2011, Minneapolis, MN, 4 pages.

Keller et al., Design of the pediatric arm rehabilitation robot ChARMin, 2014, IEEE, p. 530-535 (Year: 2014).

Miller, PH.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.

Patronik et al., "Development of a Tethered Epicardial Crawler for Minimally Invasive Cardiac Therapies," IEEE, pp. 239-240.

Rentschler et al., "In vivo Mobile Surgical Robotic Task Assistance," 1 pg.

"Peirs et al., ""A miniature manipulator for integration in a self-propelling endoscope,"" Sensors and Actuators A,2001, 92: 343-349."

Micron, http://www.micron.com, 2006, ¼-inch VGA NTSC/PAL CMOS Digital Image Sensor, 98 pp.

Ko et al., "Per-Oral transgastric abdominal surgery," Chinese Journal of Digestive Diseases, 2006; 7: 67-70.

Kantsevoy et al., "Transgastric endoscopic splenectomy," Surgical Endoscopy, 2006; 20: 522-525.

Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006.

Rentschler et al., "Mobile In Vivo Biopsy Robot," IEEE International Conference on Robotics and Automation, Orlando, Florida, May 2006, pp. 4155-4160.

Southern Surgeons Club (1991), "A prospective analysis of 1518 laparoscopic cholecystectomies," N. Eng. 1 Med. 324 (16): 1073-1078.

Suzumori et al., "Development of Flexible Microactuator and its Applications to Robotics Mechanisms," Proceedings of the IEEE International Conference on Robotics and Automation, 1991: 1622-1627.

Wolfe et al., "Endoscopic Cholecystectomy: An analysis of Complications," Arch. Surg. Oct. 1991; 126: 1192-1196.

Tendick et al., (1993), "Sensing and Manipulation Problems in Endoscopic Surgery: Experiment, Analysis, and Observation," Presence 2(1): 66-81.

Sackier et al., "Robotically assisted laparoscopic surgery," Surgical Endoscopy, 1994; 8: 63-66.

Stiff et al., "Long-term Pain: Less Common After Laparoscopic than Open Cholecystectomy," British Journal of Surgery, 1994; 81: 1368-1370.

Slatkin et al., "The Development of a Robotic Endoscope," Proceedings of the 1995 IEEE International Conference on Robotics and Automation, pp. 162-171, 1995.

Taylor et al., "A Telerobotic Assistant for Laparoscopic Surgery," IEEE Eng Med Biol, 1995; 279-287.

Way et al., (Editors), "Fundamentals of Laparoscopic Surgery," Churchill Livingstone Inc., 1995, 14 pp.

Schippers et al., (1996 "Requirements and Possibilities of Computer-Assisted Endoscopic Surgery," In: Computer Integrated Surgery: Technology and Clinical Applications, pp. 561-565.

Tendick et al., "Applications of Micromechatronics in Minimally Invasive Surgery," IEEE/ASME Transactions on Mechatronics, 1998; 3(1): 34-42.

Worn et al., "Espirit Project No. 33915: Miniaturised Robot for Micro Manipulation (MINIMAN)" , Nov. 1998; http://www.ipr.ira.ujka.de/-microbol/miniman.

Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.

Salky, "What is the Penetration of Endoscopic Techniques into Surgical Practice?" Digestive Surgery, 2000; 17:422-426.

Schurr et al., "Robotics and Telemanipulation Technologies for Endoscopic Surgery," Surgical Endoscopy, 2000; 14: 375-381.

Rosen et al., "Objective Laparoscopic Skills Assessments of Surgical Residents Using Hidden Markov Models Based on Haptic Information and Tool/Tissue Interactions," Studies in Health Technology and Infonnatics—Medicine Meets Virtual Reality, Jan. 2001, 7 pp.

Yu et al., "Microrobotic Cell Injection," Proceedings of the 2001 IEEE International Conference on Robotics and Automation, May 2001; 620-625.

Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.

Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.

Ruurda et al., "Feasibility of Robot-Assisted Laparoscopic Surgery," Surgical Laparoscopy, Endoscopy & Percutaneous Techniques, 2002; 12(1):41-45.

Ruurda et al., "Robot-Assisted surgical systems: a new era in laparoscopic surgery," Ann R. Coll Surg Engl., 2002; 84: 223-226.

Stoianovici et al., "Robotic Tools for Minimally Invasive Urologic Surgery" , Jan. 1, 2002, pp. 1-17.

Thomann et al., "The Design of a new type of Micro Robot for the Intestinal Inspection," Proceedings of the 2002 IEEE Intl. Conference on Intelligent Robots and Systems, Oct. 2002: 1385-1390.

Riviere et al., "Toward Active Tremor Canceling in Handheld Microsurgical Instruments," IEEE Transactions on Robotics and Automation, Oct. 2003, 19(5): 793-800.

Rentschler et al., "Mechanical Design of Robotic In Vivo Wheeled Mobility," ASME Journal of Mechanical Design, 2006, pp. 1-11.

(56)            References Cited

OTHER PUBLICATIONS

Rentschler et al., "Miniature in vivo Robots for Remote and Harsh Environments," IEEE Transactions on Information Technology in Biomedicine. Jan. 2006; 12(1): 66-75.

Rentschler et al., "Mobile In Vivo Camera Robots Provide Sole Visual Feedback for Abdominal Exploration and Cholecystectomy," Journal of Surgical Endoscopy, 20-1: 135-138, 2006b.

Rentschler et al., "Natural Orifice Surgery with an Endoluminal Mobile Robot," The Society of American Gastrointestinal Endoscopic Surgeons, Dallas, TX, Apr. 2006d, 14 pp.

Sharp LL-151-3D, http://www.sharp3d.com, 2006, 2 pp.

Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.

Schwartz, "In the Lab: Robots that Slink and Squirm," The New York Times, Mar. 27, 2007, 4 pp.

Yu, BSN, RN, "M2ATM Capsule Endoscopy A Breakthrough Diagnostic Tool for Small Intestine Imagining," vol. 25, No. 1, Gastroenterology Nursing, pp. 24-27.

Strong et al., "Efficacy of Novel Robotic Camera vs. a Standard Laproscopic Camera," Surgical Innovation vol. 12, No. 4, Dec. 2005, Westminster Publications, Inc., pp. 315-318.

Sodeyama et al., A shoulder structure of muscle-driven humanoid with shoulder blades, 2005, IEEE, p. 1-6 (Year: 2005).

Smart Pill "Fastastic Voyage: Smart Pill to Expand Testing," http://www.smartpilldiagnostics.com, Apr. 13, 2005, 1 pg.

"Satava, ""Surgical Robotics: The Early Chronicles,"" Surgical Laparoscopy, Endoscopy & Percutaneous Techniques, 2002; 12(1): 6-16."

Rosen et al., "Spherical Mechanism Analysis of a Surgical Robot for Minimally Invasive Surgery—Analytical and Experimental Approaches," Studies in Health Technology and Infonnatics—Medicine Meets Virtual Reality, pp. 442-448, Jan. 2005.

Rentschler et al., "Toward In Vivo Mobility," Studies in Health Technology and Infonnatics—Medicine Meets Virtual Reality, ISO Press, Long Beach, CA, 2005a, III: 397-403.

Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.

Rentschler et al., "Modeling, Analysis, and Experimental Study of In Vivo Wheeled Robotic Mobility," IEEE Transactions on Robotics, 22 (2): 308-321, 2005c.

Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.

* cited by examiner

40

42

44

46A

46B

40

42

44

46A

46

46C

46B

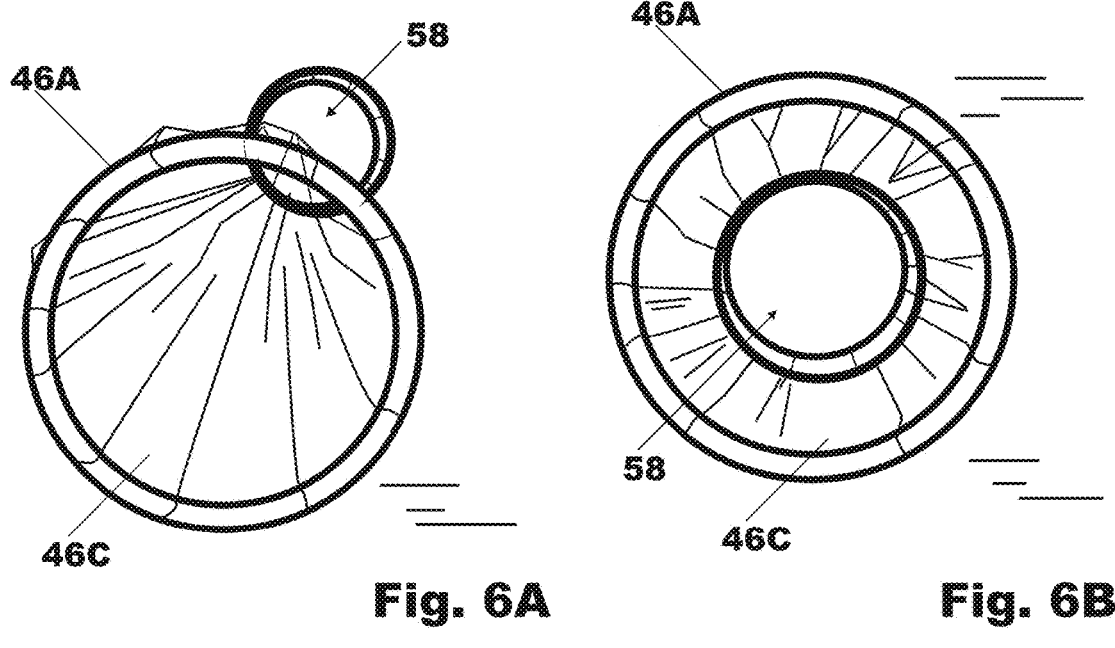
Fig. 6A          Fig. 6B
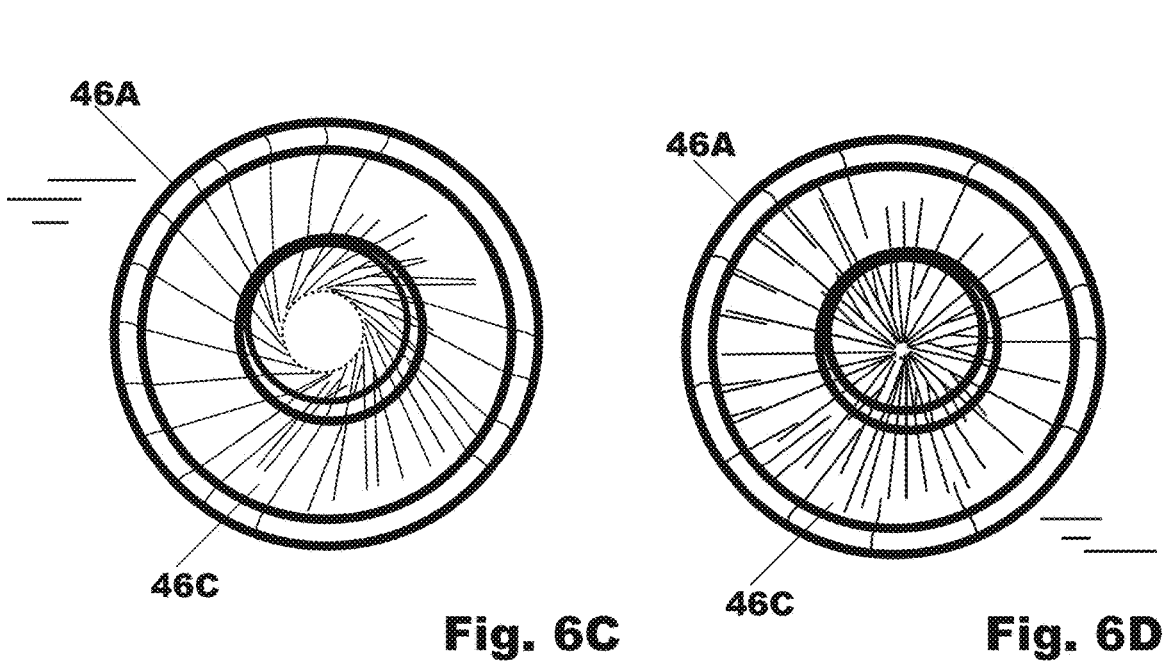
Fig. 6C          Fig. 6D

28

26

114

184

180

182

200

240    250

250    240

204    244 206

202

242

208

318

300

314

450

316

312

480

310

308

304

302

326

306

308

306

314

300

318

316

312

310

340

342

348

A

B

344

C

346

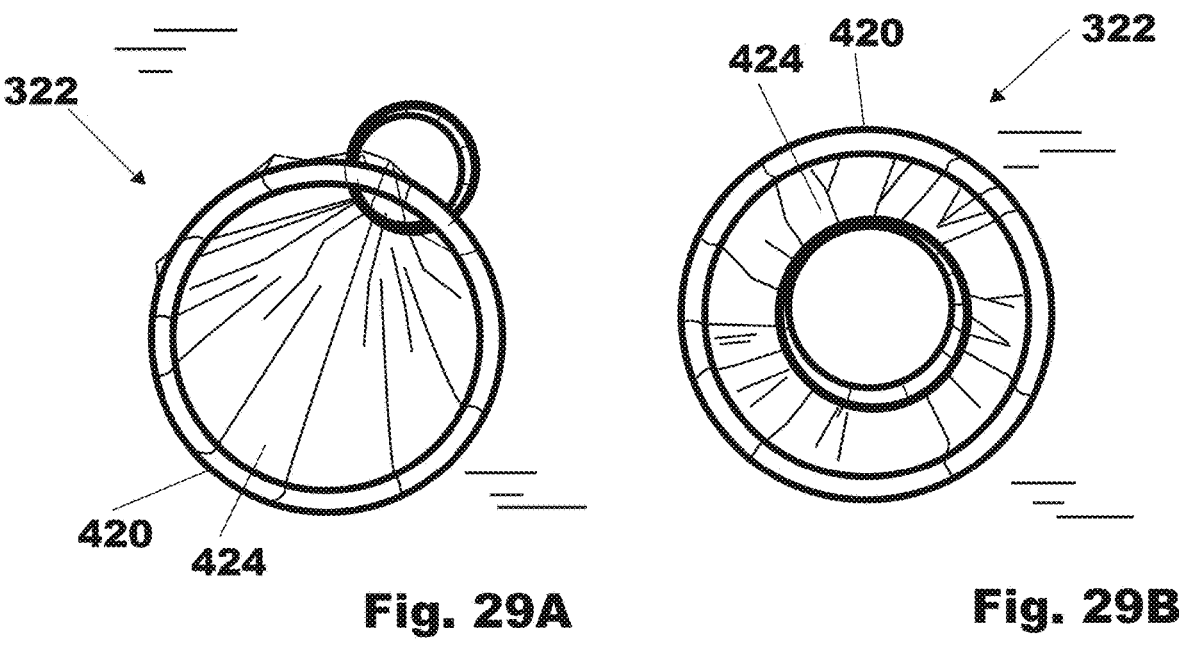
Fig. 29A          Fig. 29B
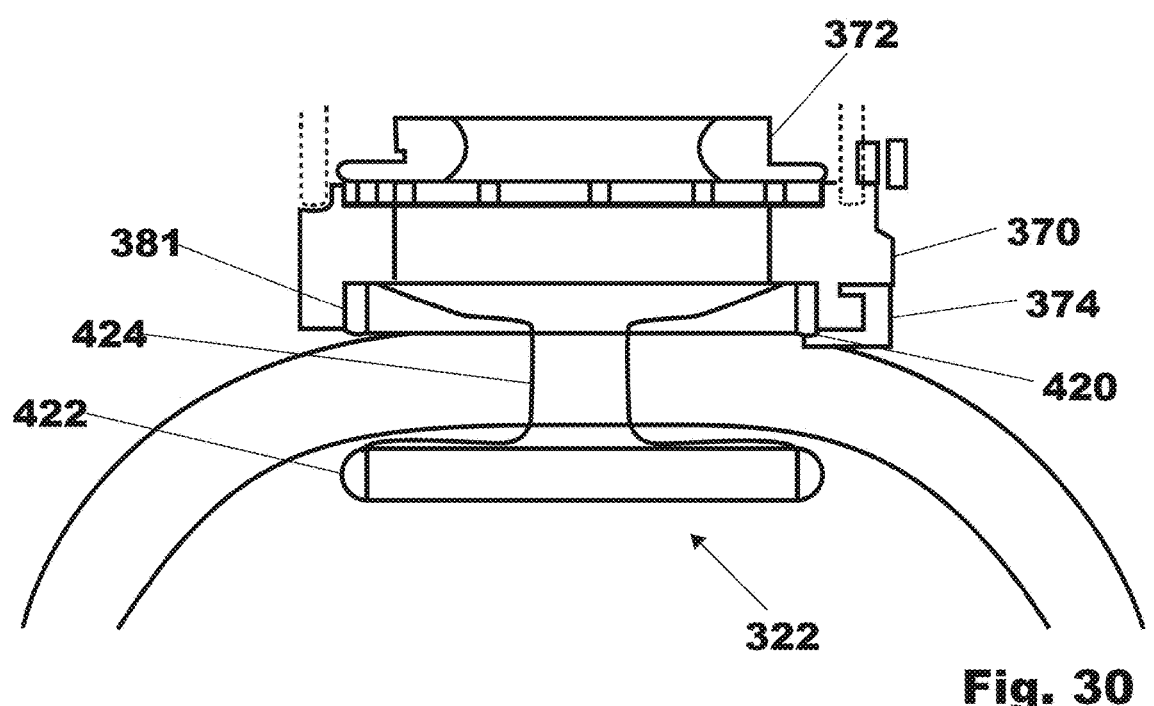
Fig. 30

370

381

374

420

472

474

504
~500
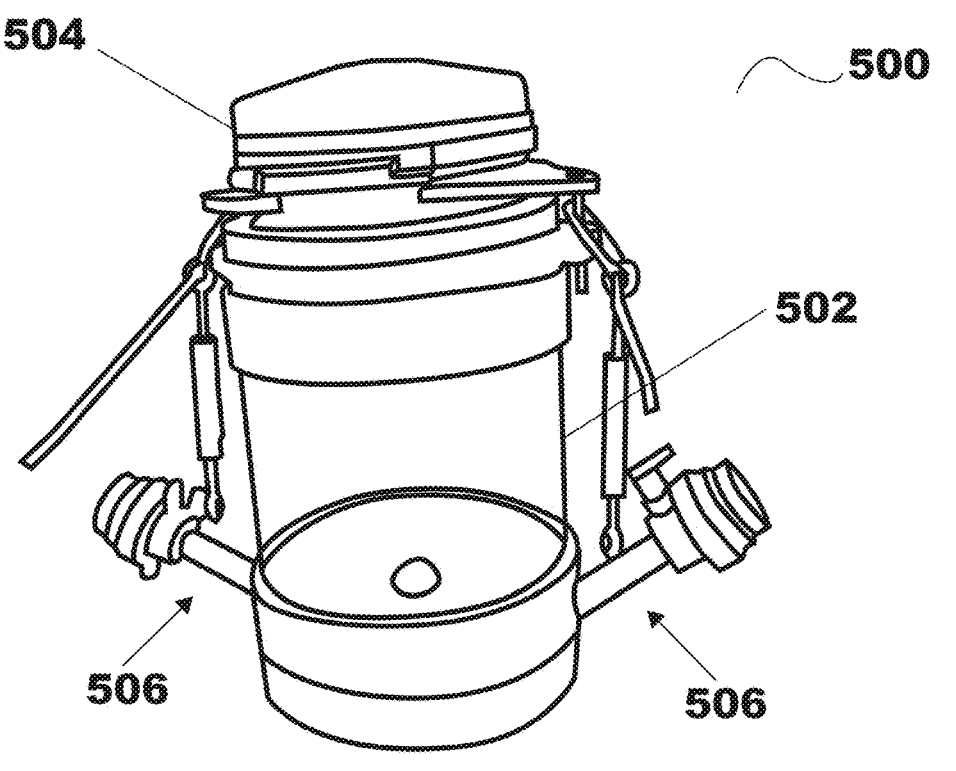
502
506          506
Fig. 39A
~500
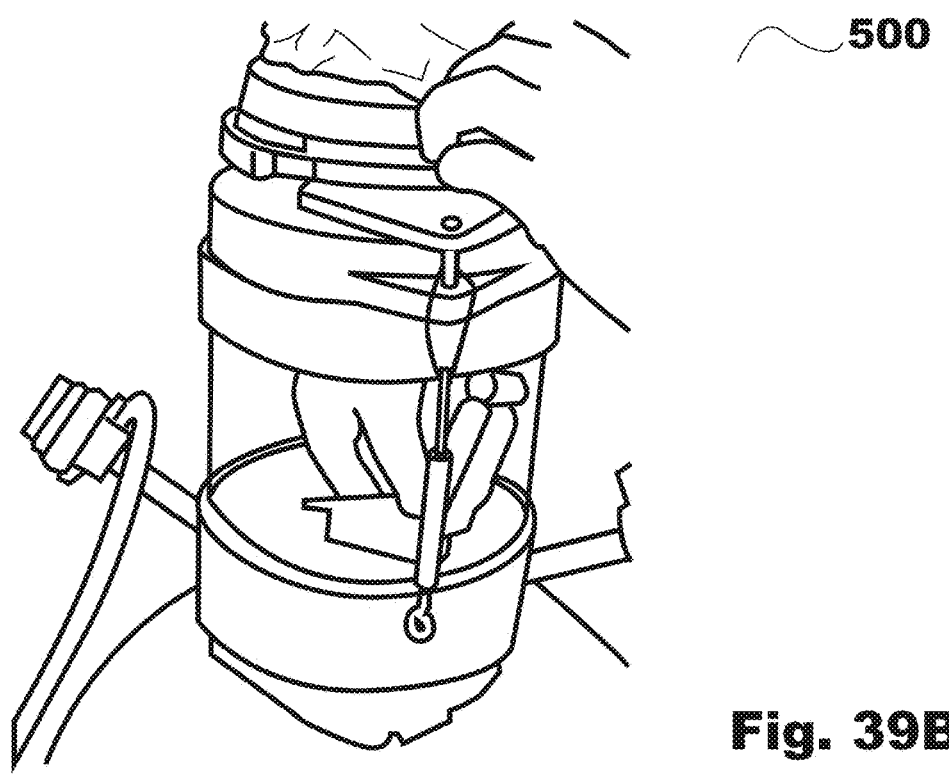
Fig. 39B

580

584

582

584

582

610

612

616

614

624

628   630

620

626

622

634     632

620

690

702

698

ABDOMINAL
WALL

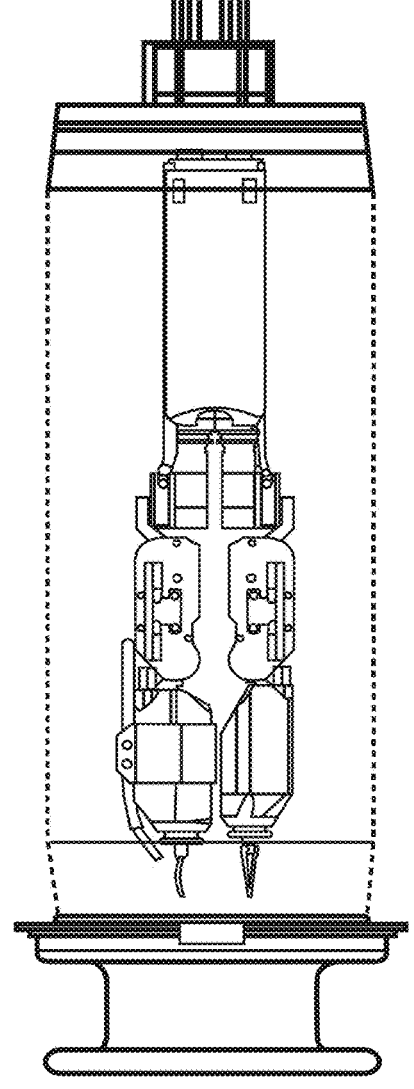
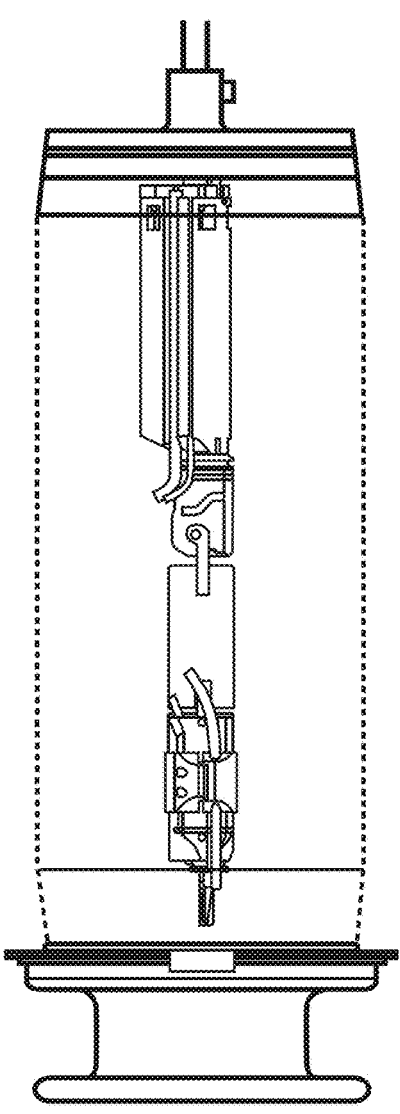
Fig. 65A　　　　　　Fig. 65B

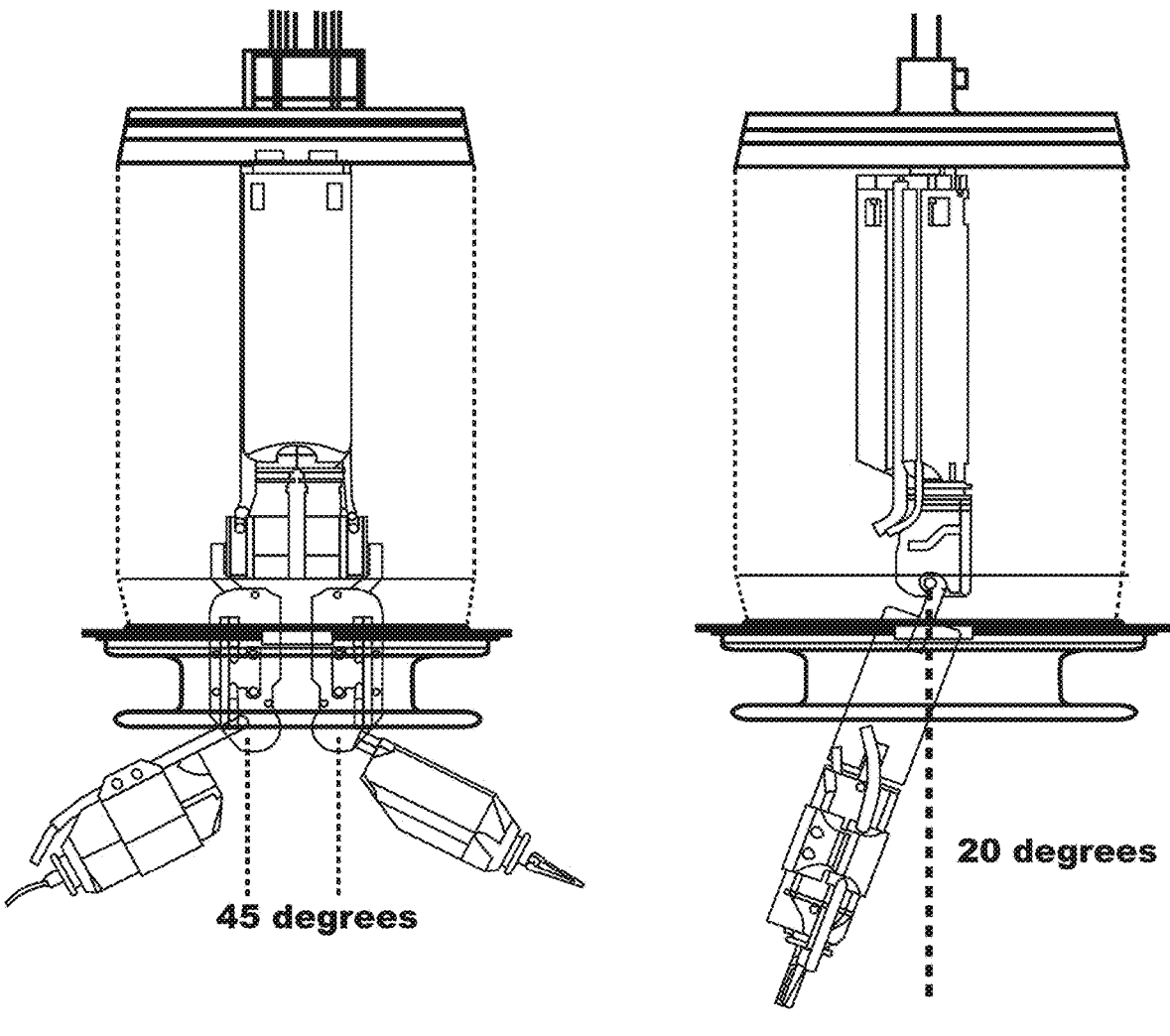
Fig. 67A        Fig. 67B

45 degrees

45 degrees

80 degrees

1054

1052

1050

1056

1062

1060

1064

1070

1074

1076A

1076

1076B

1072

1078

1098

1092

1094

1090

1100

1106

1108

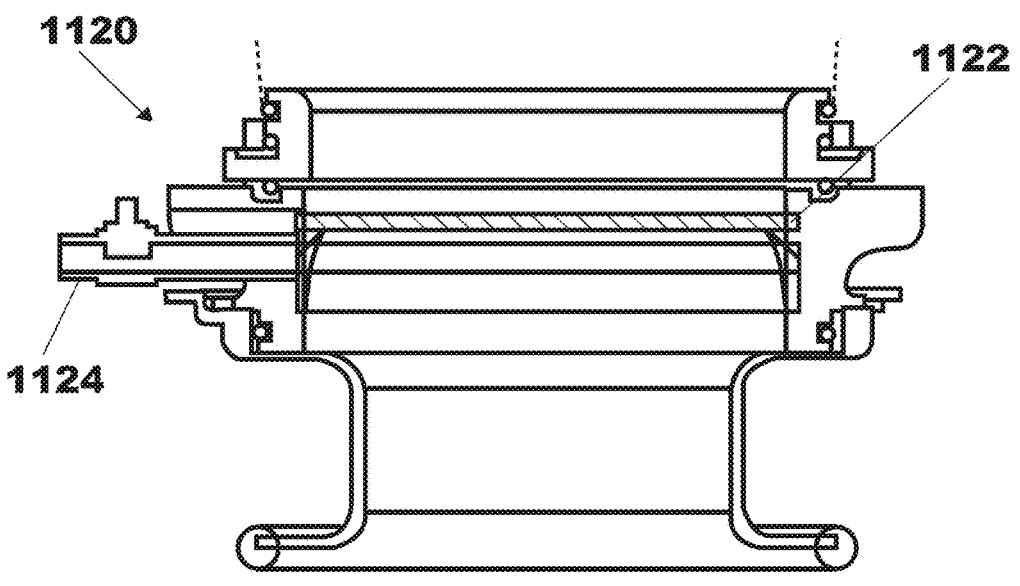
Fig. 83
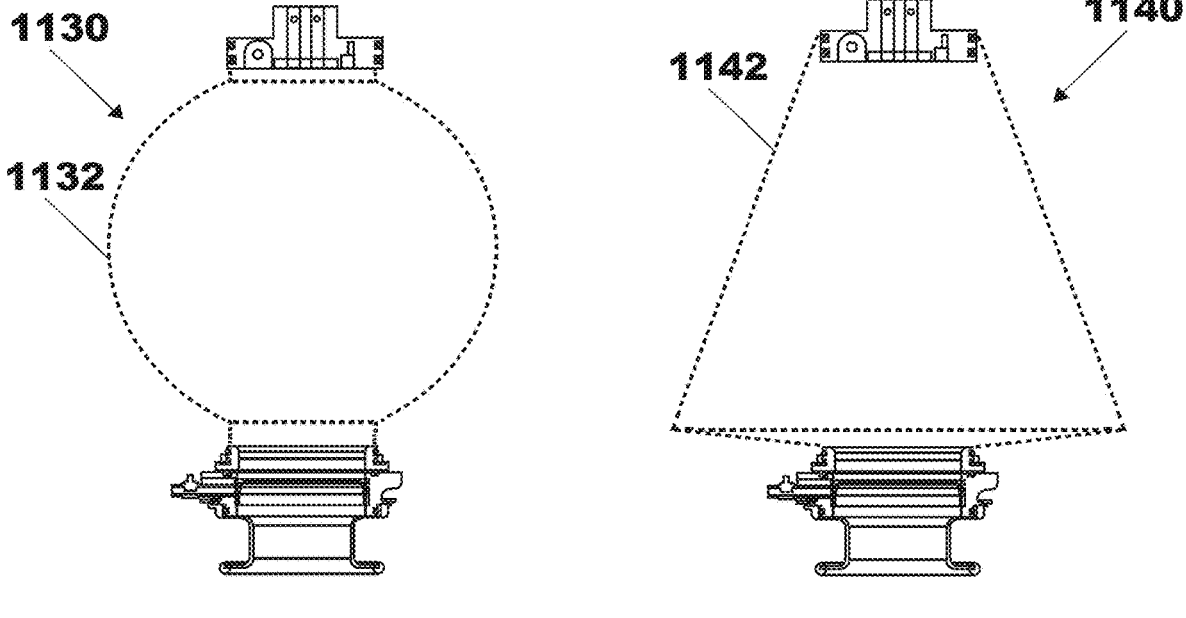
Fig. 84A            Fig. 84B

1150

1152

1154

1160

1162

1164

1170

1172

1174

1208

1200

1202

1210

1220

1226

1228

1222

1228

1220

1224

1226

1228

1240

1242

1244

1246

METHODS, SYSTEMS, AND DEVICES FOR SURGICAL ACCESS AND INSERTION

CROSS-REFERENCE TO RELATED APPLICATION(S)

This application claims priority as a continuation of U.S. patent application Ser. No. 16/999,407, filed Aug. 21, 2020 and entitled "Methods, Systems, and Devices for Surgical Access and Insertion," which claims priority as a continuation of U.S. patent application Ser. No. 15/890,860, filed Feb. 7, 2018 and entitled "Methods, Systems, and Devices for Surgical Access and Insertion," which claims priority as a continuation of U.S. application Ser. No. 14/661,465, filed Mar. 18, 2015 and entitled "Methods, Systems, and Devices for Surgical Access and Insertion;" which claims priority as a continuation of U.S. application Ser. No. 13/738,706, filed Jan. 10, 2013 and entitled "Methods, Systems, and Devices for Surgical Access and Insertion;" which claims priority to Provisional Application No. 61/584,947, filed Jan. 10, 2012; and Provisional Application No. 61/683,483, filed Aug. 15, 2012; all of which are hereby incorporated herein by reference in their entireties.

GOVERNMENT SUPPORT

This invention was made with government support under Grant No. W81XWH-09-2-0185 awarded by the U.S. Army Medical Research and Material Command and Grant Nos. NNX09A071A and NNX10AJ26G awarded by the National Aeronautics and Space Administration. The government has certain rights in the invention.

FIELD OF THE INVENTION

The various embodiments herein relate to systems, devices, and/or methods relating to surgical procedures, and more specifically for accessing an insufflated cavity of a patient and/or positioning surgical systems or devices into the cavity.

BACKGROUND OF THE INVENTION

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Further, the technologies are also limited due to difficulties relating to maintaining access to the surgical cavity while also maintaining insufflations of the cavity.

There is a need in the art for improved surgical methods, systems, and devices.

BRIEF SUMMARY OF THE INVENTION

Discussed herein are various surgical access and insertion devices and methods.

In Example 1, a surgical insertion device comprises a canister defining a lumen, a top cap coupled to a proximal end of the canister, and an incision port removably coupled to a distal end of the canister. The canister is sized to receive a surgical device in the lumen. The top cap comprises at least one lumen defined in the top cap, wherein the at least one lumen is configured to receive a support rod. The incision port comprises a fluidic sealing component configured to maintain a fluidic seal.

Example 2 relates to the surgical insertion device according to Example 1, wherein the lumen is fluidically sealed in relation to ambient air.

Example 3 relates to the surgical insertion device according to Example 1, wherein the canister comprises a flexible material or a substantially rigid material.

Example 4 relates to the surgical insertion device according to Example 1, wherein the canister comprises a flexible portion and a substantially rigid portion.

Example 5 relates to the surgical insertion device according to Example 1, wherein the canister has a cylindrical shape, a spherical shape, or a conical shape.

Example 6 relates to the surgical insertion device according to Example 1, wherein the canister comprises at least one rib structure.

Example 7 relates to the surgical insertion device according to Example 1, wherein the fluidic sealing component comprises a sealable sleeve device, a flexible seal component, a removable lid seal component, or a flap seal component.

Example 8 relates to the surgical insertion device according to Example 1, wherein the top cap comprises at least one of a pressure relief valve, at least one threaded lumen, a detachable cable harness, and a clamp projection.

Example 9 relates to the surgical insertion device according to Example 1, further comprising an outer handle set coupleable to the top cap.

Example 10 relates to the surgical insertion device according to Example 1, further comprising at least one measurement mechanism coupled to the top cap or the incision port.

Example 11 relates to the surgical insertion device according to Example 1, wherein the canister comprises at least one access port, wherein the at least one access port is a hand access port or a side access port.

In Example 12, a surgical insertion device comprises a flexible canister defining a lumen, a top cap coupled to a proximal end of the canister, an incision port removably coupled to a distal end of the canister, and a first measurement mechanism coupled with the top cap or the incision port. The canister is sized to receive a surgical device in the lumen. The top cap comprises at least one lumen defined in the top cap, wherein the at least lumen is configured to receive a support rod. The incision port comprising a fluidic sealing component is configured to maintain a fluidic seal. The first measurement mechanism is configured to measure the insertion depth of the surgical device.

Example 13 relates to the surgical insertion device according to Example 12, wherein the first measurement mechanism comprises a sensor, a string measurement system, a substantially rigid structure system, or a camera.

Example 14 relates to the surgical insertion device according to Example 12, wherein the fluidic sealing component comprises a sealable sleeve device, a flexible seal component, a removable lid seal component, or a flap seal component.

Example 15 relates to the surgical insertion device according to Example 12, wherein wherein the top cap comprises at least one of a pressure relief valve, at least one threaded lumen, a detachable cable harness, and a clamp projection.

Example 16 relates to the surgical insertion device according to Example 12, further comprising a second measurement mechanism coupled to the top cap or the incision port, the second measurement mechanism configured to measure any tilt of the flexible canister.

In Example 17, a surgical insertion device comprises a canister defining a lumen, a top cap coupled to a proximal end of the canister, and an incision port removably coupled to a distal end of the canister. The canister is sized to receive a surgical device in the lumen, wherein the surgical device is a robotic surgical device comprising two arms. The top cap comprises a pressure relief valve and at least one lumen defined in the top cap, wherein the at least one lumen is configured to receive a support rod. The incision port comprises a fluidic sealing component configured to maintain a fluidic seal.

Example 18 relates to the surgical insertion device according to Example 17, wherein the fluidic sealing component comprises a sealable sleeve device, a flexible seal component, a removable lid seal component, or a flap seal component.

Example 19 relates to the surgical insertion device according to Example 17, wherein the top cap comprises at least one of at least one threaded lumen, a detachable cable harness, and a clamp projection.

Example 20 relates to the surgical insertion device according to Example 17, further comprising at least one measurement mechanism coupled to the top cap or the incision port.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 6A is a top schematic view of a sealable sleeve device being positioned in an incision, according to one embodiment.

FIG. 6B is a top schematic view of the sealable sleeve device of FIG. 6A being positioned in an incision, according to one embodiment.

FIG. 6C is a top schematic view of the sealable sleeve device of FIG. 6A being positioned in an incision, according to one embodiment.

FIG. 6D is a top schematic view of the sealable sleeve device of FIG. 6A being positioned in an incision, according to one embodiment.

FIG. 29A is a top schematic view of a sealable sleeve device being positioned in an incision, according to one embodiment.

FIG. 29B is a top schematic view of the sealable sleeve device of FIG. 29A being positioned in an incision, according to one embodiment.

FIG. 30 is a cutaway side view of an incision port, according to one embodiment.

FIG. 39A is a perspective side view of an external pressurized device, according to another embodiment.

FIG. 39B is a perspective side view of the external pressurized device of FIG. 39A.

FIG. 65A is a side view of an external pressurized system or apparatus with a base coupling component and access port, according to one embodiment.

FIG. 65B is another side view of the external pressurized system or apparatus of FIG. 65A.

FIG. 67A is a side view of an external pressurized system or apparatus in which the forearms of the robotic device are positioned at an angle of or near 45° in relation to the upper arms, according to one embodiment.

FIG. 67B is another side view of the external pressurized system or apparatus of FIG. 67A.

FIG. 68A is a side view of an external pressurized system or apparatus in which the forearms of the robotic device are positioned in a particular position, according to one embodiment.

FIG. 68B is another side view of the external pressurized system or apparatus of FIG. 67A.

FIG. 69A is a side view of an external pressurized system or apparatus in which the forearms of the robotic device are positioned in an appropriate starting position for a procedure, according to one embodiment.

FIG. 69B is another side view of the external pressurized system or apparatus of FIG. 67A.

FIG. 70 is a side view of an external pressurized system or apparatus having a flexible container, according to another embodiment.

FIG. 71A is a perspective side view of a base coupling component, according to one embodiment.

FIG. 71B is another perspective side view of the base coupling component of FIG. 71A.

FIG. 72A is a perspective side view of a port attachment having a removable lid and an access port, according to one embodiment.

FIG. 72B is another perspective side view of the port attachment and access port of FIG. 72A.

FIG. 73A is a perspective side view of a port attachment having a removable lid and an access port, according to one embodiment.

FIG. 73B is another perspective side view of the port attachment and access port of FIG. 73A.

Figure 74A:
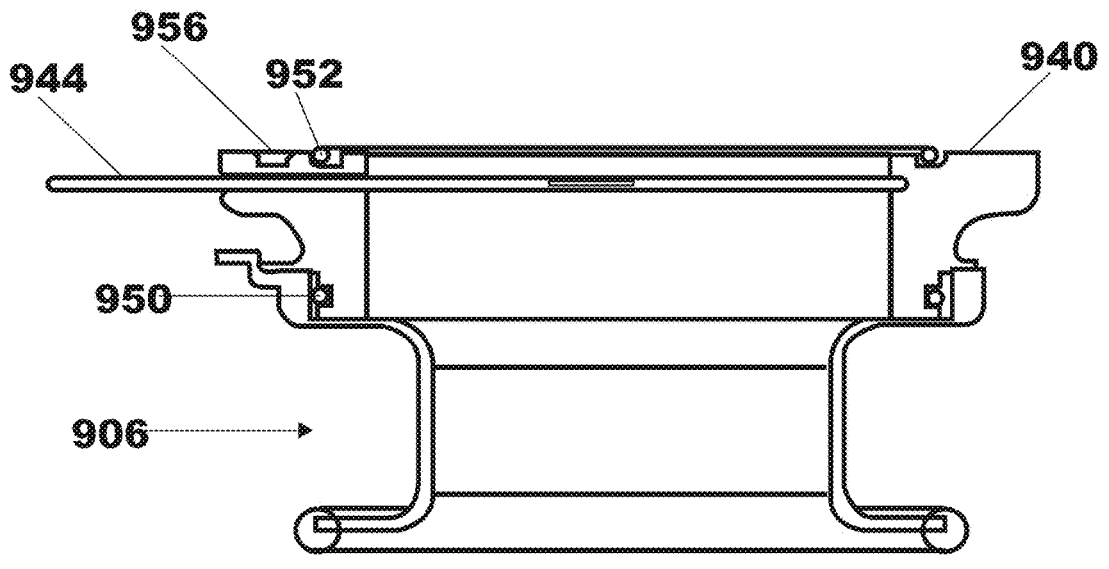

FIG. 74A is a cutaway side view of a port attachment having a removable lid and an access port, according to one embodiment.

Figure 74B:
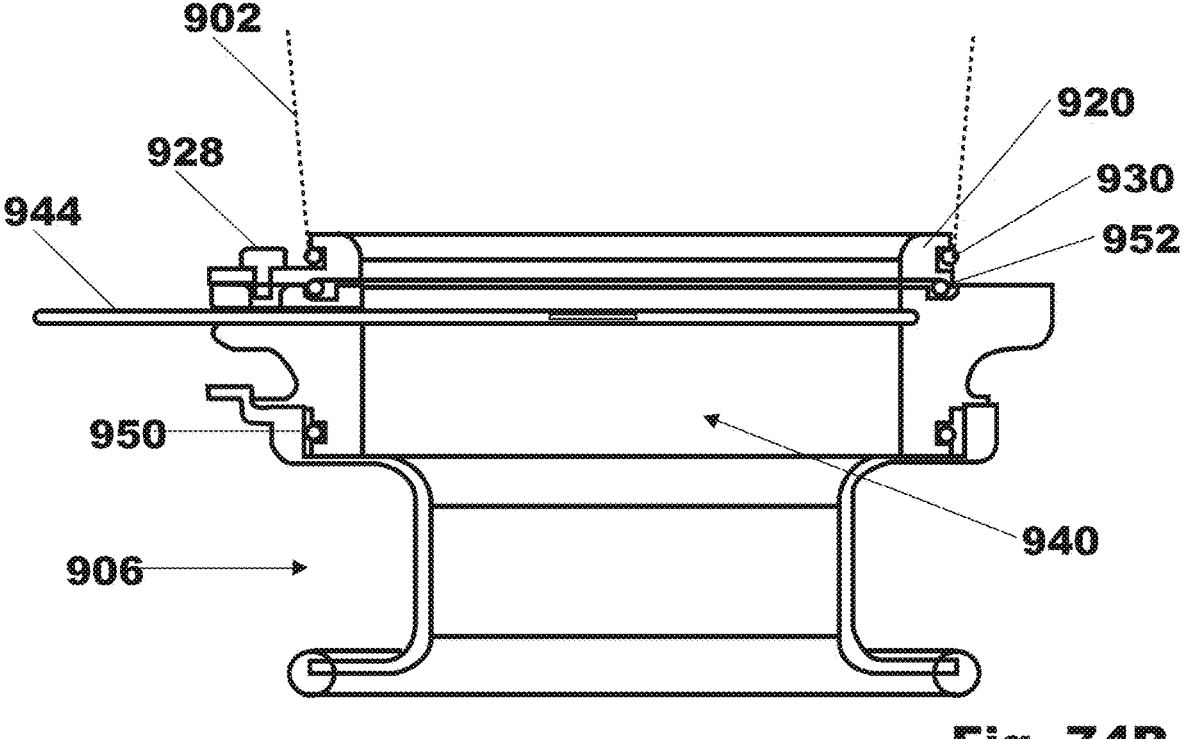

FIG. 74B is another cutaway side view of the port attachment and access port of FIG. 74A.

Figure 75A:
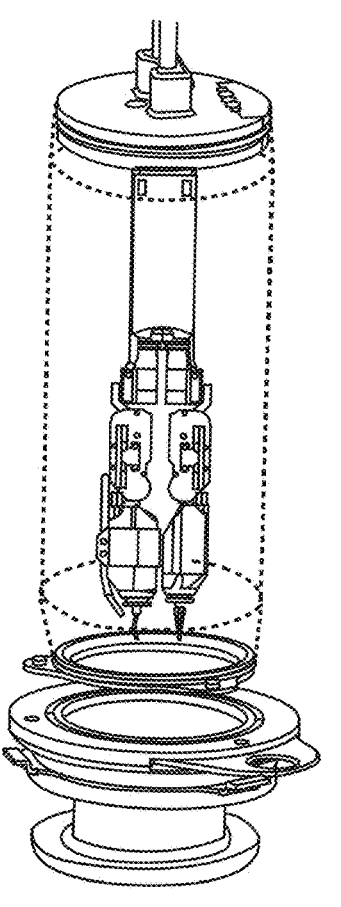

FIG. 75A is a perspective side view of an external pressurized insertion device having a port attachment with a removable lid, according to one embodiment.

Figure 75B:
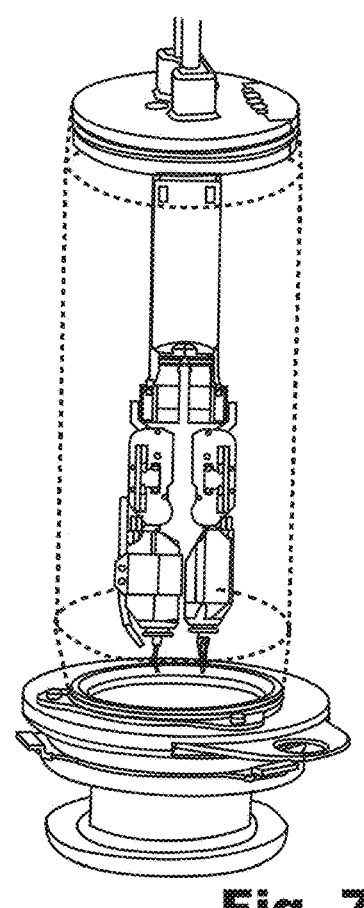

FIG. 75B is another perspective side view of the external pressurized insertion device of FIG. 75A.

Figure 75C:
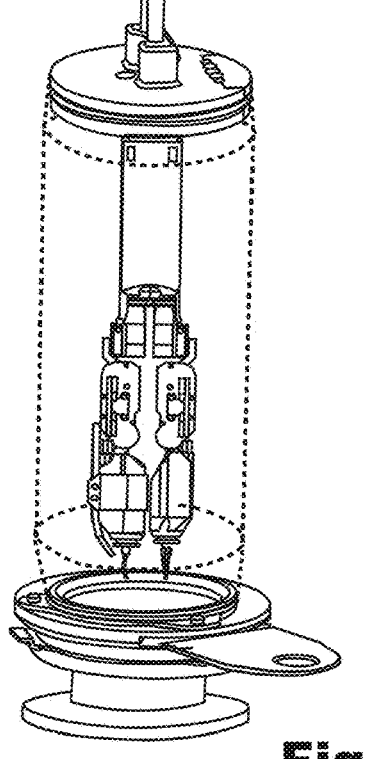

FIG. 75C is another perspective side view of the external pressurized insertion device of FIG. 75A.

Figure 76:
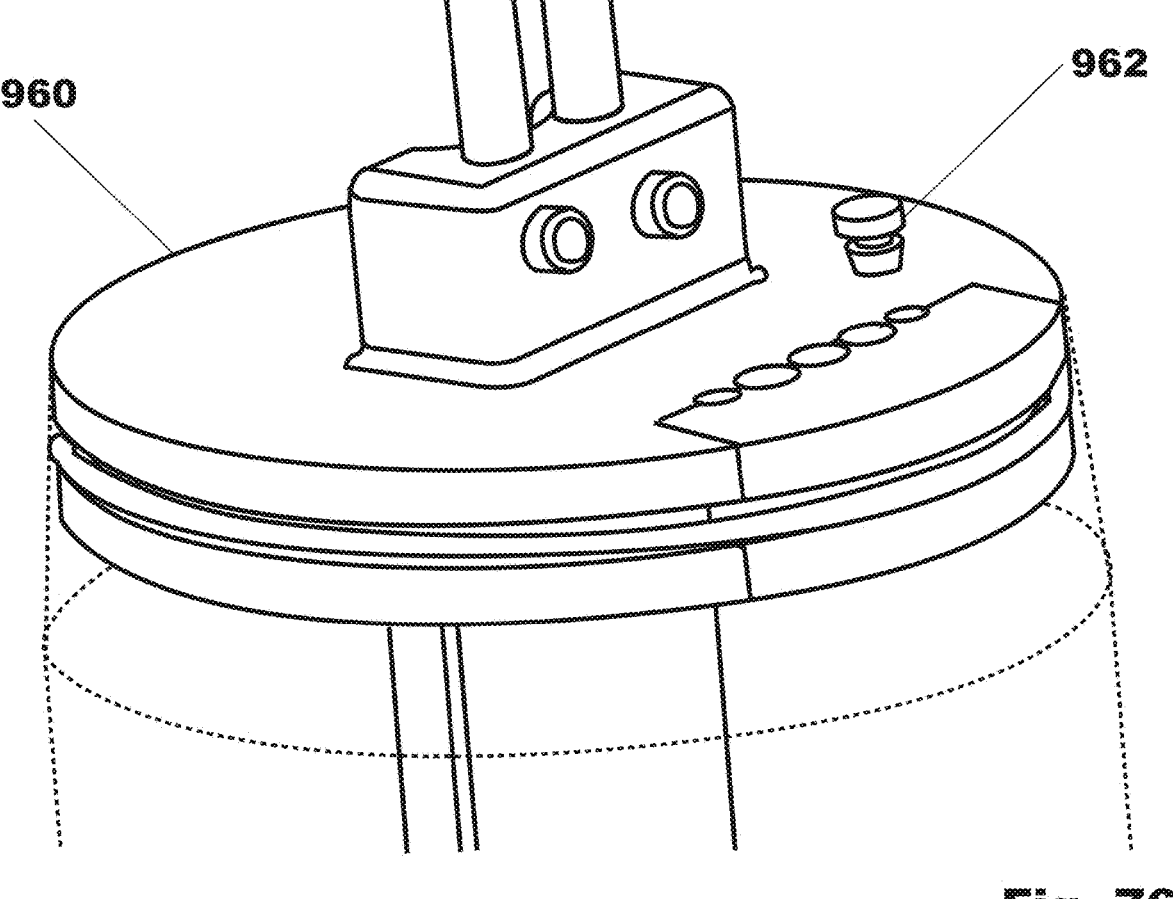

FIG. 76 is a perspective side view of a top cap having a pressure relief valve, according to one embodiment.

Figure 77A:
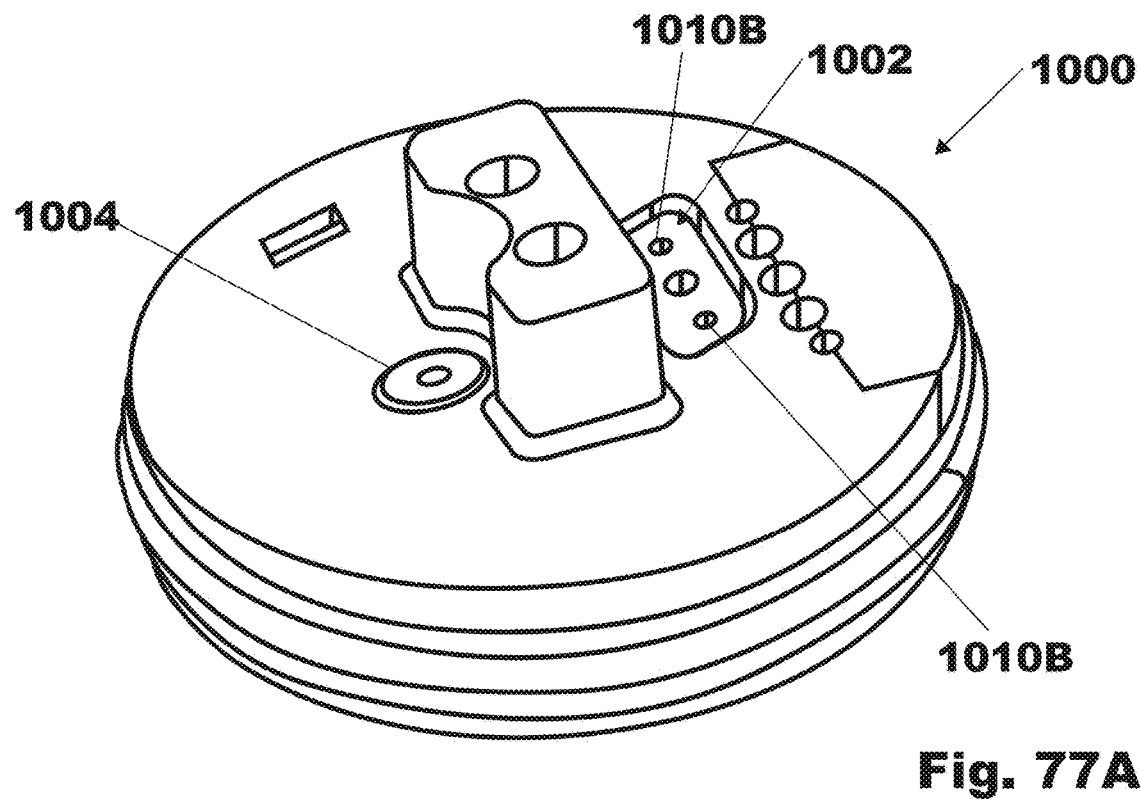

FIG. 77A is a perspective side view of a top cap having a pressure relief valve and port seal, according to one embodiment.

Figure 77B:
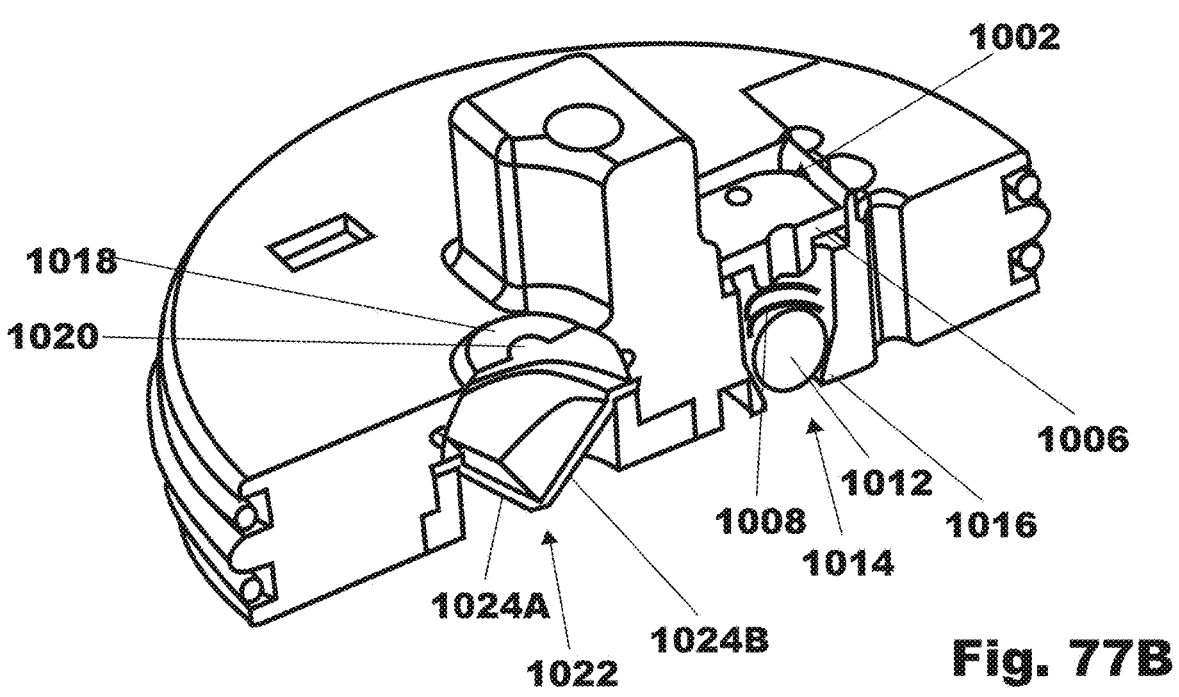

FIG. 77B is a perspective cutaway view of the top cap of FIG. 77A.

Figures 78A, 78B, 78C:
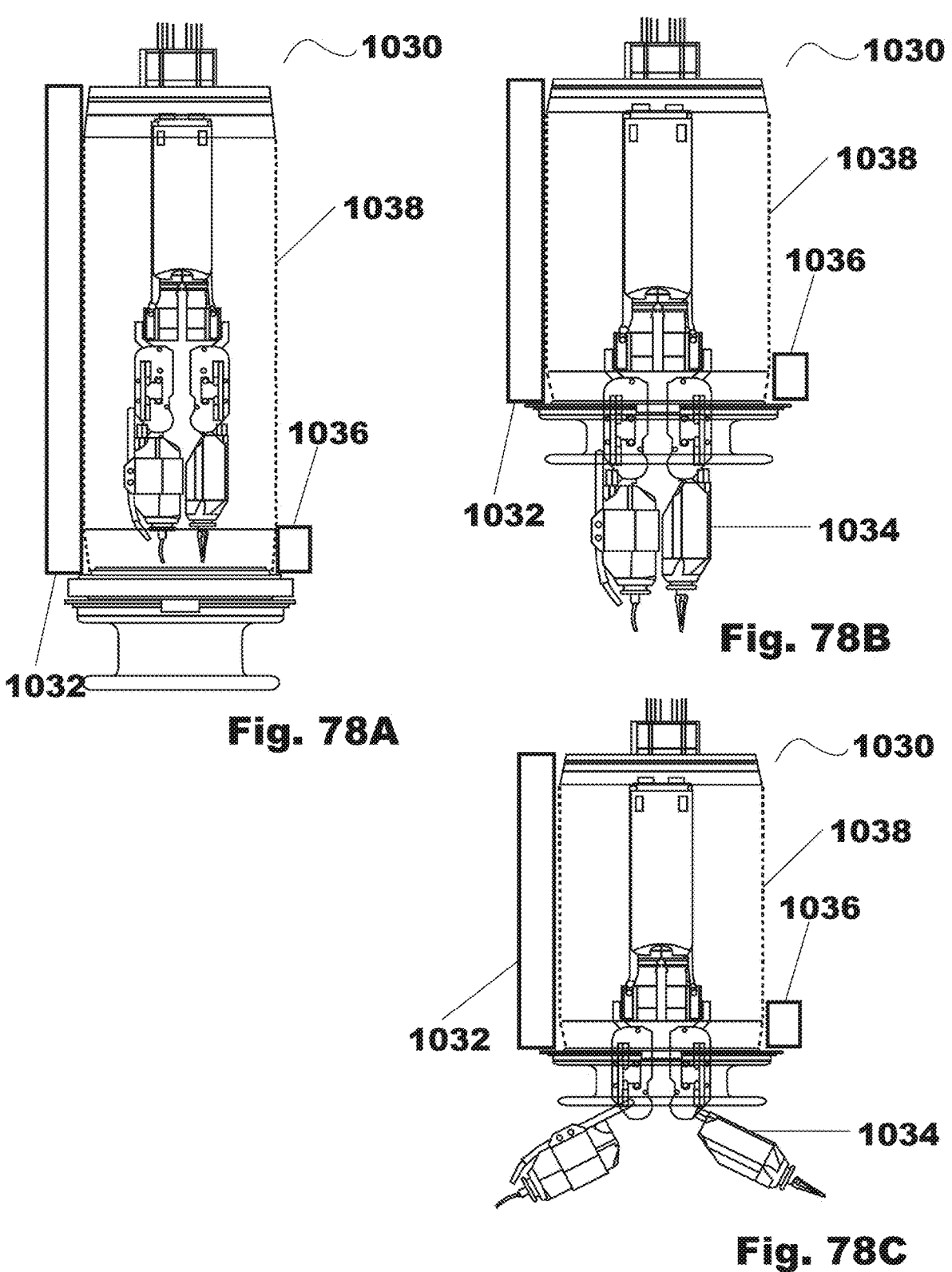

FIG. 78A is a side view of an insertion device having an actuator and sensor package.

FIG. 78B is another side view of the insertion device of FIG. 78A.

FIG. 78C is another side view of the insertion device of FIG. 78A.

Figures 79, 80:
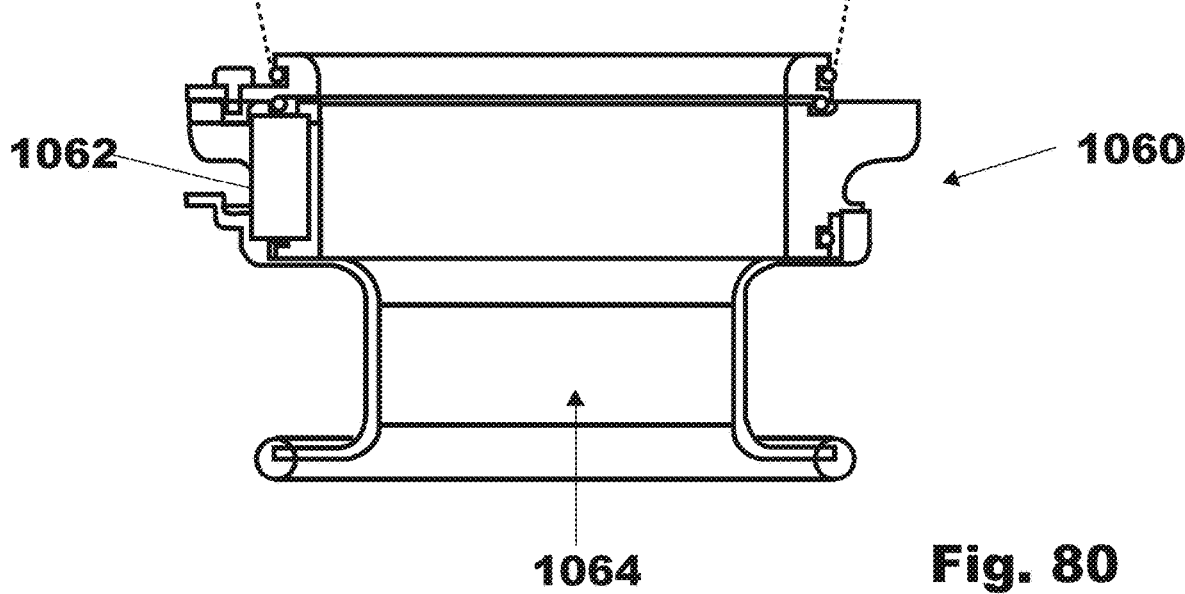

FIG. 79 is a side cutaway view of an insertion device having a measurement mechanism associated with the top cap, according to one embodiment.

FIG. 80 is a side cutaway view of an incision port of an insertion device having a measurement mechanism associated with the incision port, according to one embodiment.

Figure 81:
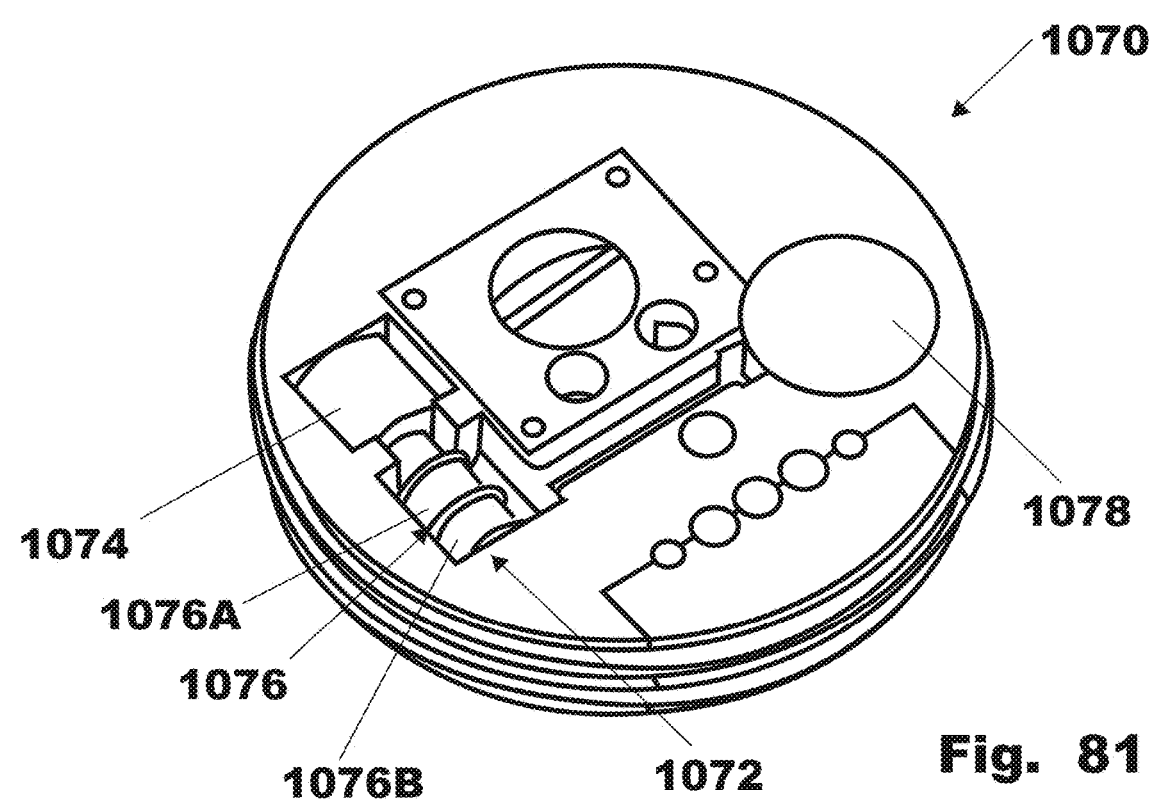

FIG. 81 is a top view of a top cap of an insertion device having a string measurement system, according to one embodiment.

Figure 82A:
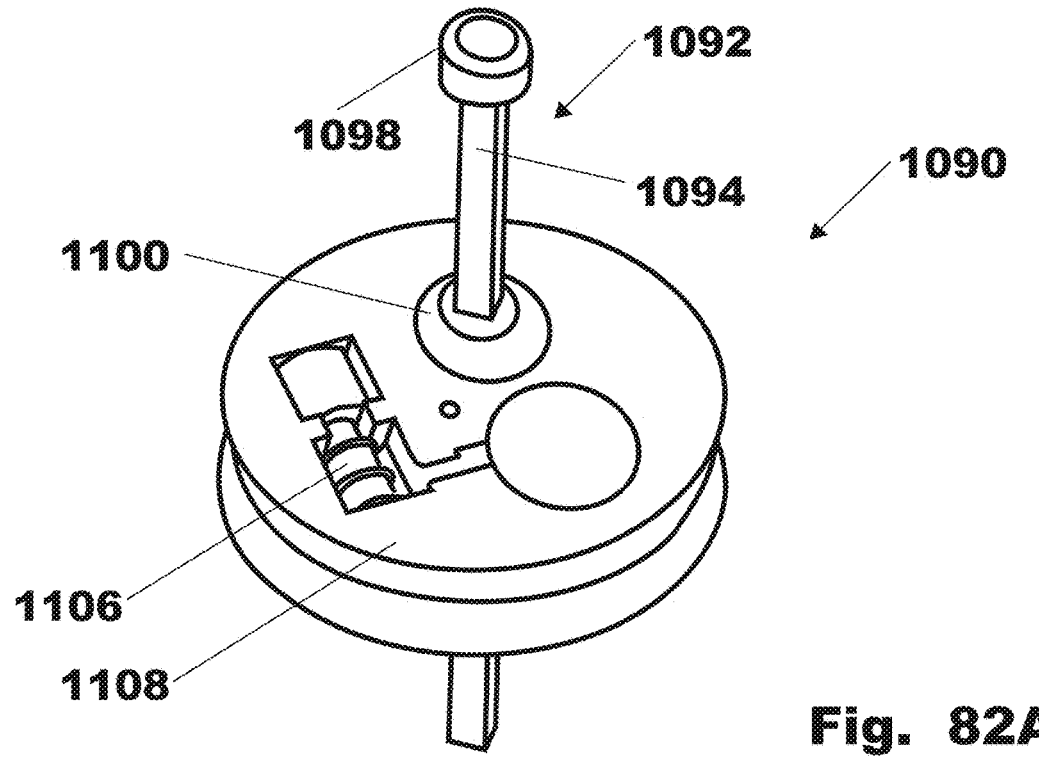

FIG. 82A is a top view of a top cap of an insertion device having a substantially rigid structure measurement mechanism, according to one embodiment.

Figure 82B:
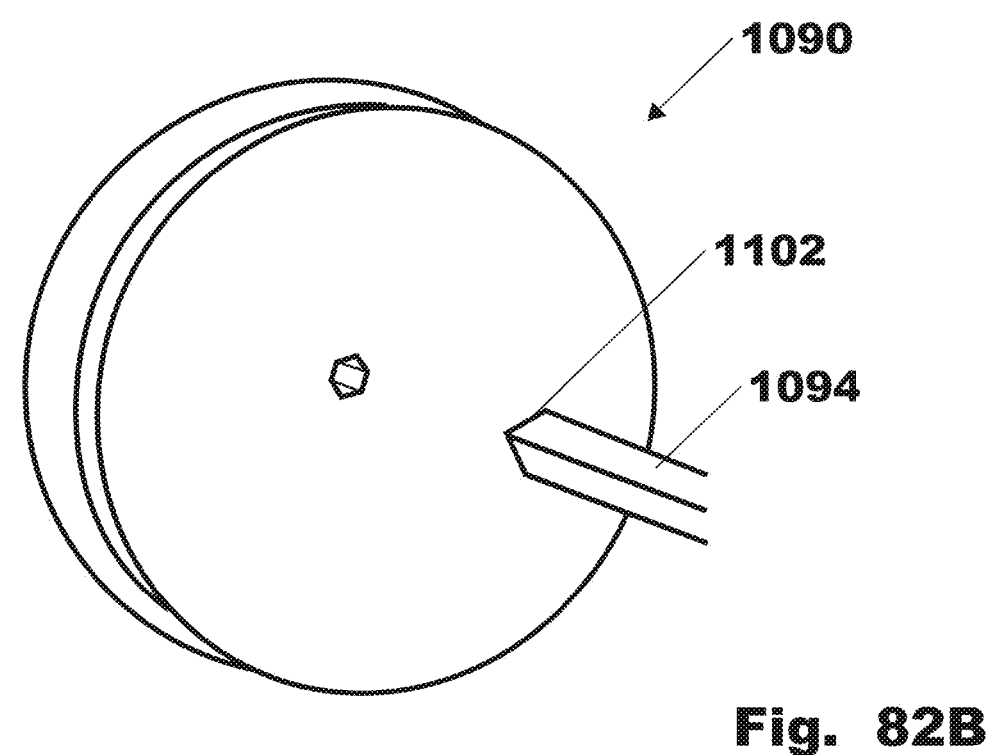

FIG. 82B is an underside view of the top cap of FIG. 82A.

Figure 82C:
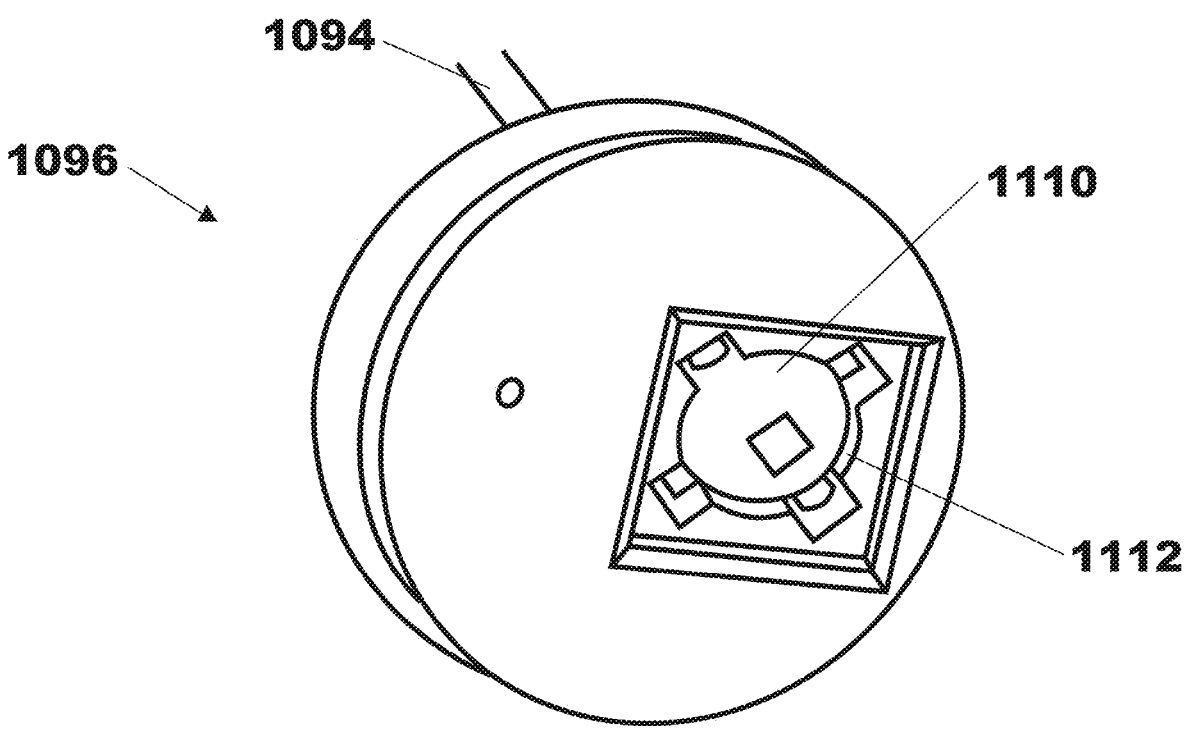

FIG. 82C is an underside view of an incision port of the insertion device of FIG. 82A.

Figure 82D:
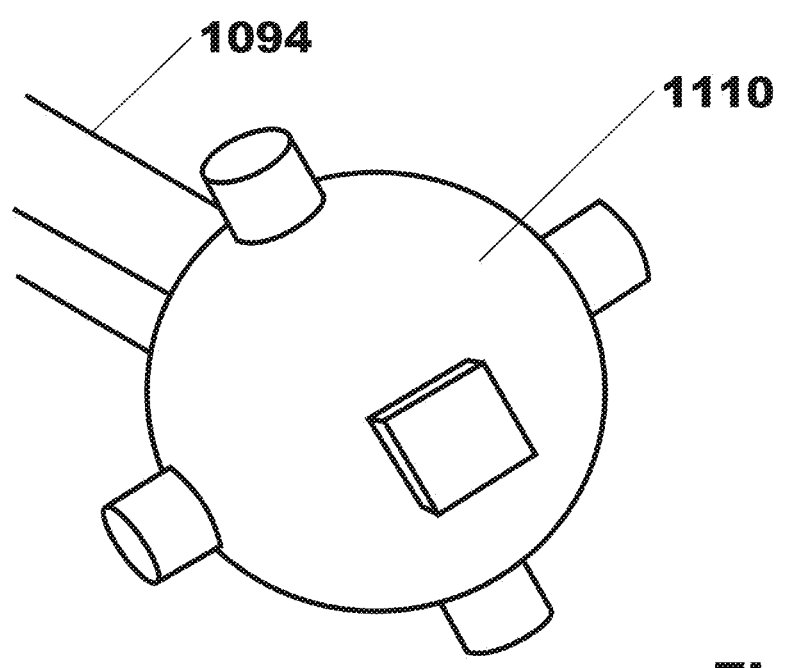

FIG. 82D is a perspective view of the substantially rigid structure having a pegged ball of the insertion device of FIG. 82A.

Figure 82E:
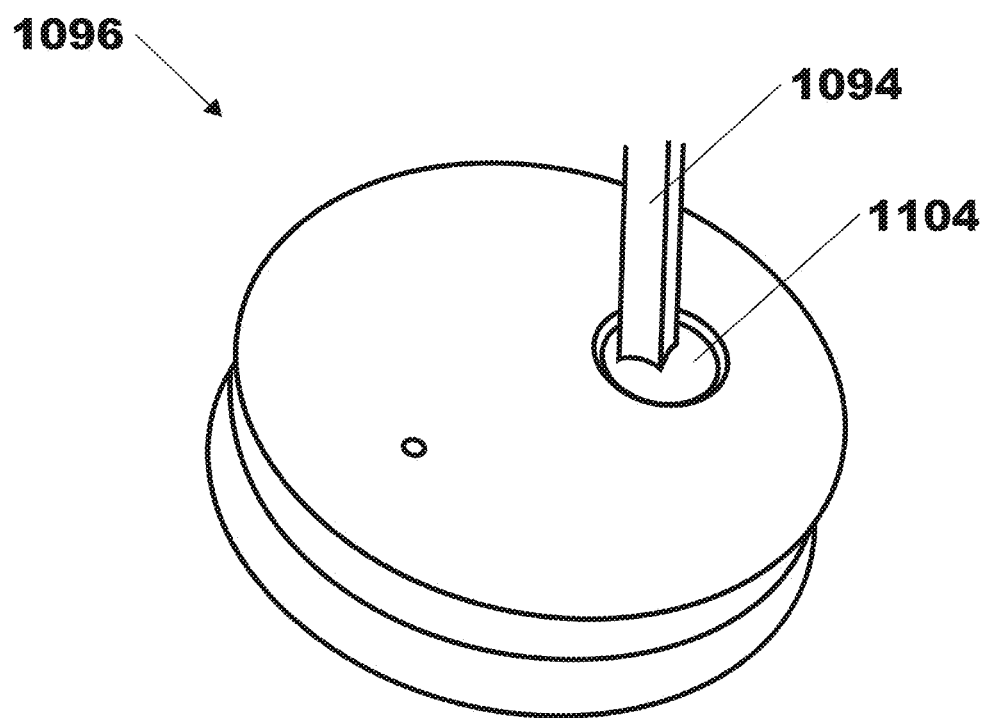

FIG. 82E is a top view of the incision port of FIG. 82C.

FIG. 83 is a cutaway side view of an incision port having an insufflations port, according to one embodiment.

FIG. 84A is a cutaway side view of an insertion device having a spherically shaped canister, according to one embodiment.

FIG. 84B is a cutaway side view of an insertion device having a conically shaped canister, according to one embodiment.

Figure 85A:
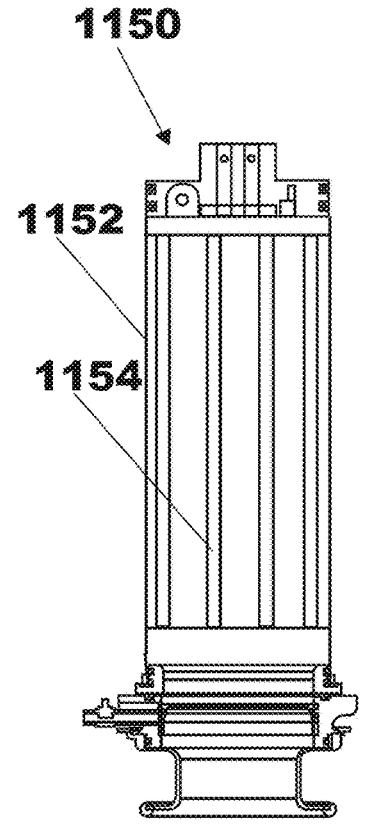

FIG. 85A is a cutaway side view of an insertion device having a canister with vertical rib structures, according to one embodiment.

Figure 85B:
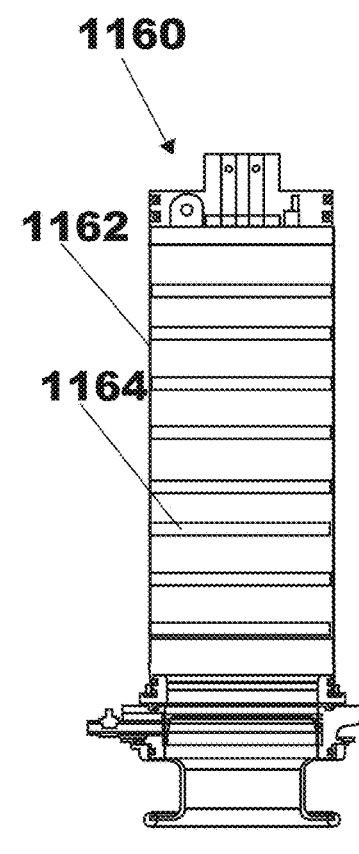

FIG. 85B is a cutaway side view of an insertion device having a canister with horizontal rib structures, according to one embodiment.

Figure 85C:
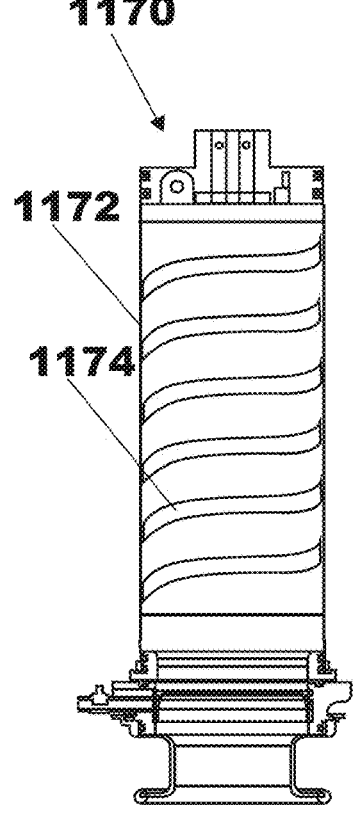

FIG. 85C is a cutaway side view of an insertion device having a canister with spiral-shaped rib structures, according to one embodiment.

Figures 86A, 86B, 86C, 86D:
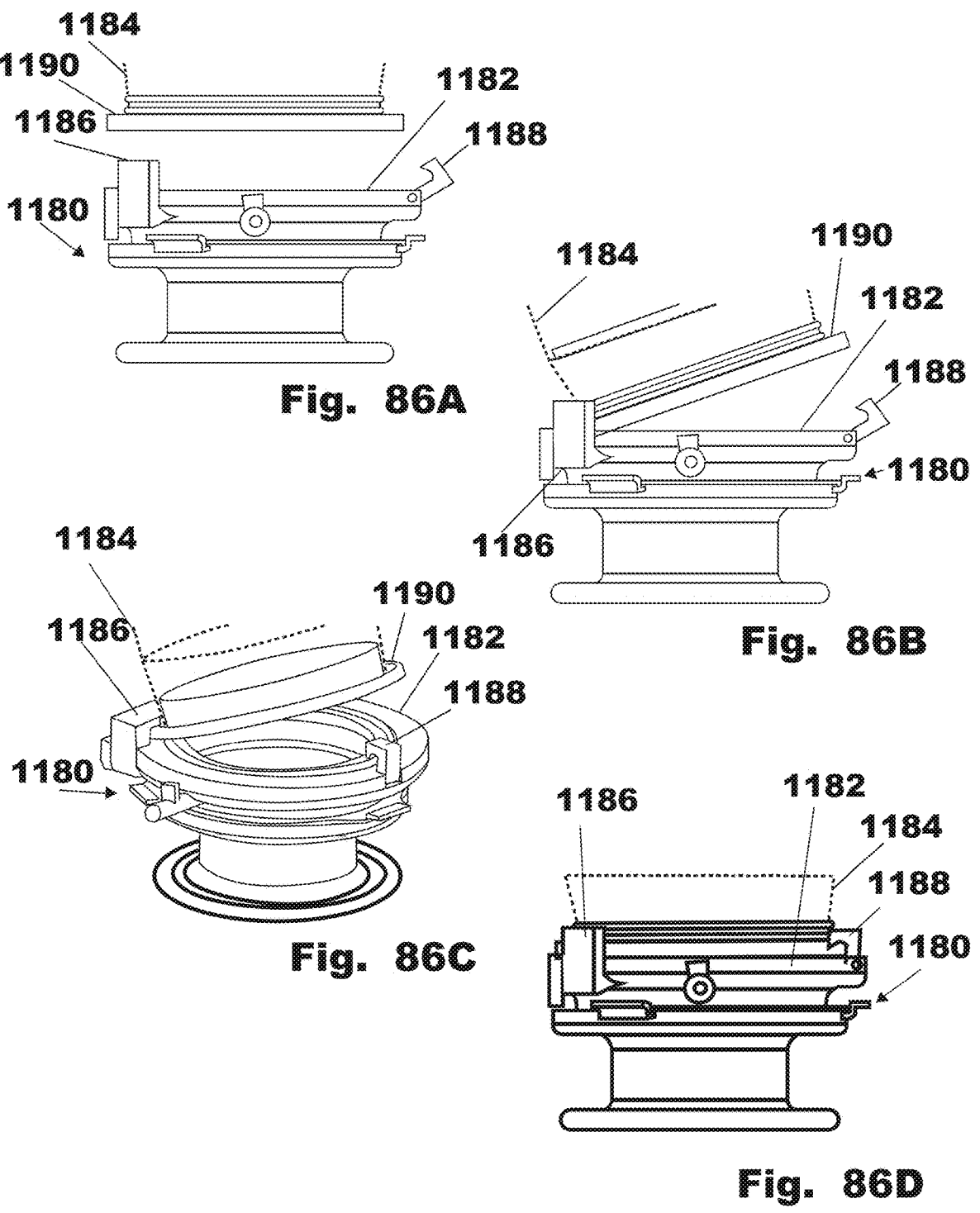

FIG. 86A is a side view of a base coupler that can be releasably coupled to a canister, according to one embodiment.

FIG. 86B is another side view of the base coupler and canister of FIG. 86A.

FIG. 86C is another side view of the base coupler and canister of FIG. 86A.

FIG. 86D is another side view of the base coupler and canister of FIG. 86A.

Figure 87A:
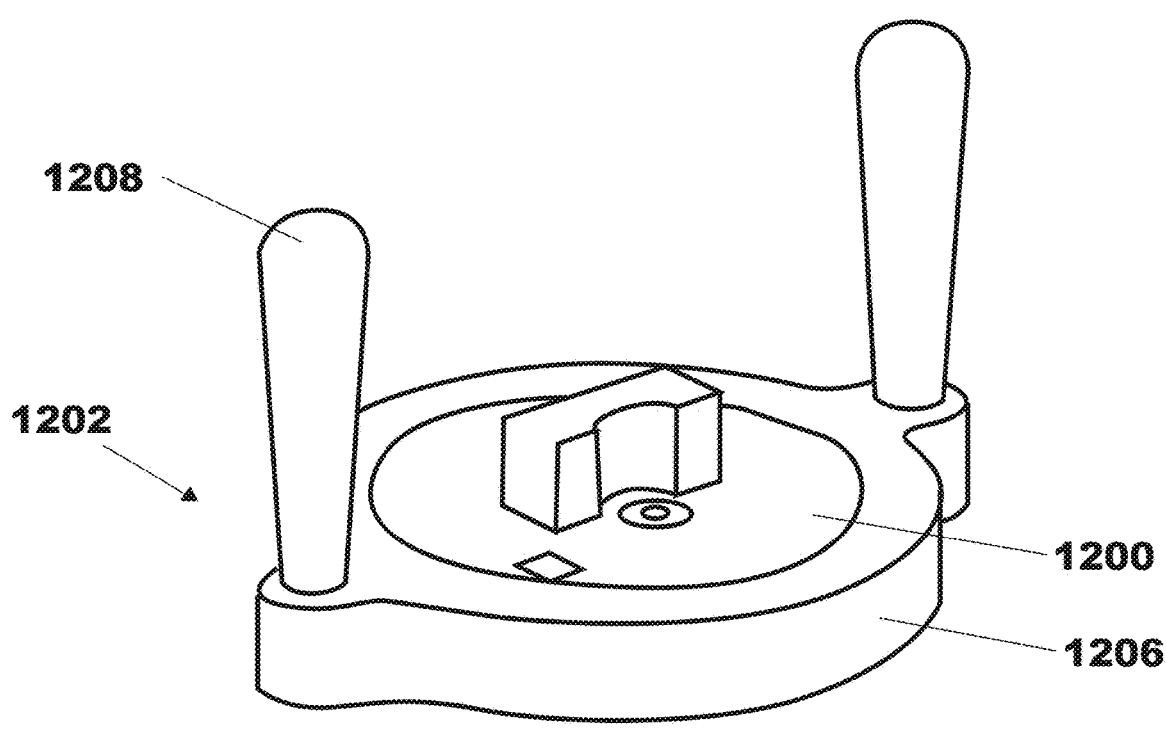

FIG. 87A is a perspective side view of a top cap and outer handle set, according to one embodiment.

Figure 87B:
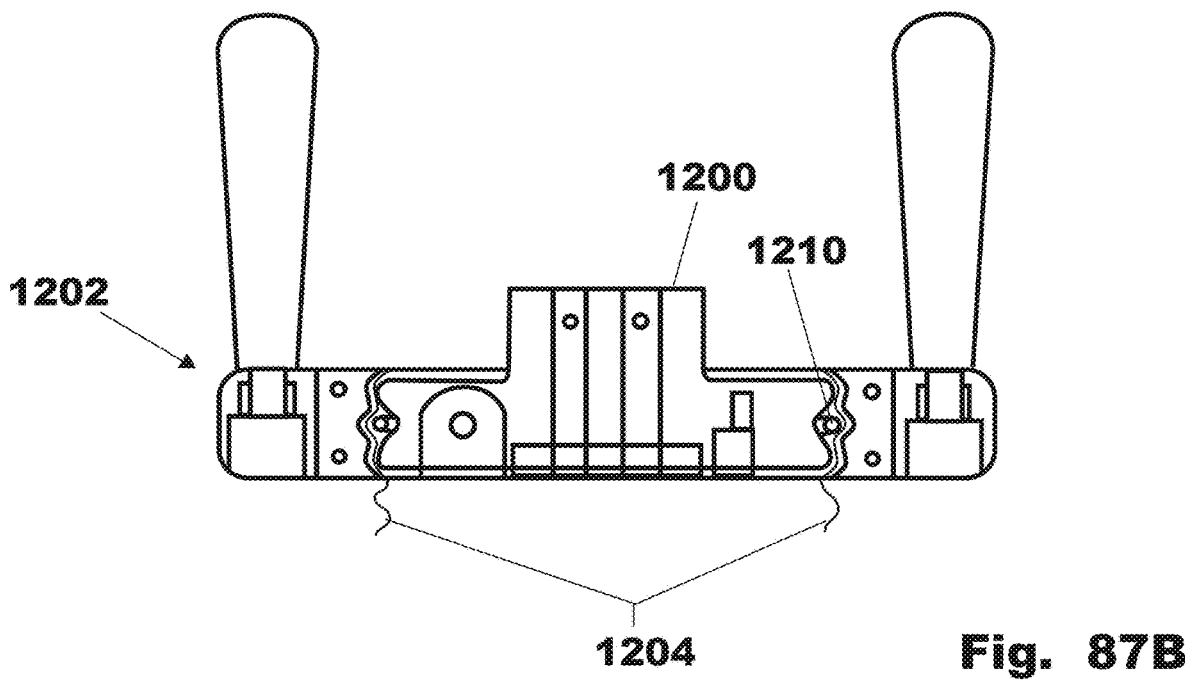

FIG. 87B is a cutaway side view of the top cap and outer handle set of FIG. 87A.

Figure 87C:
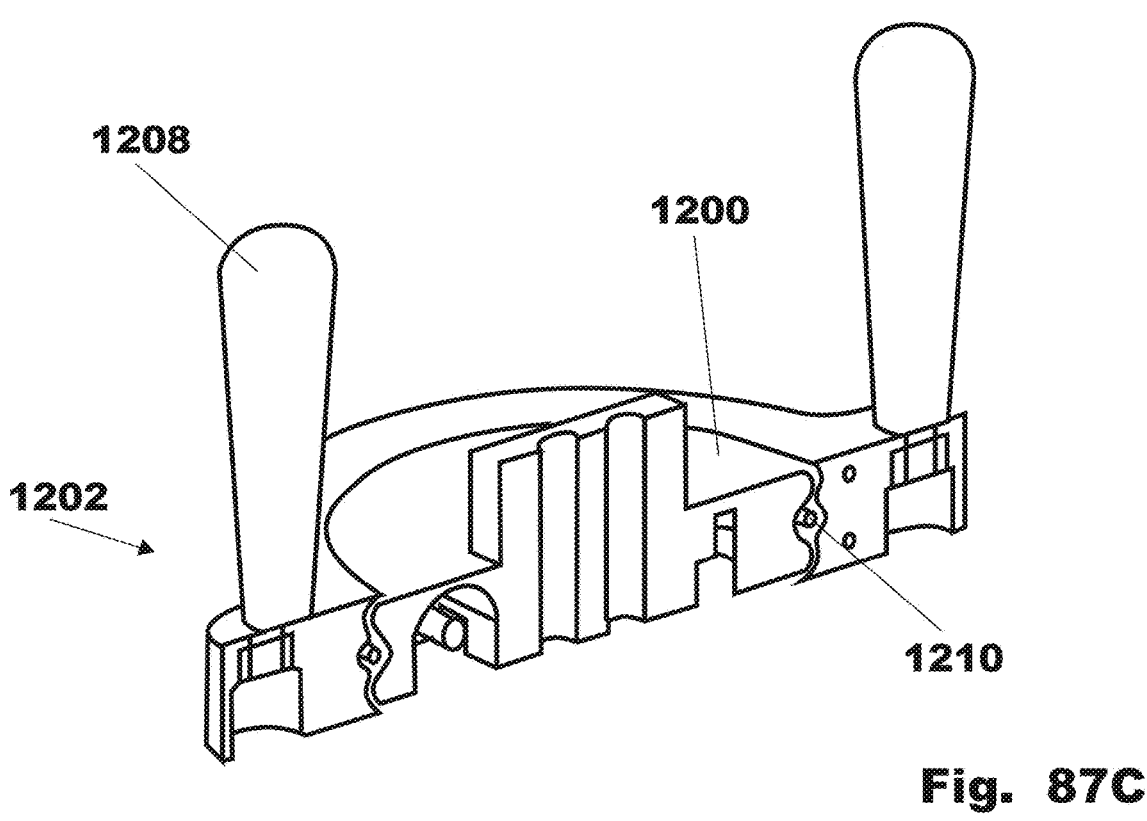

FIG. 87C is a perspective cutaway view of the top cap and outer handle set of FIG. 87A.

Figure 88A:
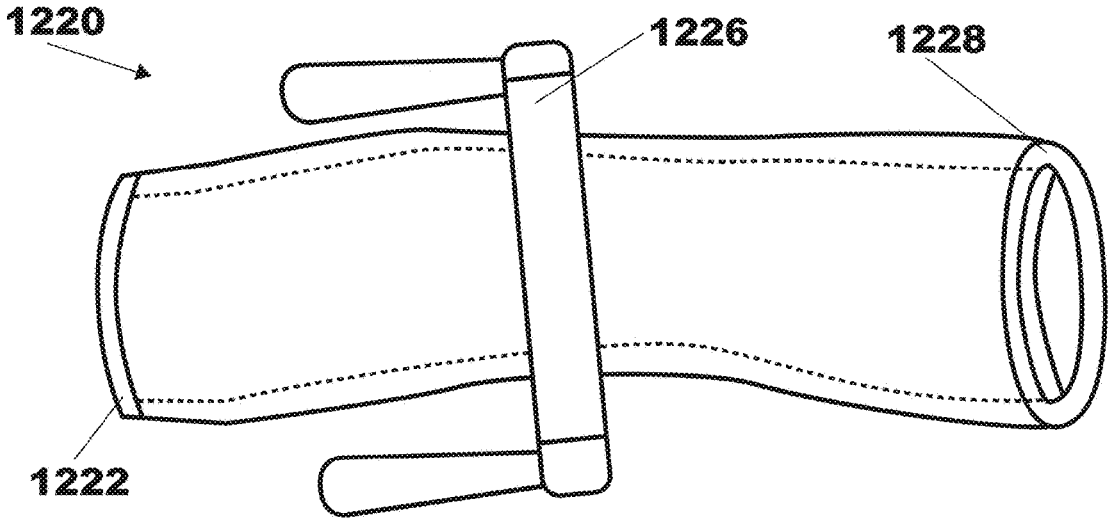

FIG. 88A is a side view of an insertion device, according to one embodiment.

Figure 88B:
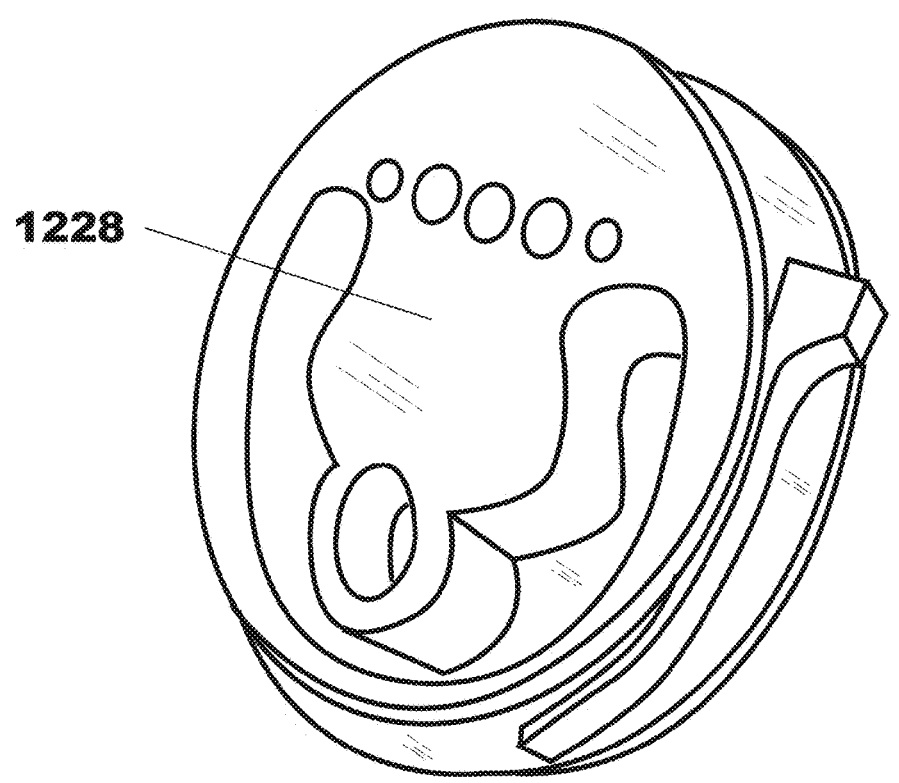

FIG. 88B is a perspective view of a top cap of the insertion device of FIG. 88A.

Figure 88C:
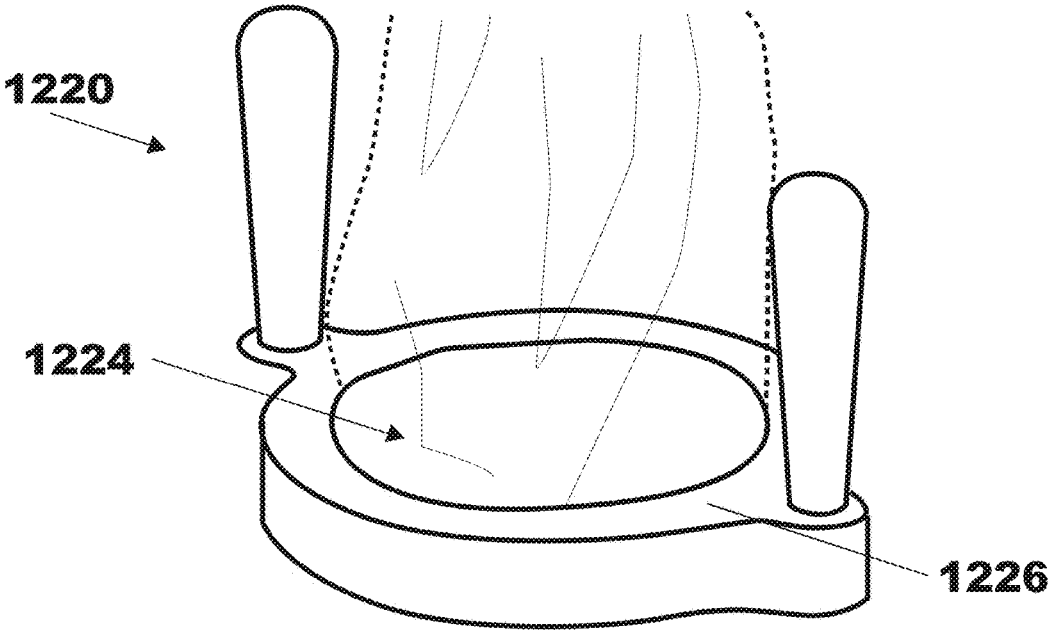

FIG. 88C is a perspective view of a mobile seal and outer handle set of the insertion device of FIG. 88A.

Figure 88D:
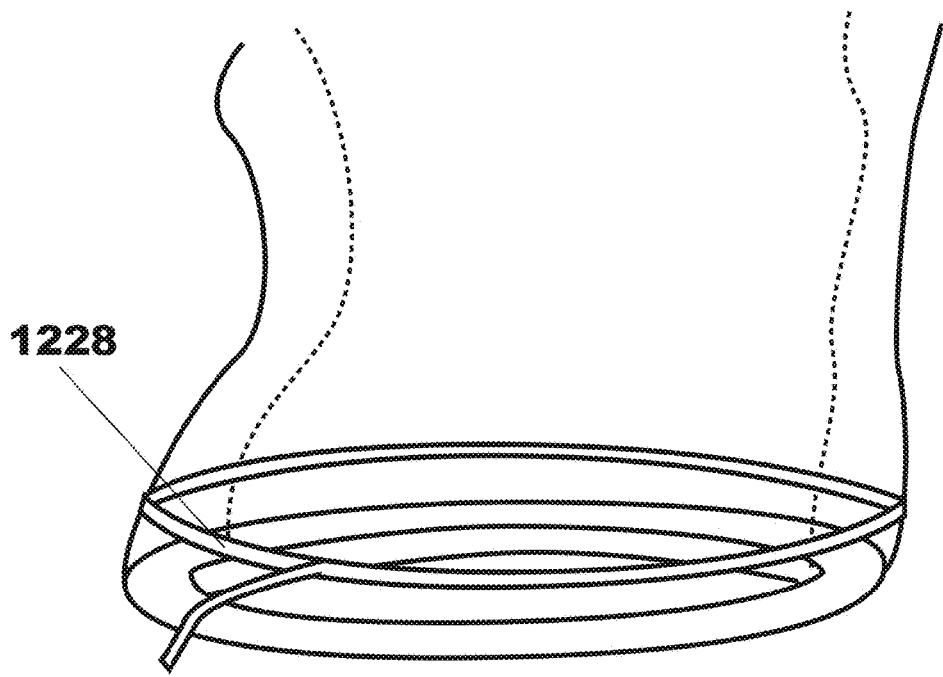

FIG. 88D is a perspective view of an incision port of the insertion device of FIG. 88A.

Figure 89:
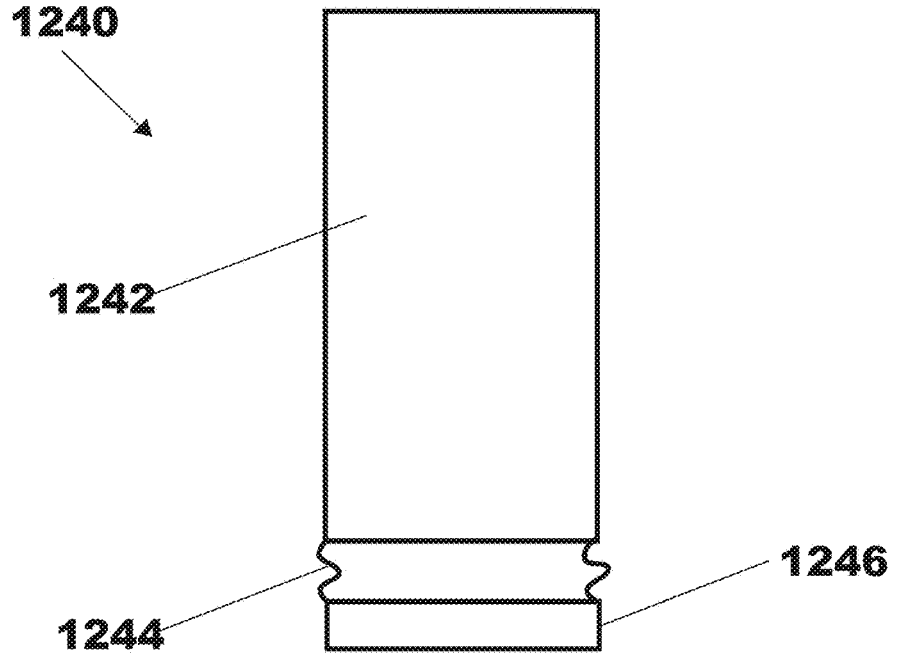

FIG. 89 is a side view of an insertion device having a substantially non-flexible canister portion and a substantially flexible canister portion, according to one embodiment.

DETAILED DESCRIPTION

The various embodiments described herein relate to systems, devices, and/or methods for accessing an insufflated cavity of a patient and/or positioning surgical systems or devices into the cavity.

Certain embodiments provide for insertion of the surgical systems/devices into the cavity while maintaining sufficient insufflation of the cavity. Further embodiments minimize the physical contact of the surgeon or surgical users with the surgical devices/systems during the insertion process. Other implementations enhance the safety of the insertion process for the patient and the systems/devices. For example, some embodiments provide visualization of the system/device as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

It is understood that any of the various embodiments disclosed herein could also be automated or made into fully automatic devices/systems and thus could be used by lightly-trained users, such as on the battlefield or during a space mission or the like.

Figure 1A:
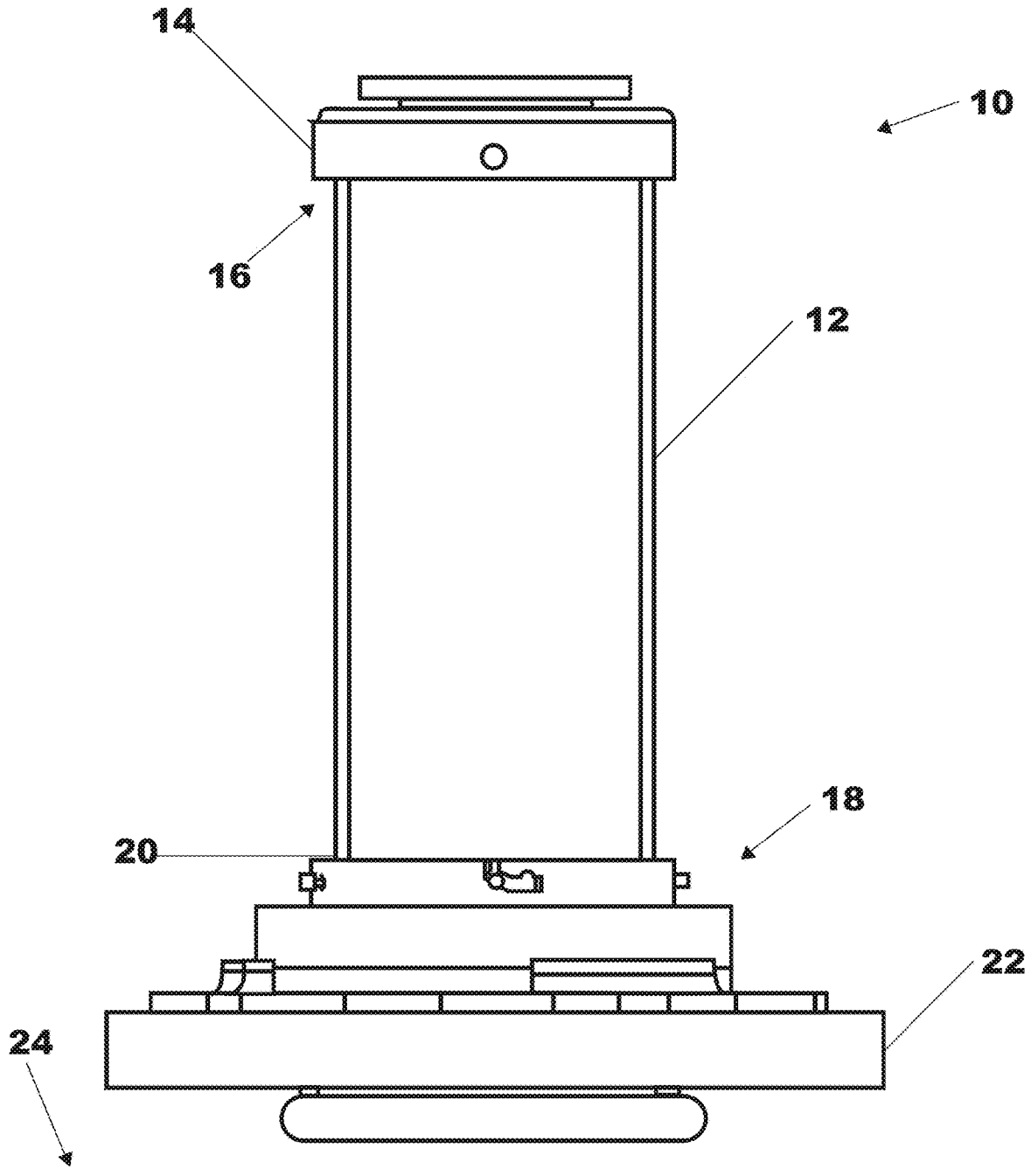
FIG. 1A is a side view of an external pressurized system or apparatus, according to one embodiment.
Figure 1B:
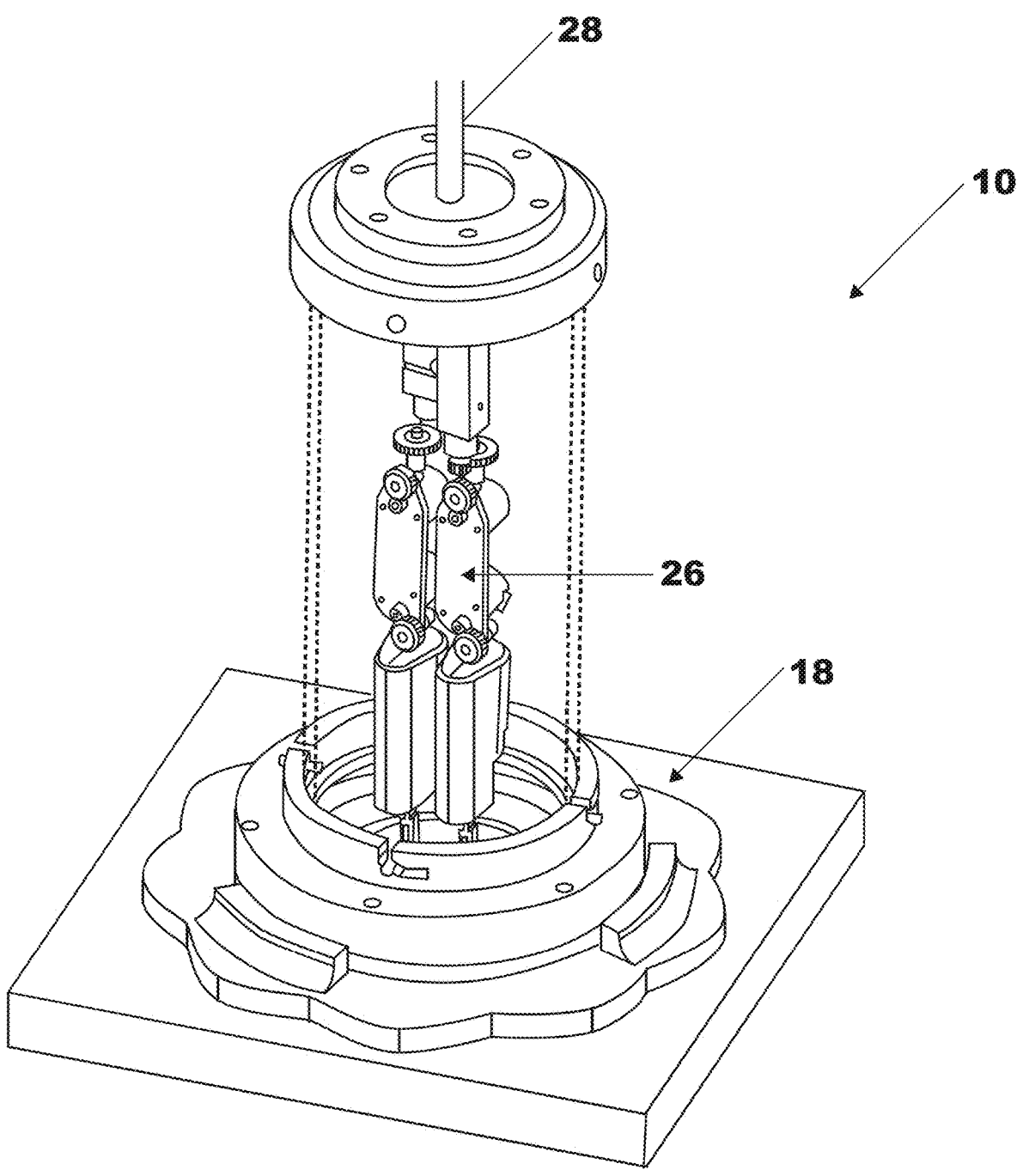
FIG. 1B is a perspective view of the external pressurized system or apparatus of FIG. 1A with a surgical device positioned therein.

One embodiment relates to an external pressurized system or apparatus. For example, one implementation of an external pressurized system or apparatus 10 is depicted in FIG. 1A. The apparatus 10 has a canister 12 with a top cap 14 coupled to a top portion 16 of the canister 12. In this embodiment, the canister 12 has a port 18 that is coupled to the canister 12 at a base portion 20 of the canister 12. The port 18 is positioned in an incision in the skin 22 of the patient, thereby providing access to a cavity 24 of the patient. As shown in FIG. 1B, the apparatus 10 is configured to receive a surgical device 26 such that the device 26 can be inserted into the patient cavity 24 through the port 18 of the apparatus 10.

In one implementation, the canister 12 is made of a hard plastic, such as, for example, poly(methyl methacrylate) ("PMMA"). Alternatively, the canister 12 can be made of any known rigid material that can be used in medical devices. It is understood that certain embodiments of the canister 12 are transparent, such as those depicted in the figures provided. The transparent canister 12 allows for the user to see the surgical device 26 during insertion. Alternatively, the canister 12 is not transparent and the device 26 can be inserted without being able to view the device 26 in the canister 12.

Figure 2A:
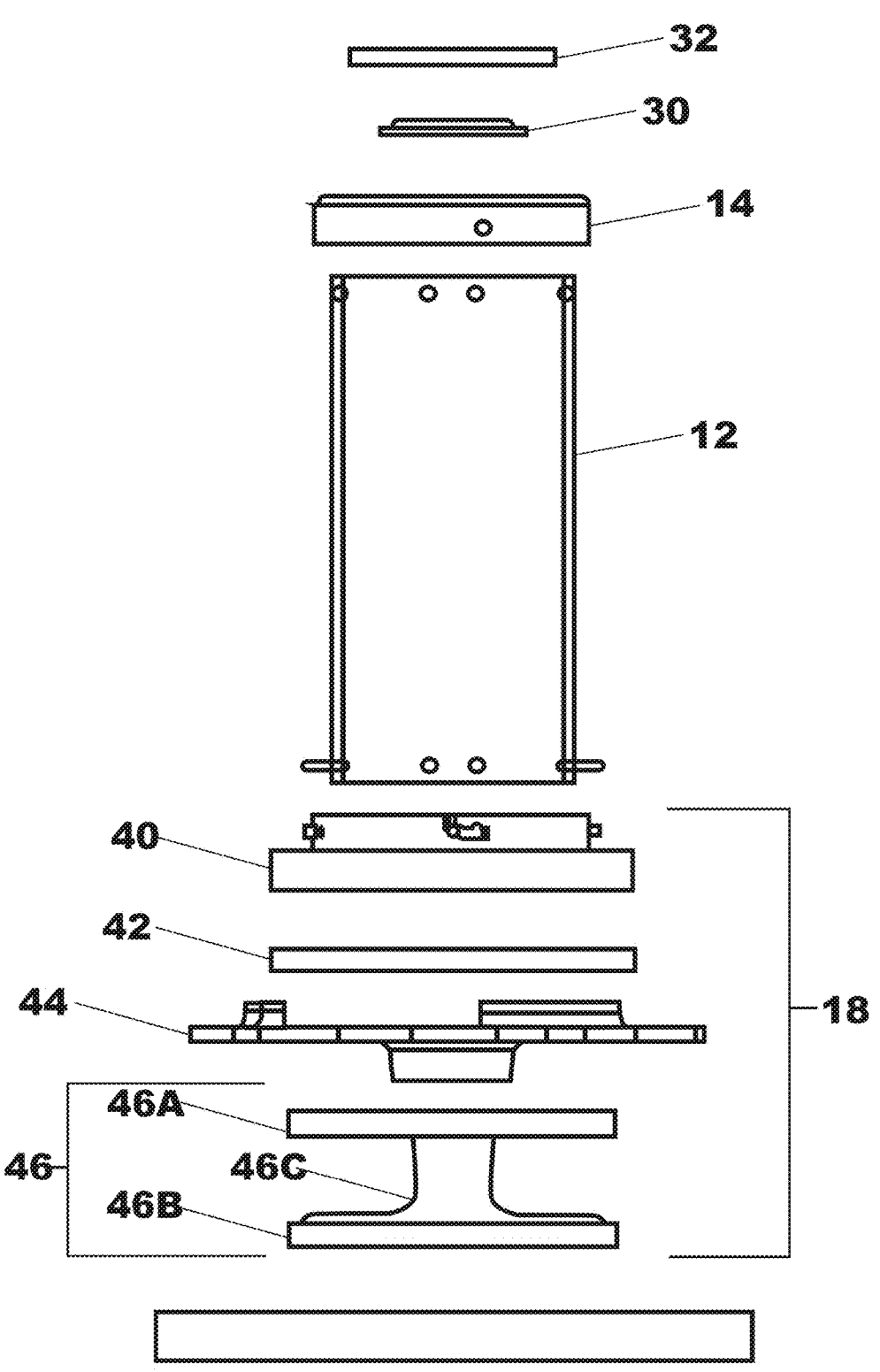
FIG. 2A is an exploded side view of the external pressurized system or apparatus of FIG. 1A.
Figure 2B:
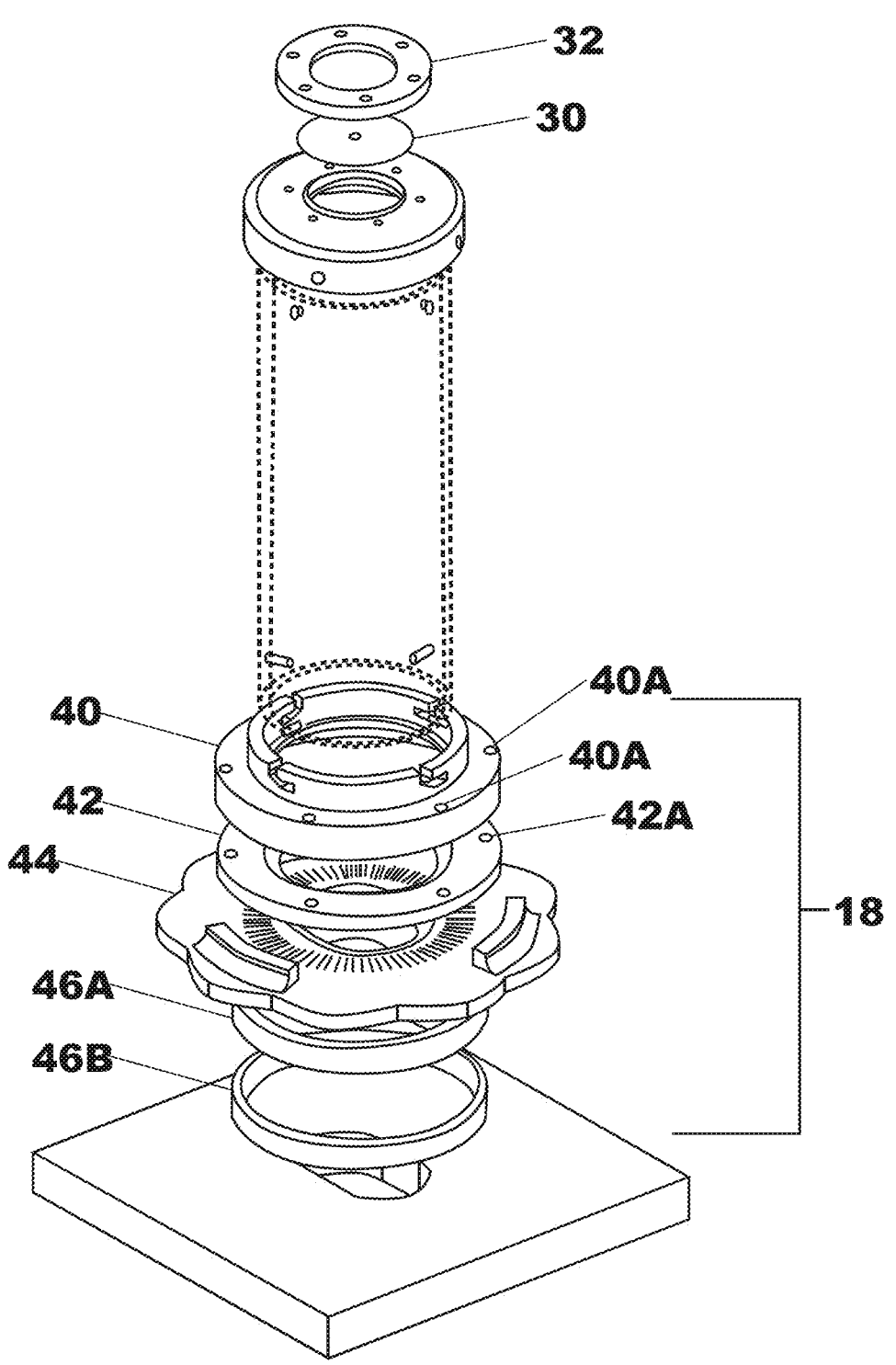
FIG. 2B is an exploded perspective view of the external pressurized system or apparatus of FIG. 1A.
Figure 3A:
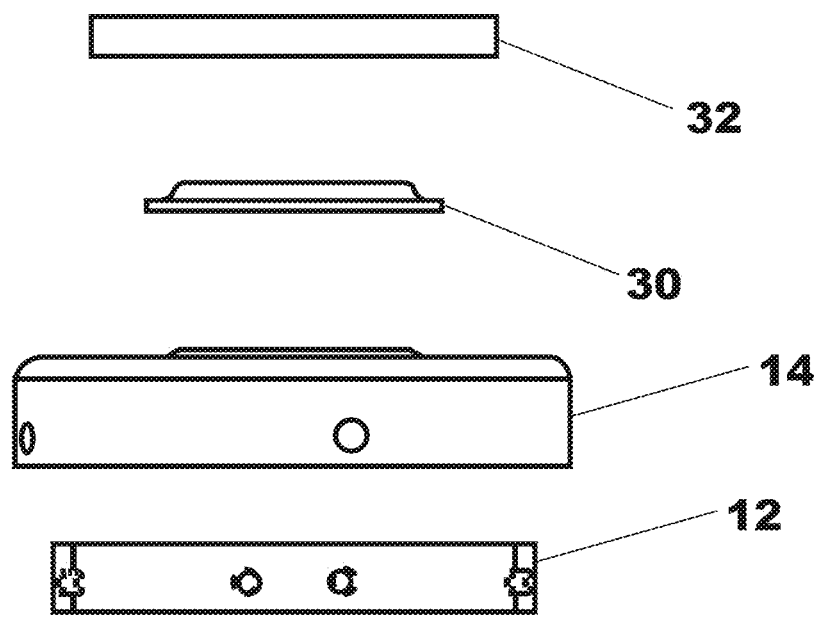
FIG. 3A is an exploded side view of a top cap, according to one embodiment.

FIGS. 2A and 2B provide an exploded view of the external pressurized apparatus 10 according to one embodiment. As discussed above, the top cap 14, also depicted in FIGS. 3A and 3B, is coupled to the top portion 16 of the canister 12. The top cap 14 has a seal 30 that is held in place with a cover 32. According to one implementation, the cover is coupled to the top cap 14 with bolts, other similar mechanical fasteners, or any other known mechanism, device, or method for coupling two such components together.

Figure 3B:
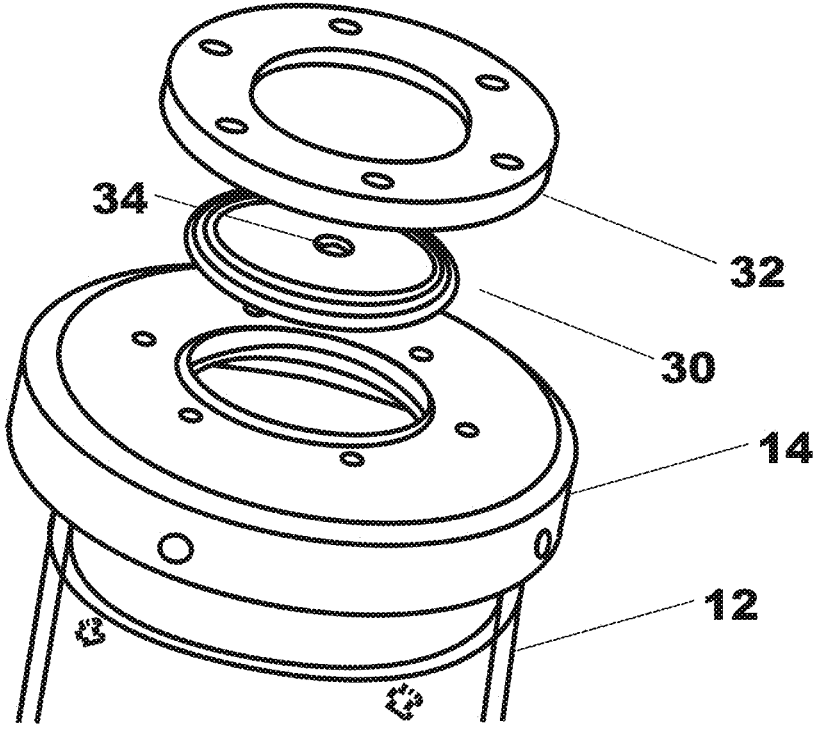
FIG. 3B is an exploded perspective view of the top cap of FIG. 3A.
Figure 4A:
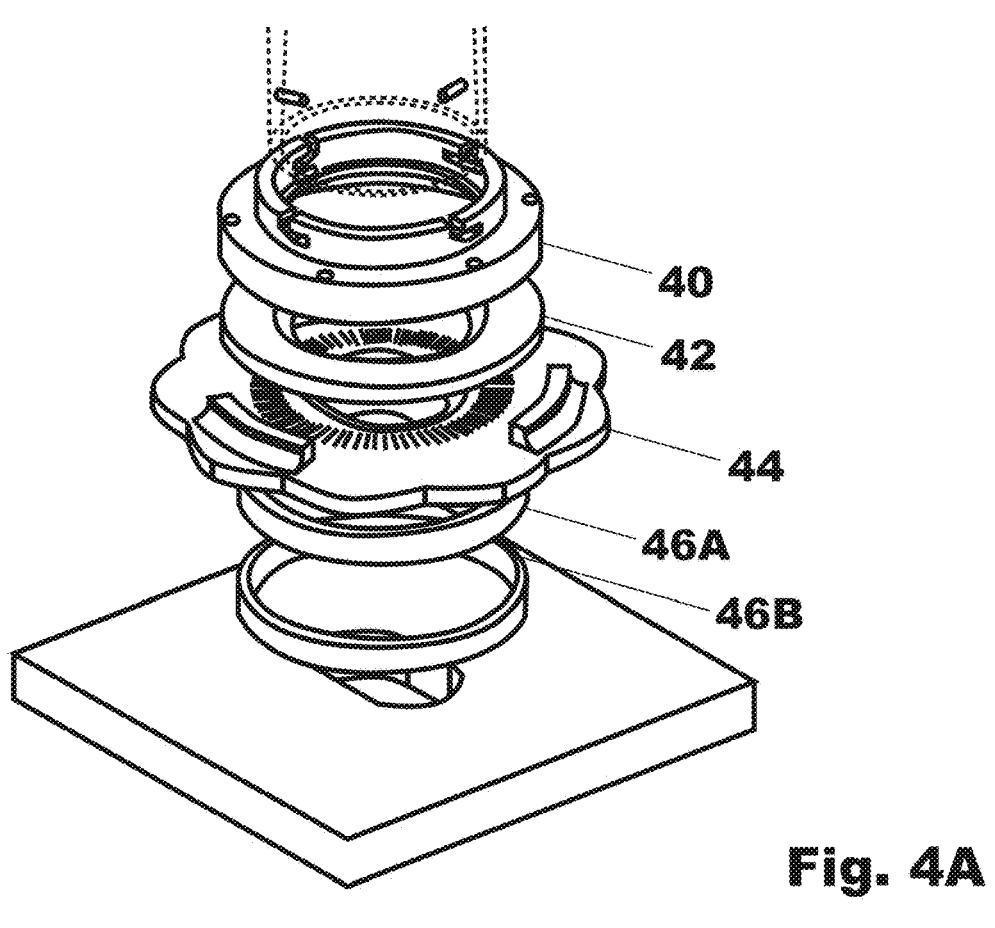
FIG. 4A is an exploded perspective view of a port, according to one embodiment.
Figure 4B:
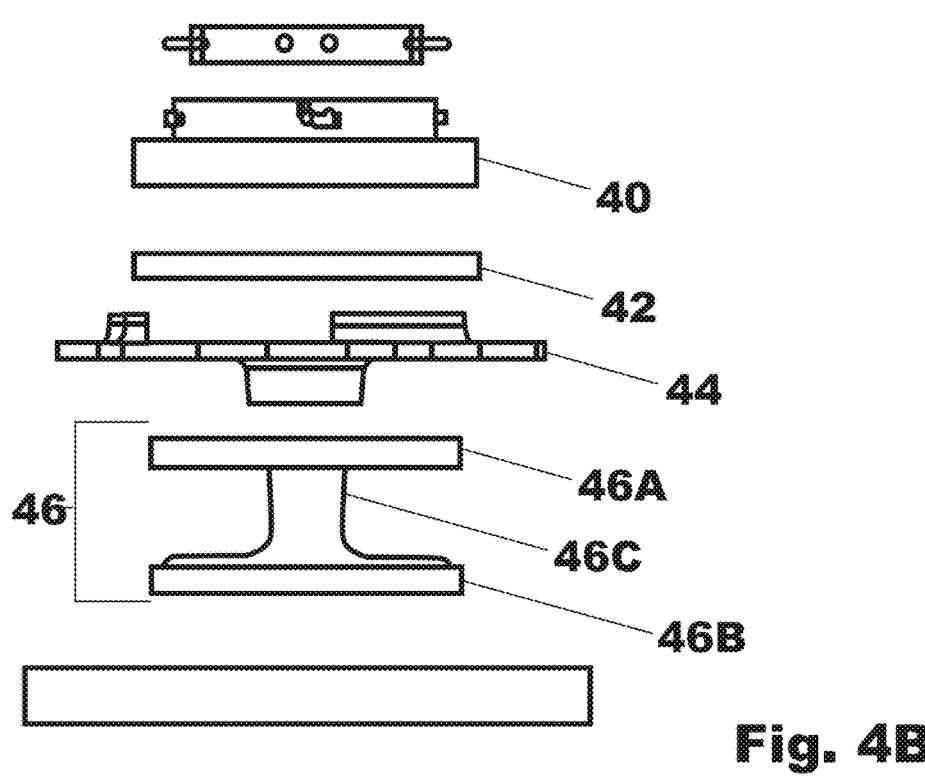
FIG. 4B is an exploded side view of the port of FIG. 4A.

In one implementation as best shown in FIGS. 2B and 3B, the seal 30 has an orifice 34 defined in the seal 34. As best shown in FIG. 1B, the orifice 34 is configured to receive a positioning rod 28, as described in further detail below. In one embodiment, the seal 30 is made of some type of rubber. Alternatively, the seal 30 can be made of any number of known materials that can be used to provide a fluid seal around a smooth rod, including a gel material or the like. In a further alternative, the top cap 14 can have any known configuration that provides a seal having an orifice or other type of access for a positioning rod 28 or the like.

Figure 5A:
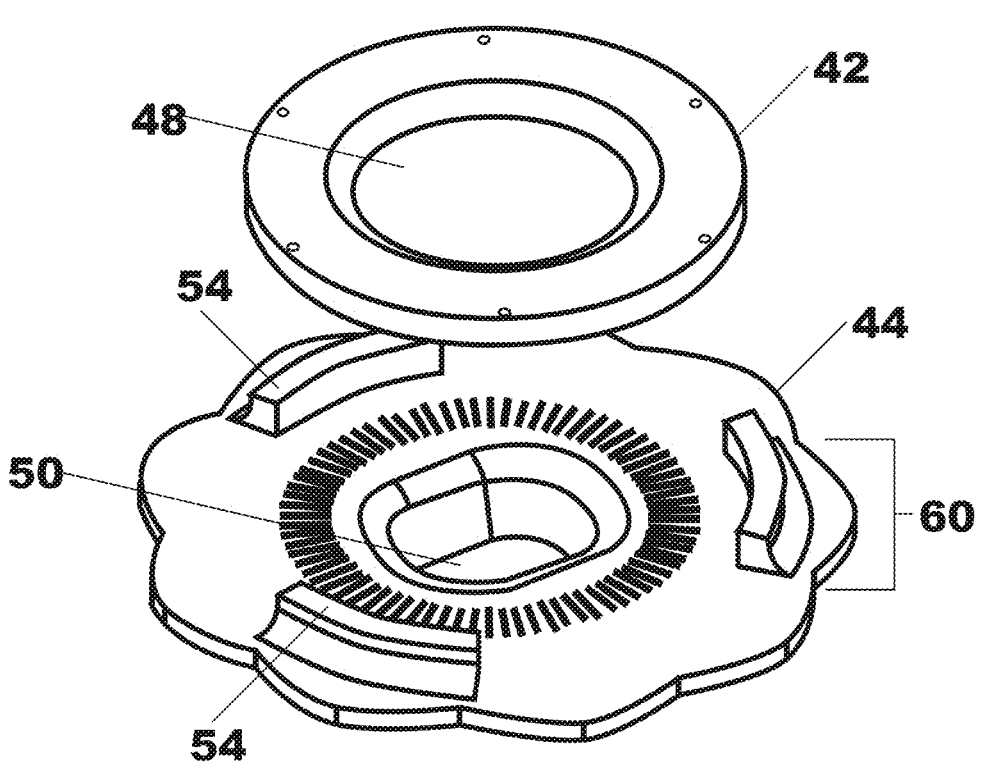
FIG. 5A is an upper perspective view of a base ring and port ring, according to one embodiment.
Figure 5B:
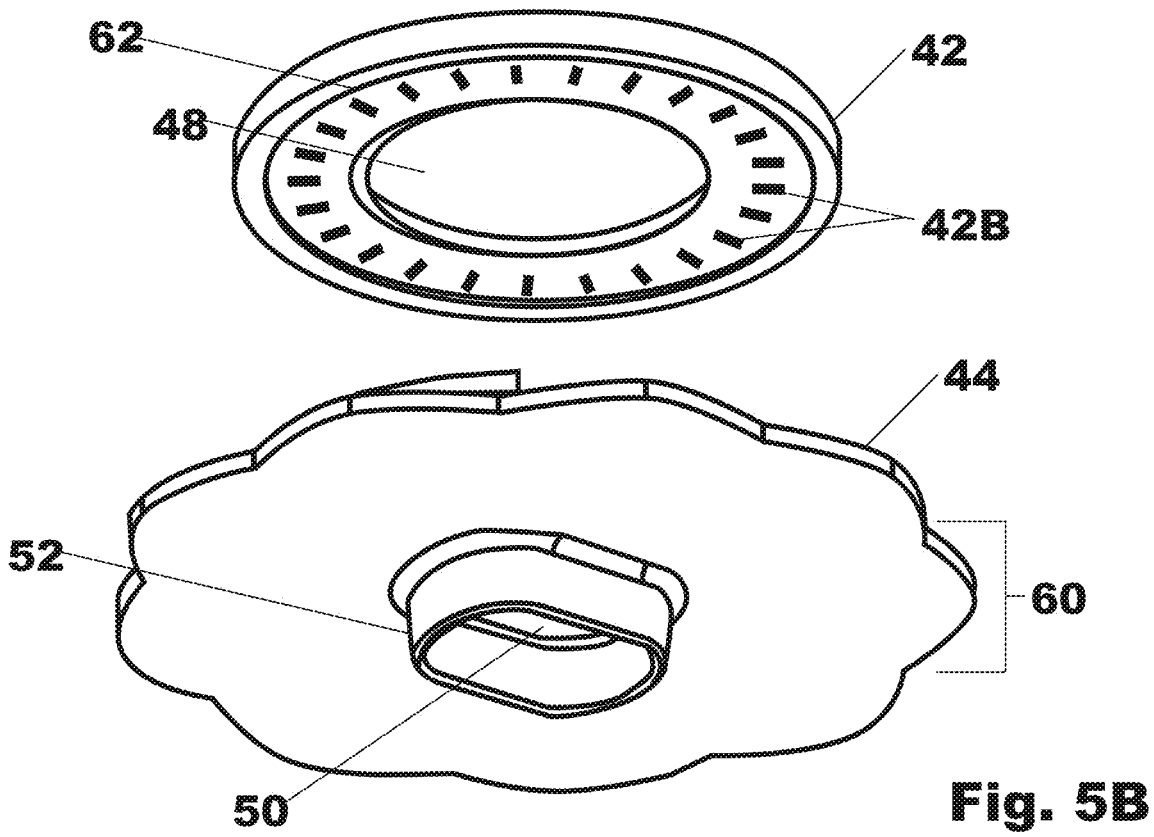
FIG. 5B is a lower perspective view of the base ring and port ring of FIG. 5A.

As best shown in FIGS. 2A, 2B, 4A, and 4B, the port 18 (also referred to herein as an "incision port"), in accordance with one implementation, has multiple components. In this particular embodiment, the port 18 has a connector ring 40, a base ring 42, a port ring 44, and a sealable sleeve device 46. The sealable sleeve device 46 has an upper sleeve ring 46A and a lower sleeve ring 46B, both of which are coupled together by a flexible sleeve 46C. In certain embodiments, the flexible sleeve 46C has elastic properties. As best shown in FIGS. 5A and 5B, the port ring 44 has multiple teeth or protrusions 44A defined in a top portion of the ring 44 in a circular configuration around a hole 50. In addition, in one embodiment, the ring 44 has a lip 52 extending from the bottom portion of the ring 44 and defining an outer edge of the hole 50. As described below, this lip 52 can be positioned within the incision made in the patient, thereby defining the smallest circumference of the incision. Further, the port ring 44 has three guide projections 54 extending from the top portion of the ring 44, which can aid in keeping the base ring 42 positioned appropriately when it is placed on top of the port ring 44 as described below. In addition, according to one embodiment, the port ring 44 can also have indentations 60 around its circumference that allow a user to grasp the port ring 44 during use as described below. Alternatively, the port ring 44 can have any exterior feature or mechanism that a user can use to better grasp the ring 44.

As also shown in FIGS. 5A and 5B, the base ring 42 has an underside that has multiple indentations 42B defined in the ring 42. In one embodiment, the indentations 42B correspond to the protrusions 44A in the port ring 44 such that the base ring 42 and port ring 44 can be coupled and rotational force can be transferred from one to the other, as described in further detail below. Alternatively, the features on the base ring 42 and the port ring 44 can be ridges that can easily couple together. In a further alternative, the features can be any known features or physical components that can be coupled together to allow for transmission of rotational force as described herein. In addition, as best shown in FIG. 5B, the underside of the base ring 42 has an exterior lip or ridge 62, according to one embodiment. When the base ring 42 is in contact with the port ring 44, the ridge 62 is in slidable contact with the port ring 44. In one implementation, the contact of the ridge 62 with the port ring 44 can provide a better seal that the ridges 42B, 44A provide alone. As such, this seal can be a secondary seal that can actually be strengthened as the sleeve device 46 is rotated and the two rings 42, 44 are urged together.

The connector ring 40 is configured to be coupleable with the canister 12, as will be described in further detail below. In addition, the connector ring 40 is coupleable to the rest of the port 18 by being configured to be coupleable to the base ring 42. In one embodiment, as best shown in FIG. 2B, the connector ring 40 has multiple threaded holes 40A defined through the ring 40 that correspond to multiple threaded holes 42A defined through the base ring 42, such that screws, bolts, or the like can be inserted into and through the threaded holes 40A, 42A of the two rings 40, 42, thereby coupling the two rings 40, 42 together. Alternatively, any known coupling components or methods can be used to couple the two rings 40, 42.

The base ring 42 is coupleable to the port ring 44. When the base ring 42 is placed on and in contact with the top of the port ring 44, the protrusions 44A are positioned in the indentations 42B and rotational friction is established such that any rotational force applied to the base ring 42 will be transmitted to the port ring 44 (or vice versa) without any slippage between the two rings 42, 44. Further, the base ring 42 and port ring 44 are coupled such that the holes 48, 50 in each ring 42, 44 correspond as well. Alternatively, any known coupling components or methods can be used to couple the two rings 42, 44 in the same fashion.

In use, the external pressurized system 10 can be used to insert a surgical device or system into a cavity of a patient. One method of insertion will now be described, but it is understood that the embodiments disclosed herein are not limited to a single procedure and instead can be used in any procedure that falls within the spirit of the various implementations contemplated herein.

In one embodiment, the port 18 is placed in an incision in the following manner to create a seal for the incision that fluidly seals the patient's cavity from the ambient air outside the patient. First, an incision is made in the patient that provides access to the patient's target cavity. In one embodiment, the cavity is the peritoneal cavity, but the target could be any known cavity. Once the incision has been made, the sealable sleeve device 46 is positioned in the incision, for example as shown in FIGS. 6A, 6B, 6C, and 6D. In this embodiment, the device 46 is positioned through incision 58. The device 46 is positioned in the incision by inserting the lower sleeve ring 46B (not shown in FIGS. 6A-6D) through the incision 58 such that the lower ring 46B is positioned within the patient and the upper ring 46A is positioned outside the patient, with the sleeve 46B extending through the incision 58. According to one embodiment, the lower sleeve ring 46B of the device 46 is a flexible ring 46B that can be deformed such that the ring 46B can be inserted through the incision 58.

In one embodiment, prior to positioning the sealable sleeve device 46 in the incision 58 as described above, the device 46 is first positioned in a similar fashion through the hole 50 in the port ring 44 and the hole 48 in the base ring 42. That is, the lower sleeve ring 46B is deformed and inserted through the hole 50 and the hole 48, thereby resulting in the upper sleeve ring 46A being positioned on the top portion of the base ring 42 (which is positioned on the top portion of the port ring 44) and the lower sleeve ring 46B being positioned on the bottom portion of the port ring 44. The lower sleeve ring 46B is then inserted through the incision 58 in the patient as described above. Alternatively, the sealable sleeve device 46 can be positioned through the hole 50 in the port ring 44 and the hole 48 in the base ring 42 after the device 46 has been positioned through the incision 58.

Once the lower ring 46B is inserted through the incision 58 as shown in FIG. 6A and further positioned in the hole 50 in the port ring 44, the upper ring 46A is positioned over the incision 58 such that the incision 58 is centered within the ring 46A, as shown in FIG. 6B. For ease of understanding, the port ring 44 is not depicted in these figures. The sealable sleeve 46 is then tightened to create a seal and position the lower ring 46B snugly to the underside of the incision 58 and the upper ring 46A snugly to the top portion of the base ring 42. This tightening occurs by rotating the upper ring 46A. In one embodiment, the upper ring 46A is less flexible (more rigid) than the lower ring 46B, thereby allowing a user to grasp it and rotate it. FIG. 6C depicts the sealable sleeve device 46 after the ring 46A has been rotated, thereby causing the sleeve 46C to gather and begin to close the opening in the sleeve 46C (or "collapse on itself"). FIG. 6D shows the sleeve device 46 after the user has successfully rotated the ring 46A to the point that a seal is formed in the sleeve 46C by closing the opening therein.

It is understood that the base ring 42 and the port ring 44 are intended to be generally rotatable relative to each other during the process of positioning the port 18 and thereby sealing the incision 58. That is, when the base ring 42 is initially positioned on the port ring 44, the two rings 42, 44 are rotatable in relation to each other. This relative rotation of the two rings 42, 44 allows for rotation of the sleeve device 46, thereby resulting in the seal created by the sleeve device 46 when it is sufficiently constricted. However, when the sleeve device 46, the port ring 44, and the base ring 42 are positioned in the incision 58 and the sealable sleeve device 46 is tightened to close the hole in the incision 58 as described above, the elasticity of the sleeve 46C urges the base ring 42 and port ring 44 together as described above, causing the bottom surface of the base ring 42 and the top surface of the port ring 44 to come into contact such that the ridges 44A on the port ring 44 couple with the ridges 42B on the base ring 42 as described above. The interfacing ridges 44A, 42B provide an interface or coupling that will result in rotational coupling of the rings 42, 44 when the rings are in contact, but also is releasable when desired. It is understood that the more force applied to urge the two rings 42, 44 together (the more that the sleeve device 46 is rotated), the more secure the coupling of the ridges 44A, 44B becomes.

Once the sleeve device 46, the port ring 44, and the base ring 42 are positioned in the incision 58 as described above, the connector ring 40 is coupled to the base ring 42. In one embodiment as described above, the connector ring 40 is coupled to the base ring 42 via nuts or bolts. Alternatively, any standard coupling device or method can be used. Once the connector ring 40 is coupled to the base ring 42, the port 18 is fully assembled, as shown in FIGS. 7A and 7B.

Figure 7A:
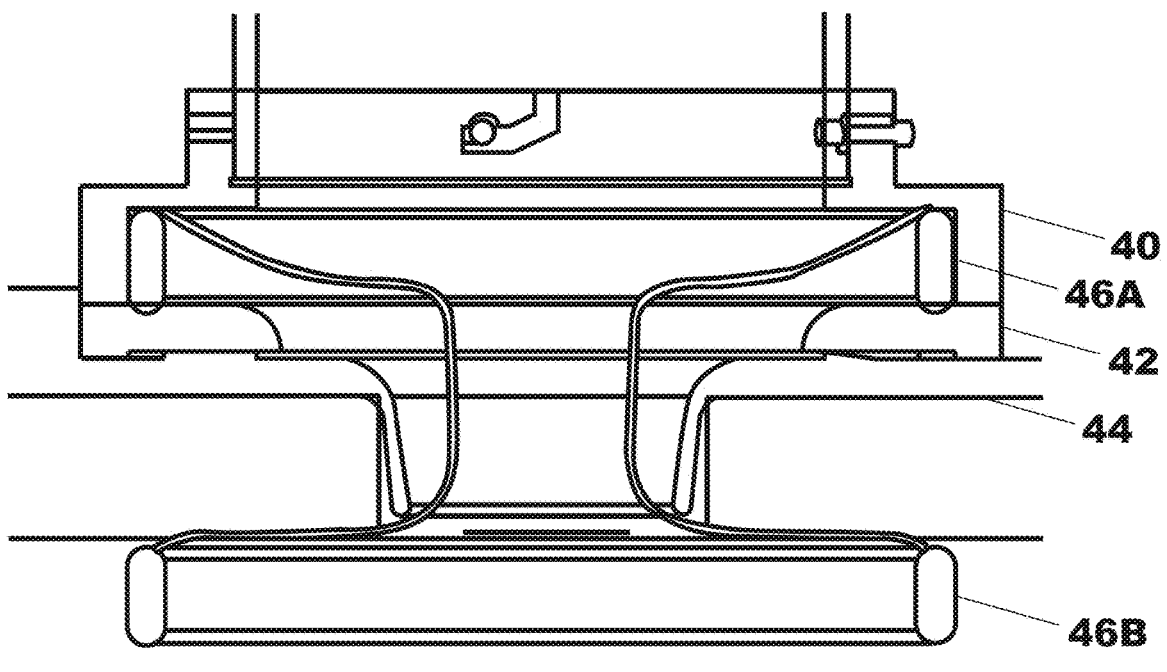
FIG. 7A is a side view of a fully assembled port, according to one embodiment.
Figure 7B:
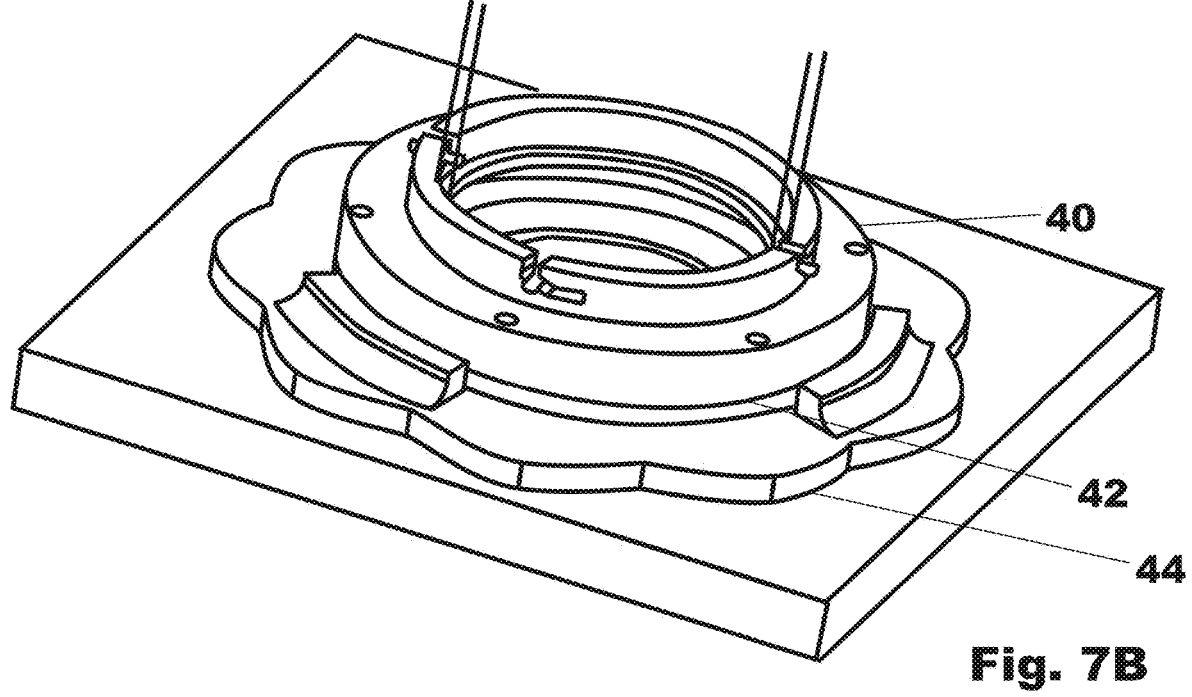
FIG. 7B is a perspective view of the fully assembled port of FIG. 7A.

According to one embodiment, the coupling of the connector ring 40 to the base ring 42 as shown in FIG. 7A, in combination with the tightening of the sleeve device 46 as described above, creates a fluid seal that seals the patient's cavity from the ambient air outside the patient. More specifically, at this point the sealable sleeve device 46 provides a seal as best shown in FIG. 6D. One of ordinary skill in the art understands that this fluidic seal is sufficient to maintain the increased air pressure of the insufflated cavity of the patient.

Once this seal is established, the canister 12 with the medical device/system 26 positioned inside can be coupled to the connector ring 40 as best shown in FIG. 1B such that the device/system 26 can then be inserted into the insufflated cavity 24 of the patient. Prior to that coupling, the device/system 26 (coupled to a positioning rod 28) must be positioned in the canister 12. While it is understood that any number of known procedures within the spirit of the embodiments contemplated herein could be used to position the device/system 26 in the canister 12, one implementation provides for-prior to coupling the canister 12 to the port 18—inserting the device/system 26 through the open end (not shown) at the base portion 20 of the canister 12 (as best depicted in FIG. 1A) and inserting the positioning rod 28 through the orifice 34 defined in the seal 30 in the top cap 14. It is understood that the positioning rod 28, in accordance with some embodiments, can have one or more lumens therein that can contain one or more connection components (such as wires, cords, or the like) that connect the device/system 26 to an external controller of some kind, thereby allowing for the controller to control the device/system 26 via the connection component(s).

Figure 8A:
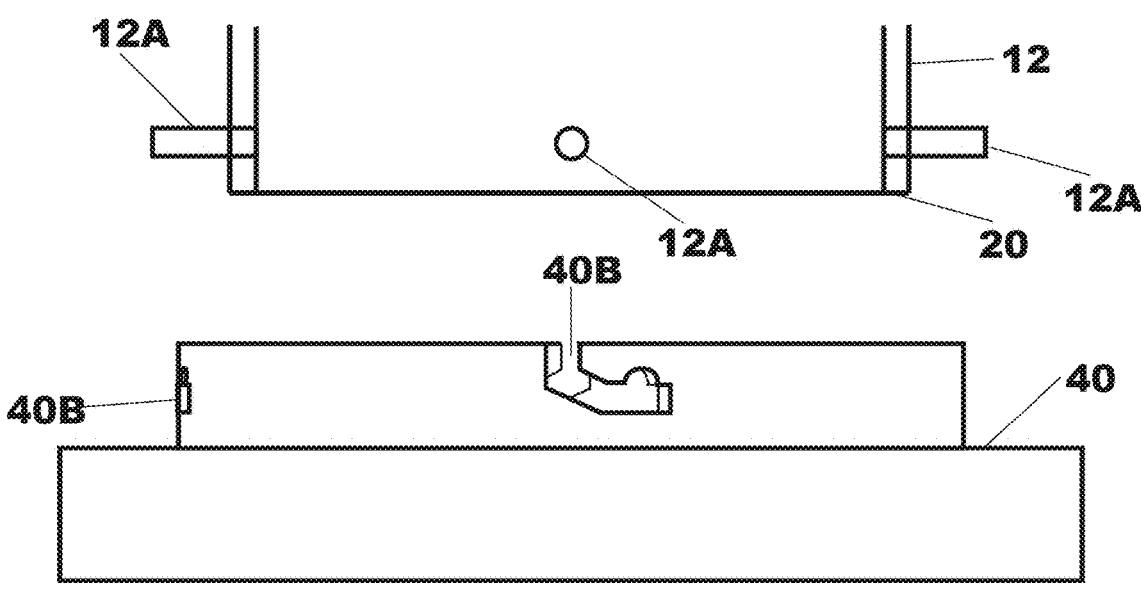
FIG. 8A is a side view of the coupling of a canister and connector ring, according to one embodiment.
Figure 8B:
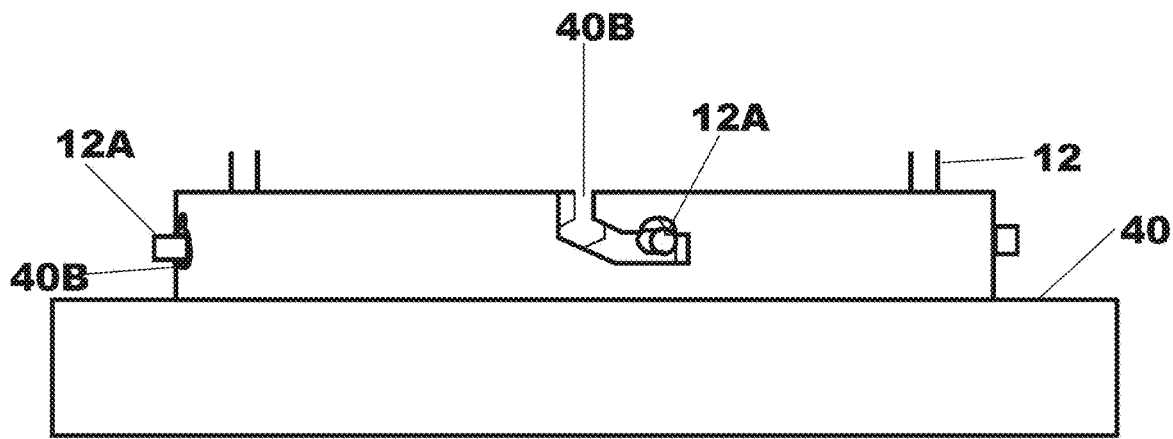
FIG. 8B is a side view of the coupling of the canister and connector ring of FIG. 8A.

Once the device/system 26 is positioned in the canister 12 with the positioning rod 28 extending out of the top cap 14 through the orifice 34 in the seal 30 as best shown in FIGS. 1B, the canister 12 can be coupled to the connector ring 40. In one embodiment as best shown in FIGS. 8A and 8B, the base portion 20 of the canister 12 has at least 2 projections 12A extending from the canister 12 that correspond to the slots 40B in the connector ring 40. More specifically, in the implementation depicted in FIGS. 8A and 8B, the canister 12 has 4 projections 12A (one of which is not shown) that correspond to 4 slots 40B in the connector ring 40. To couple the canister 12 to the ring 40, the four projections 12A are inserted into the slots 40B and the canister 12 is rotated in a counterclockwise fashion to position the projections 12A in the fully coupled position in the slots 40B as shown in FIG. 8B. Alternatively, any known coupling mechanism, device, or procedure can be used to couple the canister 12 to the ring 40.

Figure 9:
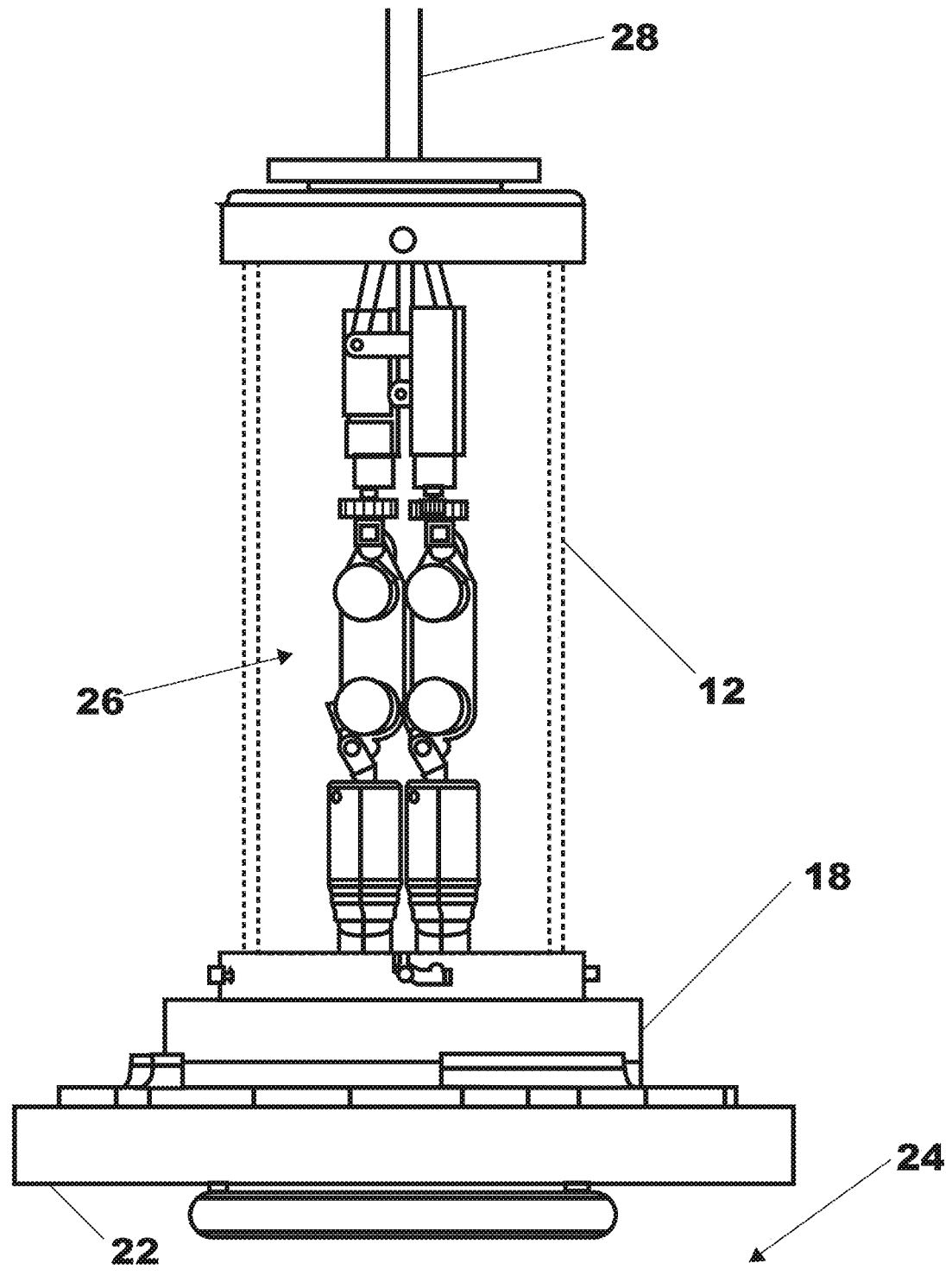
FIG. 9 is a side view of an external pressurized system or apparatus with a surgical device positioned therein, according to one embodiment.
Figure 10:
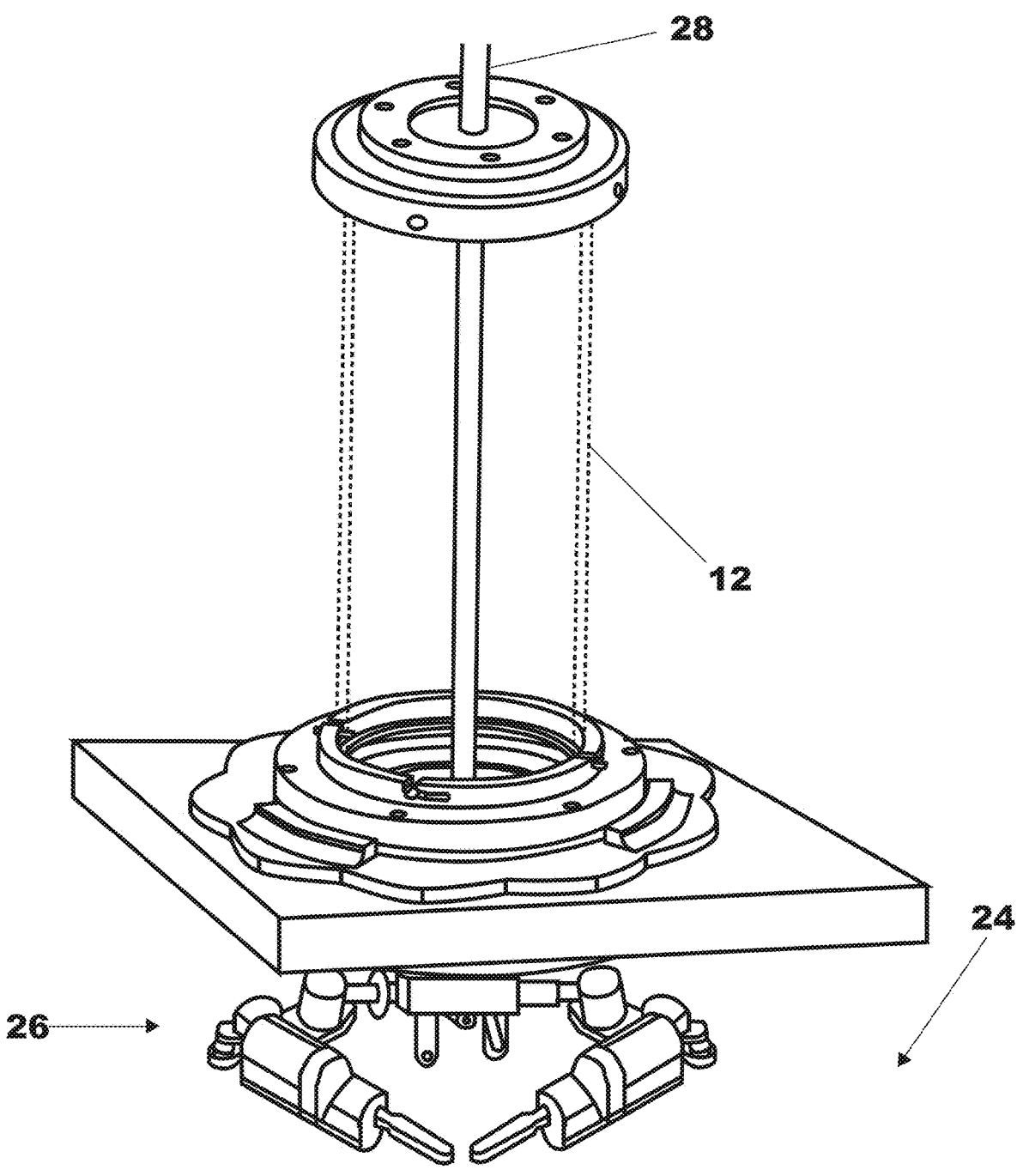
FIG. 10 is a perspective view of the external pressurized system or apparatus of FIG. 9, in which the surgical device has been urged out of the system or apparatus and into the patient's cavity.

Once the canister 12 is coupled to the port 18 as best shown in FIG. 9, a seal has been achieved that fluidically separates and seals fluid within the canister 12 from fluid outside the canister 12. At this point, the pressure inside the canister 12 is increased until it matches the pressure of the insufflated cavity 24. By equalizing the pressure in the canister 12 to the pressure in the insufflated cavity 24, the device/system 26 positioned in the canister 12 can then be inserted into the cavity 24 through the seal created by the sealable sleeve device 46 without causing a loss of pressure or loss of insufflation in the cavity 24. According to one embodiment, the fluidic seal is maintained in the canister 12 by the seal created between the canister 12 and the port 18 and further by the seal created between the positioning rod 28 and the seal 30. More specifically with respect to the positioning rod 28 and the seal 30, it is understood that the rod 28 is sized to contact the inner circumference of the orifice 34 in the seal 30, thereby resulting in an airtight fluidic seal between the rod 28 and the seal 30. It is understood that, at this point, if a user wants to adjust the positioning of the device/system 26, the user can do so using the positioning rod 28.

Once the air pressure in the canister 12 is substantially the same as the air pressure in the insufflated cavity 24, the device/system 26 is moved out of the canister 12, through the port 18 and the incision 58, and into the patient's cavity 24. According to one embodiment as best shown in FIG. 1B, the device/system 26 can be moved through the port 18 and into the cavity 24 using the positioning rod 28, which is coupled at its distal end to the device/system 26. That is, a user can grasp a proximal end of the rod 28 and move the rod 28 in a distal direction as desired to move the device/system 26 distally out of the canister 12 and into the cavity 24. In those implementations in which the device/system is a robotic device having operational arms, the device, including the arms, can be advanced through the port 18 and into the insufflated cavity 24. It is understood that the user can also turn the rod 28 to turn the device/system 26 as needed/desired as well. In this fashion, the user can position the device/system 26 as desired within the patient's cavity 24 in order to perform a procedure.

In alternative embodiments, the positioning rod 28 can be a larger rod than that depicted in these figures such that the rod 28 can have multiple lumens defined within the rod 28, including one or more larger lumens that could be used for tool and/or camera insertion. Insufflation after removal of the canister 12 could also be accomplished through such a rod 28. In a further alternative, instead of a rod, a port such as a known SILS port could be used.

Figure 11:
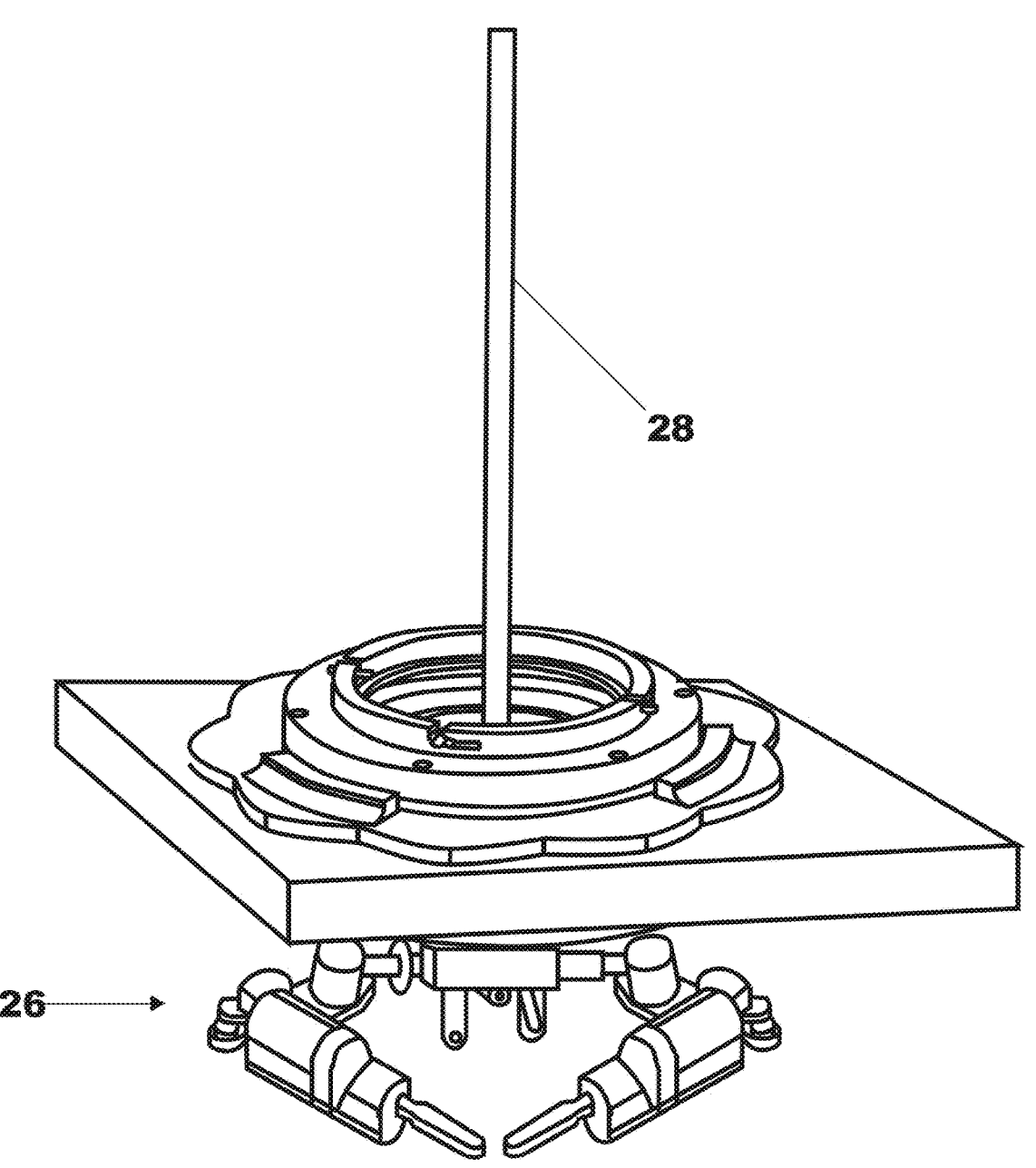
FIG. 11 is a perspective view of the external pressurized system or apparatus of FIG. 10, in which the canister has been removed.

Once the device/system 26 has been inserted into, and is positioned as desired in, the patient's cavity 24, the fluidic seal is re-established between the insufflated cavity 24 and the interior of the canister 12 via the sealable sleeve device 46. As a result, the pressure inside the canister 12 can be lowered until it is substantially equal to the ambient pressure. At that point, the canister 12 can be de-coupled from the connector ring 40. That is, according to one embodiment, the canister 12 is rotated in the clockwise direction, thereby urging the projections 12A out of the slots 40B in the ring 40. Once the canister 12 is removed, as best shown in FIG. 11, only the port 18 itself remains with the fluidic seal established by the combination of the port 18 components, including the sealable sleeve device 46 as described above. Thus, the user can freely position and operate the device/system using the positioning rod 28 (and, in some embodiments, the external controller (not shown) connected to the device/system via the connection component(s)). For example, the removal of the canister 12 can provide for additional accessibility and freedom of movement for the rod 28. As such, the medical procedure using the system/device 26 is typically performed once the canister 12 is removed as shown in FIG. 11.

Figure 12:
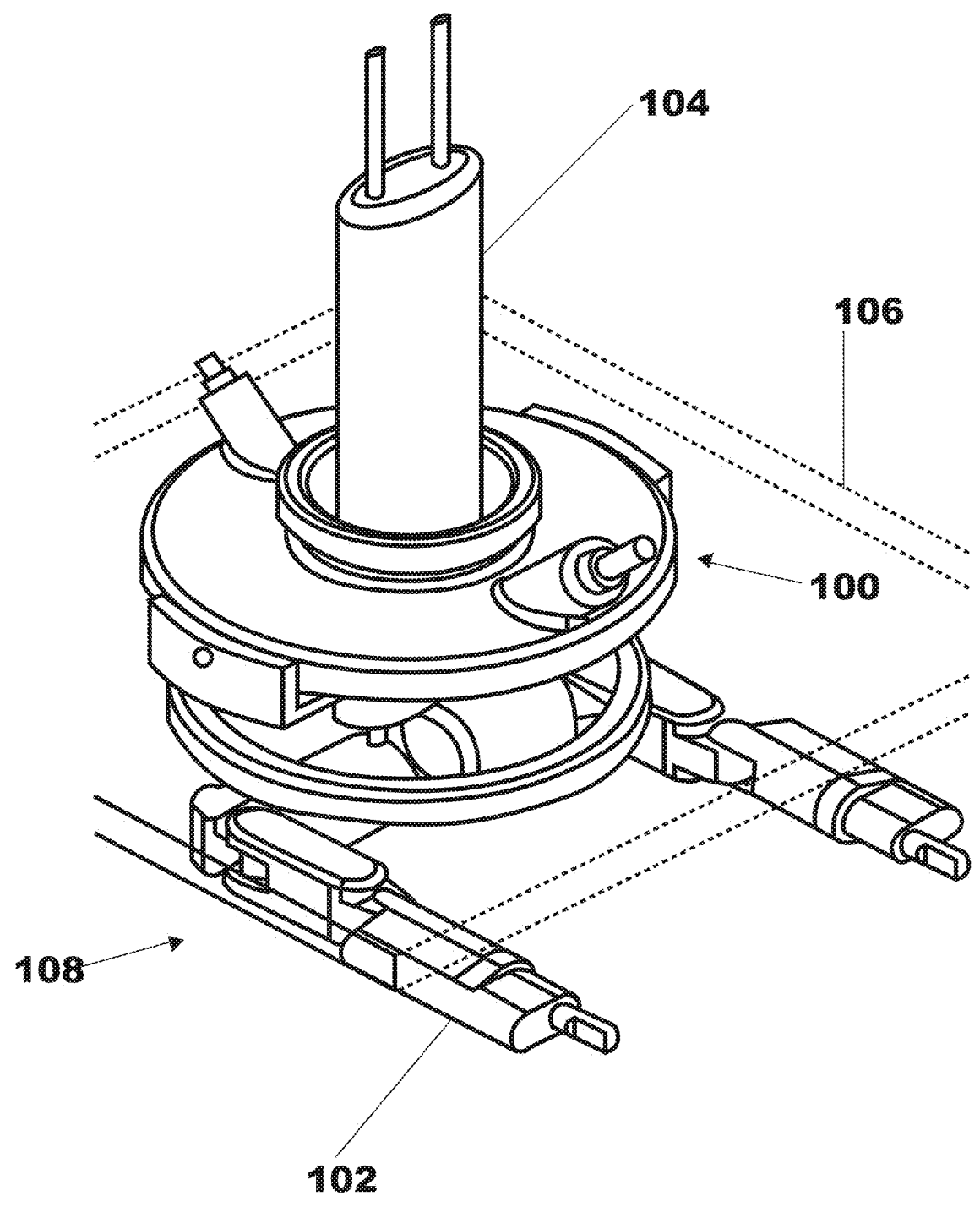
FIG. 12 is a perspective view of an balloon seal insertion system or apparatus, according to one embodiment.

Another access and insertion embodiment relates to a balloon seal insertion method and device for inserting a surgical device/system into a patient's cavity and performing a surgical procedure using a balloon seal insertion device that operates to maintain a fluidic seal around the surgical device such that the higher air pressure of the insufflated cavity is not lost during the procedure. One example of a balloon seal insertion device 100 being used to position and operate a surgical device 102 in a patient's insufflated cavity 106 is depicted in FIG. 12. As depicted, the insertion device 100 is positioned on the patient's skin (schematically depicted as 106) and through the incision in the skin (not shown). The connecting rod 104 coupled to the device 102 is positioned through the insertion device 100, with the surgical device 102 positioned within the patient's insufflated cavity 108.

Figure 13A:
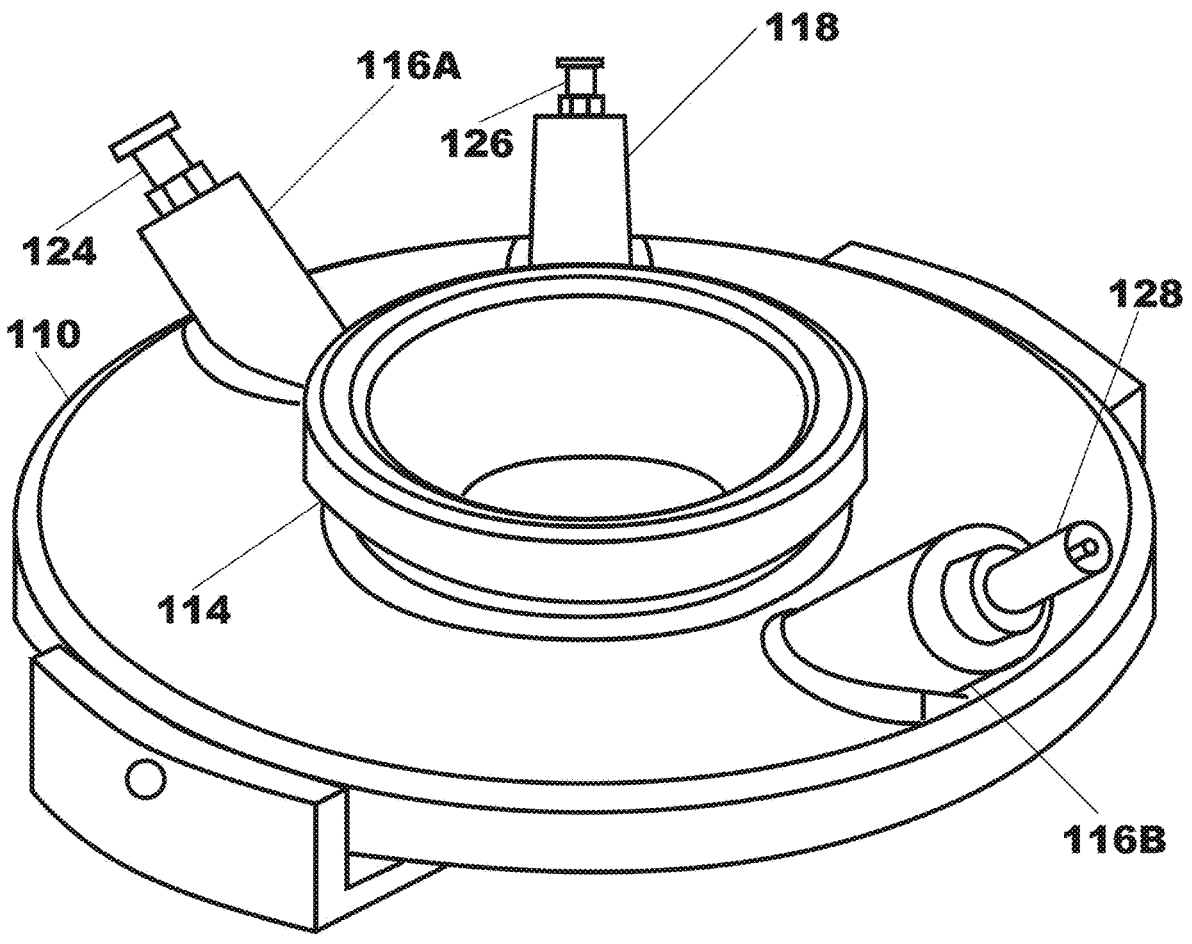
FIG. 13A is a perspective view of an balloon seal insertion system or apparatus, according to one embodiment.
Figure 13B:
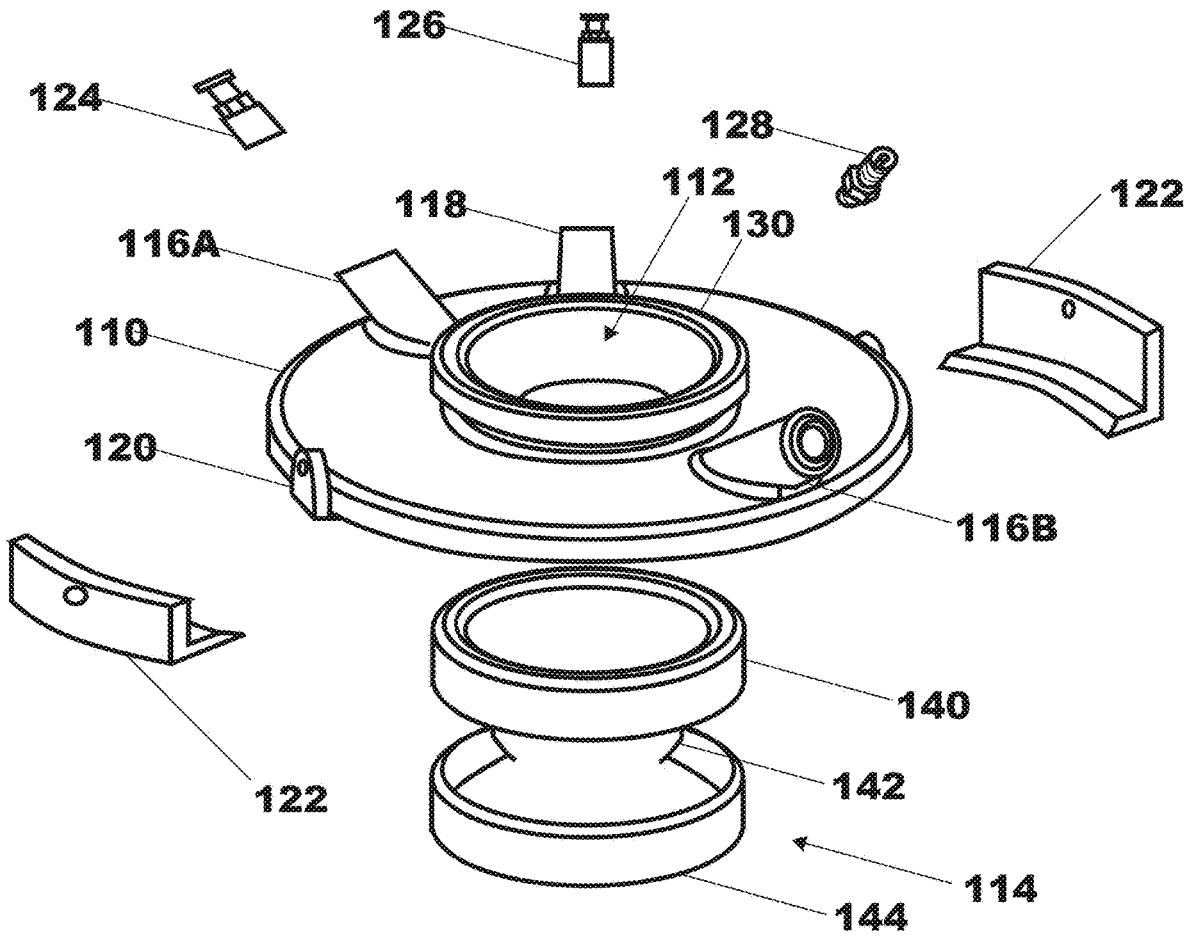
FIG. 13B is an exploded perspective view of the balloon seal insertion system or apparatus of FIG. 13A.

As best shown in FIGS. 12, 13A, and 13B, the insertion device 100 can maintain a fluidic seal during a surgical procedure because the device 100 has an expandable seal 114 (also referred to as an "expandable balloon" or "balloon" herein) disposed through a hole 112 defined in the port housing 110 of the device 100. The balloon 114 provides a fluidic seal around any surgical device positioned through the hole 112 because the balloon 114 is flexible, expandable, and elastic. As such, as the balloon 114 is inflated, it provides "odd geometry molding," which means it can be expanded around, come into contact with, and conform to the shape of any object positioned through the hole 112, thereby creating a fluidic seal around that object, regardless of its shape.

As best shown in FIG. 13B, the insertion device 100 comprises a port housing 110 that defines a hole 112 as discussed above. As also discussed above, the balloon 114 is positioned within the hole 112. The housing 110 further has two balloon inflation/deflation ports 116A, 116B and a cavity insufflation/deflation port 118. In addition, the housing 110 has two attachment components 120 configured to allow for the attachment of the coupling components 122. The coupling components 122 are used to couple the housing 110 to a standard sealable sleeve 46 as will be discussed below.

The ports 116A, 116B, 118 are configured to receive various types of standard valves and/or connections such as Luer locks, each of which is configured to provide an interface for external tubes, hoses, or the like for providing inflation or deflation as desired/needed. In this specific embodiment, two connections 124, 126 are Luer locks and one connection 128 is a Schrader valve. According to one implementation, a Schrader valve is used for connection 128 in port 116B to accommodate connection to a standard air pump while also providing a release valve to deflate the balloon seal 114 when necessary. It is understood that any other known valves or connections used with medical devices-such as, for example, any connections using standard UNF or NPT size fittings—can be used in place of connections 124, 126, 128 with various implementations of this device 100.

It is understood that the various ports 116A, 116B, 118 are intended to couple to external hoses, tubes, or the like, one or more of which are in turn coupled to external air pressure sources. It is further understood that one or all of the external air pressure sources can be an insufflation device or an air pump typically used for inflation of a medical device. In one embodiment, the external air pressure source is a self-regulating device that self-regulates the level of the air pressure. Alternatively, the external air pressure source can be any known air pressure source that is used with inflatable medical devices.

According to one embodiment, the balloon 114 has a top ring 140, a bottom ring 144, and an expandable body 142 connecting the two rings 140, 144. It is understood that these parts of the balloon 114 can be part of a single integral piece that makes up the balloon 114. Alternatively, the balloon 114 can be made up of separate components. The top ring 140 is positioned on and coupled to the top lip 130 on the top portion of the hole 112, while the bottom ring 144 is positioned on and coupled to the bottom lip 132 on the bottom portion of the hole 112, as best shown in FIGS. 14B and 14C. In accordance with one implementation, the rings 140, 144 can be coupled to the lips 130, 132 chemically (a glue or other type of adhesive) or mechanically (clamps, screws, or any other known mechanical attachment mechanisms). Alternatively, the expandable seal 114 can be any known expandable device or component that is used with medical devices and can provide a fluidic seal via odd geometry molding. In one embodiment, the balloon 114 is comprised of latex or some type of rubber. Alternatively, the balloon 114 can be made of any known material used in medical devices that is expandable, elastic, and can provide a fluidic seal via odd geometry molding.

In one implementation, the thickness of the seal 114 can be modified to influence how the seal 114 operates. For example, various parts of the seal 114 can have different thicknesses to influence the way in which the seal 114 expands when it is inflated. Alternatively, the seal 114 can have a single thickness that can be varied to influence the resistance of the seal 114 when an object is inserted through it. Alternatively, the thickness can be varied for other reasons as well. In a further alternative embodiment, in addition to at least one expandable elastic material, an additional material or materials can be added to the seal 114. For example, a fabric or other type of material that is less elastic and/or less expandable can be included in the seal 114 to influence or control the way the seal 114 expands when it is inflated. For example, a fabric could be included in a top and bottom portion of the seal 114 to prevent the seal 114 from expanding vertically (up or down) and thereby influence the seal 114 to expand horizontally.

In the embodiment as shown, the attachment components 120 are threaded holes configured to receive screws or bolts or the like. Further, in this implementation, the threaded holes 120 are positioned on opposite sides of the housing 110. Alternatively, any appropriate known attachment component 120 can be used to allow for attachment of the coupling components 122 to the housing 110. Further, it is understood by one of ordinary skill that the number and positioning of the attachment components 120 on the housing can vary as desired to allow for different configurations and different types of coupling components 122.

Figure 14A:
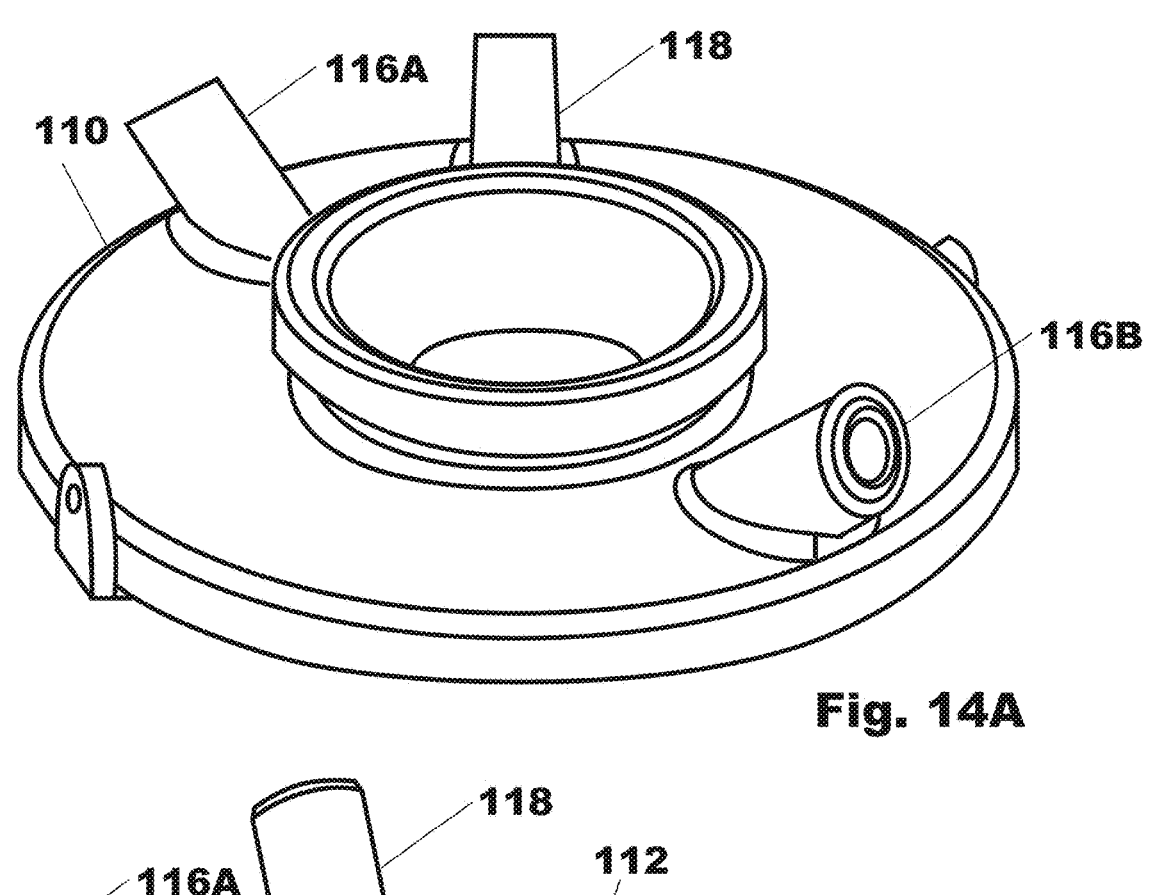
FIG. 14A is a perspective view of a port housing, according to one embodiment.
Figure 14B:
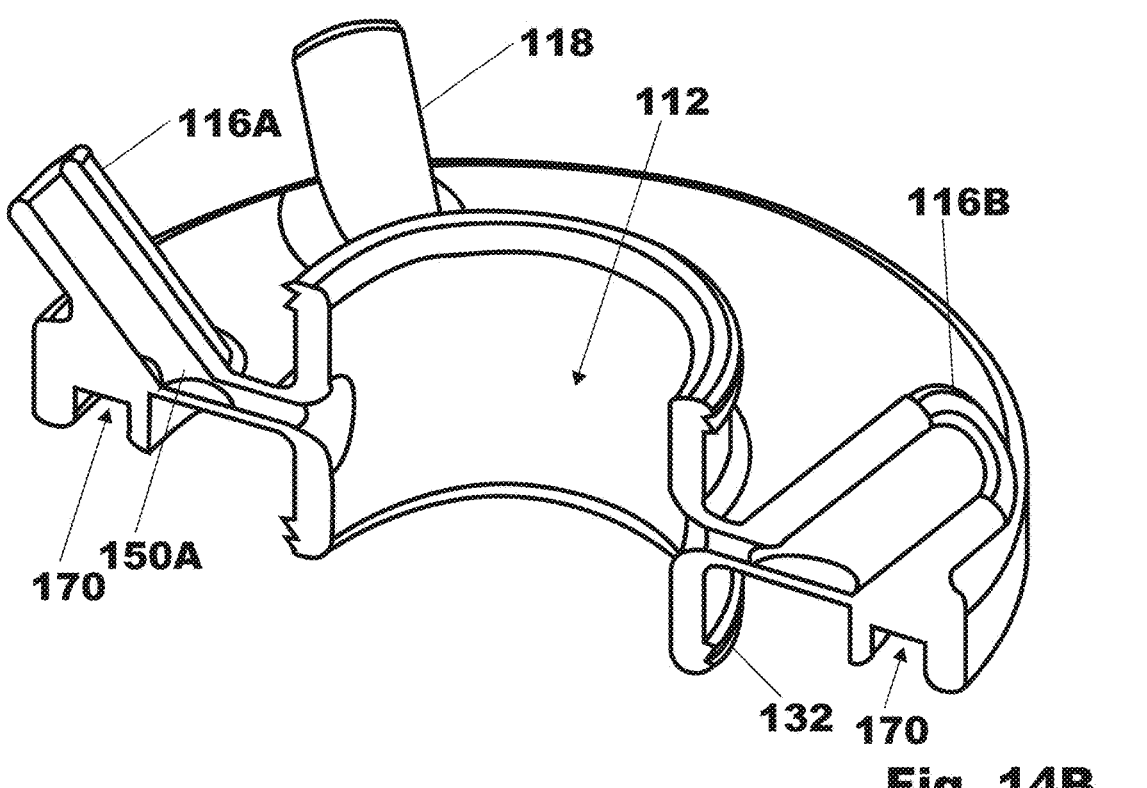
FIG. 14B is a cutaway perspective view of the port housing of FIG. 14A.
Figure 14C:
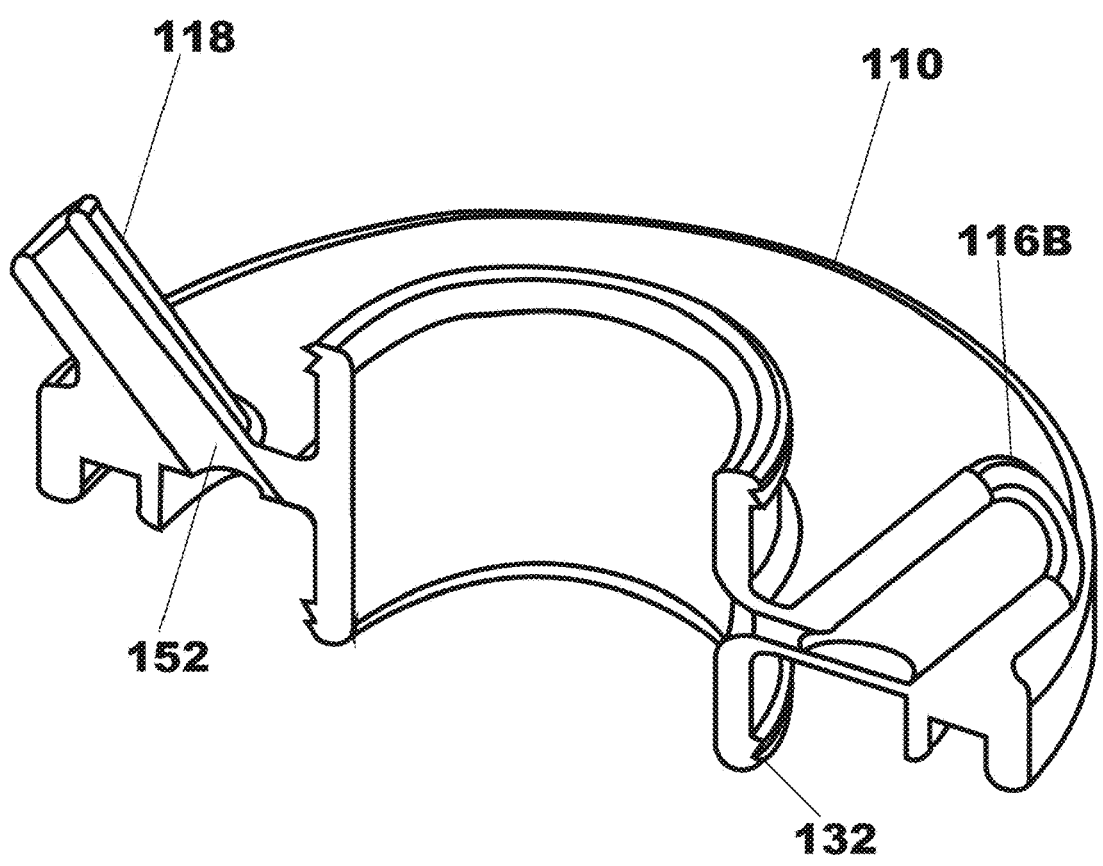
FIG. 14C is a cutaway perspective view of the port housing of FIG. 14A.

FIGS. 14A, 14B, and 14C depict additional details about the configuration of the port housing 110, according to one embodiment. More specifically, as best shown in FIG. 14B (which depicts a cross-section of the housing 110), the port housing 110 has two balloon inflation/deflation lumens 150A, 150B defined in the housing 110. The balloon inflation/deflation lumen 150A provides a fluid connection between the balloon inflation/deflation port 116A and the hole 112, thereby allowing for inflation or deflation of the expandable seal 114 via the port 116A. Similarly, the balloon inflation/deflation lumen 150B provides a fluid connection between the balloon inflation/deflation port 116B and the hole 112, thereby also allowing for inflation or deflation of the expandable seal 114 via the port 116B.

As best shown in FIG. 14C (which depicts a different cross-section of the housing 110), the port housing 110 also has a cavity insufflation/deflation lumen 152 defined in the housing 110 that provides a fluid connection between the cavity insufflation/deflation port 118 and patient's cavity 108 which is in fluid communication with the underside of the housing 110 when the housing is positioned on the incision in the patient. This lumen 152 thus allows for insufflation or deflation of the patient's cavity 108 via the port 118.

Figure 15:
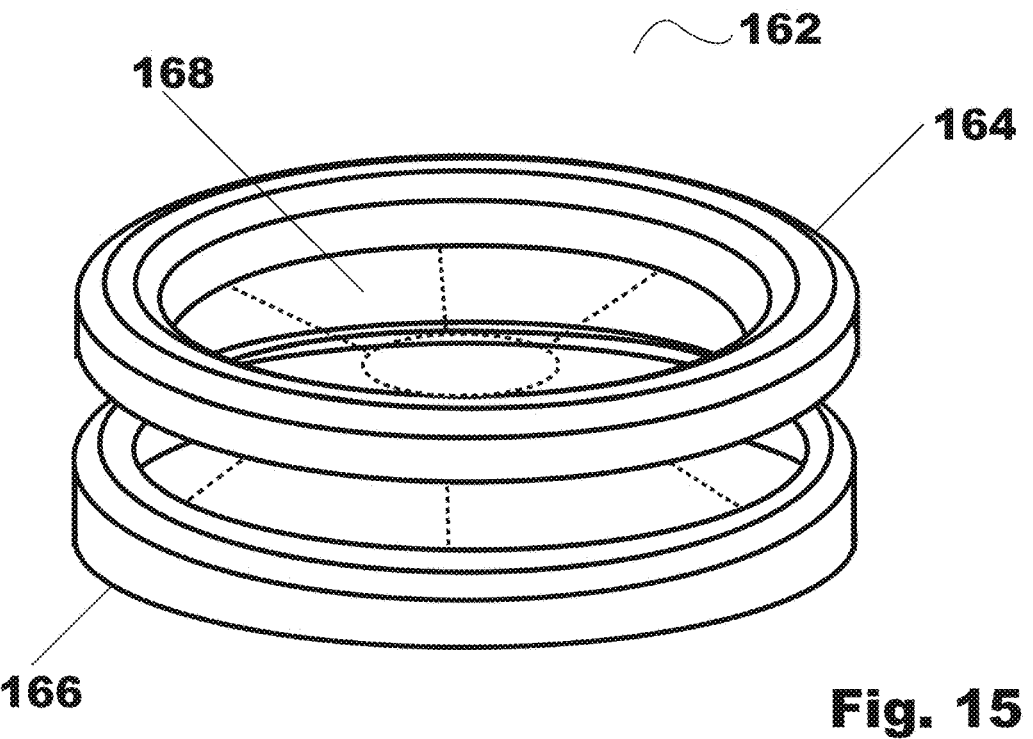
FIG. 15 is a perspective view of a standard sealable sleeve device, according to one embodiment.
Figure 16A:
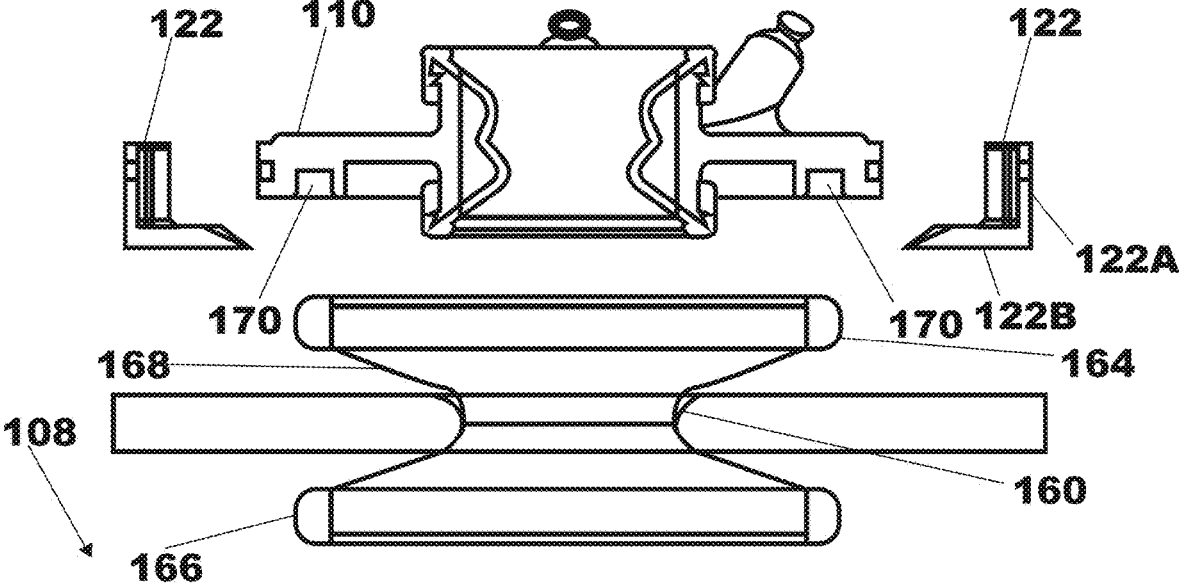
FIG. 16A is a cutaway side view of a balloon seal insertion system or apparatus, according to one embodiment.
Figure 16B:
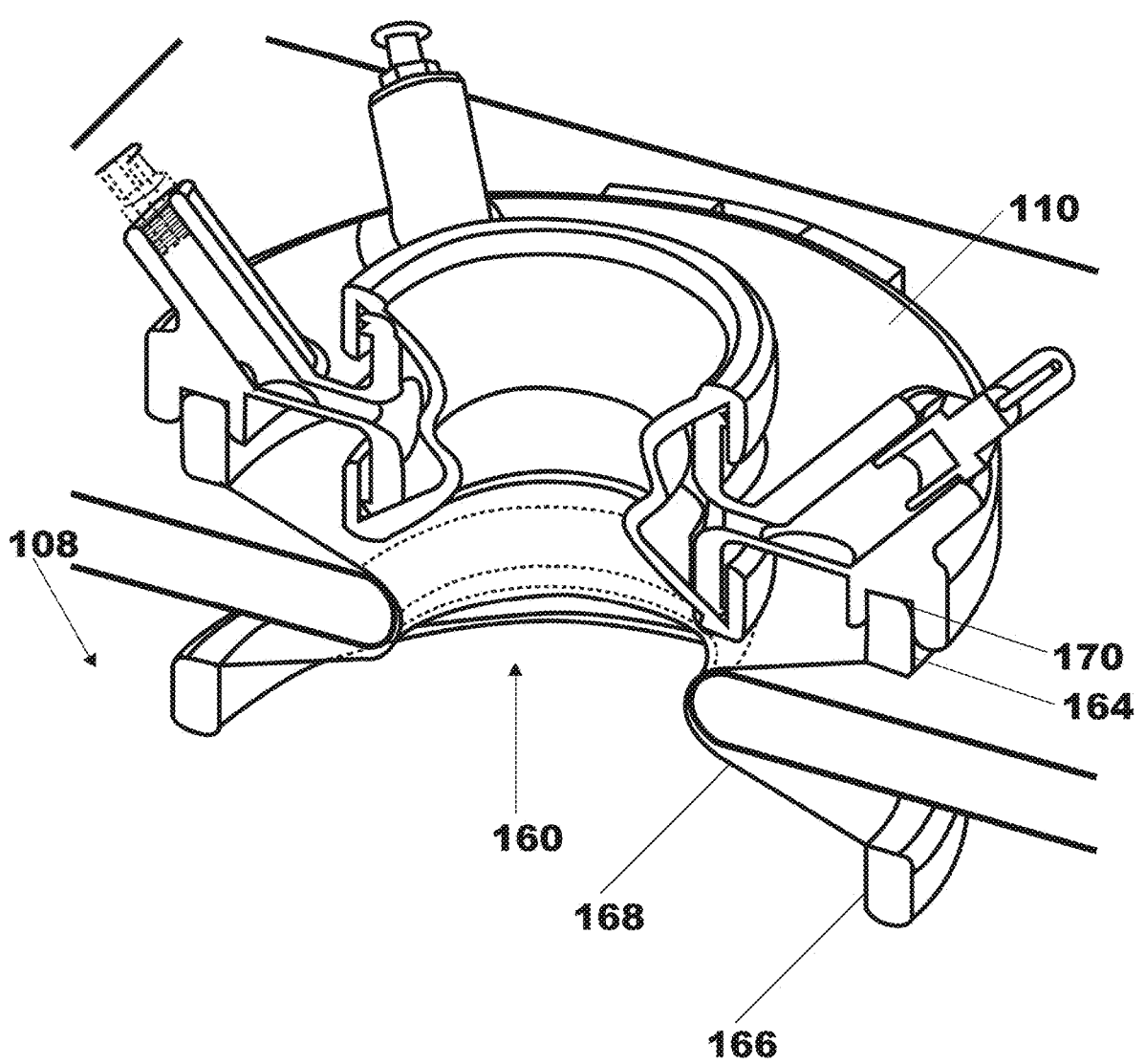
FIG. 16B is a cutaway perspective view of the balloon seal insertion system or apparatus of FIG. 16A.

In use, the device 100 is positioned on the incision 160 in the patient in combination with a standard sealable sleeve device 162 as best shown in FIGS. 16A and 16B. The standard sealable sleeve device 162 is shown in FIG. 15. It has an upper ring 164 and a lower ring 166 that are coupled together by a flexible sleeve 168. According to one embodiment, the device 162 is substantially similar to the sealable sleeve device described above with respect to FIGS. 2A, 2B, 6A, 6B, 6C, and 6D.

In one implementation, the sealable sleeve device 162 is first positioned in the incision 160. It is understood that the sleeve device 162 can be inserted using steps similar to those described above. Alternatively, any known insertion steps can be used to insert the device 162 into the incision such that the upper ring 164 is positioned outside of the incision 160 and the lower ring 166 is positioned inside the patient's cavity, with the sleeve 168 disposed through the incision 160 itself, as best shown in FIG. 16A.

Once the sleeve device 162 is positioned in the incision 160, the housing 110 is coupled to the sleeve device 162 as best shown in FIGS. 16A and 16B. More specifically, according to one implementation, the housing 110 is positioned over the upper ring 164 of the sleeve device 162 such that the upper ring 164 is positioned into the circular indentation or notch 170 defined in the bottom of the housing 110. The configuration of the notch 170 corresponds to the configuration of the upper ring 164 and thus is configured to receive the upper ring 164 such that the ring 164 fits snugly into the notch 170.

Once the ring 164 is positioned in the notch 170, the coupling components 122 are coupled to the attachment components 120 on the housing 110 and thereby firmly couple the housing 110 to the sleeve device 162. The coupling components 122 in this embodiment are components having a vertical piece 122A and a horizontal piece 122B. The vertical pieces 122A are coupled to the attachment components 120 using a screw or bolt or similar mechanism. As best shown in FIG. 16a, when the vertical pieces 122A are coupled to the attachment components 120, the horizontal pieces 122B are positioned under the housing 110 such that they are also positioned under the upper ring 164 disposed in the notch 170. As such, the coupling components 122 operate to retain or lock the upper ring 164 in the notch 170. As a result, the retention of the upper ring 164 into the notch 170 can provide a fluidic seal between the housing 110 and sleeve device 162. Alternatively, any appropriate known interface between the housing 110 and sleeve device 162 that provides a fluidic seal can be used.

Once the housing 110 and sleeve device 162 are coupled, the balloon 114 can be inflated using either port 116A or port 116B or both. When the balloon 114 has been sufficiently inflated such that the expandable body 142 of the balloon 114 contacts itself, a fluidic seal is created between the patient's cavity and the ambient air outside the patient's body. Once this fluidic seal is established, the patient's cavity 108 can be insufflated using port 118 to the desired pressure inside the cavity 108 and the appropriate devices and/or instruments can be inserted into the cavity 108 through the expanded balloon 114 seal with loss of pressure inside the cavity 108.

Figure 17A:
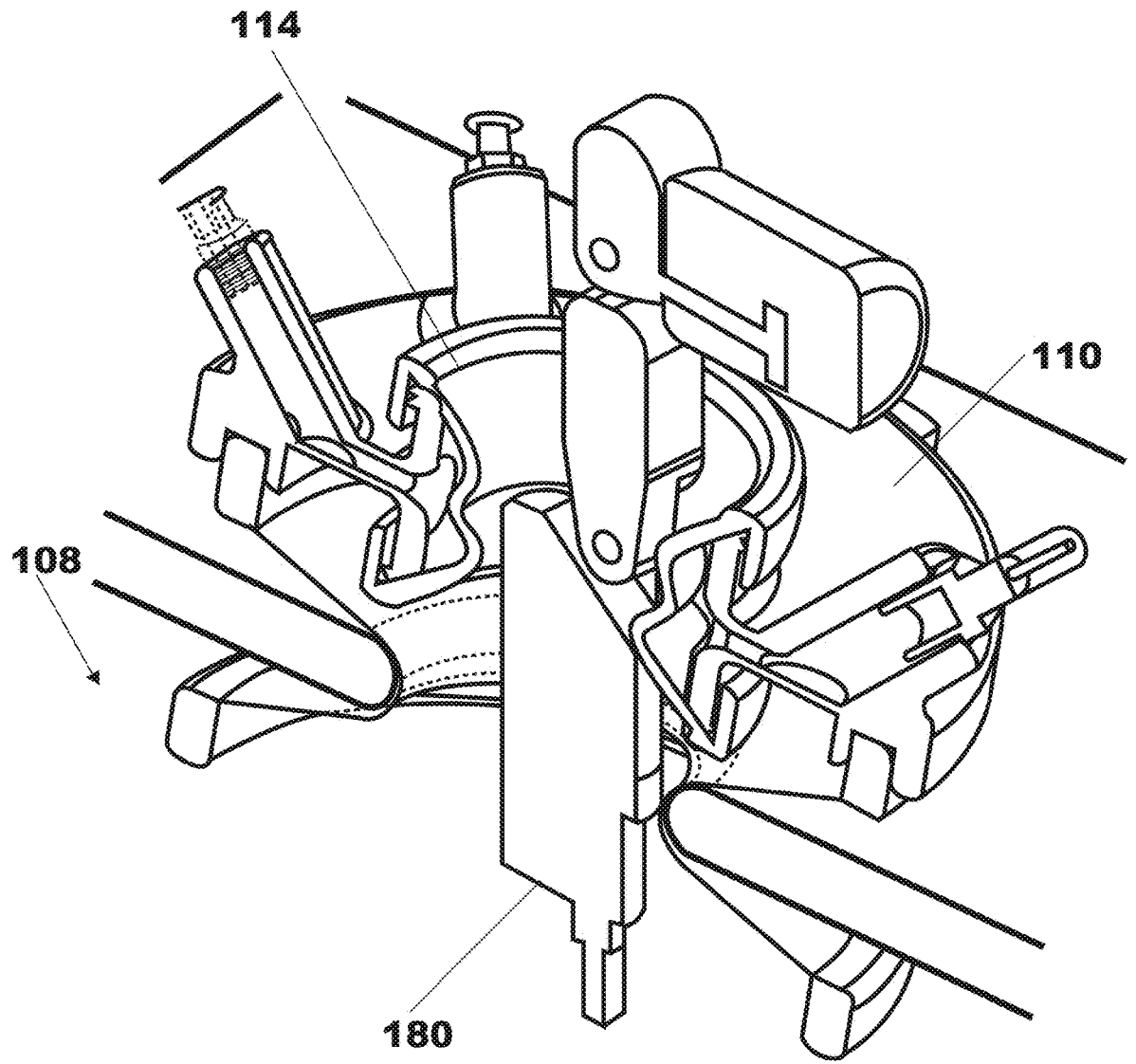
FIG. 17A is a cutaway perspective view of a balloon seal insertion system or apparatus with a first arm of a surgical device disposed therethrough, according to one embodiment.
Figure 17B:
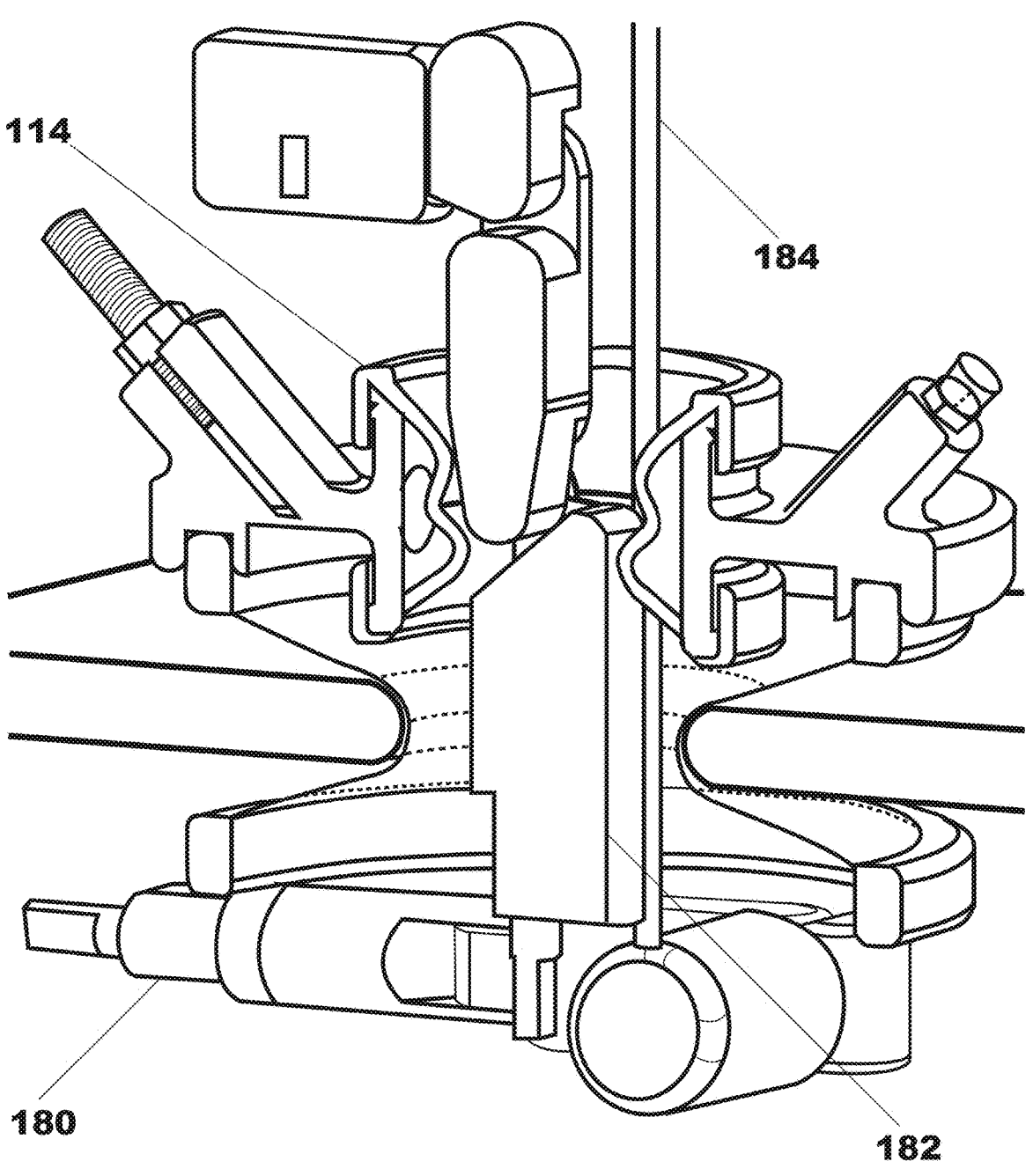
FIG. 17B is a cutaway perspective view of the balloon seal insertion system or apparatus of FIG. 17A in which the first arm is positioned using a connection rod.

In one particular example as depicted in FIGS. 17A and 17B, a device/system having two robotic arms 180, 182 are positioned in the patient's cavity 108 through the expanded balloon 114 seal. More specifically, the first robotic arm 180 is inserted into the expanded balloon 114 seal in FIG. 17A. Due to the odd geometry formation of the expanded balloon 114, the fluidic seal is maintained even as the first arm 180 is being inserted through the balloon 114. Once the first arm 180 is successfully inserted into the cavity 108 and positioned as desired as shown in FIG. 17B using a connection rod 184, the second arm 182 is inserted into the balloon 114 seal. Again, the odd geometry formation of the balloon 114 allows this to occur without losing the fluidic seal and thus without losing the higher pressure of the insufflated cavity 108.

Returning to FIG. 12, this figure depicts a final position of the robotic system having two arms 180, 182. With the arms 180, 182 positioned as desired, the system can now be operated by a user or surgeon to perform the desired procedure.

It is contemplated that alternative embodiments of the balloon seal devices could have more than one balloon seal provided in a single device. Those two or more balloon seals could be provided in various configurations. For example, in one configuration, in addition to the central seal similar to that described above, a second seal could be provided off to one side of the first seal and positioned at an angle so that any device or object inserted through the second seal would be inserted at an angle. It is understood that these two or more balloon seals could be pneumatically connected to the same air pressure source(s), or, alternatively, each seal could be pneumatically separate so that each has its own pressure source and can be set at its own independent level of air pressure.

Another access and insertion embodiment relates to a rubber seal insertion method and device for inserting a surgical device/system into a patient's cavity and performing a surgical procedure using a rubber seal access/insertion device that operates to maintain a fluidic seal at the incision such that the higher air pressure of the insufflated cavity is not lost during the procedure. One example of a rubber seal access/insertion device 200 is depicted in cross-sectional view in FIG. 18. As depicted, the access/insertion device 200 is positioned on the patient's skin (schematically depicted as 202) over the incision 206 in the skin 202 and is coupled to a standard sealable sleeve device 204, which is disposed through the incision 206.

Figure 19A:
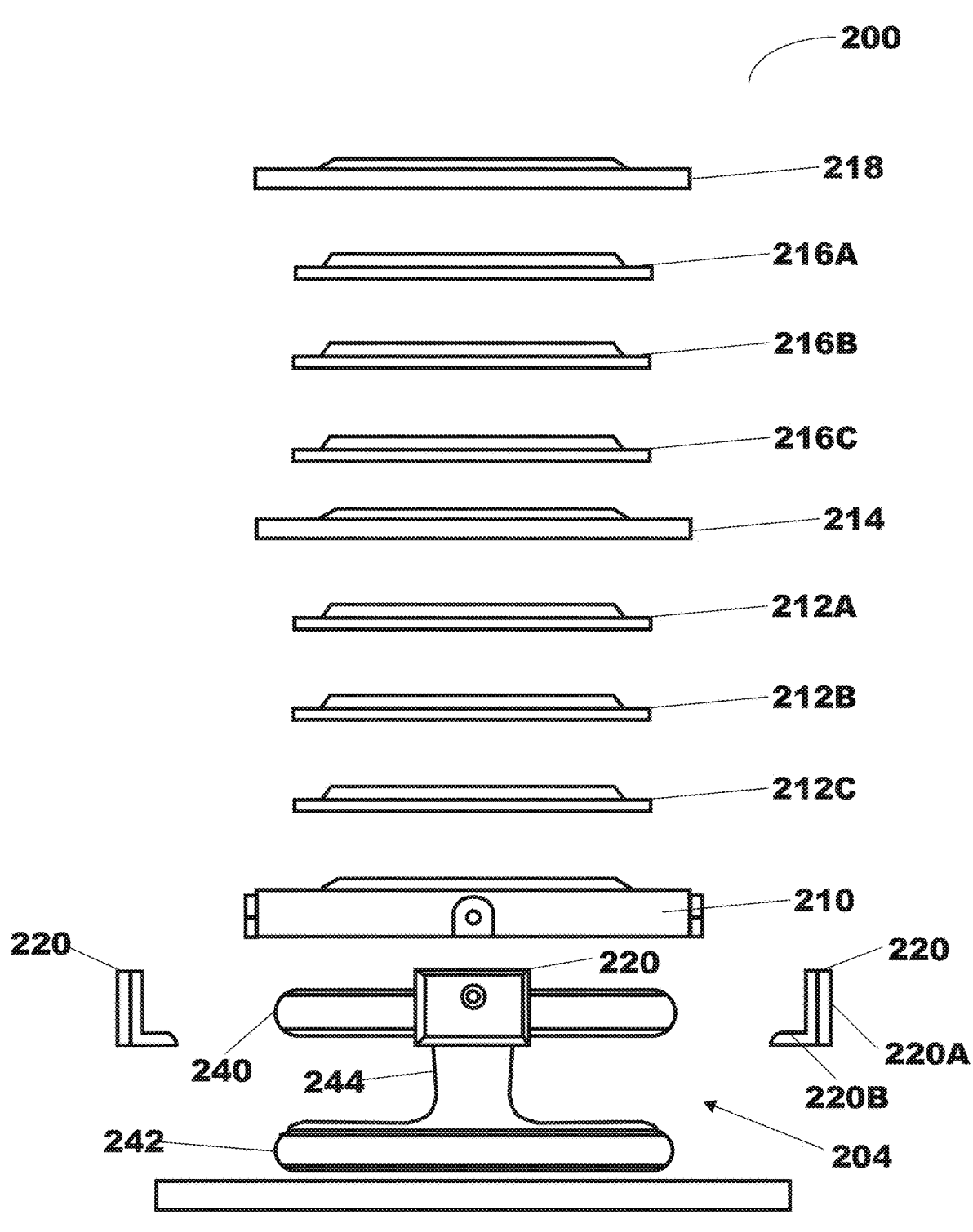
FIG. 19A is an exploded side view of a rubber seal access/insertion device, according to one embodiment.
Figure 19B:
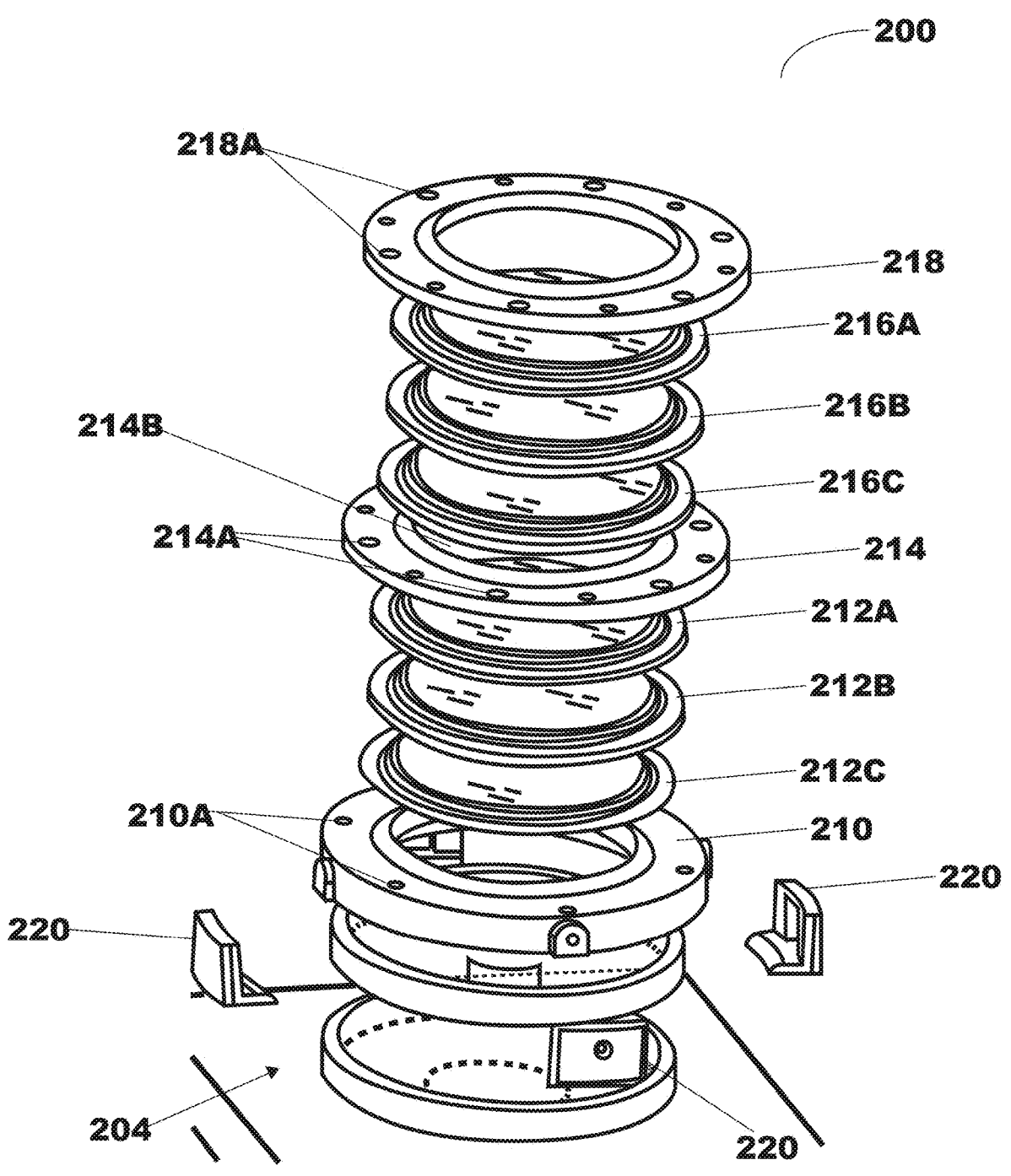
FIG. 19B is an exploded perspective view of the rubber seal access/insertion device of FIG. 19A.

As best shown in FIGS. 19A and 19B, the access/insertion device 200 has a base ring 210 that is coupleable to the sleeve device 204. The device 200 also has three seals 212A, 212B, 212C positioned between the base ring 210 and the first top ring 214. In some embodiments, the device 200 has only the first set of seals (212A, 212B, 212C) and the first top ring 214. In alternative embodiments such as the implementation as shown, the device 200 also has a second set of three seals 216A, 216B, 216C positioned between the first top ring 214 and a second top ring 218. In this implementation, the first and second top rings 214, 126 are coupled to the base ring 210, thereby maintaining the first set of seals 212A, 212B, 212C and second set of seals 216A, 216B, 216C in place such that each of the sets of seals 212, 216 and the two top rings 214, 218 maintain a fluidic seal. According to one embodiment, a set of screws or bolts are positioned through the holes 210A, 214A, 218A defined in the outer circumference of each of the base ring 210, the first top ring 214, and the second top ring 218, respectively, and fastened to fix the rings 210, 214, 218 in place. Alternatively, any known device or mechanism for holding or fixing the rings 210, 214, 218 (and thus the seals 212, 214) in place can be used.

Figure 20:
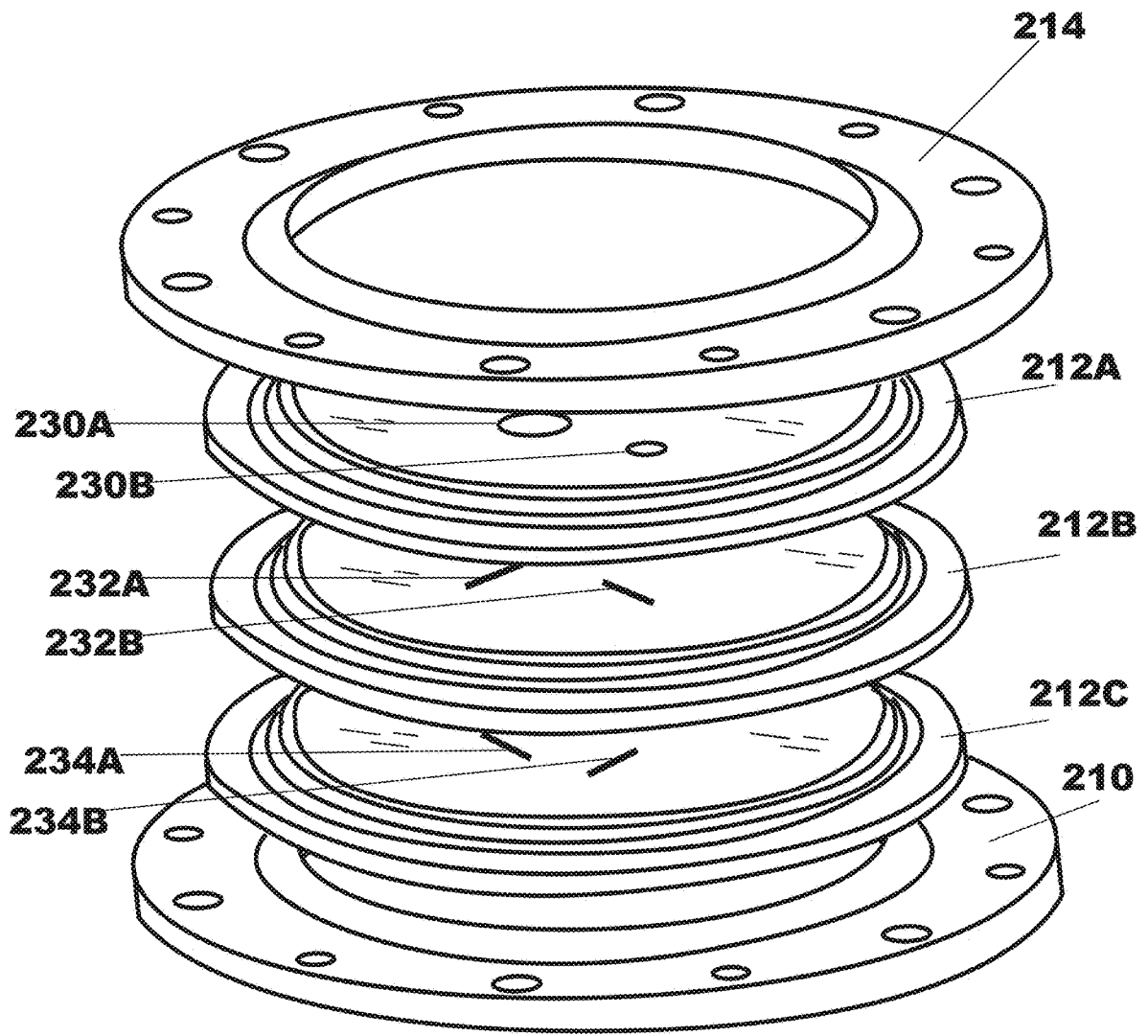
FIG. 20 is an exploded perspective view of the separate rubber seals of a rubber seal access/insertion device, according to one embodiment.

According to one embodiment, the fluidic seal created by the set of seals (212A, 212B, 212C, for example) is created by providing separate rubber seals having different types of openings defined in each such seal. For example, as best shown in FIG. 20, in this implementation, the seals 212A, 212B, 212C each have two different openings formed through them that are different from the corresponding openings in the other seals. Seal 212A has two substantially circular holes 230A, 230B formed through the seal 212A.

The hole 230A is larger, is positioned more centrally on the seal 212A, and is intended to receive a surgical device or system such as a robotic surgical device. The hole 230B is smaller, is positioned closer to an edge of the seal 212A, and is intended to receive a peripheral device or component such as a trocar, a camera, or some other accessory tool. These holes 230A, 230B are intended to provide a fluidic seal around the perimeter of any object(s) passed through them.

In contrast, seal 212B has two slits 232A, 232B formed through the seal 212B. The slit 232A is larger and is positioned in a location that corresponds to hole 230A, while slit 232B is smaller and is positioned in a location that corresponds to hole 230B. Similarly, seal 212C has a larger slit 234A positioned in a location corresponding to hole 230A and slit 232A and further has a smaller slit 234B positioned in a location corresponding to hole 230B and slit 232B. In addition, the slits 234A, 234B in seal 212C are positioned at a 90 degree angle with respect to the slits 232A, 232B in seal 212B. According to one implementation, the combination of the slits 232A, 232B in seal 212B with the slits 234A, 234B in seal 212C results in a stronger fluid seal that can withstand the increased pressure of the insufflated cavity 208 of the patient without the slits opening and allowing that increased pressure to be lost.

By incorporating two sets of seals 212, 216 as shown in FIGS. 19A, 19B, the overall fluidic seal created by the device 200, even when surgical devices are inserted through the device 200, is further strengthened. More specifically, as best shown in FIG. 19B, the first top ring 214 defines a hole 214B at its center. When the first top ring 214 is positioned between the first set of seals 212 and the second set of seals 216, the hole 214B in the first top ring 214 creates a cavity between the two sets of seals 212, 214. As such, according to one embodiment, any loss of the fluidic seal in one set of the seals (either 212 or 214) will not cause a loss of the overall fluidic seal or leak pressure directly from the patient's cavity 208 into the ambient air outside the patient. Hence, the cavity created by the first top ring 214 can minimize the overall pressure loss from any such leak.

In accordance with one implementation, each of the seals 212A, 212B, 212C, 216A, 216B, 216C is a relatively thin sheet of rubber. Alternatively, each of the seals can be made of any known flexible material that can serve as a seal in a medical device. In one exemplary embodiment, each of the seals is about 0.125 inches thick. Alternatively, the thickness of each of the seals can vary between about 0.0625 and about 0.25 inches thick. In a further alternative, each set of three seals 212, 216 can be replaced with a single seal having a thickness ranging from about 0.1875 inches to about 0.75 inches. This thickness in a single seal, according to some embodiments, can provide substantially the same type of fluidic seal strength as the set of three thin seals.

As discussed above, according to certain embodiments, the device 200 has only one set of seals 212A, 212B, 212C and only the first top ring 214. While such embodiments do not have the cavity created by the first top ring 214 as described above, the device 200 with a single set of seals 212 can still provide a sufficient fluidic seal. For example, such a device 200 would provide a sufficient fluidic seal for insertion of any robotic device having sufficiently smooth external features and surfaces. In addition, a device 200 with a single set of seals 212 can reduce the size of the overall device 200 and can potentially reduce any trauma to the surgical device inserted through the device 200 as a result of only having to pass through a single set of seals 212.

Figure 21:
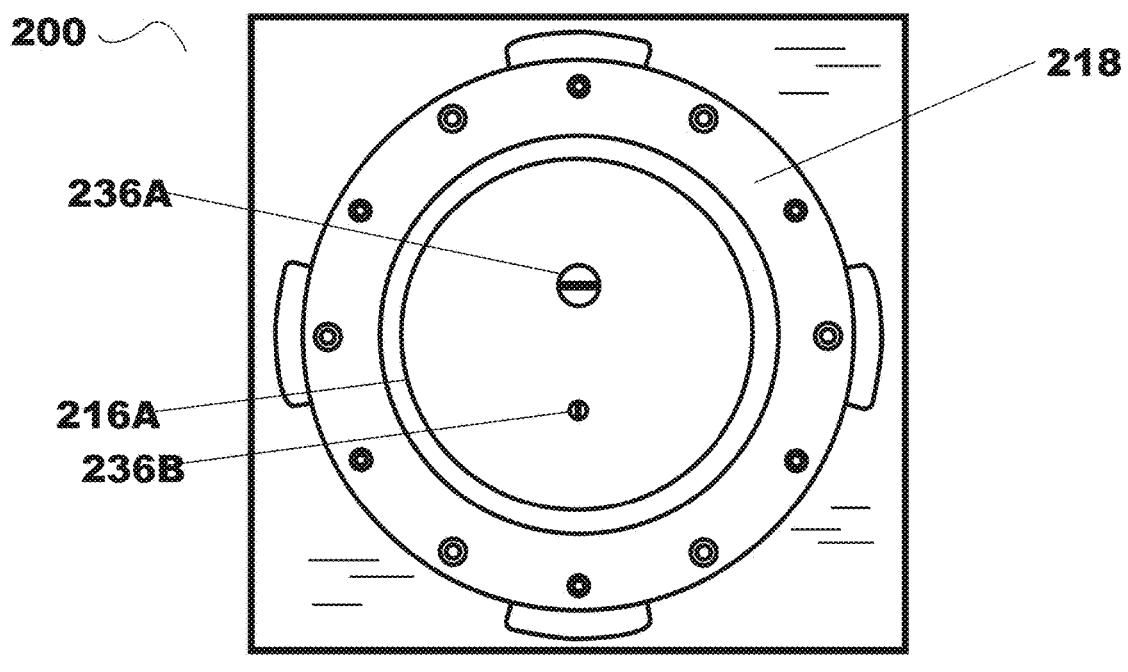
FIG. 21 is a top view of a rubber seal access/insertion device, according to one embodiment.

FIG. 21, according to one implementation, depicts a top view of the device 200. More specifically, FIG. 21 shows the second top ring 218 positioned over the seal 216A. The holes 236A, 236B in the seal 216A are visible as well.

In use, the rubber seal access/insertion device 200 can be positioned for use in the following manner. First, as described above with respect to other embodiments, according to one implementation, the sealable sleeve device 204 is first positioned in the incision 206. It is understood that the sleeve device 204 can be inserted using steps similar to those described above. Alternatively, any known insertion steps can be used to insert the device 204 into the incision such that the upper ring 240 is positioned outside of the incision 206 and the lower ring 242 is positioned inside the patient's cavity, with the sleeve 244 disposed through the incision 206 itself, as best shown in FIG. 18.

Figure 18:
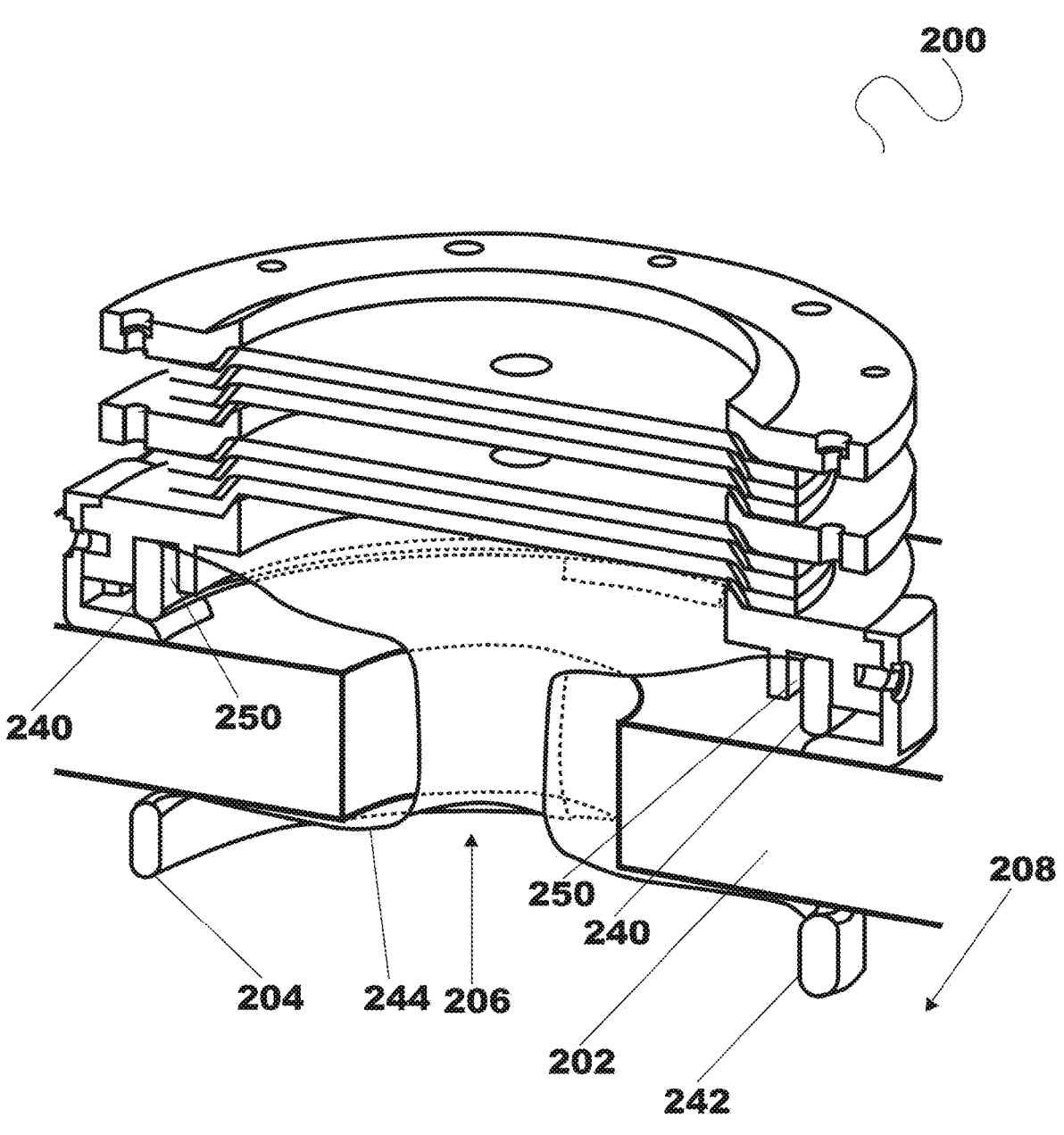
FIG. 18 is a cutaway perspective view of a rubber seal access/insertion device, according to one embodiment.
Figure 22:
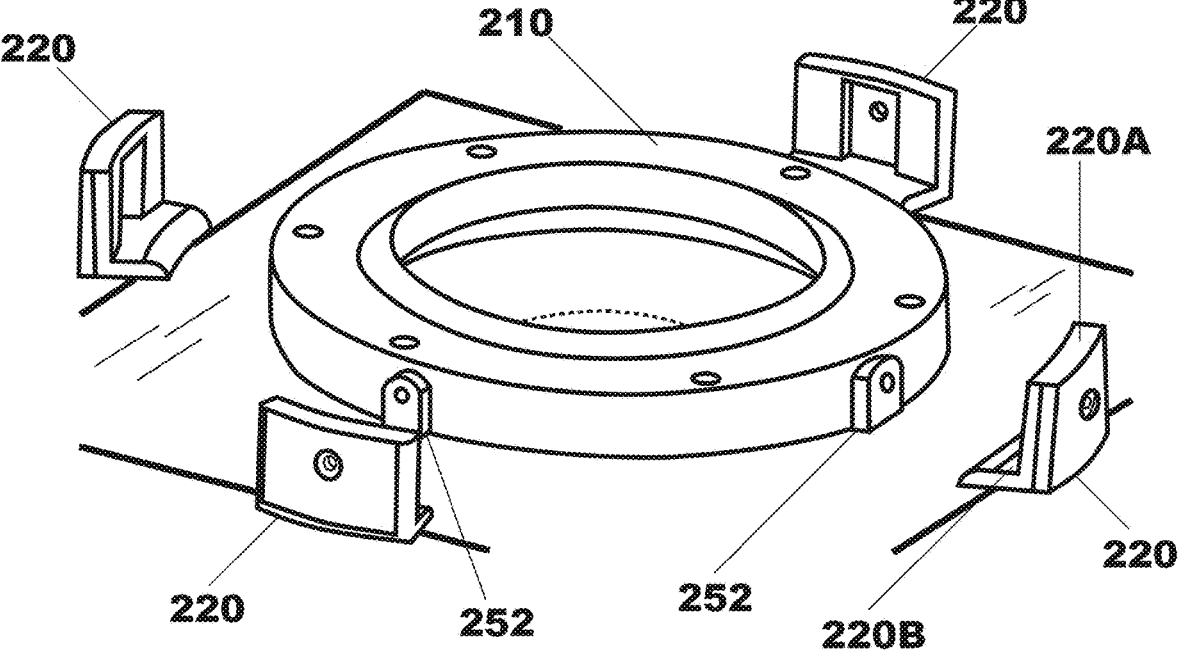
FIG. 22 is a base ring of a rubber seal access/insertion device, according to one embodiment.

Once the sleeve device 204 is positioned in the incision 206, the base ring 210 (and thus the entire device 200) is coupled to the sleeve device 204 as best shown in FIGS. 18 and 22. More specifically, according to one implementation, the base ring 210 is positioned over the upper ring 240 of the sleeve device 204 such that the upper ring 240 is positioned into the circular indentation or notch 250 defined in the bottom of the base ring 210. The configuration of the notch 250 corresponds to the configuration of the upper ring 240 and thus is configured to receive the upper ring 240 such that the ring 240 fits snugly into the notch 250.

Once the upper ring 240 is positioned in the notch 250, the coupling components 220 are coupled to the attachment components 252 on the base ring 210 and thereby firmly couple the base ring 210 to the sleeve device 204. The coupling components 220 in this embodiment are components having a vertical piece 220A and a horizontal piece 220B as best shown in FIG. 19A or 22. The vertical pieces 220A are coupled to the attachment components 252 using a screw or bolt or similar mechanism. As best shown in FIG. 18, when the vertical pieces 220A are coupled to the attachment components 252, the horizontal pieces 220B are positioned under the base ring 210 such that they are also positioned under the upper ring 240 disposed in the notch 250. As such, the coupling components 220 operate to retain or lock the upper ring 240 in the notch 250. As a result, the retention of the upper ring 240 into the notch 250 can provide a fluidic seal between the base ring 210 and sleeve device 204. Alternatively, any appropriate known interface between the base ring 210 and sleeve device 204 that provides a fluidic seal can be used.

Figure 23:
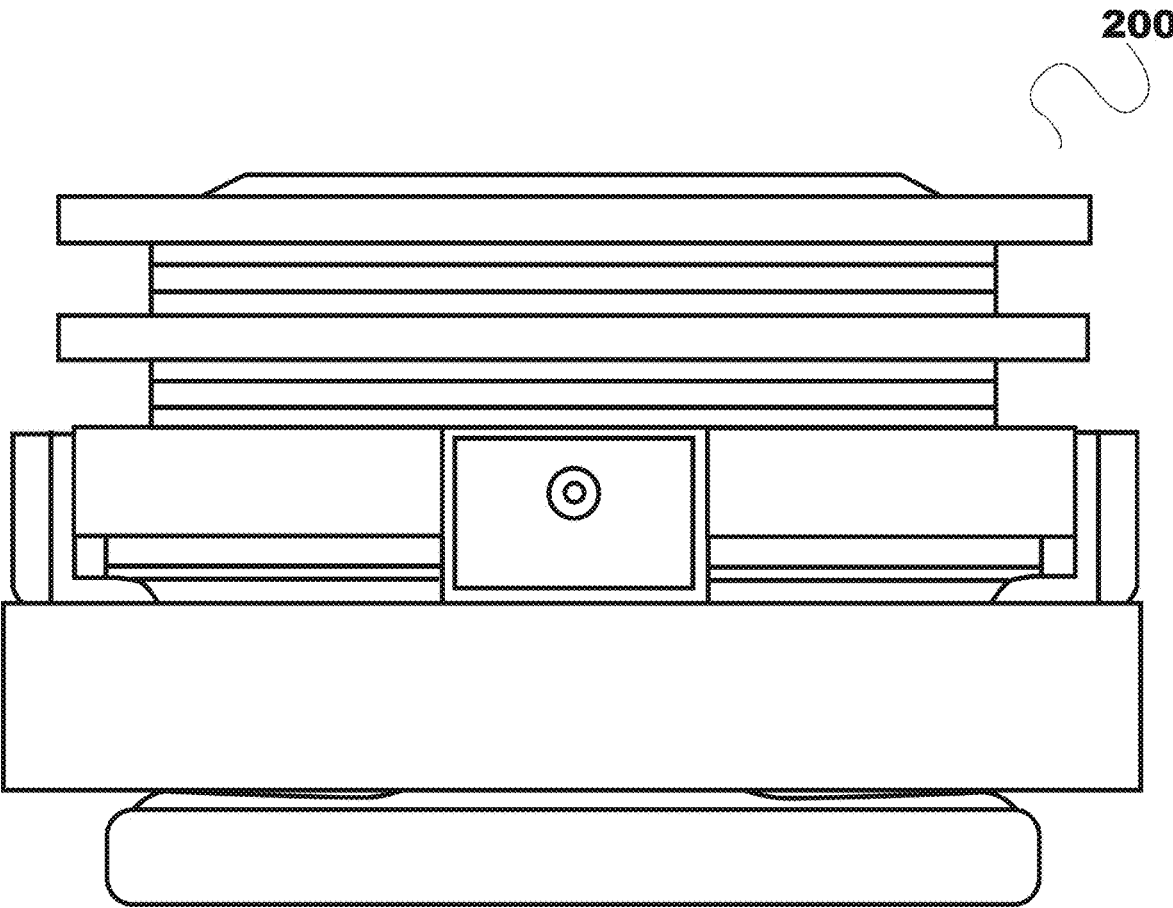
FIG. 23 is a side view of a rubber seal access/insertion device, according to one embodiment.

Once the device 200 and sleeve device 204 are coupled as best shown in FIGS. 18 and 23, a fluidic seal has been established between the patient's cavity 208 and the external air outside of the patient. At this point, the patient's cavity can be insufflated to the desired amount of air pressure. Subsequently, one or more surgical devices can be inserted through the seals 212, 216 at the appropriate holes/slits and into the patient's insufflated cavity 208. In one embodiment, each arm of a robotic surgical device can be separately and consecutively inserted through the larger hole (and larger slits) of the seals and into the cavity 208. Alternatively, any known devices can be inserted into the cavity 208 so long as they fit through the holes and slits as contemplated herein.

Another embodiment of an access/insertion device relates to another external pressurized system or apparatus similar to the system or apparatus depicted in FIGS. 1-11 and described in detail above. Like the device in FIGS. 1-11, the instant device is coupled to a port that is positioned over and/or in an incision in the skin of the patient, thereby providing access to a cavity of the patient. However, in the instant implementations as shown in FIGS. 24A-38 and discussed below, the external pressurized system/apparatus has a external body having one or more access ports for the insertion of not only surgical devices, but also additional equipment and/or the hands of one or more users or medical professionals, providing access to the interior of the pressurized system/apparatus without loss of the higher pressure inside the system/apparatus.

Figure 24A:
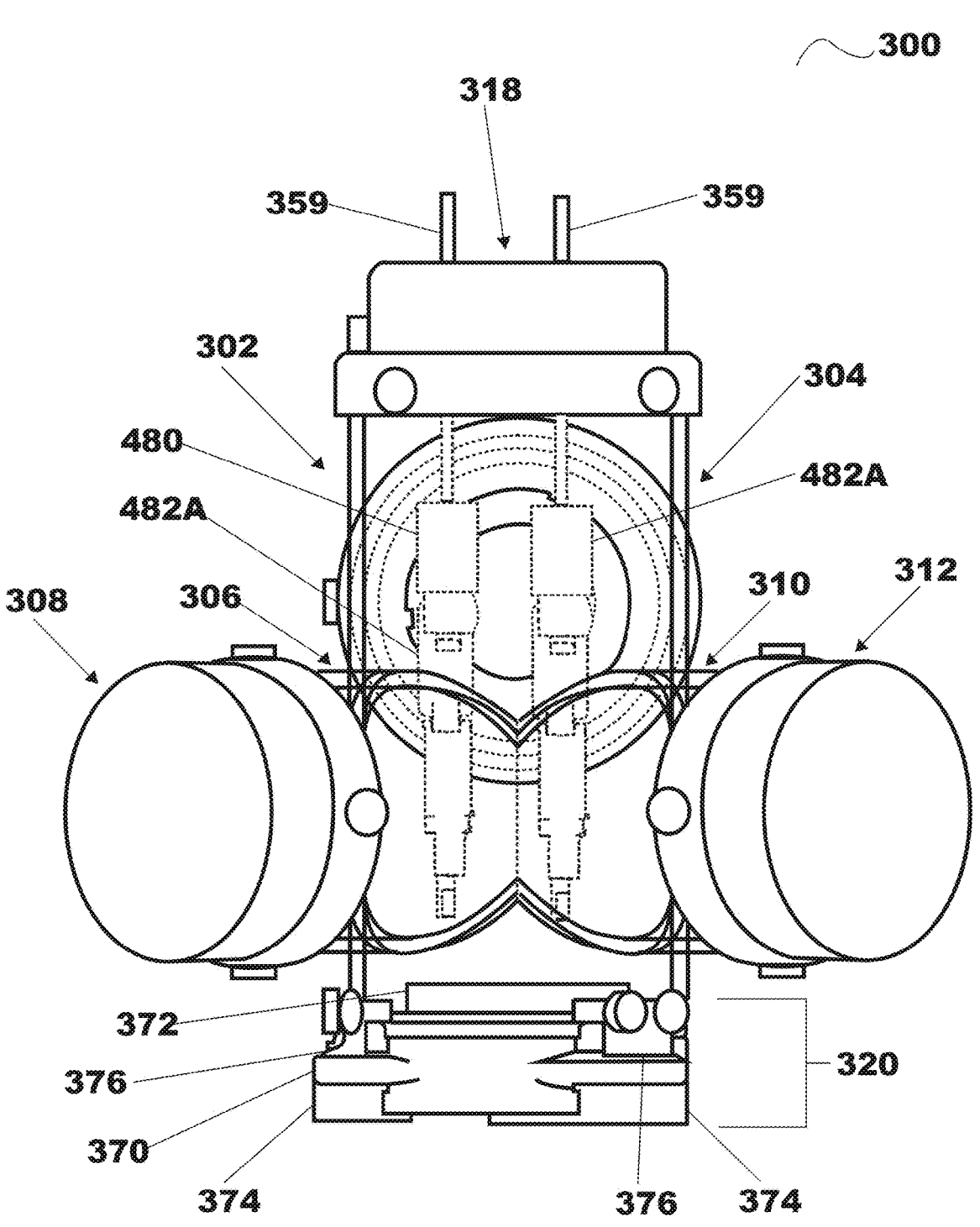
FIG. 24A is a side view of an external pressurized system or apparatus having one or more additional access ports, according to one embodiment.
Figure 24B:
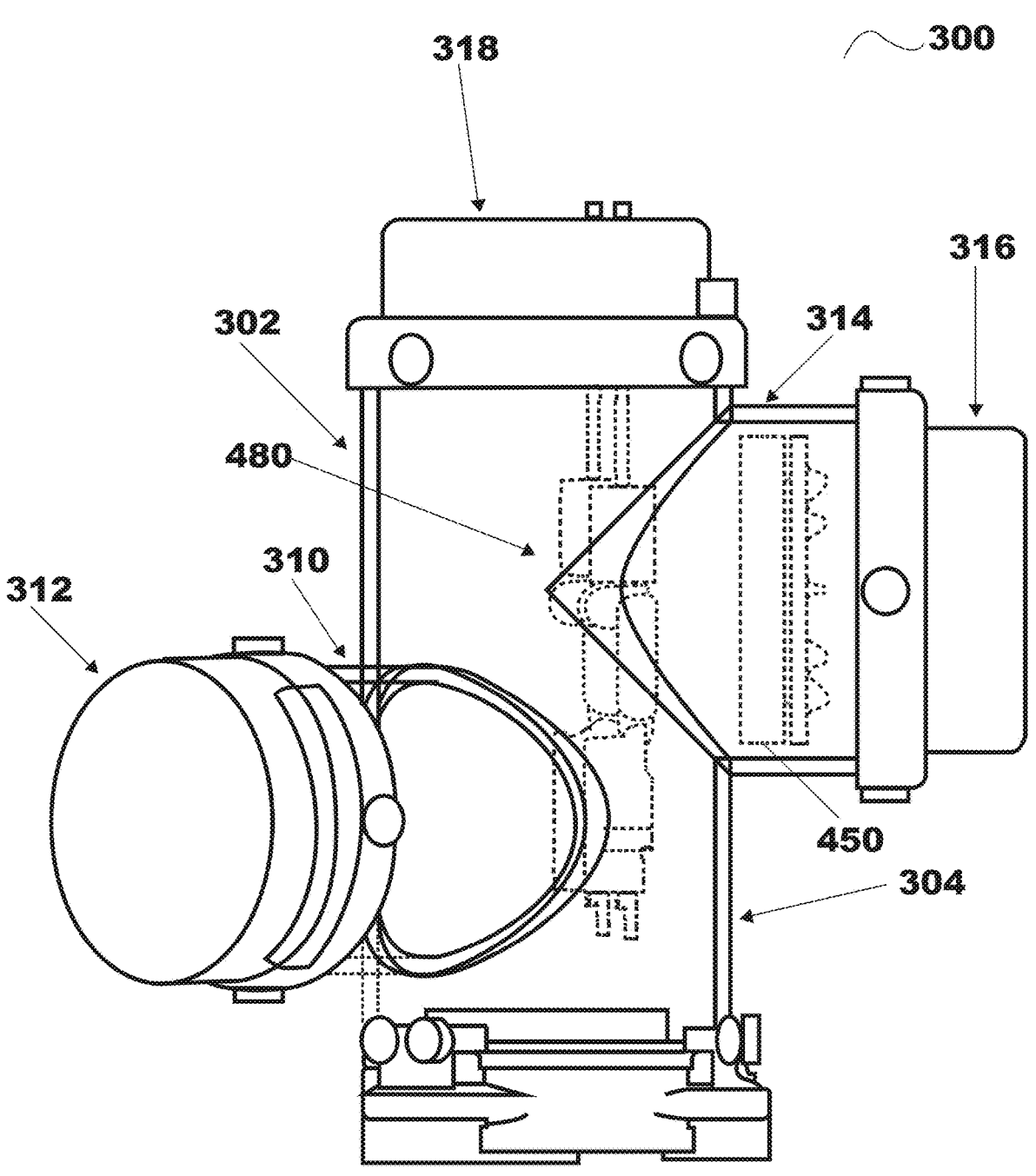
FIG. 24B is another side view of the external pressurized system or apparatus of FIG. 24A.
Figure 24C:
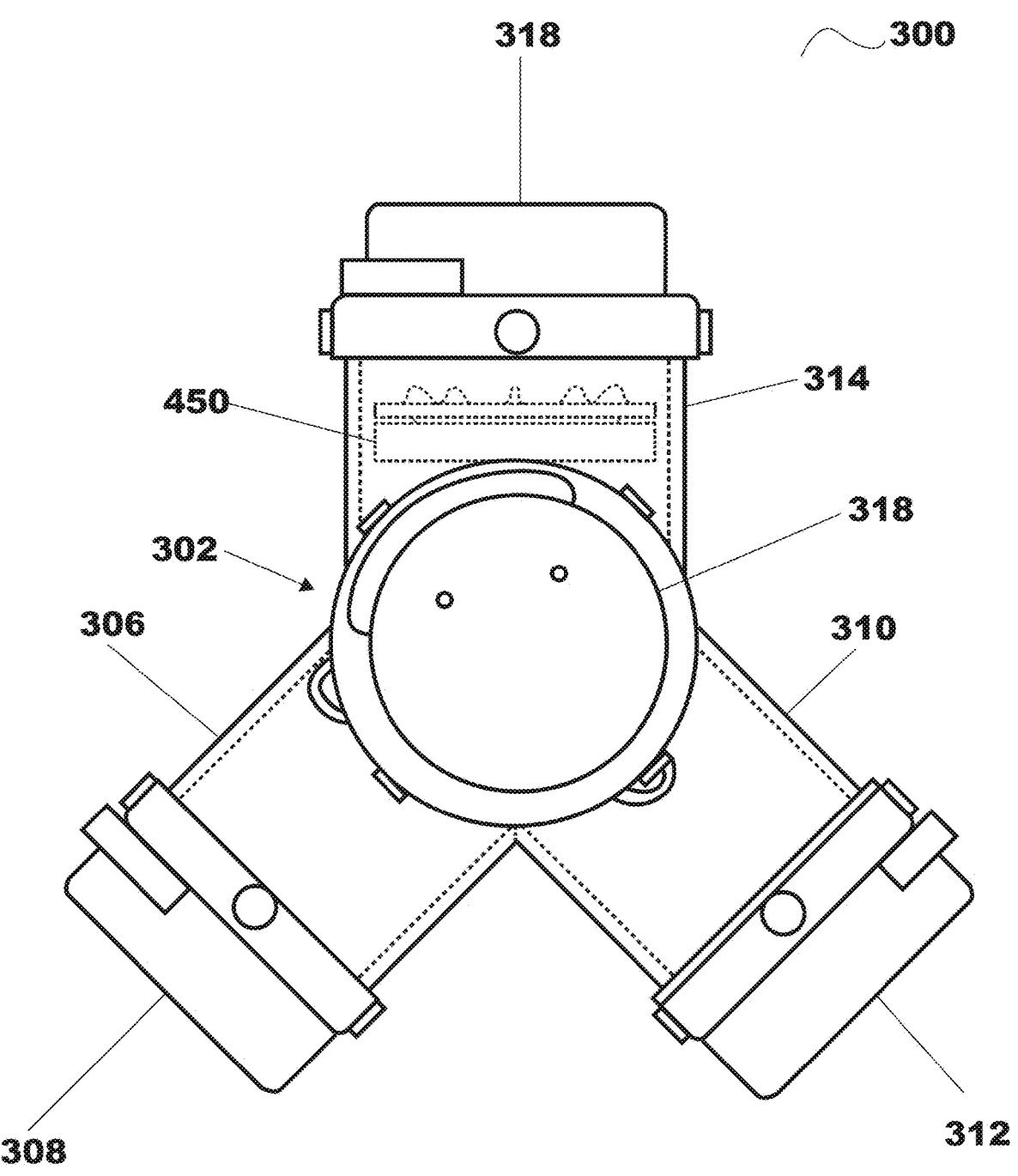
FIG. 24C is a top view of the external pressurized system or apparatus of FIG. 24A.

For example, one implementation of such an external pressurized system or apparatus 300 is depicted in FIGS. 24A-24F. As best shown in FIGS. 24C (top view) and 24D (perspective view), the device 300 has an external body 302 having a main tube (also referred to as the "canister") 304, a left hand tube 306 with a left hand access port 308, a right hand tube 310 with a right hand access port 312, and a side access tube 314 with a side access port 316. In addition, the main tube 304 has a device port 318 coupled to a top portion of the tube 304.

Figures 24D, 24E:
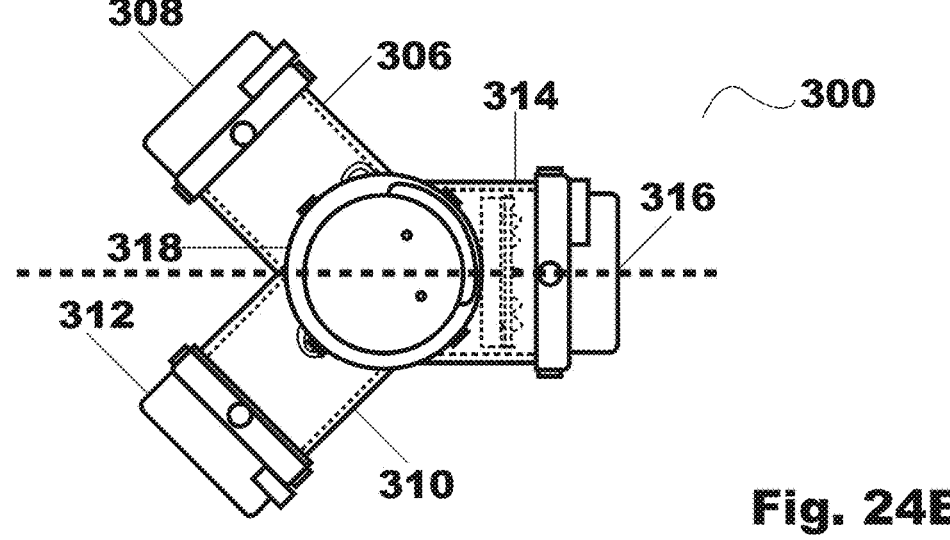
FIG. 24D is a perspective view of the external pressurized system or apparatus of FIG. 24A.
FIG. 24E is another top view of the external pressurized system or apparatus of FIG. 24A.
Figure 24F:
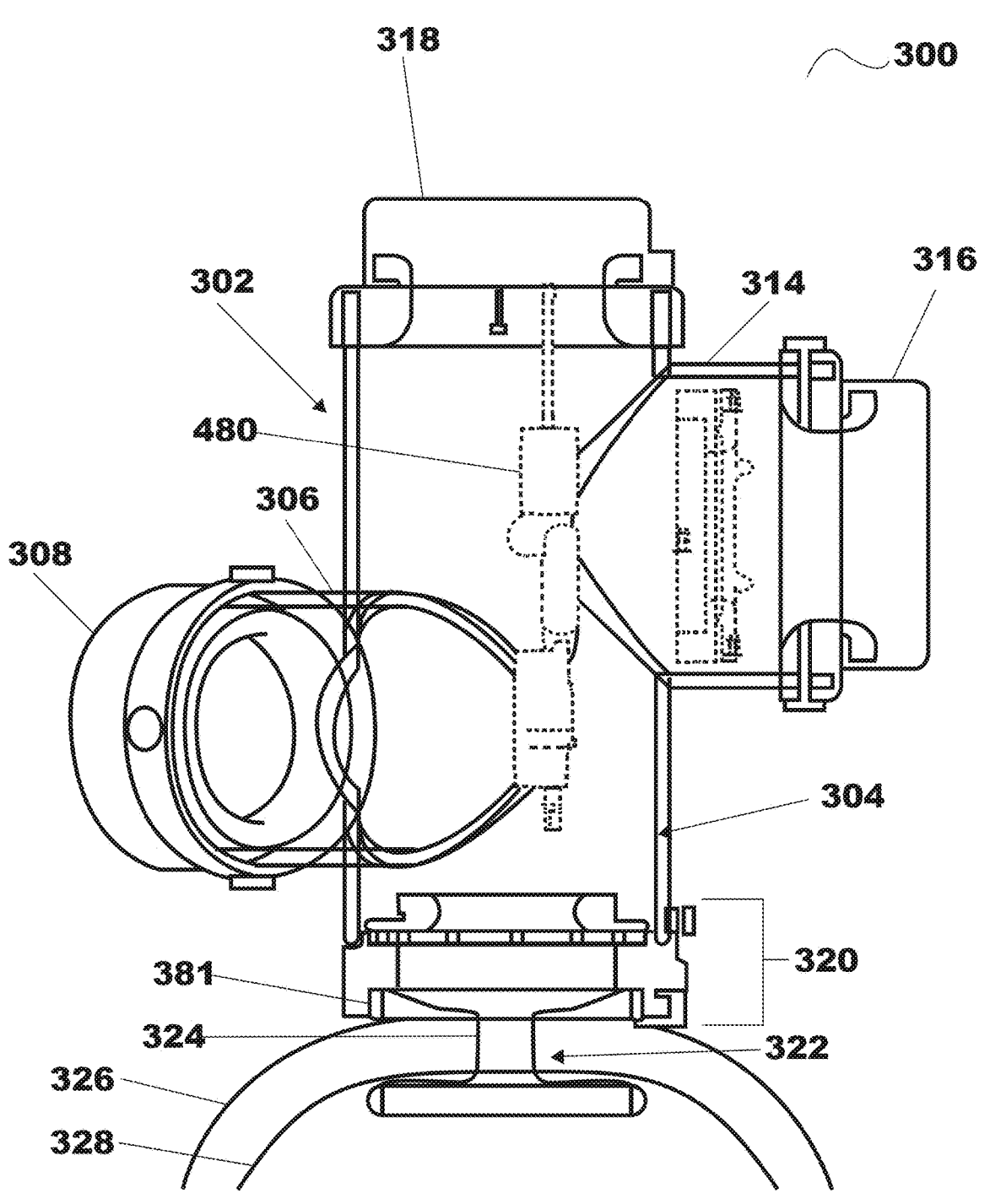
FIG. 24F is a cutaway side view of the external pressurized system or apparatus of FIG. 24A along the cross-section shown with the dotted line in FIG. 24E.

The bottom portion of the main tube 304 is coupleable to an incision port 320, as best shown in FIGS. 24A and 24B. In turn, as best shown in FIG. 24F, the incision port 320 is coupleable to a standard sealable sleeve device 322, which can be positioned in the incision 324 made in the patient's skin 326 to access a target cavity 328 of the patient. The incision port 320 and its coupling to both the main tube 304 and the sealable sleeve device 322 are described in detail below.

In the depicted implementation, the left and right hand access ports 308, 312 can be configured to allow a user or medical professional to insert her or his hands through the ports 308, 312 and into the interior of the body 302. Further, the side access tube 314 with access port 316 can be used for storage of equipment and/or for assistance of another user by inserting her or his hand through the port 316. In addition, the device access port 318 can be configured such that various medical devices/systems can be inserted into the body 302 through the port 318. Alternatively, any of the access ports 308, 312, 316, 318 can be configured to allow for insertion of hands and/or equipment/devices. Further, in various alternative embodiments, it is understood that the body 302 could have a main tube 304 with one, two, or more than three additional tubes with access ports for various uses, including any of those discussed above. It is also understood that various embodiments contemplated herein include tubes and/or ports that are different sizes or shapes than those depicted. For example, in some implementations, the tubes and/or ports could be square or oval in shape.

In one implementation, the external body 302 (the main tube 304 and the access tubes 306, 310, 314) is made of a hard plastic, such as, for example, poly(methyl methacrylate) ("PMMA"). Alternatively, the body 302 can be made of any known rigid material that can be used in medical devices. It is understood that certain embodiments of the body 302 are transparent, such as those depicted in the figures provided. The transparent body 302 allows for the user to see the interior of the tubes 304, 306, 310, 314 including any equipment or devices being inserted during the procedure. Alternatively, the body 302 is not transparent and the equipment/devices can be inserted without being able to view them in the device 300.

According to one implementation, the sealable sleeve device 322, as best shown in FIGS. 24F, 29A, 29B, and 30, can be a standard, commercially available device as described in the various embodiments above. The device 322 has an upper ring 420 and a lower ring 422 that are coupled together by a flexible sleeve 424. According to one embodiment, the device 322 is substantially similar to the sealable sleeve device described above with respect to FIGS. 2A, 2B, 6A, 6B, 6C, and 6D.

Figure 25:
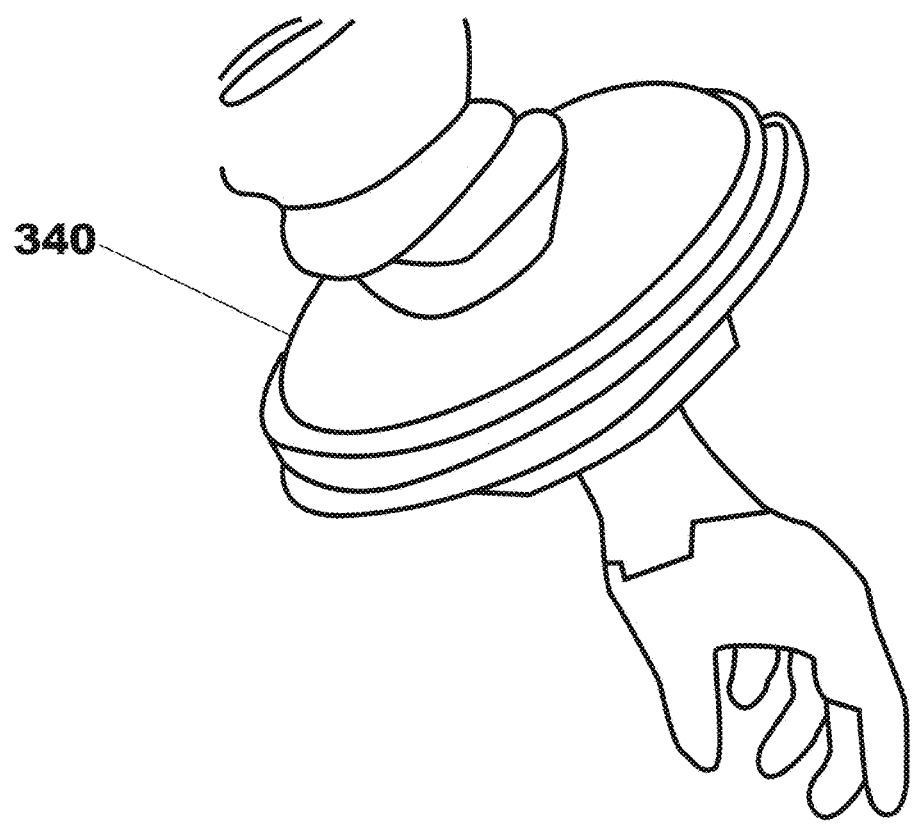
FIG. 25 is a perspective view of an access port with a hand disposed therethrough, according to one embodiment.
Figure 26:
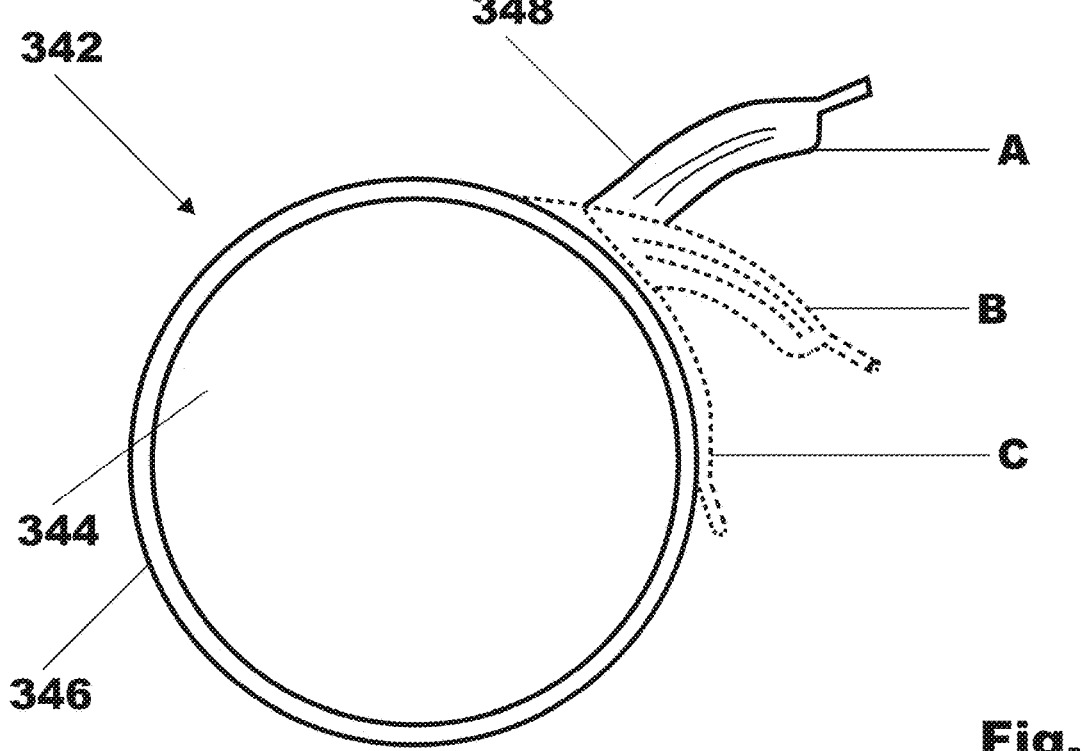
FIG. 26 is a top view of another access port, according to another embodiment.

According to one embodiment, the access ports 308, 312, 316, 318 are standard commercially-available ports that allow various objects, including devices or hands, to be inserted through them and into a surgical space. One example of an access port 340 in use is depicted in FIG. 25. As shown in that figure, the port 340 allows for insertion of a hand through the port 340. Another exemplary access port 342 is depicted in FIG. 26. This port 342 is the GelSeal® port that is commercially available from Applied Medical in Rancho Santa Margarita, CA. In this embodiment, the port 342 has a body 344, a rigid support ring 346, and a moveable clamp lever 348 that can be used to tighten the port 342 and thus secure the port 342 to any ringed object to which it is attached. More specifically, the clamp lever 348 is depicted in three different positions. In position A, the lever 348 is in the open position A and the port 342 thus has its widest circumference. In position B, the lever 348 is midway between the open position A and the closed position C and the port 342 has a circumference that is less than when it is in the open position A. Finally, in position C, the lever 348 is positioned against the port 342 in the closed position C and the port 342 has its smallest circumference. In use, the lever 348 is typically in position A when the port 342 is positioned and then the lever 348 is moved to position C to clamp the port 342 in place. In one embodiment, the body 344 is made of the soft, gel-like material in the product as provided by Applied Medical. Alternatively, the body 344 can be made of any material that allows for objects and/or hands to be inserted through the material such that the fluidic seal is maintained so that the higher pressure of the surgical cavity is not lost when an object is inserted through the material.

Figure 27A:
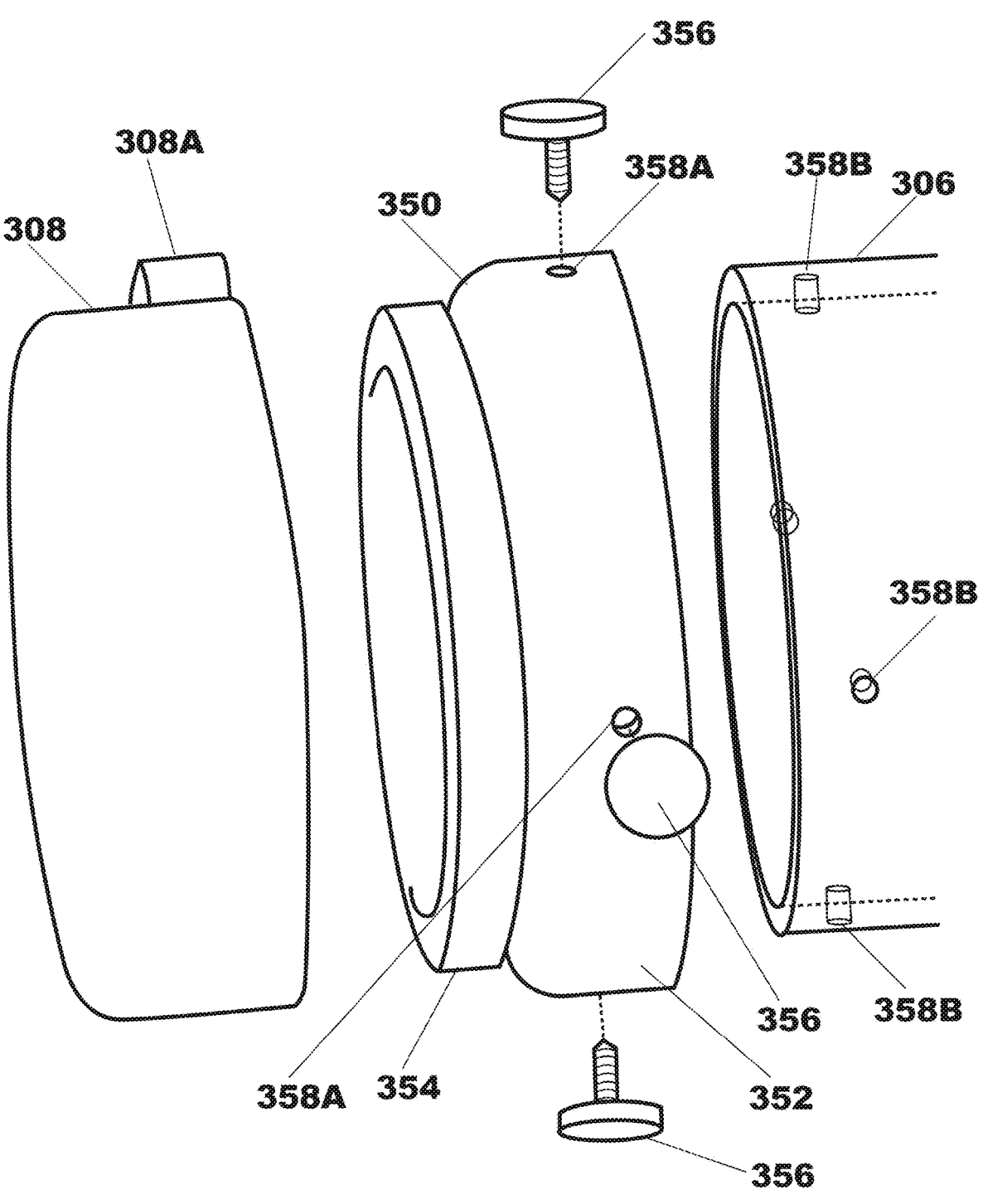
FIG. 27A is a perspective view of a port adaptor ring coupling an access port to a tube, according to one embodiment.

In accordance with one implementation as shown in FIG. 27A, the access ports 308, 312, 316, 318 are coupled to the tubes 304, 306, 310, 314 via a port adaptor ring 350. The port adaptor ring 350 has a first ring portion 352 that is sized to mate with any one of the tubes 304, 306, 310, 314 of the body 302. (In this particular depiction, the left hand access tube 306 is used as an example.) The ring 350 also has a second ring portion 354 that is sized to mate with a port—in this case the left hand access port 308.

According to one embodiment, the first ring portion 352 is coupled to the tube 306 by positioning the first ring portion 352 over the end of the tube 306 and holding the first ring portion 352 in place using thumb screws 356 that are inserted through threaded holes 358A in the first ring portion 352 and into threaded holes 358B in the tube 306. Alternatively, any attachment devices or mechanisms, such as bolts, clamps, or the like, can be used to attach the first ring portion 352 to the tube 306 (and, by extension, to any of the tubes 304, 306, 310, 314). In one embodiment, a gasket (not shown), such as a foam or rubber gasket, is positioned between the tube 306 and the first ring port 352 to ensure that a fluidic seal is established between the two components.

The access port 308, in accordance with one implementation, is coupled to the second ring portion 354 in a fashion similar to that described above. That is, the clamp lever 308A on the port 308 is placed in position A, and the port 308 is positioned over the second ring portion 354. Then the lever 308A is moved into the closed position-position C-such that the port 308 is clamped onto the second ring portion 354. Alternatively, any known mechanism or method for coupling a port similar to port 308 to a device component can be used.

Figure 27B:
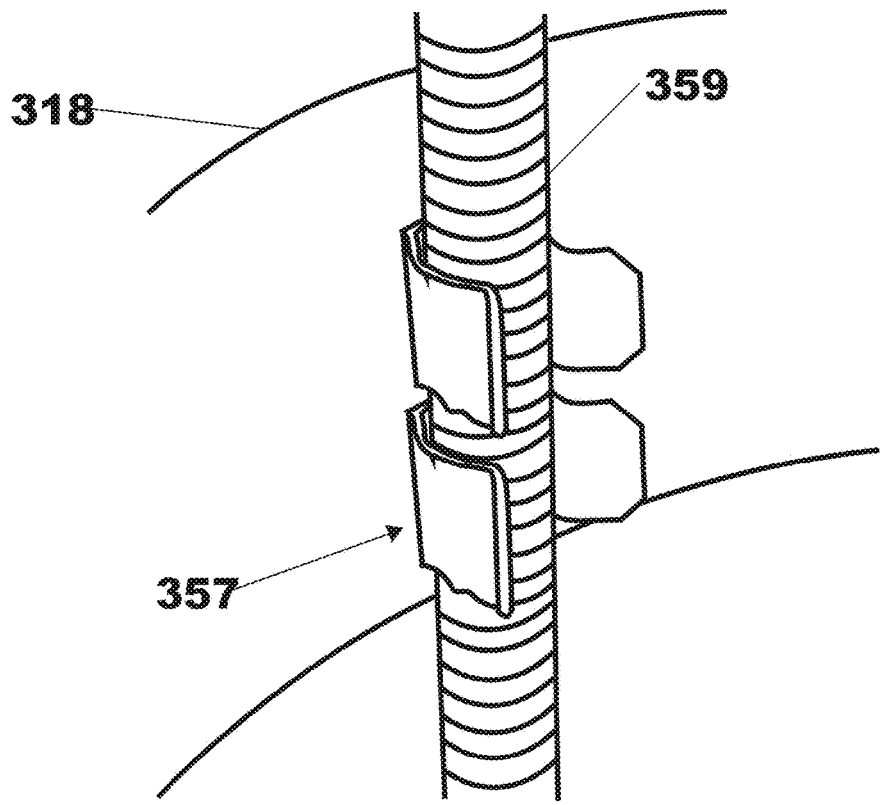
FIG. 27B is a perspective view of a device access port having a device attachment component, according to one embodiment.

According to one embodiment as shown in FIG. 27B, the device access port 318 can have one or more additional structures to allow a user to easily stabilize or position a surgical device within the body 302 of the device 300 prior to or during use. More specifically, the device access port 318 in certain implementations has one or more device attachment components 357 (also referred to as "device clips") positioned along the inner lumen of the port 318. The device clip 357 is configured to retain a device such as a positioning rod 359 within the clip 357, thereby providing a way to couple a portion of the surgical device being used for the intended procedure to the interior of the body 302. In one embodiment, the attachment component 357 is an actual clip as shown in FIG. 27B. Alternatively, the component 357 can be a notch or other type of specifically configured indentation 357 defined in the inner lumen of the port 318 that is configured to receive a medical device such as a positioning rod 359 or the like. In a further alternative, the attachment component 357 can be any mechanical or structural mechanism or component that allows for coupling to a medical device. In further embodiments, such attachment components 357 can be positioned elsewhere in the body 302, such as, for example, on an interior port of another access port or elsewhere on an interior portion of one of the tubes.

Figure 28A:
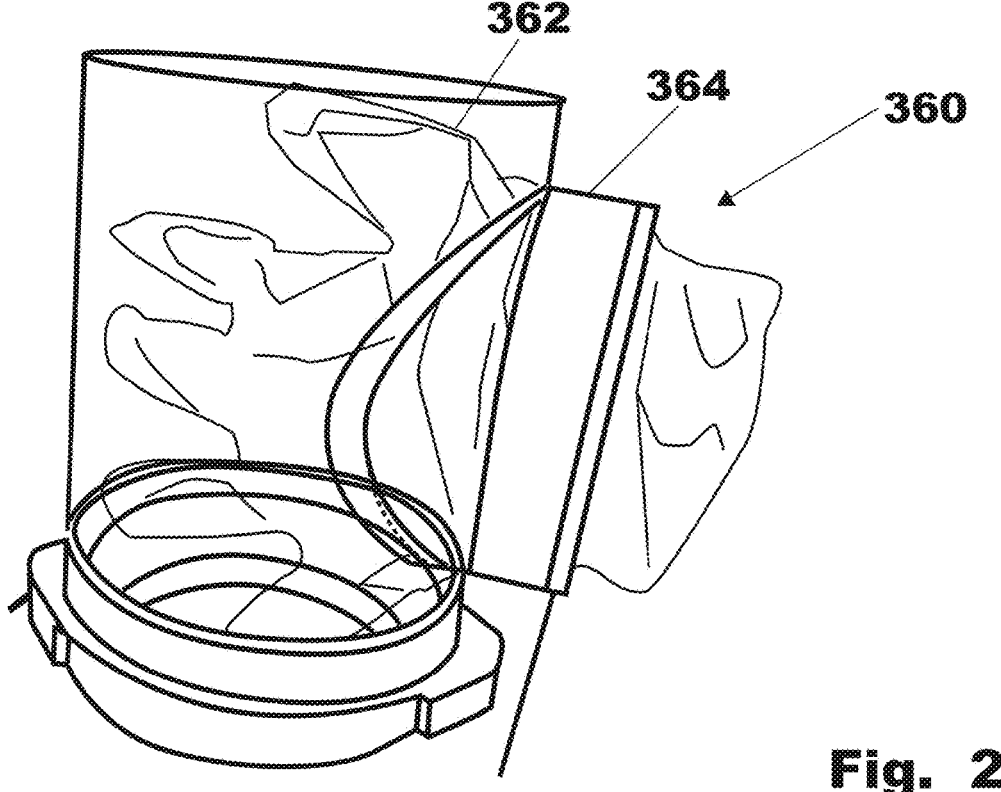
FIG. 28A is a perspective view of a glove port, according to one embodiment.
Figure 28B:
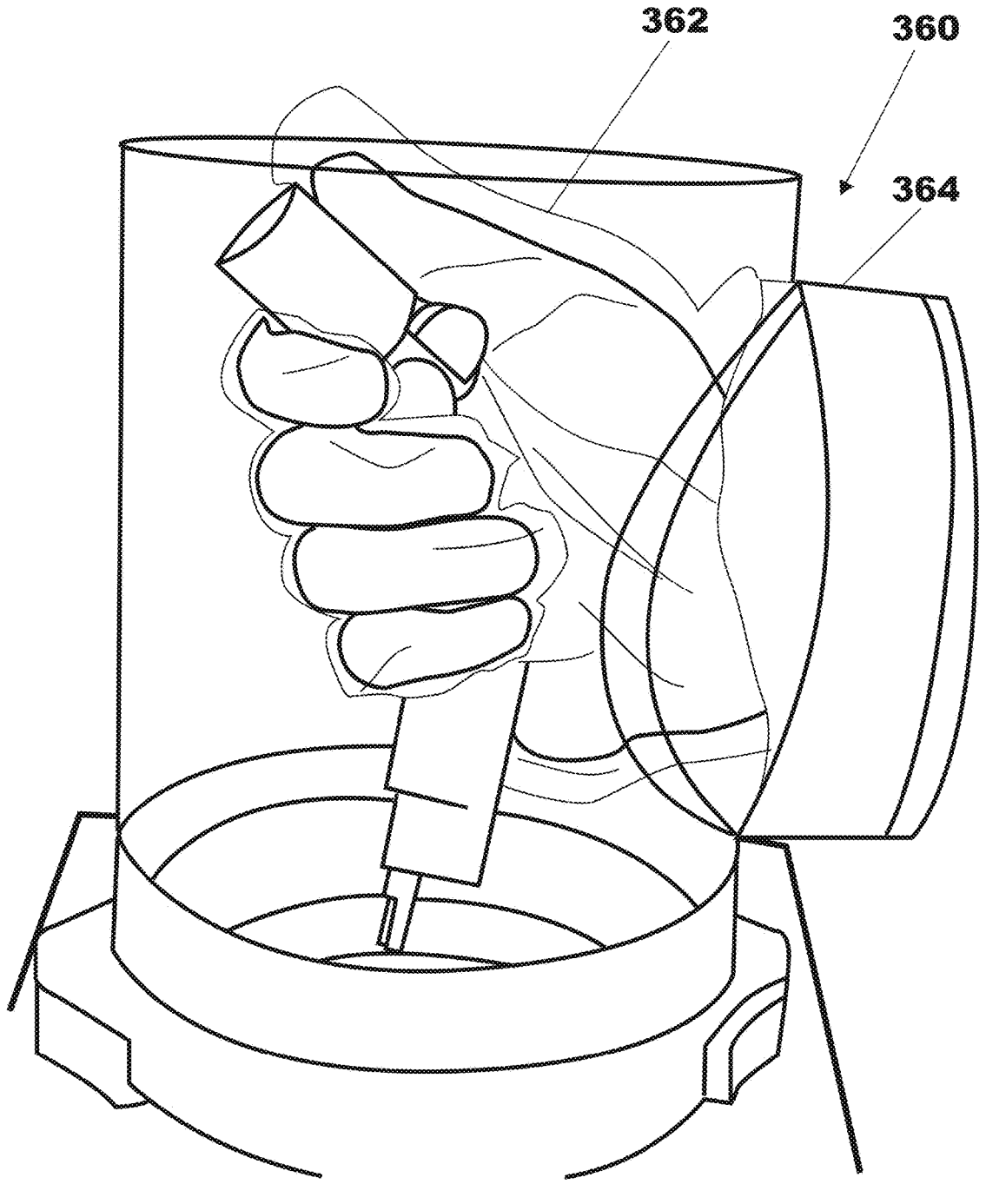
FIG. 28B is a perspective view of the glove port in FIG. 28A in use.

In various alternative embodiments, other types of access ports can be used instead of the ports described above and depicted in FIGS. 24-27B. For example, in one specific alternative implementation, one or more glove ports can be used such as the glove port 360 depicted in FIGS. 28A and 28B. The glove port 360 has a glove component 362 coupled to a glove port ring 364. In various embodiments, the glove port 360 could be coupled at the glove port ring 362 to one or more of the tubes 304, 306, 310, 314 on the body 302. In one embodiment, the glove port ring 362 is coupled to the tube via a clamp lever similar to the clamp lever described with respect to FIG. 26. Alternatively, any known coupling mechanism can be used. Unlike the access ports 308, 312, 316, 318, the glove port 360 does not require that a fluidic seal be established around the surgeon's arm or whatever object is inserted through it. As such, the glove port 360 can help to ensure that the pressure differential between the patient's cavity and the ambient air outside the patient will be maintained. In one embodiment, the glove port 360 has a pressure relief valve (not shown) that can be used to adjust the volume, thereby accounting for the volume change caused when a user inserts her or his hand into the body 302 using the glove component 362. FIG. 28B depicts the glove port 360 in use.

As mentioned above, the incision port 320 is configured to be coupleable to both the main tube 304 and to the sealable sleeve device 322, as shown in FIGS. 24F and 29. As best shown in FIGS. 24A and 30, the incision port 320 has a base ring 370. The upper portion of the base ring 370 can be coupled to an internal coupling component 372, which can couple to the port seal 450 as described in further detail below. Further, the lower portion of the base ring 370 can be coupled to external coupling components 374 (also referred to in certain embodiments as "sleeve clamps"), which couple the ring 370 to the sealable sleeve device 322. In addition, the base ring 370 can also be coupled to coupling components 376 (also referred to in certain embodiments as "tube brackets"), which couple the ring 370 to the main tube 304 of the device 300.

Figure 31A:
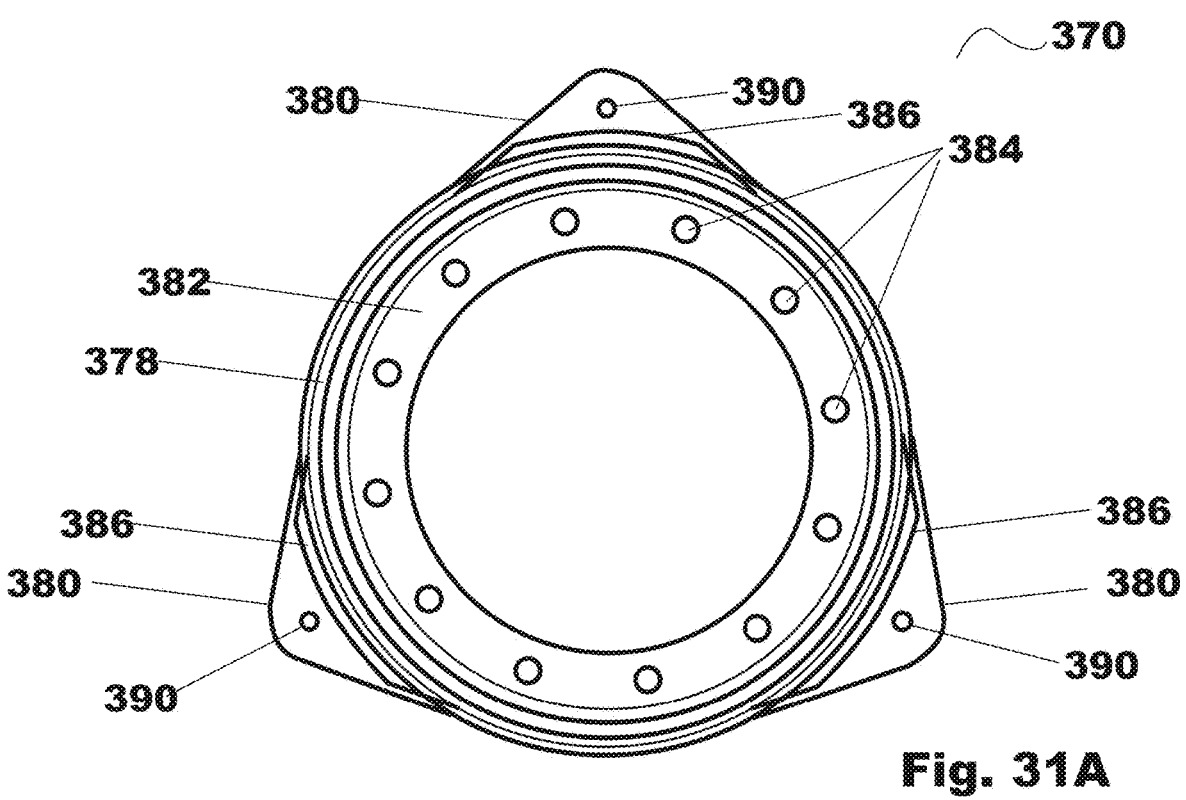
FIG. 31A is a top view of a base ring of an incision port, according to one embodiment.
Figure 31B:
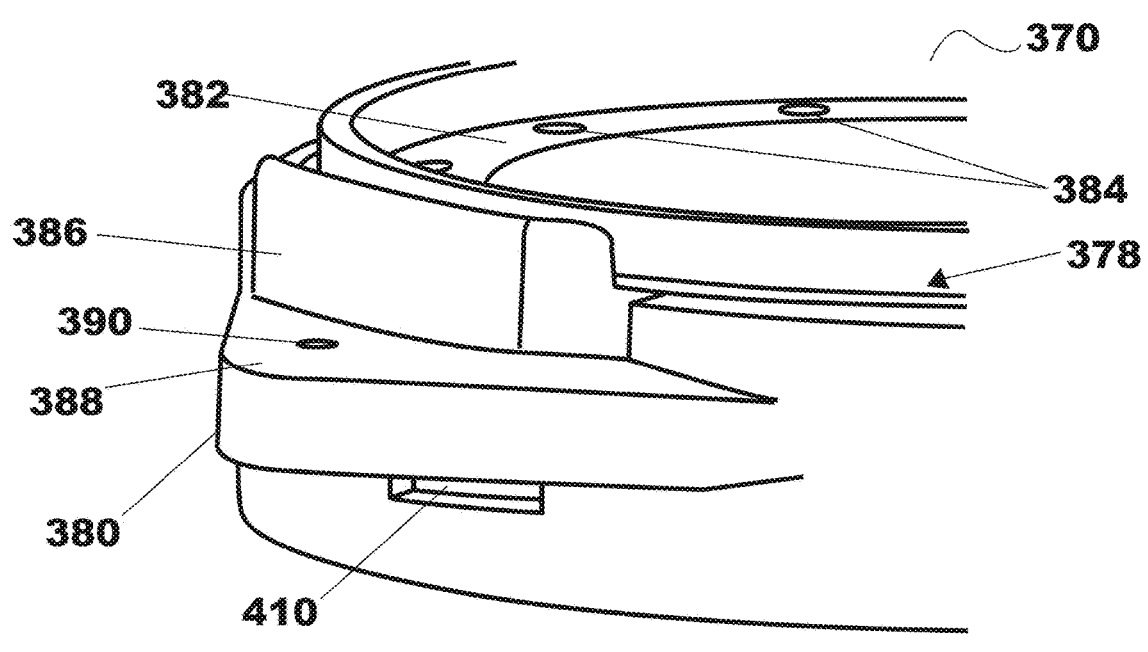
FIG. 31B is a perspective view of the base ring of FIG. 31A.
Figure 35:
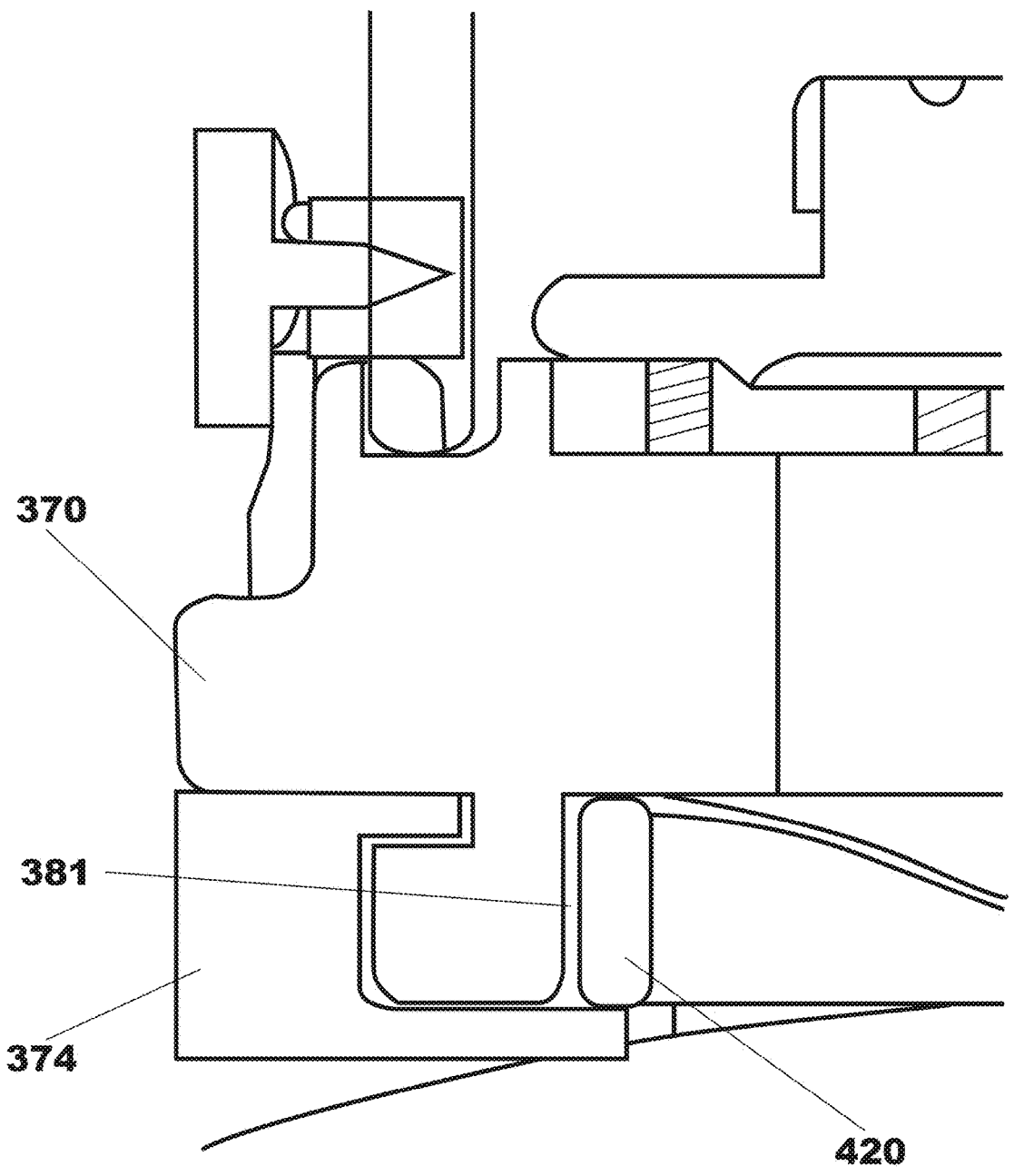
FIG. 35 is a cutaway side view of an incision port, according to one embodiment.

FIGS. 31A and 31B depict the base ring 370, according to one implementation. The ring 370 has a curved indentation or notch 378 configured to receive and couple with the bottom portion of the main tube 304. In addition, the ring 370 has three bracket receiving components 380 configured to receive the tube brackets 376. Further, as best shown in FIGS. 24F, 30, and 35, the bottom portion of the ring 370 defines a circular indentation or lumen 381 that is configured to be positioned over and receive the upper ring 420 of the sleeve device 322. The ring 370 also has multiple holes 384 defined in an interior ring 382. The multiple holes 384 correlate to holes 436 in the base plate 430 of the internal coupling component 372, as described in detail below. Each of the bracket receiving components 380 have a projection 386 and horizontal portion 388 on which the tube bracket 376 is positioned and a hole 390 that corresponds to the hole 394 in the tube bracket 376 as described in detail below. In one embodiment, a gasket (not shown), such as a silicon, foam or rubber gasket, is provided between the notch 378 and the bottom portion of the main tube 304 to strengthen the fluidic seal between the two components.

Figure 32:
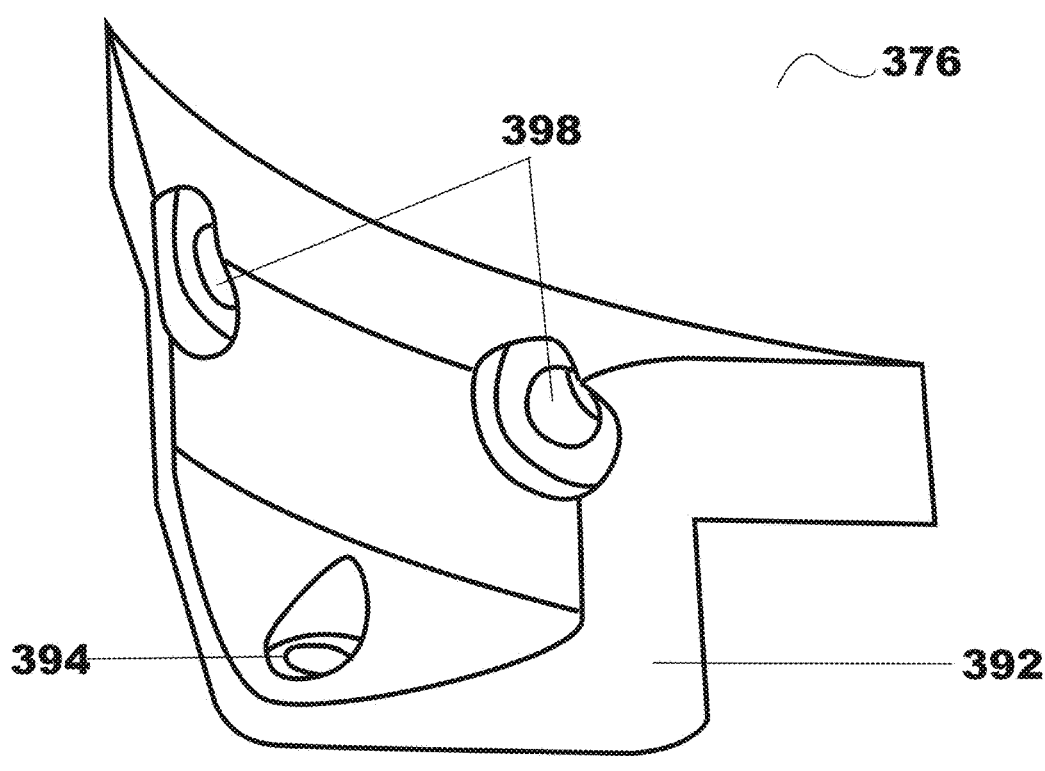
FIG. 32 is a perspective view of a tube bracket, according to one embodiment.

FIG. 32 depicts a tube bracket 376, according to one embodiment. The tube bracket 376 has a base portion 392 having a hole 394 defined therein that corresponds to the hole 390 in the bracket receiving component 380 on the base ring 370. The bracket 376 also has a tube contacting portion 396 having two holes 398 defined therein that correspond to the holes 404 in the bottom portion of the main tube 302, as described below.

Figure 33:
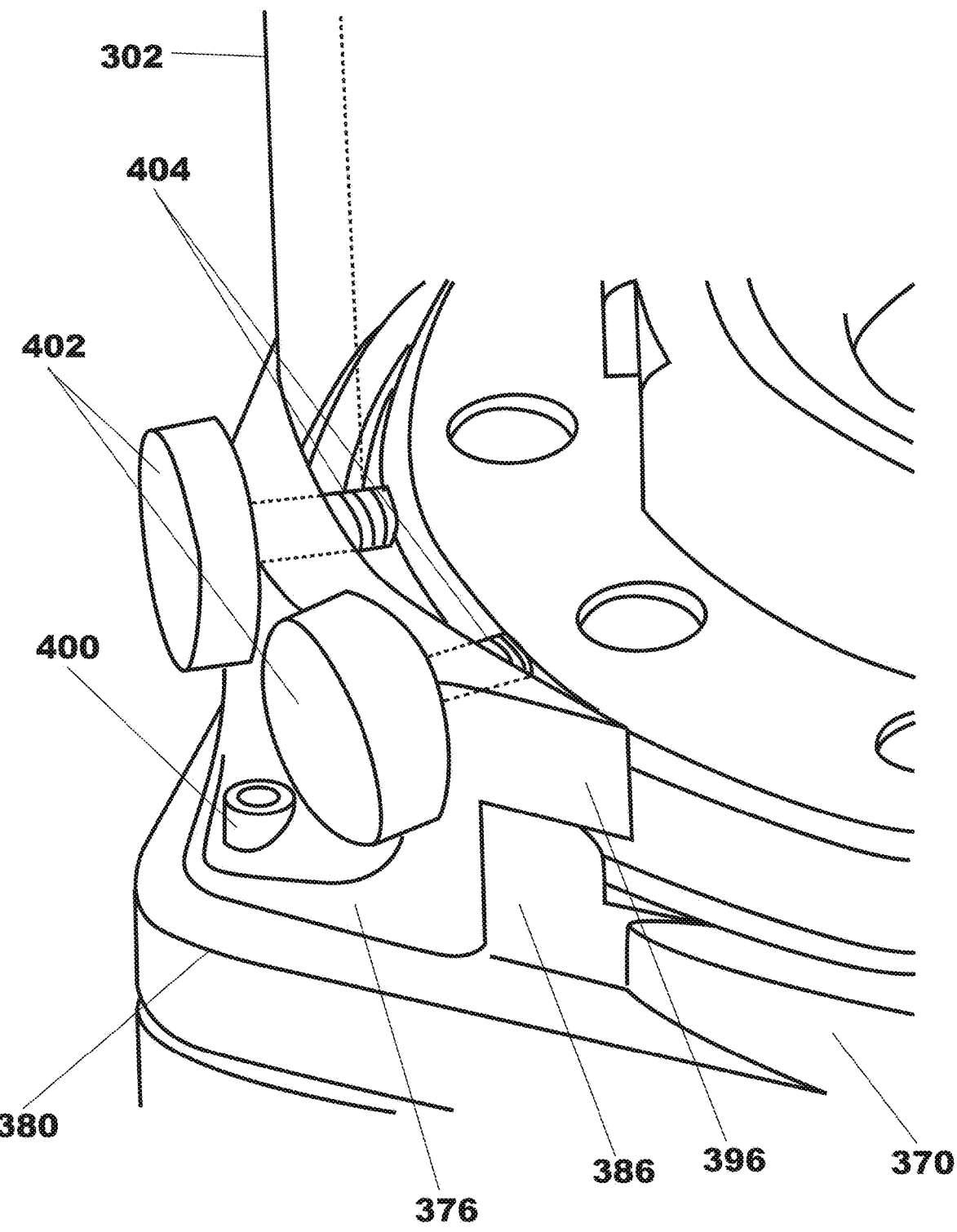
FIG. 33 is a perspective view of a tube bracket coupling a main tube to a base ring, according to one embodiment.

According to one embodiment, the tube bracket 376 is used to couple the main tube 302 to the base ring 370, as shown in FIG. 33. More specifically, the tube bracket 376 is positioned on the bracket receiving components 380, with the base portion 392 of the bracket 376 positioned on the horizontal portion 388 and the tube contacting portion 396 positioned on the projection 386. In that position, the bracket 376 is coupled to the base ring 370 by inserting a threaded screw 400 through hole 394 in the bracket 376 and into hole 390 in the ring 370. Further, the bracket 376 is coupled to the main tube 302 by inserting two threaded screws 402 through holes 398 in the bracket 376 and into holes 404 in the tube 302. Thus, the tube 302 is attached in position against the incision port 320 and specifically the base ring 370 using the brackets 376. In the embodiments depicted in FIGS. 24A-24F, there are three tube brackets 376—spaced about 120 degrees from each other around the circumference of the port 320—that are used to couple the tube 302 to the port 320. Alternatively, two brackets or more than three brackets could be used in different positions around the port 320. In a further alternative, any known type of coupling mechanism could be used to keep the tube 302 coupled to the port 320.

Figure 34:
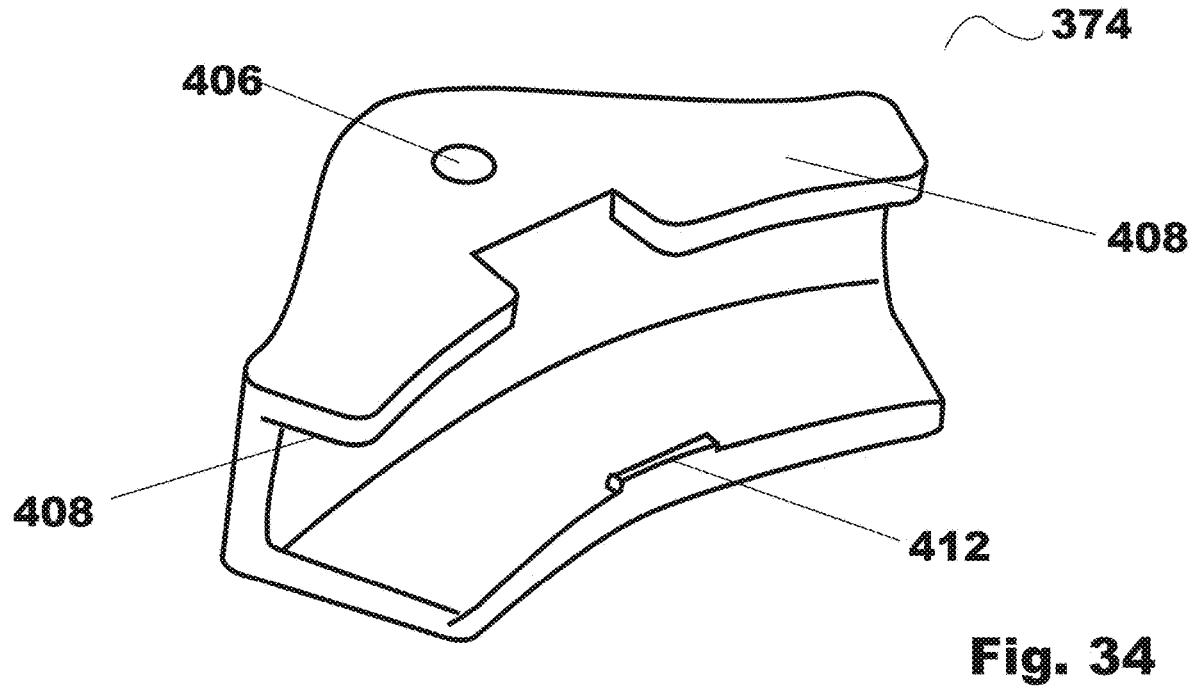
FIG. 34 is a perspective view of a sleeve clamp, according to one embodiment.

As discussed above, the incision port 320 is coupled to the sealable sleeve device 322 using the sleeve clamps 374. FIG. 34 depicts one embodiment of a sleeve clamp 374. The clamp 374 has a hole 406 defined in a top portion of the clamp 374, projections 408 configured to fit into the notches 410 defined under the bracket receiving components 380 on the base ring 370 (as best shown in FIG. 31B), and a projection 412 configured to help retain the upper ring 420 of the sealable sleeve device 322 in position on the clamp 374, as discussed below. The hole 406 corresponds to the hole 394 in the bracket 376 and the hole 390 in the base ring 370 such that when the sleeve clamp 374 is positioned under the bracket receiving component 380 of the base ring 370 and the threaded screw is inserted through hole 394 and hole 390, it is also threaded into hole 406 such that the sleeve clamp 374 is coupled to the base ring 370.

As best shown in FIGS. 30 and 35, when the port 320 is positioned over the sleeve device 322 such that the upper ring 420 is positioned within the lumen 381 on the bottom portion of the base ring 370, the sleeve clamp 374 can be coupled to the base ring 370 as described and the upper ring 420 of the sealable sleeve device 322 is contacted by the clamp 374 and thereby retained in its desired position as shown. Further, the notch 412 in the clamp 374 can further help to retain the upper ring 420. In one embodiment, a gasket (not shown), such as a foam, rubber, or silicone gasket, is placed between the upper ring 420 and the underside of the base ring 370, thereby providing a stronger fluidic seal between the two components.

Figure 36:
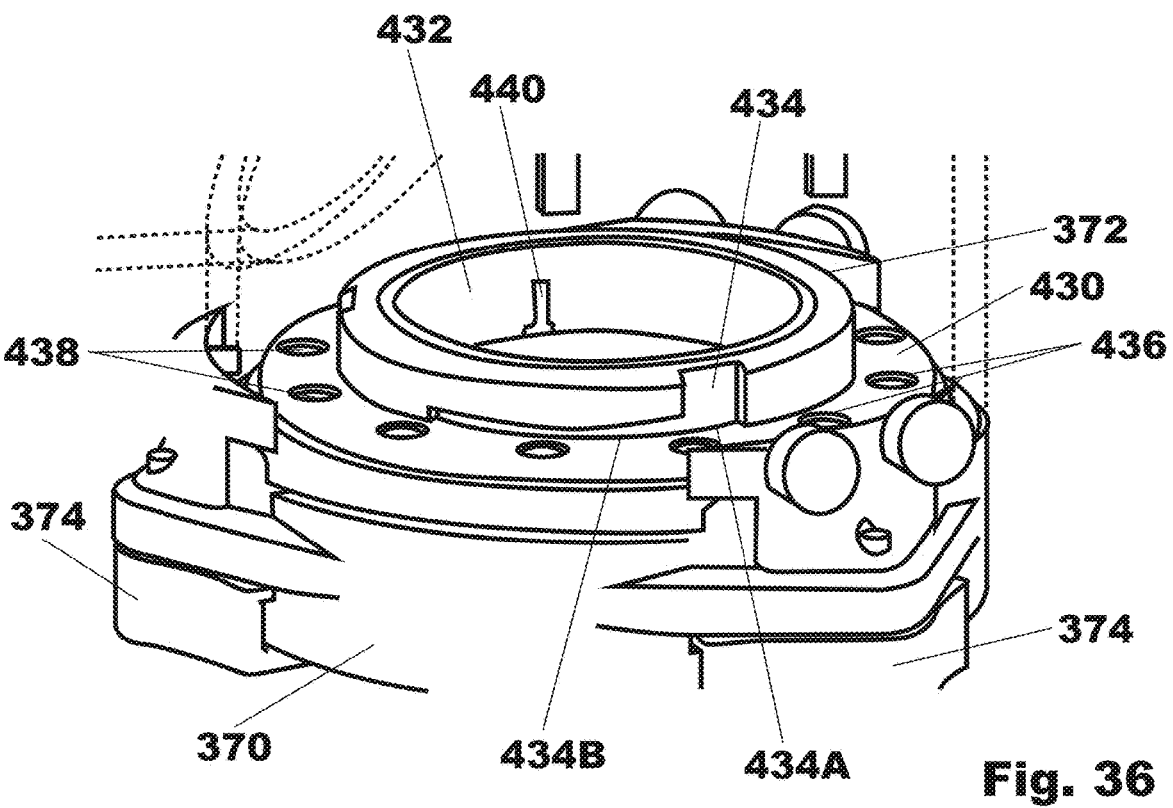
FIG. 36 is a perspective view of an incision port with an internal coupling component, according to one embodiment.

As discussed above, according to one embodiment, the upper portion of the base ring 370 can be coupled to an internal coupling component 372, as best shown in FIGS. 24A, 30, and 36. The internal coupling component 372 has a base plate 430 and a male component 432 projecting from the base plate 430. The base plate 430 has multiple holes 436 defined in the plate 430. These holes 436 correspond to the holes 384 defined in the interior ring 382 of the base ring 370 such that screws 438 (or bolts or any other known coupling mechanisms) can be used to couple the base plate 430 to the interior ring 382 of the base ring 370 as shown. In addition, the interior portion of the male component 432 has two device attachment components 440 (also referred to herein as "device clips") (only one such clip 440 is shown in FIG. 36). Each device clip 440 is configured to be able to allow a user to couple a positioning rod (as described elsewhere herein) or some other device component to the clip 440 before or during a surgical procedure, thereby stabilizing or maintaining the position of the device.

As best shown in FIG. 36, the male component 432 has three notches 434 formed or engineered on its outer circumference (one of which is fully depicted in FIG. 36). The notches 434 have a vertical portion 434A and a horizontal portion 434B in communication with the vertical portion 434A. Each notch 434 is configured to received a corresponding projection formed on an internal circumference of any device intended to couple with the male component 432. As such, to couple the device to the male component 432, the device is positioned over the male component 432 with the projections on the device positioned over the corresponding notches 434 on the male component 432. The device is then positioned onto the male component 432 such that each projection moves along the vertical portion 434A of the notch 434 until it reaches the horizontal portion 434B. At that point, the device can be rotated and thereby move each projection circumferentially along the horizontal portion 434B of the notch 434, thereby coupling the device to the male component 432 of the internal coupling component 372.

Figure 37A:
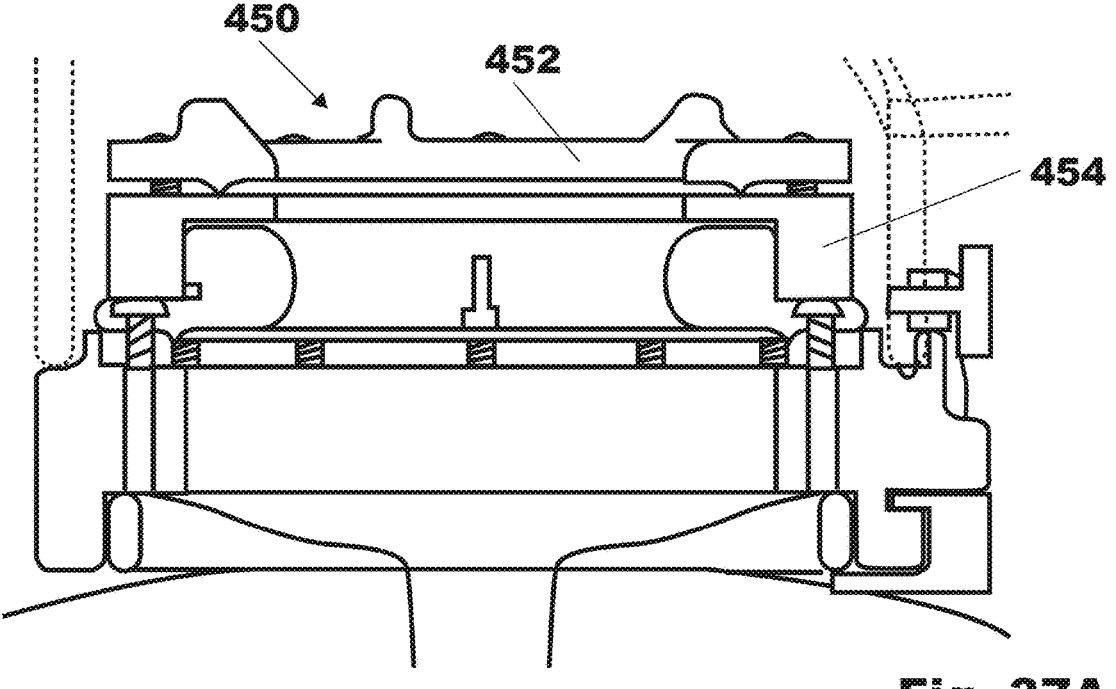
FIG. 37A is a cutaway side view of an incision port coupled to a port seal, according to one embodiment.
Figure 37B:
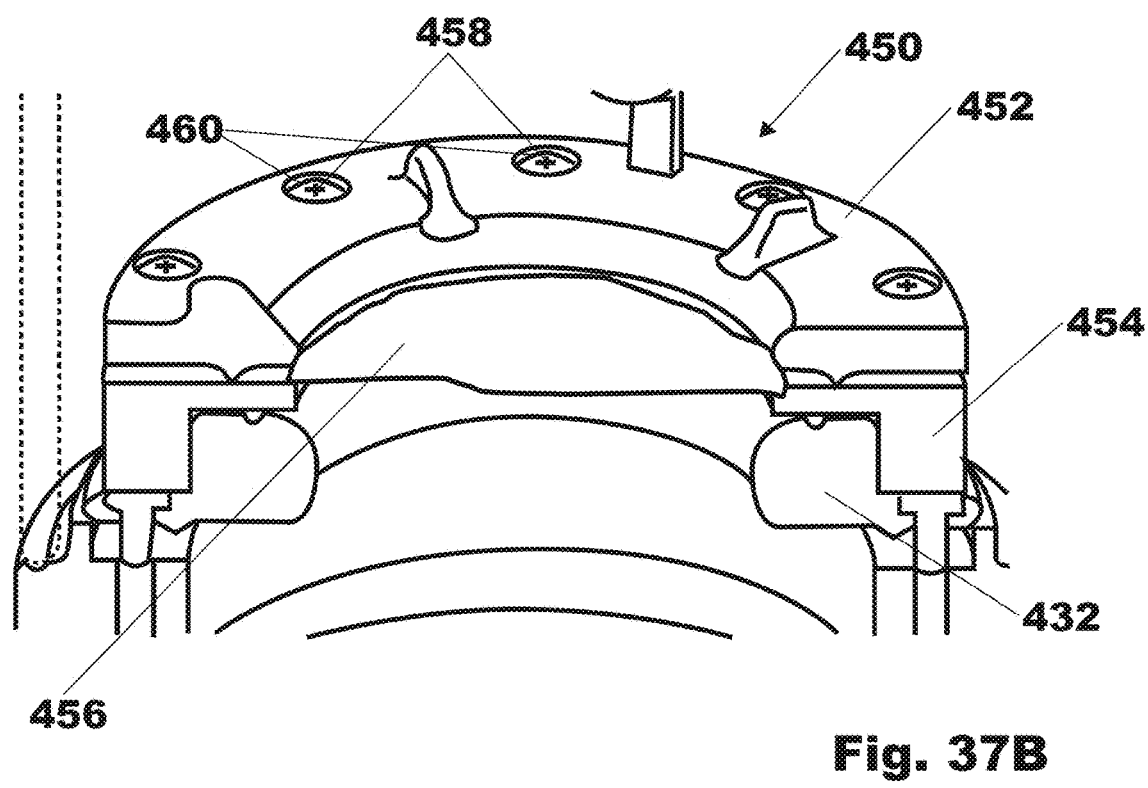
FIG. 37B is a cutaway perspective view of the incision port and the port seal of FIG. 37A.
Figure 37C:
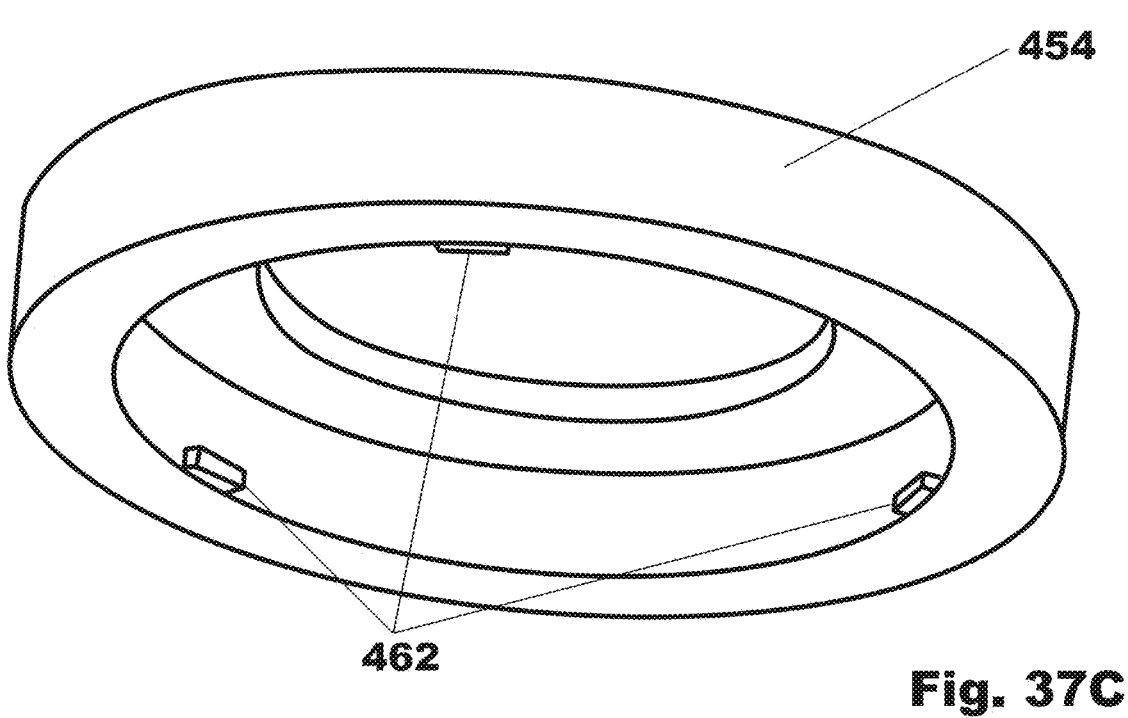
FIG. 37C is a perspective view of the underside of a base seal ring, according to one embodiment.

In one implementation, as best shown in FIGS. 37A, 37B, and 37C, one of the components that can be coupled to the internal coupling component 372 is a port seal 450. The port seal 450 has a seal clamp 452 coupled to a base seal ring 454. A seal component 456 is positioned between the clamp 452 and the ring 454 so that the coupling of the clamp 452 to the ring 454 fixes the seal component 456 in place in the port seal 450. In one embodiment as shown, the seal clamp 452 has multiple holes 458 defined in the clamp 452 that correspond to holes (not shown) in the base seal ring 454 such that threaded screws 460 (or bolts, or the like) can be inserted through the holes 458 and into the holes in the ring 454 to couple the two components together. Alternatively, any other known attachment mechanisms can be used. In one embodiment, a gasket (not shown), such as a foam, silicone, or rubber gasket, can be positioned between the male component 432 and the base seal ring 454 to strengthen the fluidic seal between the two components.

The seal clamp 452, in one embodiment, has multiple projections 464 extending from the top surface of the clamp 424. These projections 464 can be easily grasped by a user to place the port seal 450 on the male component 432 or remove it therefrom. Further, as best shown in FIG. 37C, the underside of the base seal ring 454 has three projections 462 disposed on the inner circumference of the ring 454. The three projections 462 correspond to the three notches 434 defined in the outer circumference of the male component 432 such that the base seal ring 454 can be coupled to the male component 432 as described above.

According to one implementation, the seal component 456 (also referred to herein as a "flexible seal component" or an "elastic seal component") is a circular sheet of flexible or elastic material that is configured to allow a device or other equipment to be inserted through the seal component 456 (or to allow the seal component 456 to be positioned over such equipment, like a positioning rod, as described in further detail below). In one embodiment, the seal component 456 is a circular rubber sheet having a small hole (not shown) in the sheet through which equipment can be inserted. Alternatively, the seal component 456 can be any known material configured to maintain a fluidic seal when a device or equipment is inserted through the seal component 456.

Figure 38A:
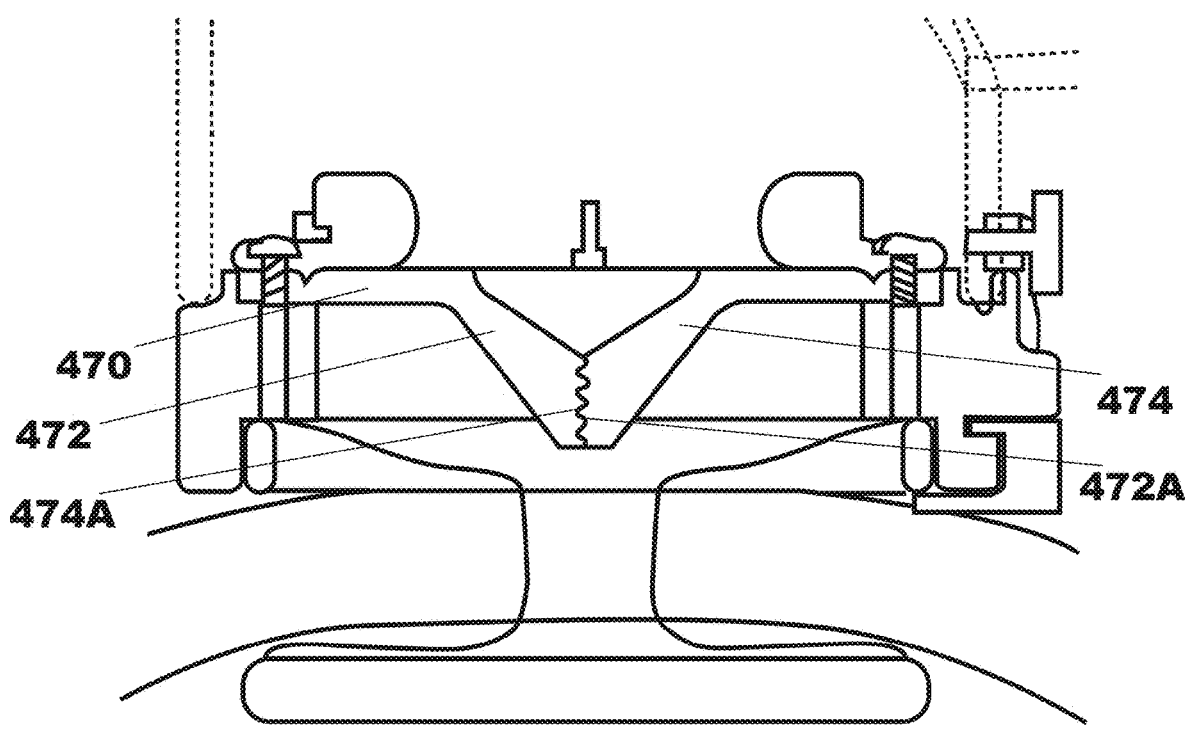
FIG. 38A is a cutaway side view of an incision port having a flap seal component, according to one embodiment.
Figure 38B:
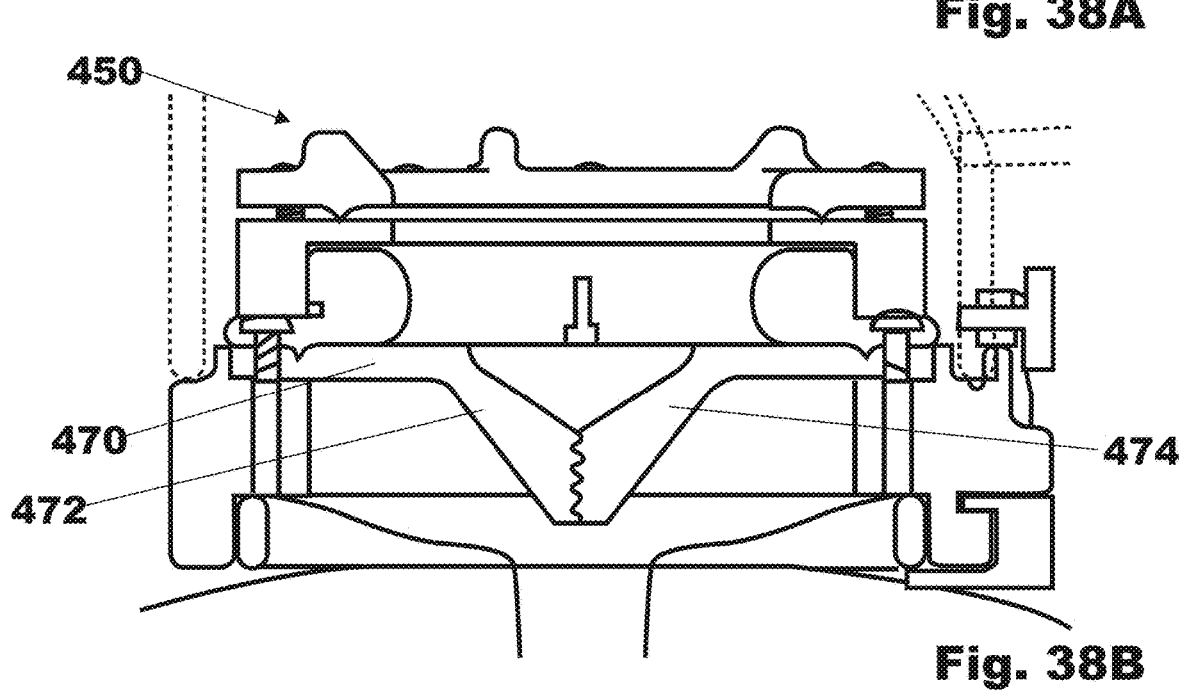
FIG. 38B is a cutaway side view of an incision port having a flap seal component and coupled to a port seal, according to one embodiment.
Figure 38C:
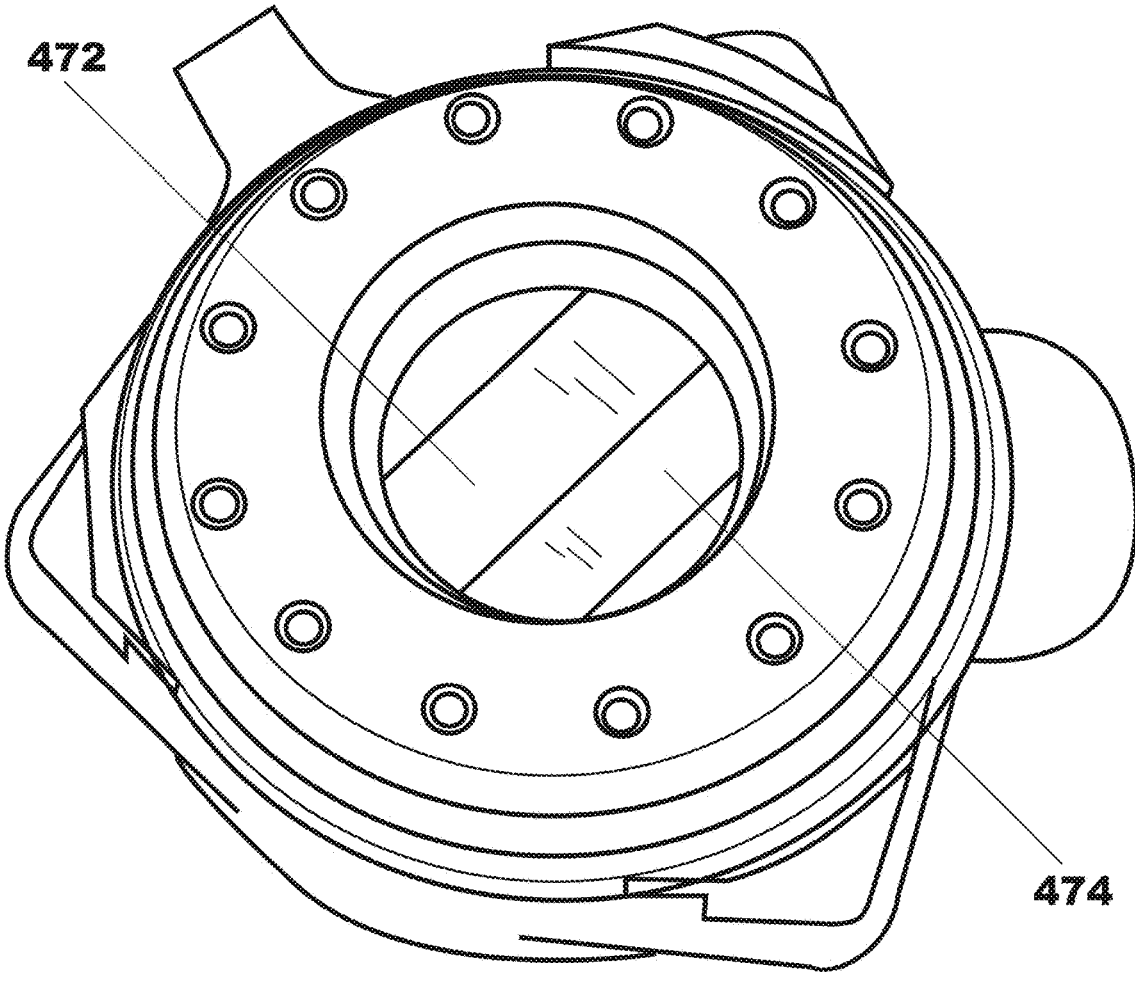
FIG. 38C is a perspective top view of the incision port and a port seal of FIG. 38B.

In accordance with one embodiment, a different type of seal component can also be incorporated into the device 300. As shown in FIGS. 38A, 38B, and 38C, a flap seal component 470 is provided. The flap seal component 470 has two flaps—a first flap 472 and a second flap 474—that contact each other at a midpoint in the component 470. Each of the flaps 472, 474 has ridges or teeth 472A, 474A on the surfaces that are in contact such that the ridges 472A on flap 472 correspond to the ridges 474A on flap 474 and thus interface or couple with each other. In one implementation as shown, the flap seal component 470 is positioned between the base ring 370 and the internal coupling component 372. According to one implementation, the configuration of the flaps 472, 474 extended downward toward the patient's cavity and the coupled ridges 472A, 474A can provide structural strength to prevent a mechanical failure (also referred to as a "blowout") in which the flaps 472, 474 are forced outward by the higher air pressure until the flaps 472, 474 are extending outward away from the patient's cavity and the fluidic seal is lost.

In one embodiment as shown in FIG. 38A, the flap seal component 470 can be incorporated into the incision port 320 and used when the port seal 450 is not coupled to the port 320. Alternatively, as shown in FIG. 38B, the flap seal component 470 can be incorporated into the incision port 320 and used when the port seal 450 is coupled to the port 320.

In use, the various embodiments disclosed or contemplated herein relating to access and insertion systems, devices, and methods that relate specifically to an external device having one or more ports for the insertion of not only medical devices, but also related equipment and/or the hands of one or more medical professionals to access the interior of the device during medical procedures while being able to maintain a higher air pressure within the device that is substantially the same as the insufflated cavity of the patient. According to one implementation, the high pressure is around 18 mmHg above atmospheric pressure, which is around the amount of pressure that is used to insufflate a patient's abdominal cavity during a laparoscopic procedure. Alternatively, any known higher pressure amount that is used during medical procedures can be used.

The method of using the device 300, according to one embodiment, includes at least some of the following steps. First, as described above with respect to other embodiments, according to one implementation, the sealable sleeve device 322 is first positioned in the incision 324 (see FIGS. 24F, 29A, 29B, and 30). It is understood that the sleeve device 322 can be inserted using steps similar to those described above. Alternatively, any known insertion steps can be used to insert the device 322 into the incision 324 such that the upper ring 420 is positioned outside of the incision 324 and the lower ring 422 is positioned inside the patient's cavity, with the sleeve 424 disposed through the incision 324 itself, as best shown in FIG. 30.

Next, the incision port 320 and the device 300 are coupled to the sealable sleeve device 322. As best shown in FIGS. 30, 33, and 35, the base ring 370 of the incision port 320 is positioned over the upper ring 420 of the sleeve device 322 such that the upper ring 420 is positioned in the lumen 381 on the bottom portion of the base ring 370. In addition, the bottom portion of the main tube 304 of the device body 302 can be positioned in the curved notch 378 on the base ring 370. At this point, both the device 300 and the sleeve device are positioned as desired with respect to the incision port 320 and must be coupled to the port 320. To do so, the tube brackets 376 and the sleeve clamps 374 are positioned on the base ring 370 as described above and fixed in place using the threaded screws 400. Then the threaded screws 402 are placed as well. As such, the incision port 320 is coupled to both the device 300 and the sleeve device 322 and a fluidic seal is created between the interior of the body 302 and the exterior.

According to one embodiment, at least one medical device or piece of equipment that will be used during the procedure can be placed in the body 302 prior to coupling the body 302 to the incision port 320. For example, in one embodiment, the device 480 disposed within the body 302 as best shown in FIGS. 24A, 24B, 24D, and 24F can be positioned within the body 302 and, in some implementations, secured to a device clip 357 (as shown in FIG. 27B). More specifically, in the particular embodiment depicted in FIGS. 24A, 24B, 24D, and 24F, the device 480 is made up of two arms 482A, 482B that are positioned within the body 302. Alternatively, any medical device that will be used for the surgical procedure could be positioned within the body 302 in the same or a similar fashion.

It is understood, in accordance with one implementation, that the port seal 450 is not coupled to the internal coupling component 372 (which is coupled to the incision port 320) at this point during the placement of the device 300. As such, according to one embodiment, the port seal 450 is stored in the side access tube 314 while the body 302 is being coupled to the port 320, as best shown in FIGS. 24B, 24C, and 24D. Alternatively, the port seal 450 can be uncoupled from the internal coupling component 372 and placed in the side access tube 314 prior to positioning the medical device inside the body 302 and coupling the body 302 to the incision port 320.

Once the device 300 is coupled to the incision port 320 and the incision port 320 is coupled to the sealable sleeve device 322, the fluidic seal within the device 300 has been established, and the patient's cavity can be insufflated. This insufflation will result in an increase in air pressure within the patient's cavity and within the device 300 (because neither the port seal 450 nor the flap seal 470 is not coupled to the internal coupling component 372).

Once insufflation is achieved, the device 480 is positioned through the incision port 320 and into the patient's cavity. More specifically, the user or medical professional inserts her or his hands into the left and right hand access ports 308, 312 and moves the medical device through the incision port 320 and into position within the cavity. At this point, if the medical device has a positioning rod 359, that rod 359 can be coupled to a device clip 440 on the interior of the male component 432 of the internal coupling component 372 of the port 320, thereby establishing, maintaining, or fixing the position of the medical device within the patient's cavity. Alternatively, the device can be positioned and maintained in that position using any type of mechanism or method, including some type of device or method independent of the device 300.

Once the medical device is positioned as desired, the port seal 450 can be positioned in place over the device (or the positioning rod 359—or rods—of the device). That is, the user reaches in through the hand access ports 308, 312 and removes the seal 450 from the side access tube 314 and placed over the device/rod 359 so that the device and/or rod 359 is inserted through the seal component 456 of the seal 450 and then coupled to the male component 432 of the internal coupling component 372 as described above.

Once the port seal 450 is in place, the body 302 can be removed from the incision port 320. More specifically, the user can remove the threaded screws 402 and then remove the main tube 304 from the port 320. The fluidic seal between the patient's cavity and the ambient air outside the patient's body is maintained by the port seal 450.

The user/medical professional can then begin performing the medical procedure.

An alternative external pressurized device embodiment is depicted in FIGS. 39A and 39B. In this embodiment, the device 500 is a single tube 502 having a single access port 504 disposed at the top of the tube 502. The access port 504 serves to establish a fluidic seal when a medical device or a surgeon's hand is inserted through the port 504. The tube 502 also has two camera ports 506 extending from a bottom portion of the tube 502. According to one implementation, the tube 502 is configured to couple to an incision port, including any incision port disclosed elsewhere herein or any known incision port.

Figure 40:
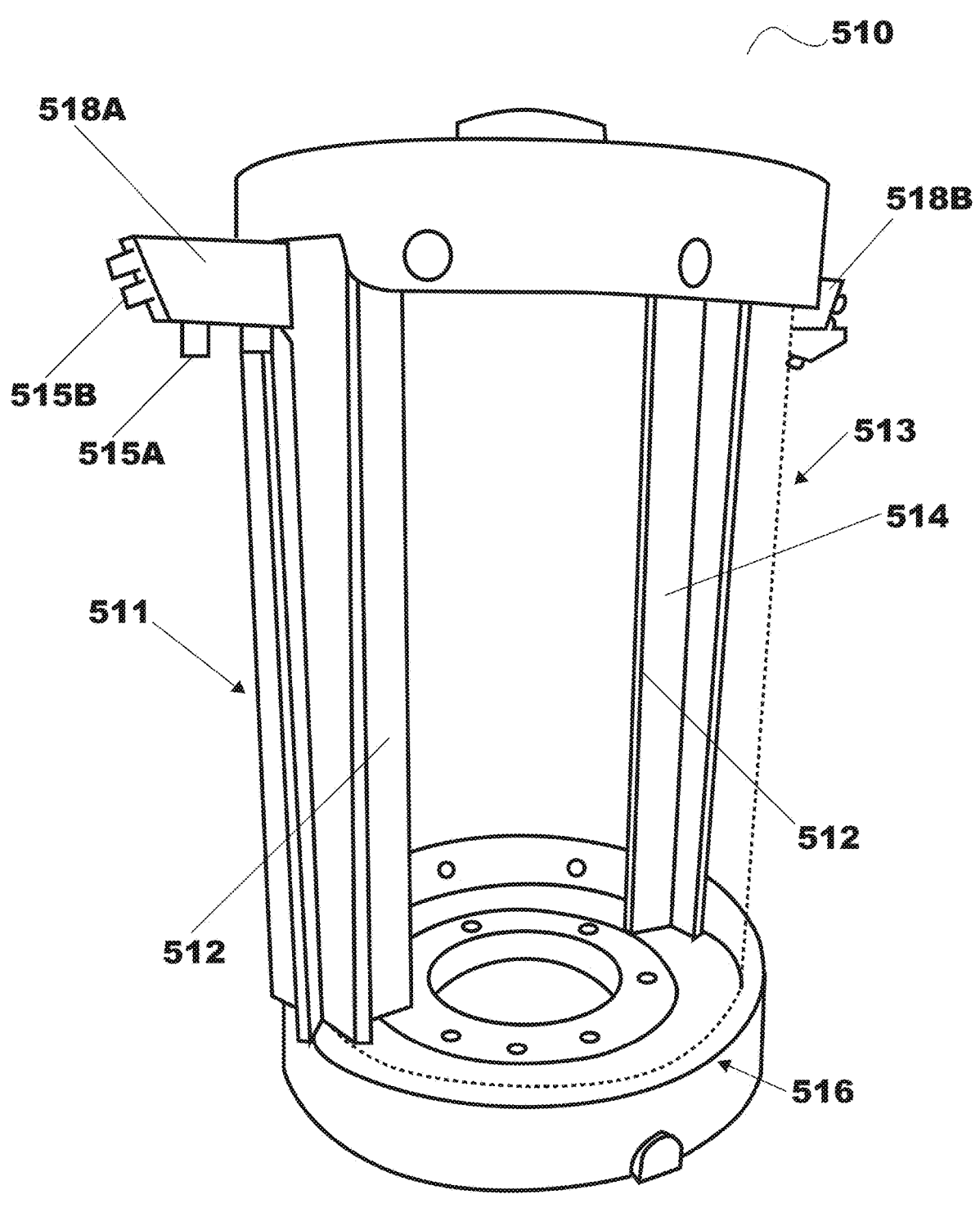
FIG. 40 is a side view of an external pressurized device having two slots, according to a further embodiment.

A further embodiment depicted in FIG. 40 is another alternative external pressurized device 510. The device 510 has a tube 514 that is coupleable to an incision port 516 and has two slots 511, 513 formed on opposite sides of the tube 514. These slots 511, 513 provide fluid communication between the interior of the tube 514 and the exterior of the tube 514. In one embodiment, the rod slots 512 are each configured to receive a positioning rod. The device 510 further has two slot seals 512, with one seal 512 positioned in each of the slots 511, 513. These slot seals 512 are configured to maintain a fluidic seal at each of the slots 511, 513 such that an object can be positioned through either or both slots 511, 513 and the fluidic seal is not lost. The tube 514 also has two sets of device attachment components 518A, 518B (also referred to as "rod clips"). Each set of rod clips 518A, 518B has two device clips—a horizontal clip 515A and an angled clip 515B.

In use, a device can be positioned within the tube 514 such that a positioning rod coupled to the device extends out of the tube 514 through one of the slots 511, 513. The device can be fixed in position in the tube 514 by coupling the positioning rod to the horizontal clip 515A. The patient's cavity can then be insufflated. When ready, the positioning rod can be moved down the slot (511 or 513) such that the device is being moved down the interior of the tube 514 and inserted through the port 516 and into the patient's cavity. At this point, the positioning rod is angled upward and clipped to the angled clip 515B, thereby fixing the positioning of the device inside the patient's cavity.

Figure 41A:
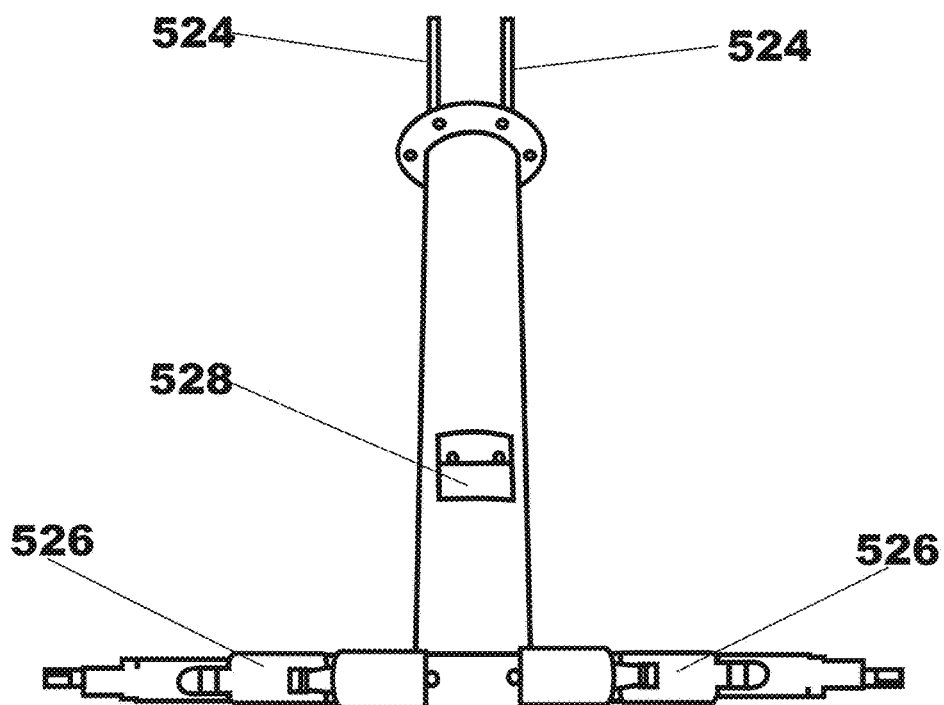
FIG. 41A is a side view of a positioning tube, according to one embodiment.
Figure 41B:
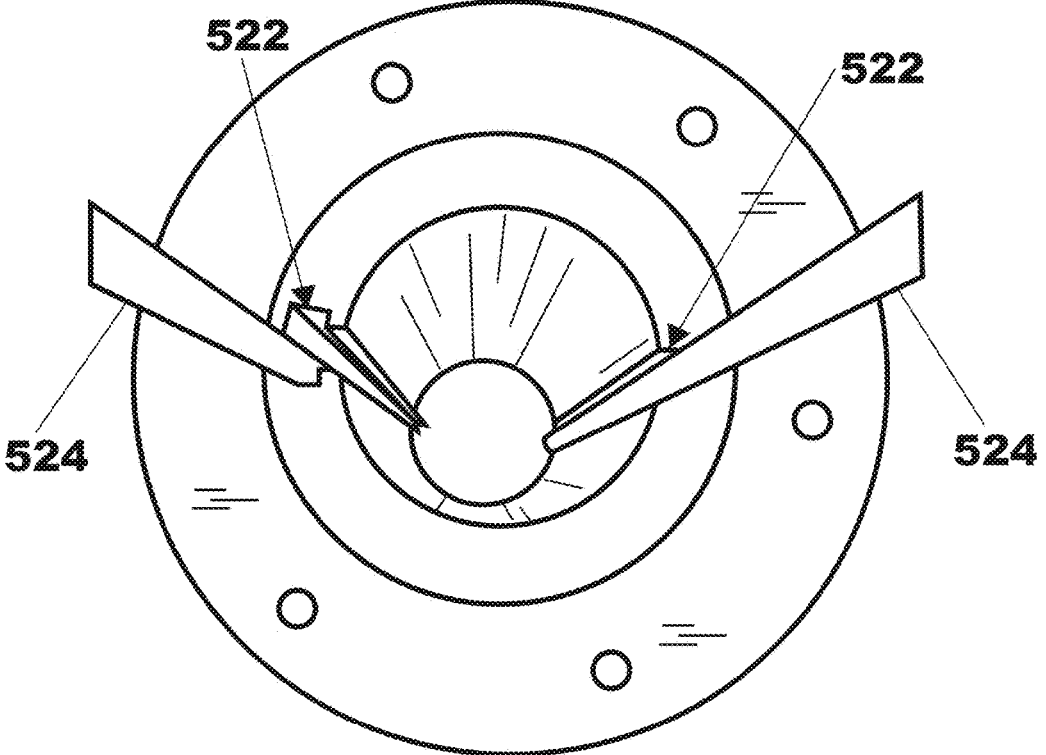
FIG. 41B is a top view of the positioning tube of FIG. 41A.

Another implementation relates to a positioning tube 520 as depicted in FIGS. 41A and 41B. In this embodiment, the positioning tube 520 can also act as a large positioning rod. The tube 520 has two guide slots 522 defined in or attached to an inner portion of the tube 520. The guide slots 522 are each configured to receive a positioning rod 524. In this implementation, each device 526 (or device arm) is coupled to an end of one of the positioning rods 524 and can be inserted through the tube 520 and into the patient's cavity. Due to the size of the tube 520, the devices 526 must be inserted one at a time. Alternatively, the tube 520 can be sized so that both devices 526 can be inserted at the same time. The tube 520 also has an air lock 528 disposed in the tube 520. The air lock 528 is configured to be capable of fluidically dividing the tube 520 into two fluidically separate compartments when the air lock 528 is closed.

In use, the positioning tube 520 (having a robotic arm 526 disposed within the tube 520) can be inserted through any of the various incision ports described elsewhere herein. When the tube 520 is positioned so that the distal end of the tube 520 is extending into the patient's cavity, a seal is created at the top of the top by placing a seal cap (not shown) on the top of the tube 520. Once the inside of the tube 520 is sealed, the positioning rod 524 can be urged distally and thereby the arm 526 is urged out of the tube 520 and into the patient's cavity. If a second arm 526 is going to be inserted, the air lock 528 is then closed. That is, the air lock 528 is closed to create a fluidic seal between the top of the tube 520 and the bottom of the tube 520. Once the air lock 528 is in place, the seal cap is removed, and the second arm 526 can be positioned in the tube 520. At this point, the seal cap can be replaced, the air lock 528 can be released, and the second arm 526 can be inserted into the patient's cavity.

Figure 42:
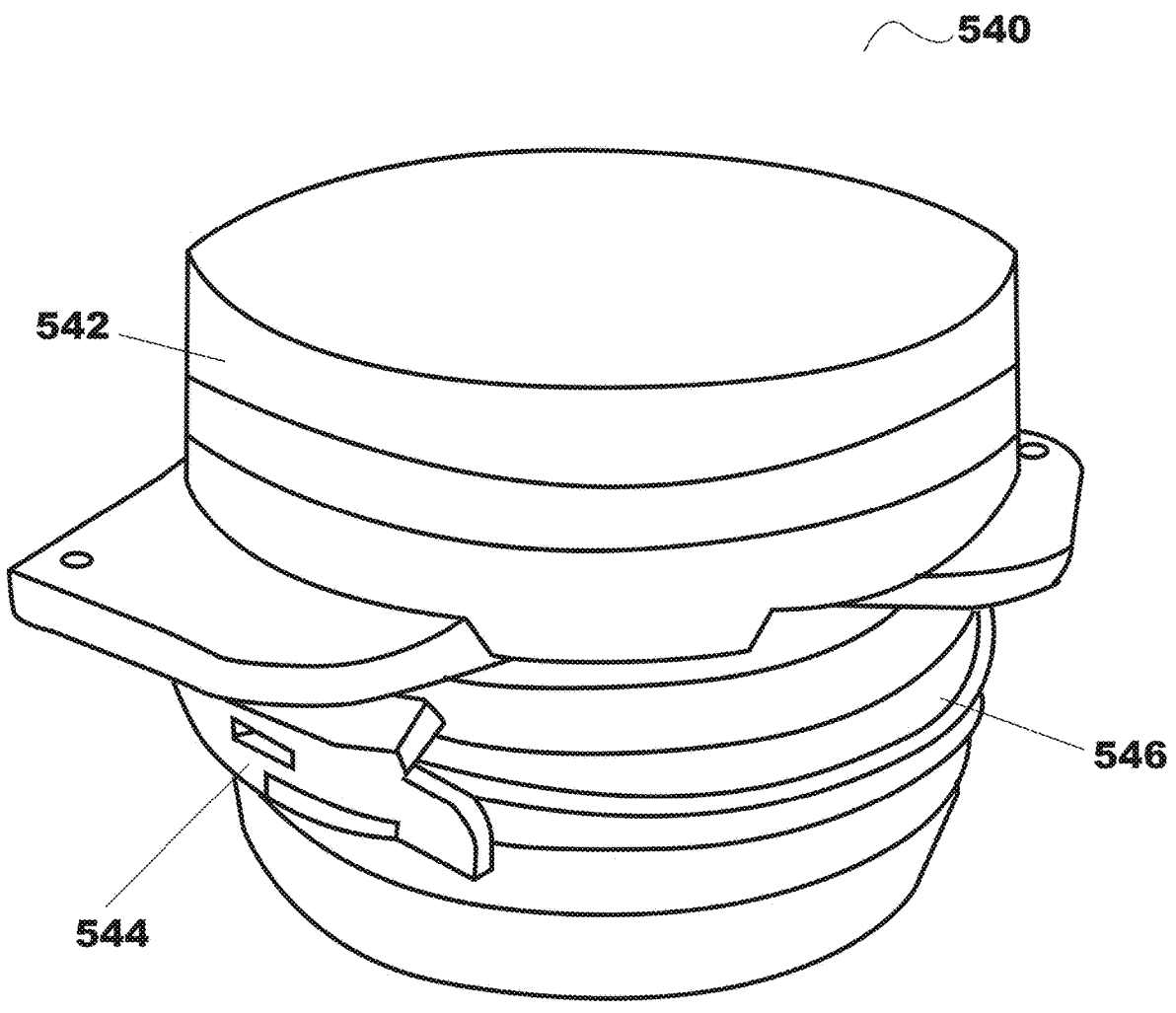
FIG. 42 is a perspective view of a stacked incision port, according to one embodiment.

Several additional embodiments relate to various types of incision ports. For example, FIG. 42 depicts a stacked incision port 540. The port 540 actually has two access ports 542, 544 that are coupled together, with a cavity 546 between the two access ports 542, 544. In one embodiment, the access ports 542, 544 are commercially available Gel-Seal® ports. The cavity 546 between the two access ports 542, 544 strengthens the overall fluidic seal of the port 540. In other words, the cavity 546 reduces the amount of air pressure loss because any air pressure loss is lost in the cavity and not lost to the ambient air, thereby reducing the overall loss.

Figure 43:
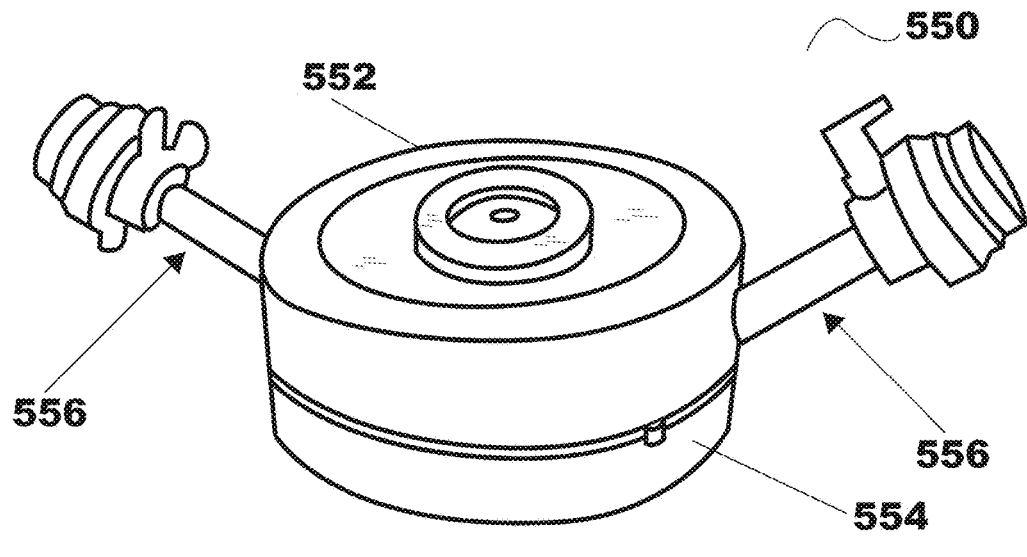
FIG. 43 is a perspective view of an incision port having two seals, according to one embodiment.

Another incision port embodiment is depicted in FIG. 43. This incision port 550 actually has two seals combined in the port: a rubber seal 552 and a flap seal 554. The port 550 also has two camera ports 556 extending out from the port 550. In one embodiment, the rubber seal 552 has three different rubber disks (not shown) similar to the different disks depicted in FIG. 20 and described above. The disks in this rubber seal 552 can have openings/incisions that differ for each disk in the same fashion as the disks shown in FIG. 20. Alternatively, the rubber seal 552 can be similar to any rubber or flexible seal described elsewhere herein. The flap seal 554, according to one embodiment, is similar to the flap seal depicted in FIGS. 38A-38C.

Figure 44:
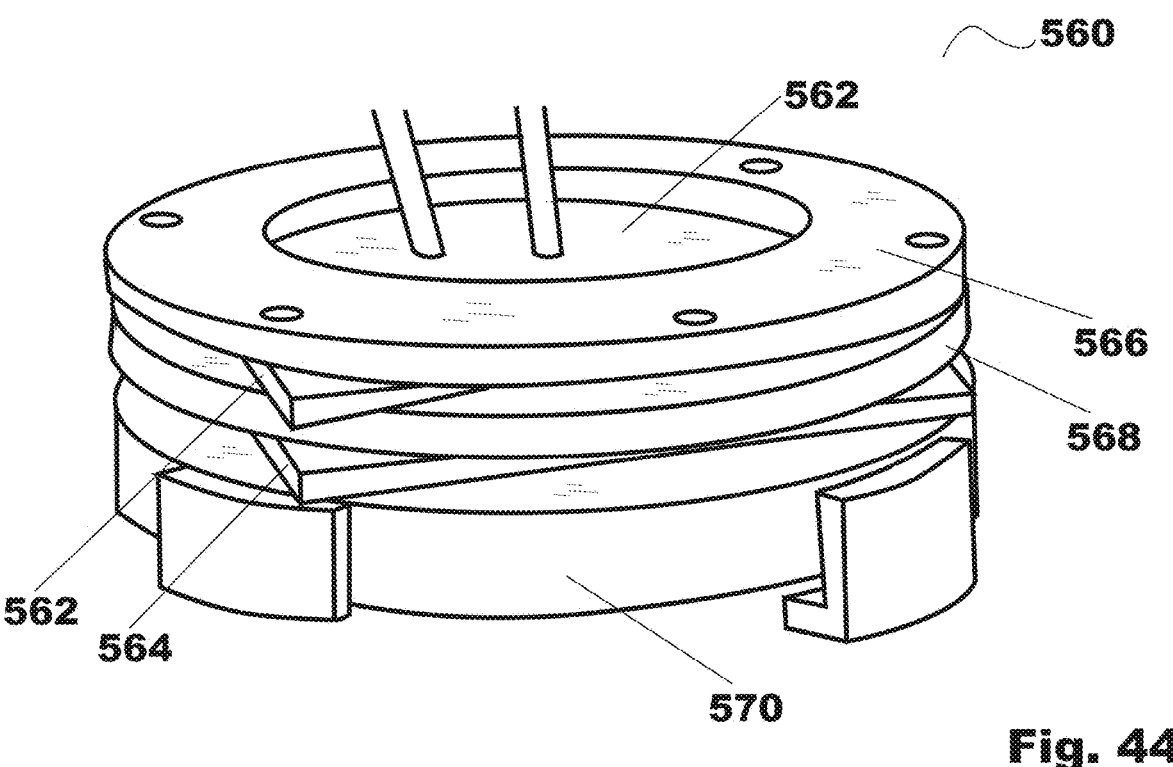
FIG. 44 is a perspective view of an incision port having two seals, according to another embodiment.

FIG. 44 depicts another incision port embodiment. More specifically, this port is a two-seal port 560 having a first rubber seal 562 and a second rubber seal 564. The port 560 also has a base ring 570, a middle ring 568, and a top ring 566. The middle ring 568 creates a cavity (not shown) between the two seals 562, 564 that is configured to compartmentalize any lose of pressure by either of the seals 562, 564. The presence of the cavity makes this embodiment fairly similar to the incision port depicted in FIG. 42.

According to one embodiment, each sheet of rubber 562, 564 is about 0.5 inches thick and has a single slit (not shown) formed through the middle of it. Alternatively, each sheet 562, 564 can have two openings (not shown) formed through the middle of it.

Figure 45A:
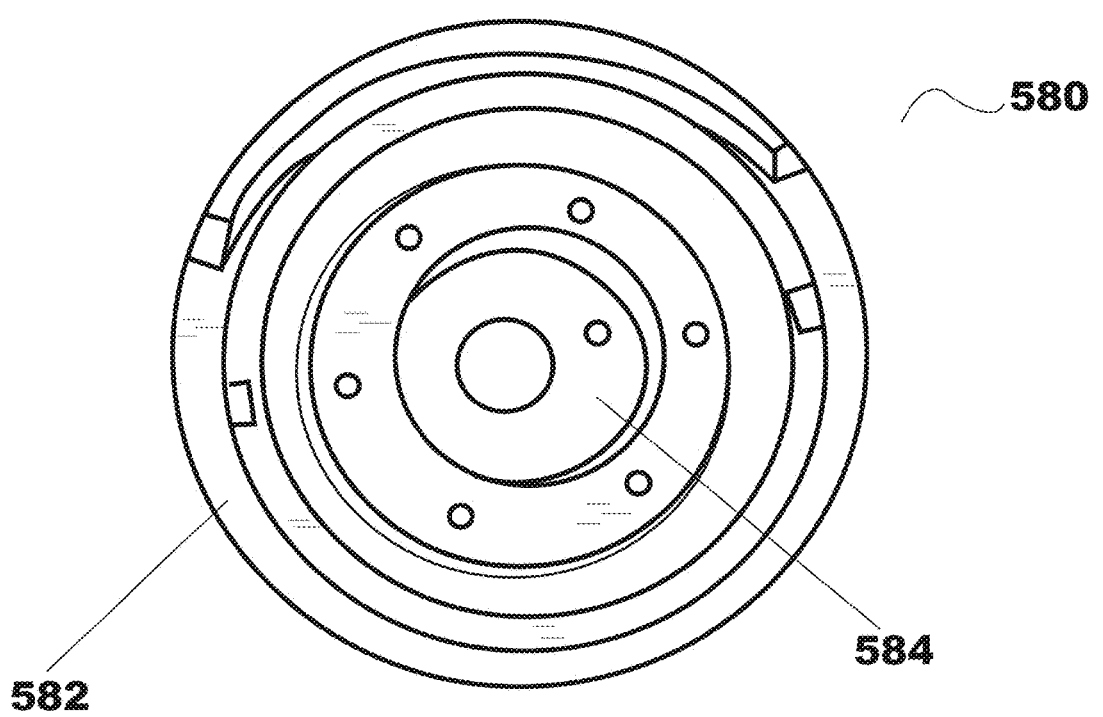
FIG. 45A is a top view of an incision port, according to a further embodiment.
Figure 45B:
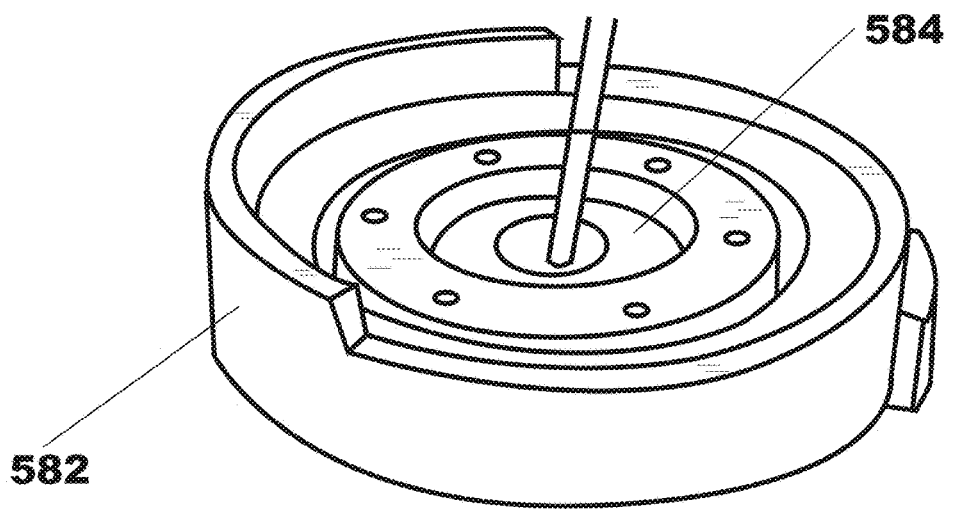
FIG. 45B is a perspective view of the incision port of FIG. 45A.

FIGS. 45A and 45B depict a further incision port embodiment. This port is a three-sheet rubber seal port 580 having a single ring 582 in which three sheets of rubber (only the top sheet 584 is shown). In one embodiment, each of the three sheets has an opening in it that corresponds to the openings in the other two sheets. In a further embodiment, the openings are similar to those depicted in FIG. 20 and described. Alternatively, each sheet can have two corresponding openings.

Figure 46A:
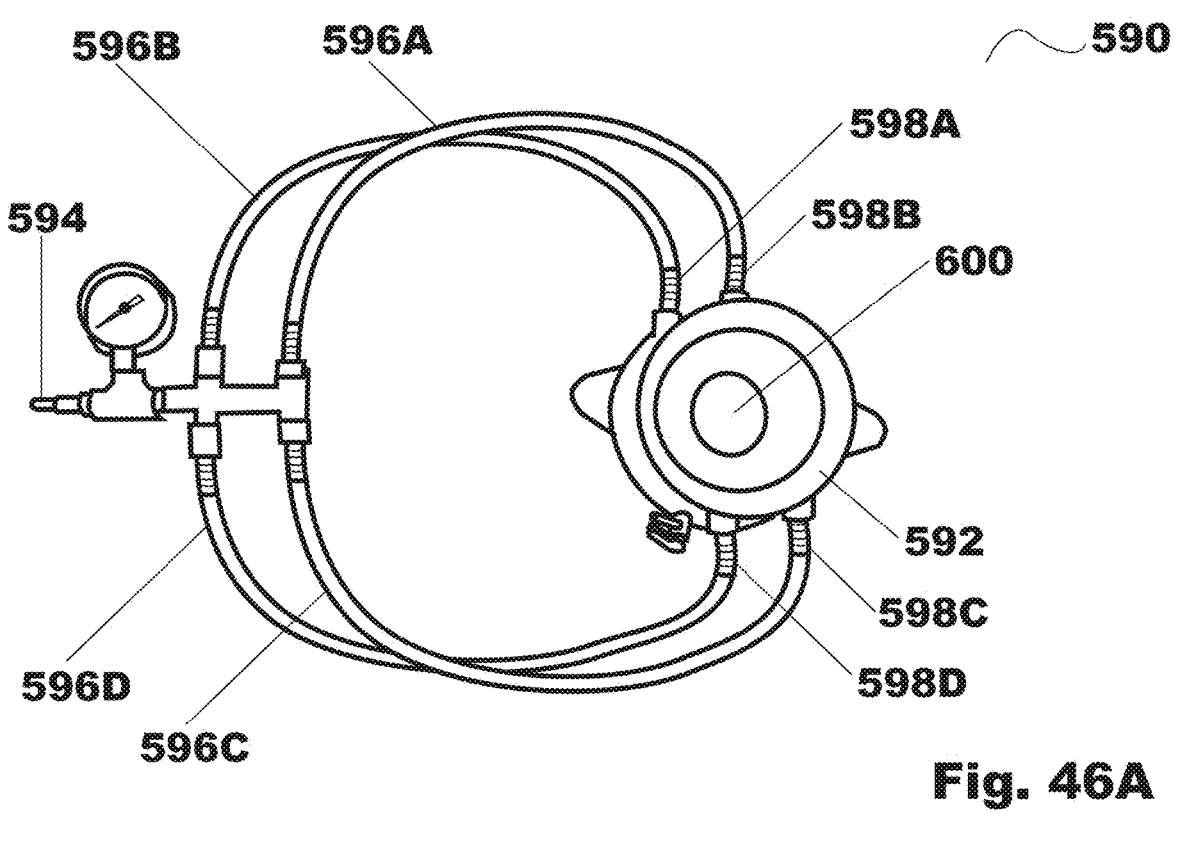
FIG. 46A is a top view of an air barrier incision port system, according to one embodiment.
Figure 46B:
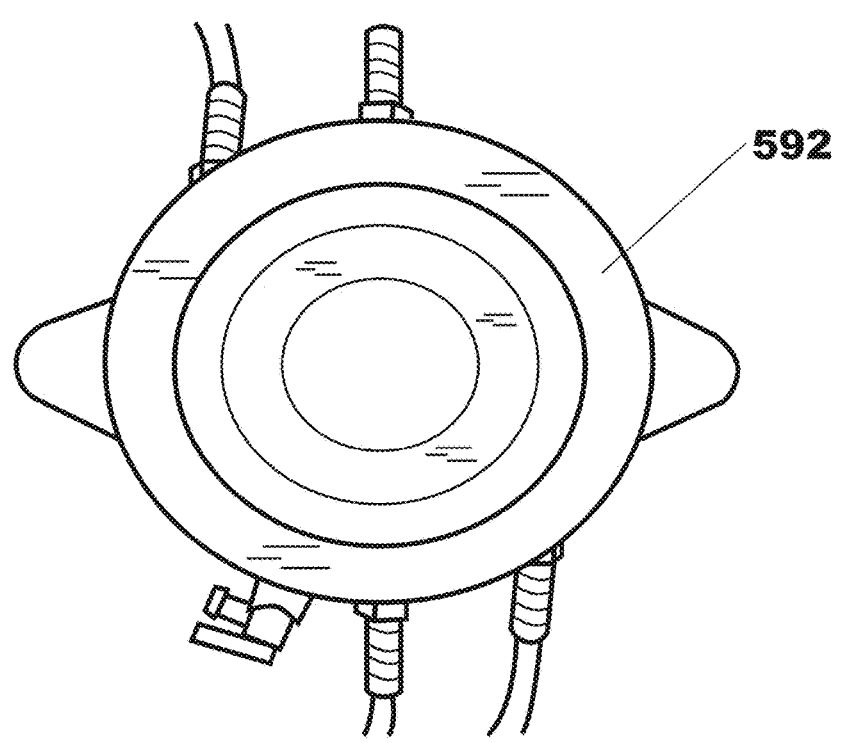
FIG. 46B is a top view of the air barrier port of the port system of FIG. 46A.

FIGS. 46A and 46B depict a further incision port system embodiment. This system is an air barrier port system 590 having an air barrier port 592. This port 592 is coupled to four air tubes 596A, 596B, 596C, 596D that are coupled to an air intake port 594. In operation, high pressure air is provided at the air intake port 594 and is forced through the four tubes 596A-D and into the port 592. The four tube connections 598A, 598B, 598C, 598D are positioned on the port 592 such that the air is forced into a channel (not shown) that encircles the hole 600 in the port 592. The air is then forced through a circular nozzle (not shown) in communication with the channel (not shown) that projects the air out of the nozzle and across the hole 600. The air flow projected across the hole 600, according to one implementation, is both directed and has a high velocity-both of which have an impact on the creation of an air barrier. As a result, an air barrier is created in the hole 600 defined in the port 592. That is, the high velocity air movement across or within the hole 600 creates a fluidic seal that is sufficient to maintain the insufflation of a patient's cavity.

Figure 47:
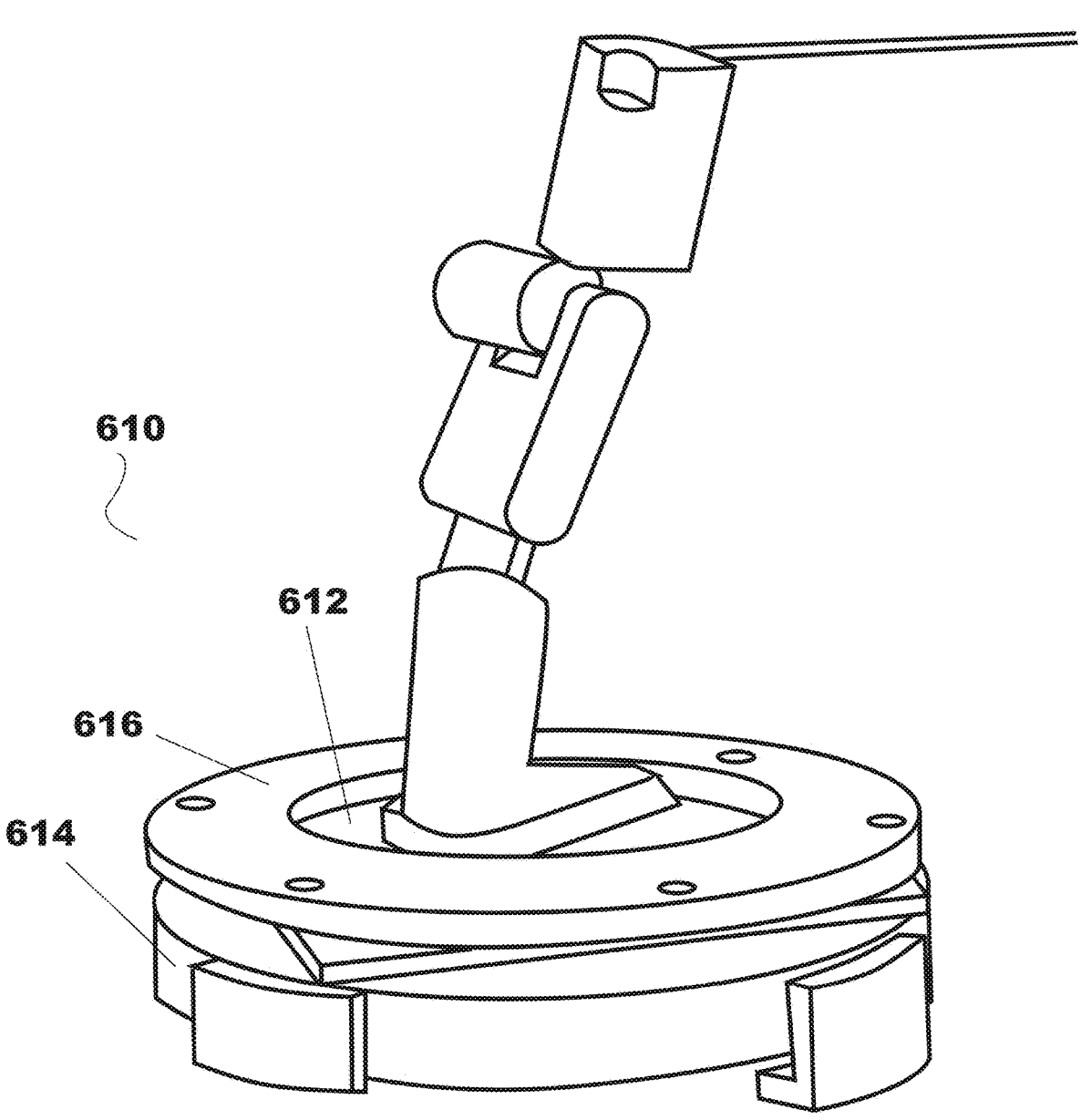
FIG. 47 is a perspective side view of a rubber seal incision port, according to one embodiment.

FIG. 47 depicts another incision port embodiment—in this case, a one-sheet rubber seal port 610 having a single sheet of rubber 612 (other other flexible seal material) positioned between a base ring 614 and a top ring 616. In one embodiment, the sheet has slit (not shown) formed in it through which a surgical device or other equipment can be inserted. Alternatively, the sheet can have two slits or other types of openings.

Figure 48A:
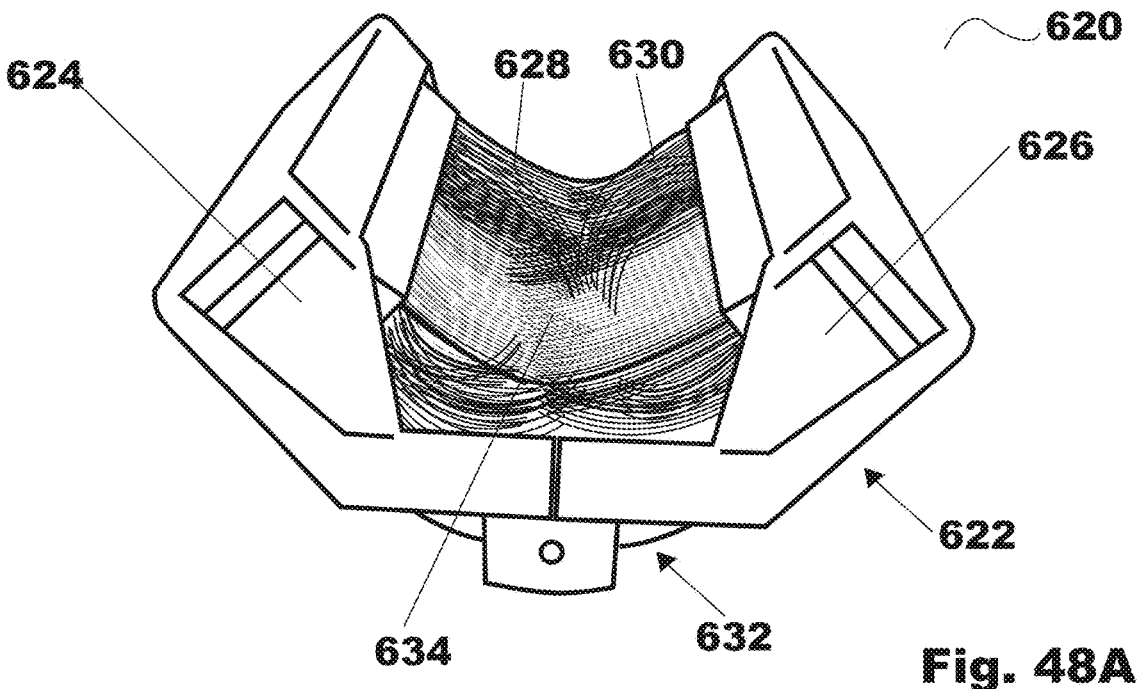
FIG. 48A is a perspective side view of a dual brush incision port, according to one embodiment.
Figure 48B:
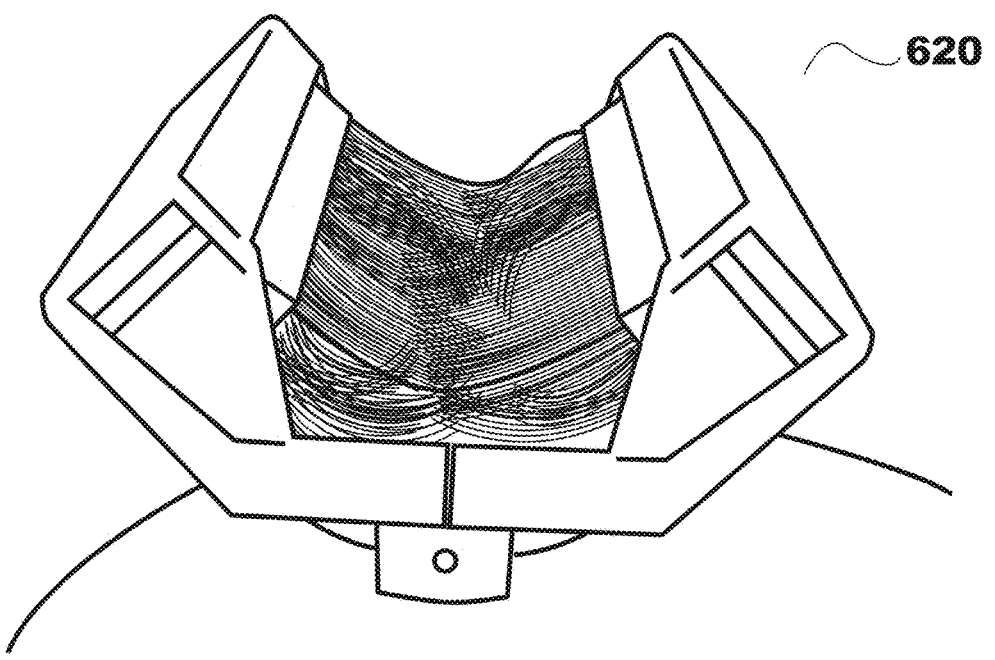
FIG. 48B is another perspective side view of the dual brush incision port of FIG. 48A.

Another incision port embodiment is shown in FIGS. 48A and 48B. This port is a dual brush port 620. This port 620 has a body 622 with a first brush holder 624 and a second brush holder 626. The first brush 628 is positioned in the first brush holder 624 and the second brush 630 is positioned in the second brush holder 626. Further, the body 622 has an opening 632 formed in a bottom portion of the body 622 that can provide access to the patient's cavity. The brush bristles of the two brushes 628, 630 are mingled and meshed together at the brush seal 634 such that the mesh of bristles creates a fluidic seal that is sufficient to maintain a patient's insufflated cavity.

Figure 49A:
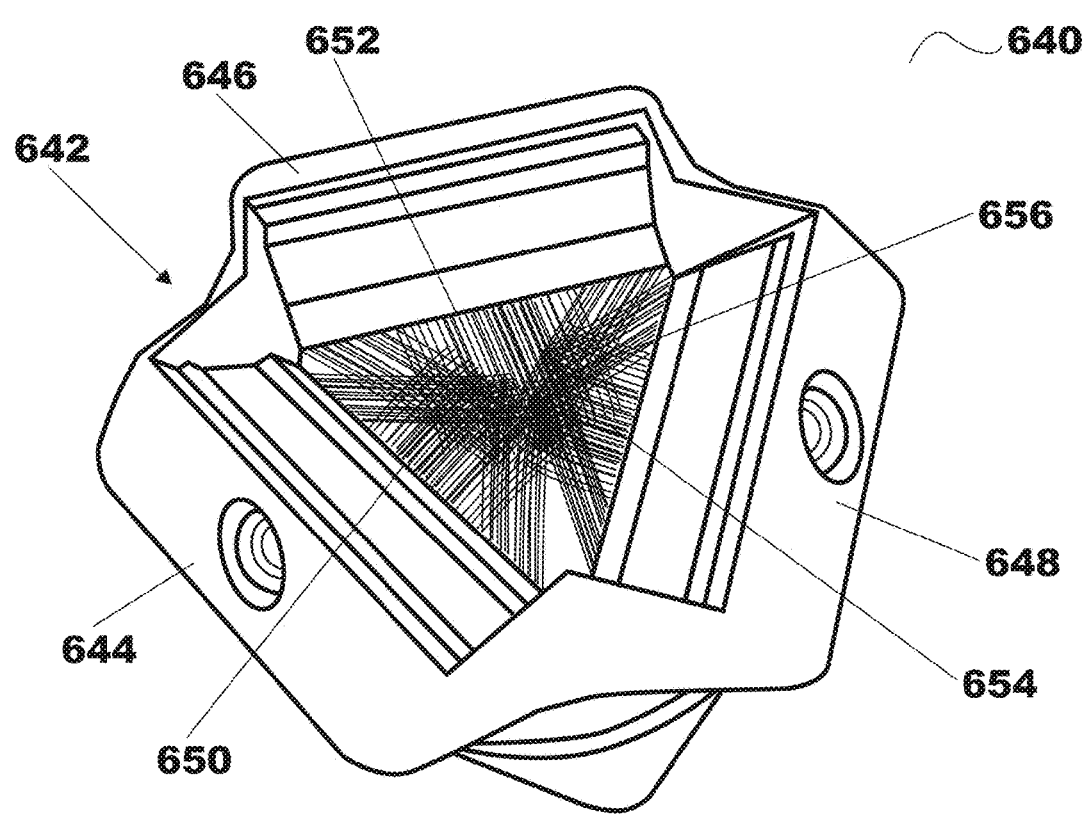
FIG. 49A is a perspective top view of a triple brush incision port, according to one embodiment.
Figure 49B:
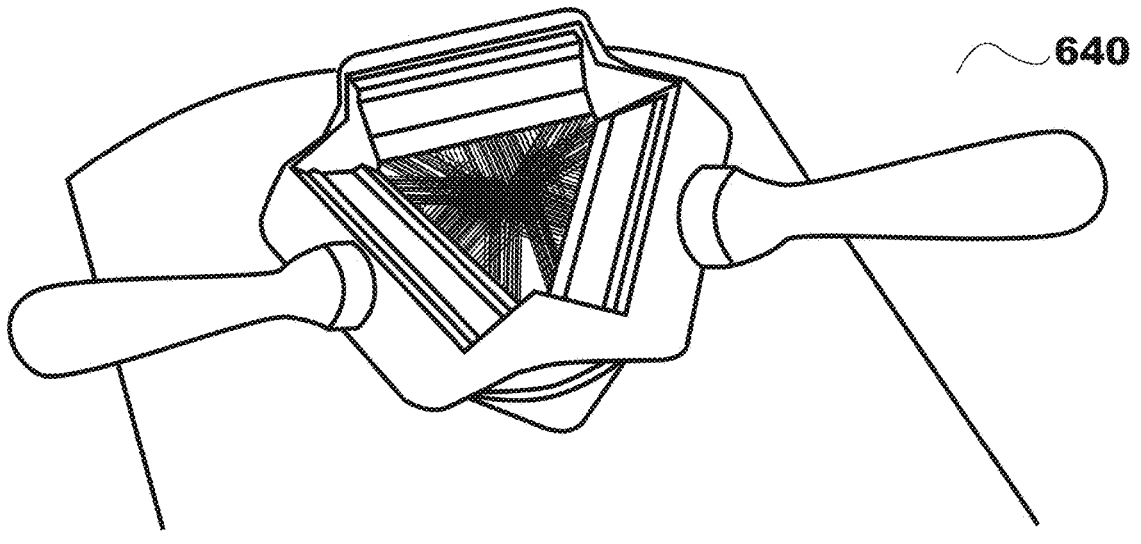
FIG. 49B is a perspective side view of the triple brush incision port of FIG. 49A.

FIGS. 49A and 49B depict another brush port—in this case, a triple brush port 640. This port 640 has a body 642 with first, second, and third brush holders 644, 646, 648. The first brush 650 is positioned in the first brush holder 644, the second brush 652 is positioned in the second brush holder 646, and the third brush 654 is positioned in the third brush holder 648. Further, the body 642 has an opening (not shown) formed in a bottom portion of the body 642 that can provide access to the patient's cavity. The brush bristles of the three brushes 650, 652, 654 are mingled and meshed together at the brush seal 656 such that the mesh of bristles creates a fluidic seal that is sufficient to maintain a patient's insufflated cavity.

Figure 50A:
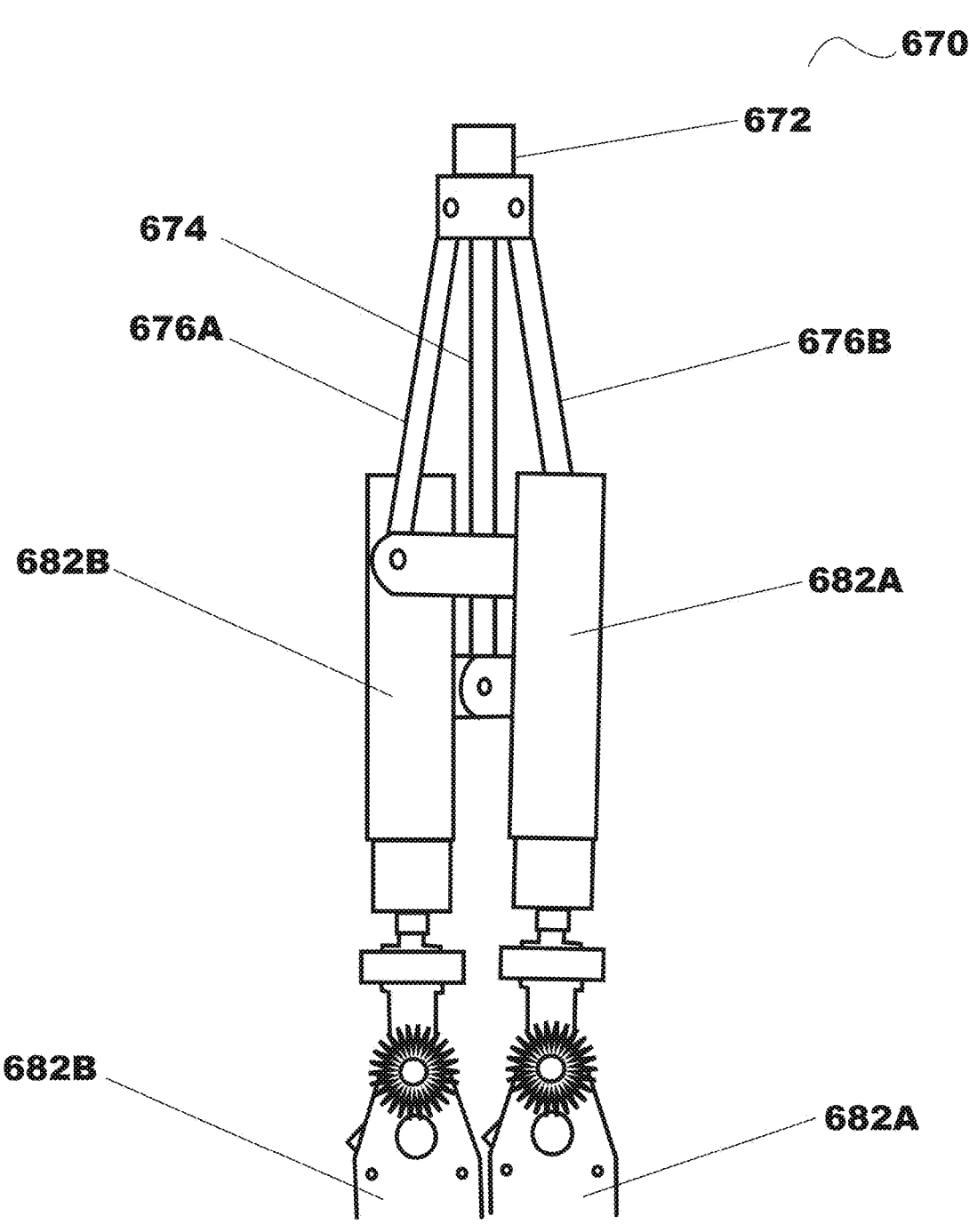
FIG. 50A is a side view of an insertion device, according to one embodiment.
Figure 50B:
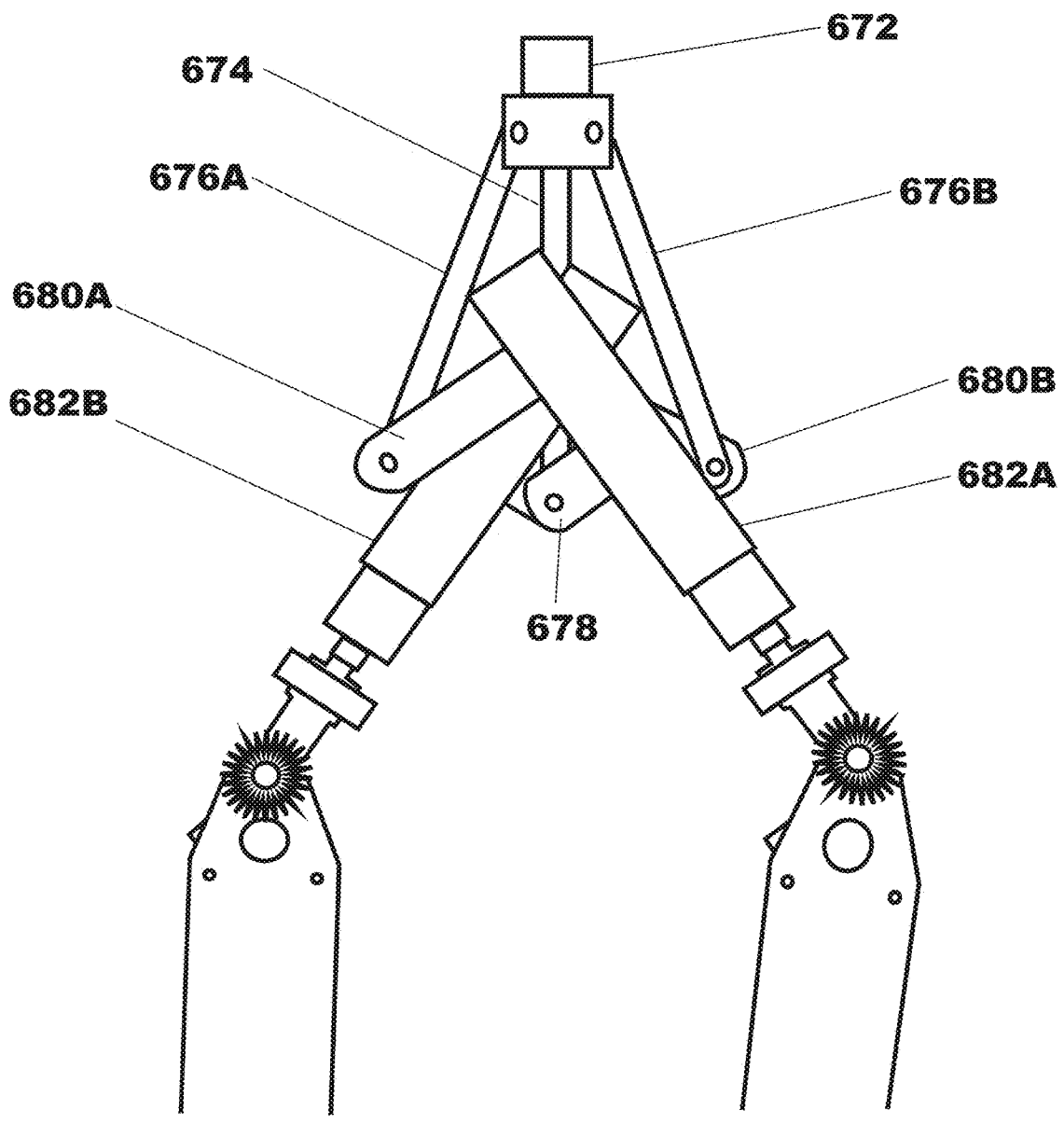
FIG. 50B is another side view of the insertion device of FIG. 50A.
Figure 50C:
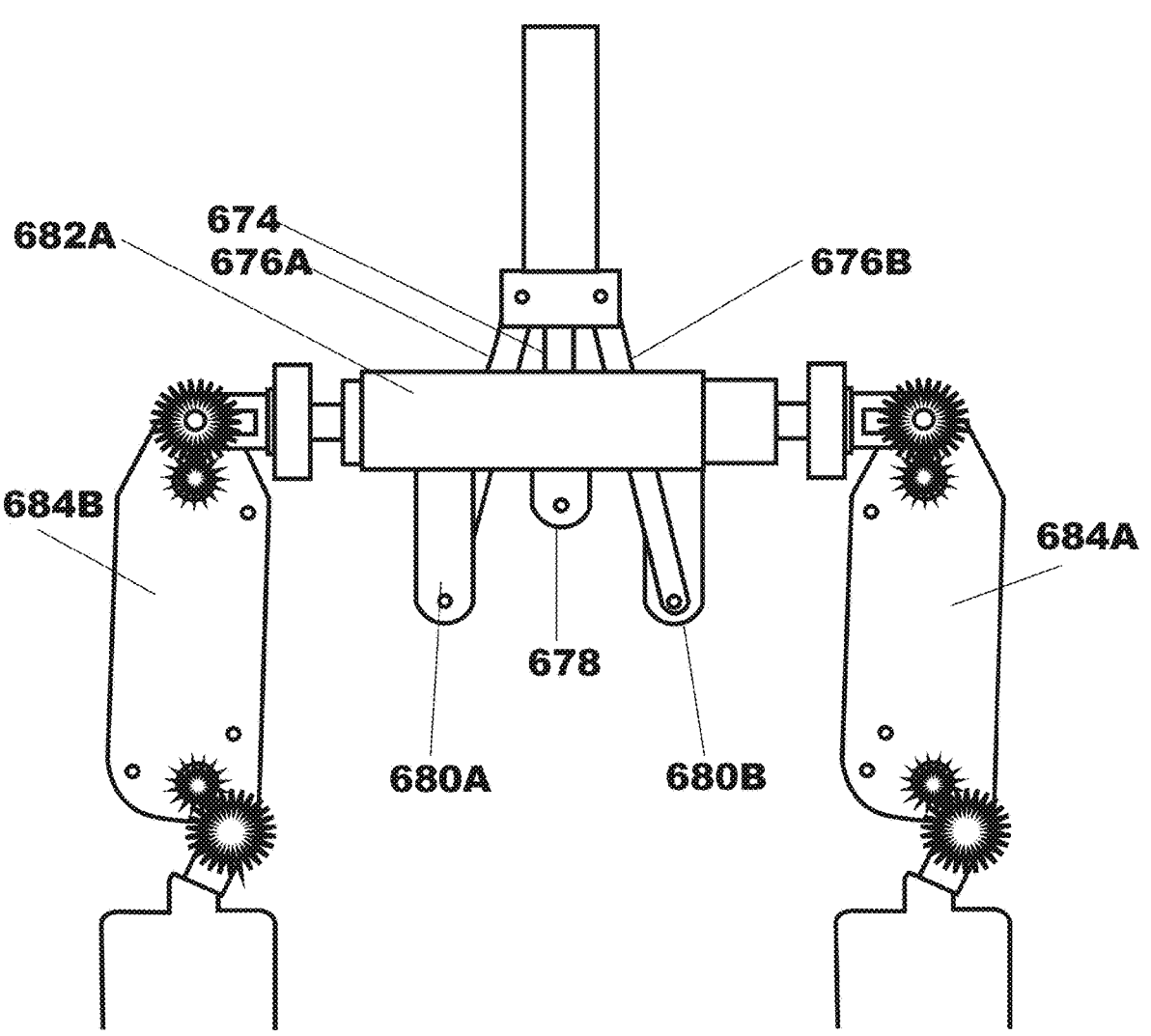
FIG. 50C is another side view of the insertion device of FIG. 50A.

According to another implementation, FIGS. 50A, 50B, and 50C depict an insertion device 670 that can be used to insert both arms of a robotic surgical device into a patient's cavity. The insertion device 670 has an insertion tube 672 through which an insertion rod 674 is slidably disposed. In addition, the device has a first arm 676A and a second arm 676B, both of which are coupled to the distal end of the tube 672. The first arm 676A is coupled to an end bracket 680A coupled to an end of the first device body 682A, while the second arm 676B is coupled to an end bracket 680B coupled to an end of the second device body 682B. Further, the insertion rod 674 is coupled to two center brackets (only bracket 678A is visible in the figures)—one center bracket 678A coupled to a middle portion of the first body 682A and a second center bracket (not shown) coupled to a middle portion of the second body 682B.

In use, the insertion device 670 can be used to insert a two-armed surgical device through a hole (such as an incision, a port, or the like) and into a patient's cavity prior to operating the device within the cavity. To accomplish this insertion, the insertion device 670 initially maintains an insertion configuration (as best shown in FIG. 50A) such that the surgical device has its smallest circumferential profile, thereby allowing it to pass through smaller holes. Once the surgical device has been inserted into the patient's cavity, the insertion device 670 can be moved into its deployed configuration (as best shown in FIG. 50C) such that the surgical device is in its operational configuration. To accomplish this, a user or surgeon retracts the insertion rod 674 in a proximal direction (away from the surgical device. This retraction of the rod 674 urges the two center brackets (with only center bracket 678A of body 682A depicted) in the same proximal direction. Because the two end brackets 680A, 680B are retained in substantially the same position by the two arms 676A, 676B, the result is that the two device bodies 682A, 682B move through a transition depicted in FIG. 50B and into the operational configuration depicted in FIG. 50C. At this point, the user or surgeon can use the surgical device, including its two arms 684A, 684B to perform the planned surgery or procedure.

There are numerous device access and insertion devices and methods disclosed in the instant application. All of the various devices and methods that allow for access to a cavity and insertion of devices having two arms can also generally be used with respect to devices that can be uncoupled into separate arms so as to allow each arm to be inserted individually. In one embodiment, one advantage of inserting each arm separately is that inserting a first arm and then a second arm in a serial manner (and possibly more arms) can likely be accomplished through a smaller incision when compared to inserting both arms simultaneously.

Figure 51A:
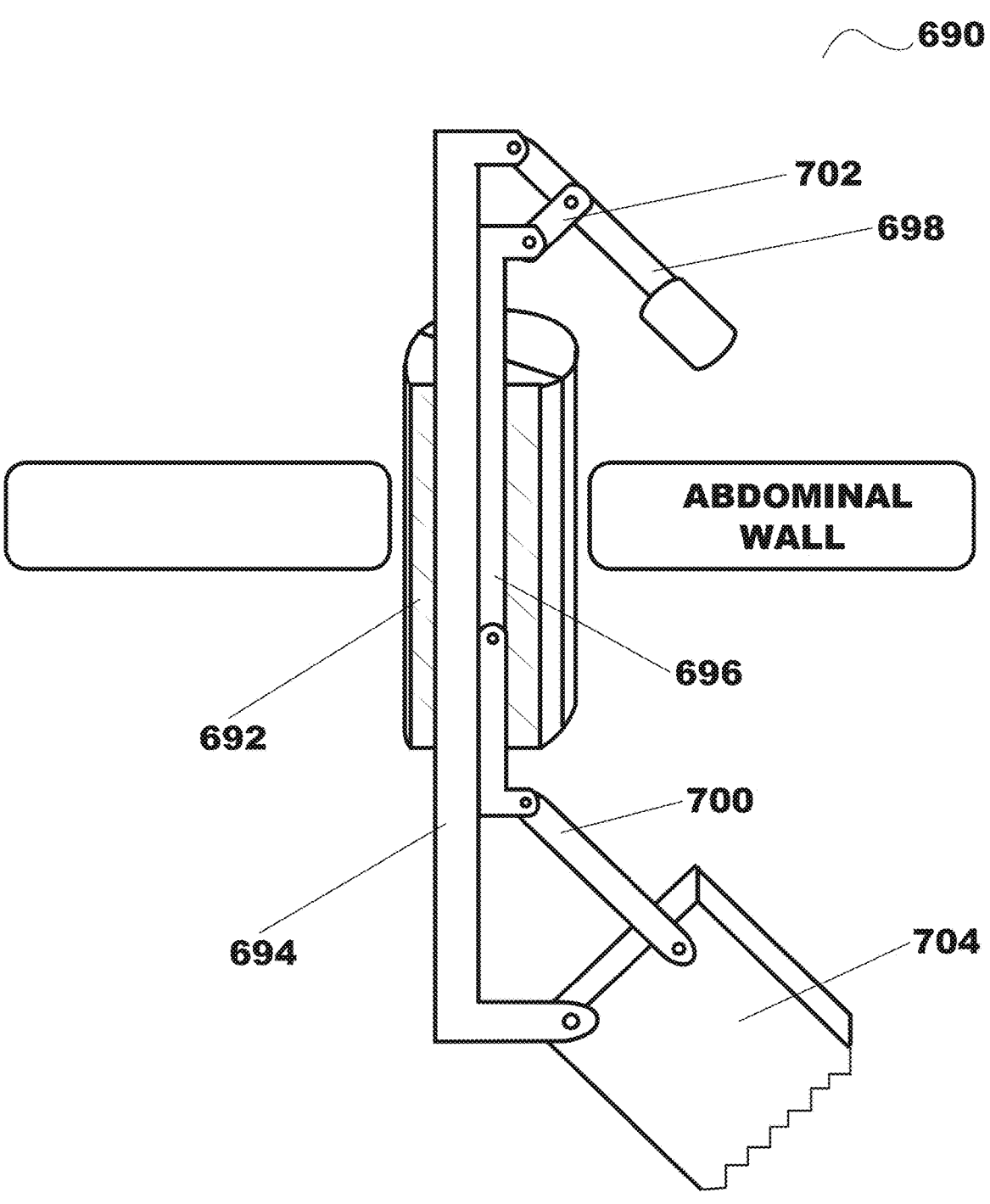
FIG. 51A is a side view of an insertion device, according to another embodiment.
Figure 51B:
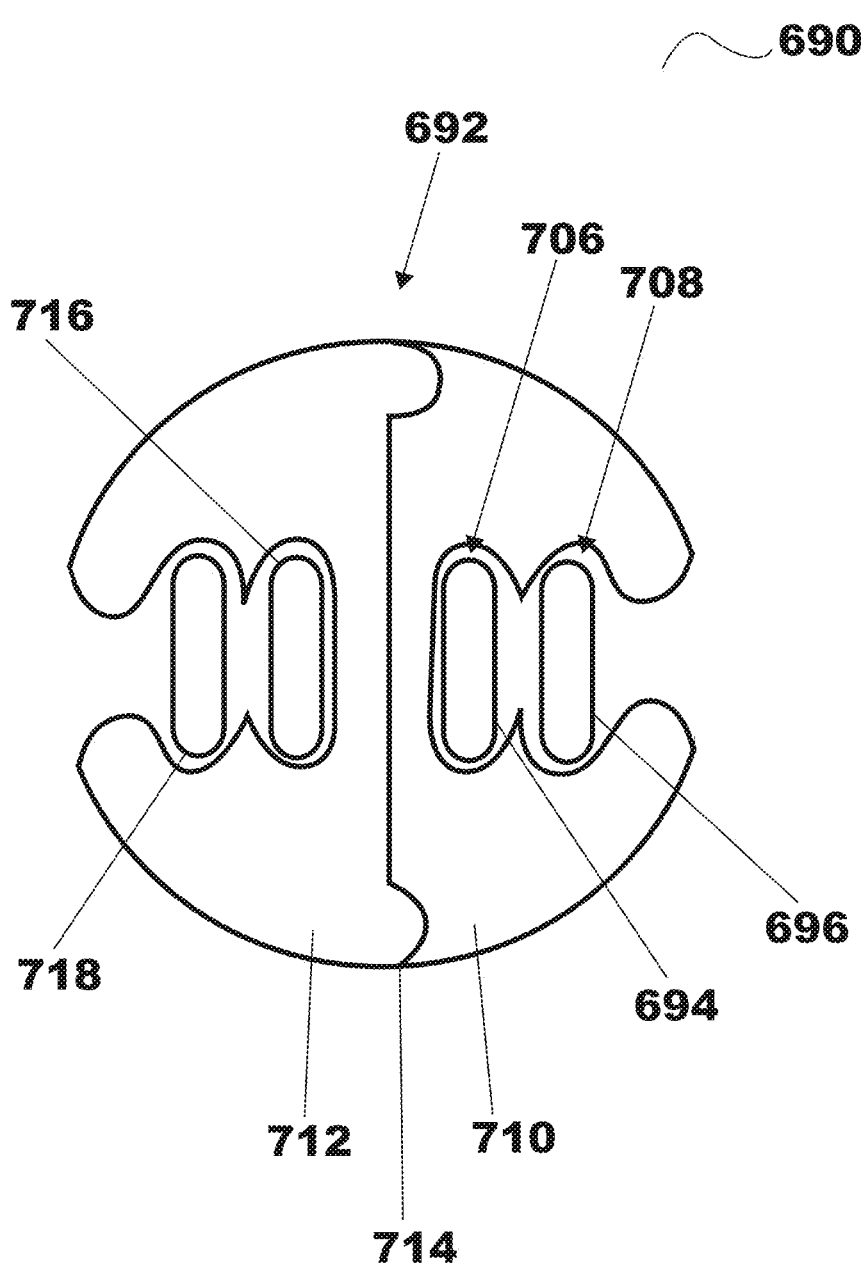
FIG. 51B is a top view of the insertion device of FIG. 51A.

FIGS. 51A and 51B depict an alternative embodiment of an insertion device 690 (in the same spirit as the insertion device depicted in FIGS. 50A-C). While the above embodiment in FIGS. 50A-C depict an insertion device for use with a two-armed device, this insertion device 690 is used with a single arm 704 or with two arms that are inserted separately. That is, in this embodiment, a single device arm 704 is coupled to the insertion device 690. As shown, this device is positioned through an insertion tube 692 (which can also be a positioning or support rod). The device has two moveable rods 694, 696 slidably disposed within the support rod 692. The first moveable rod 694 is coupled at its distal end to a first robotic arm 704 and at its proximal end to a control lever 698. The second moveable rod 696 is coupled at its distal end to a coupling link 700 (that is coupled to the arm 704) and at is proximal end to a coupling link 702 (that is coupled to the lever 698).

In use, the lever 698 can be actuated to cause the first and second rods 694, 696 to move in relation to each other. This movement of the rods 694, 696 can be used to move the arm 704 and thereby position the arm 704 as desired or needed inside the patient's cavity.

As shown in FIG. 51B, which is a cross-section of the support rod 692, showing that the support rod 692 can have two separate lumens 706, 708 or slots, one for each of the moveable rods 694, 696. In one embodiment, the first moveable rod 694 is positioned in the first lumen 706 and the second moveable rod 696 is positioned in the second lumen 708.

In a further embodiment, it is understood that this support rod 692 could have two halves—a right half 710 and a left half 712—that are coupleable at the mating feature 714. Alternatively, the two halves can be coupleable by any known mechanical means. The right half 710 is configured to hold the first and second rods 694, 696 relating to the first (or right) arm 704, while the left half is configured to hold the first and second rods 716, 718 relating to a second (or left) arm (not shown). This embodiment can thus be used with two arms, with each arm being inserted and positioned separately.

Figure 52:
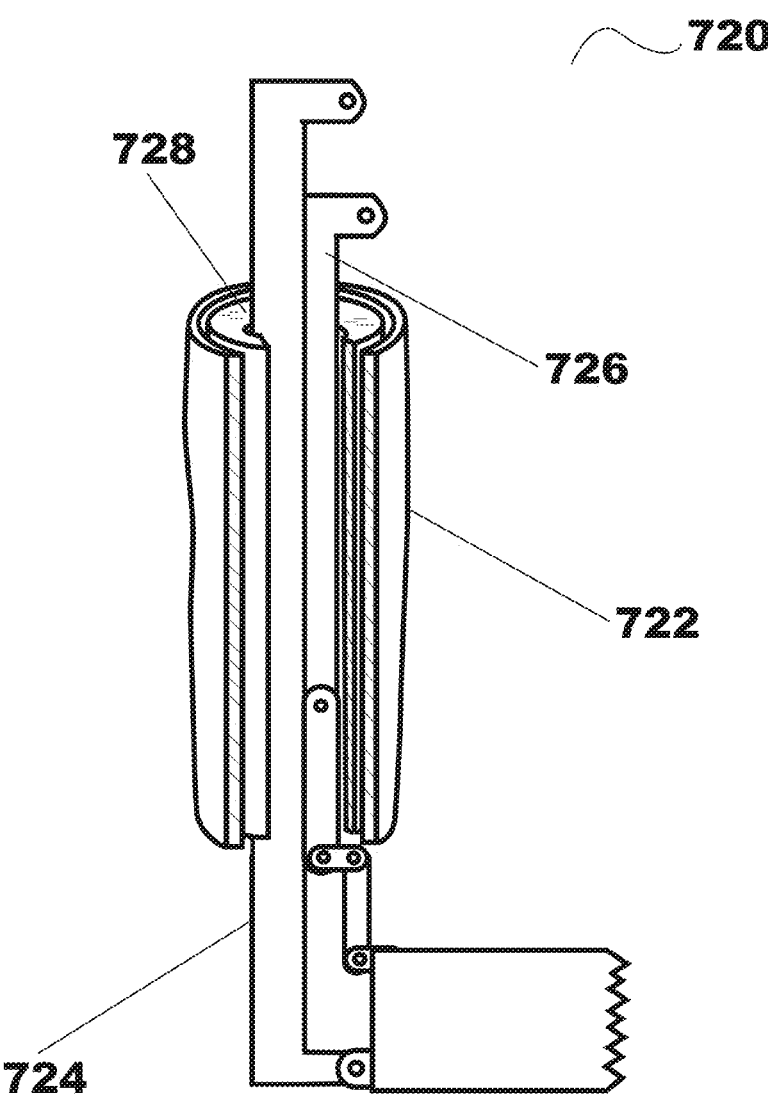
FIG. 52 is a side view of an insertion device, according to a further embodiment.

FIG. 52 depicts another embodiment in which two separate arms can be inserted and positioned separately by using an overtube 722. In this device 720, the first moveable rod 724 and second moveable rod 726 are still positioned within a support rod 728. However, in this embodiment, the support rod 728 is positioned within an overtube 722. The overtube 722 can be pass over the top of the support rod 728 in order to couple the support rod 728 to a second support rod (not shown) or another half of a support rod. This embodiment is another way to couple the two support rods or two halves of a support rod just as the mating feature 714 accomplishes that task in the prior embodiment.

Figure 53:
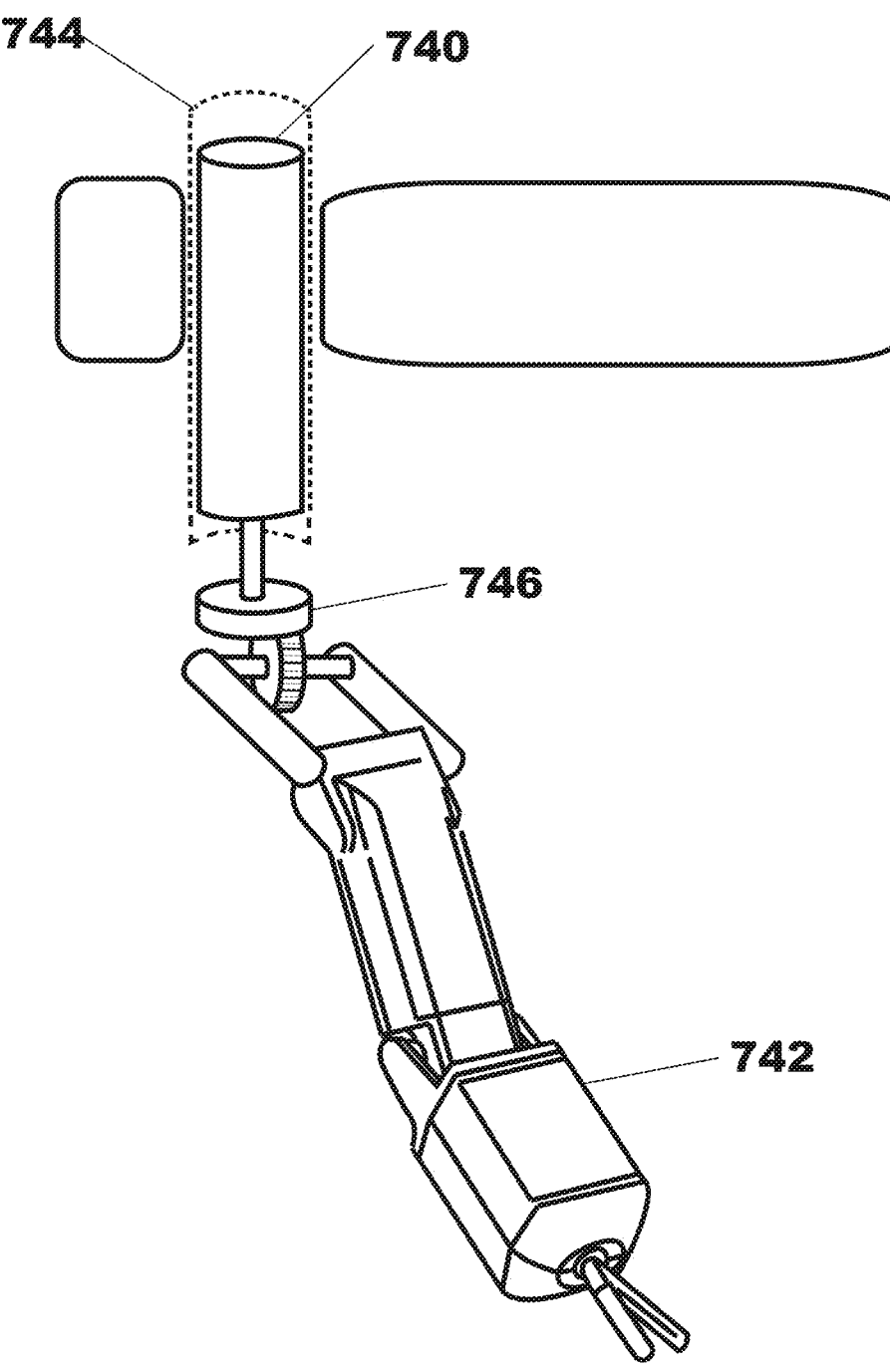
FIG. 53 is a side view of a surgical device positioned in a positioning rod, according to one embodiment.

Of course, as shown in FIG. 53, in any embodiment in which the surgical device or robotic arm has a motor 740 provided that can be positioned in the positioning or support rod 744 and is coupled to the robotic arm 742, there is no need for a separate insertion device. Instead, the arm 742 can easily be positioned by actuating the motor 740 and transfer the motive force through the beveled gears 746 and to the arm 742.

Figure 54:
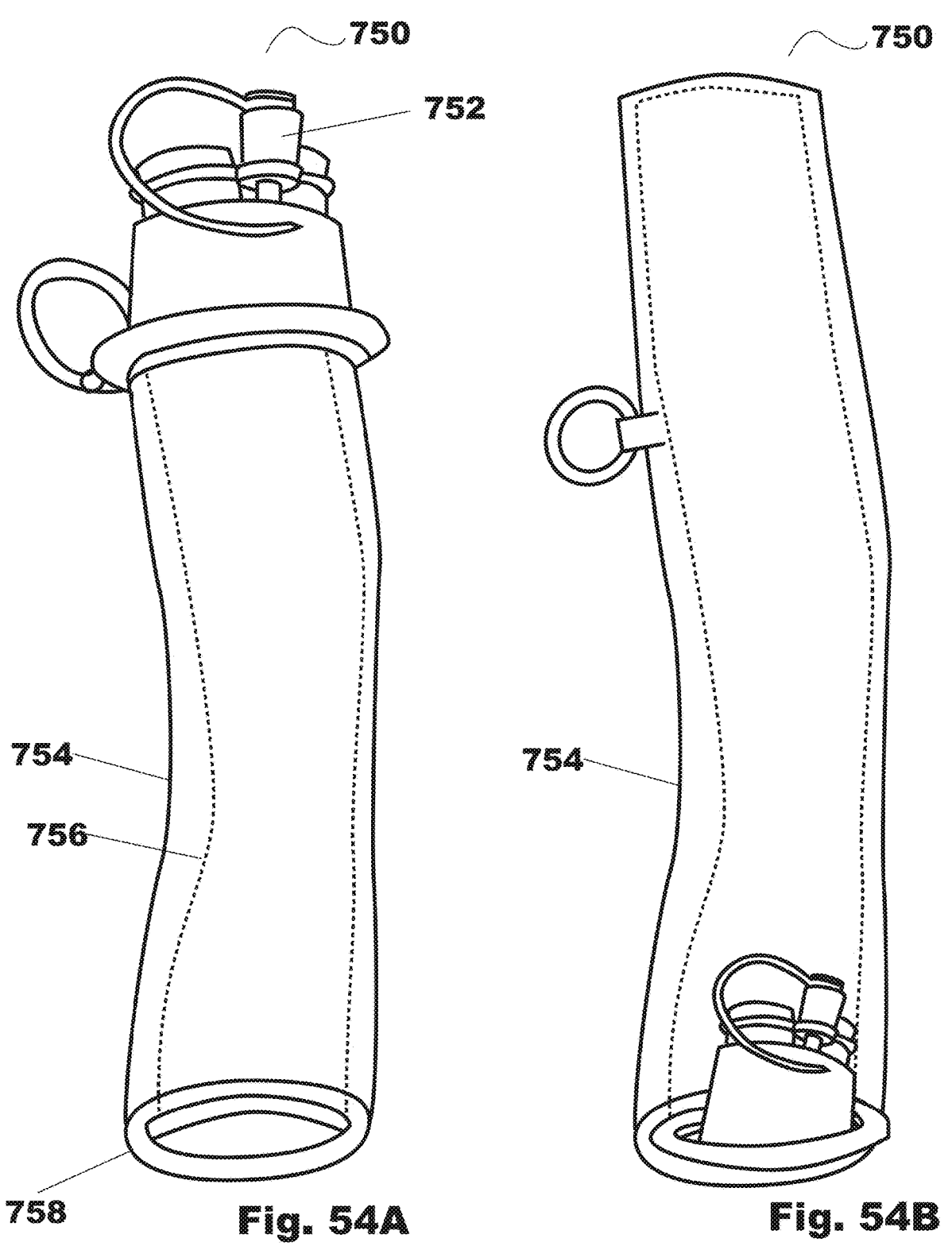
FIG. 54A is a side view of an internal pressurized bag device, according to one embodiment.
FIG. 54B is another side view of the internal pressurized bag device of FIG. 54A.

FIGS. 54A and 54B depict a different type of access/insertion device in comparison to the devices described above. Unlike the above devices, which are generally incision ports or devices positioned outside the patient's cavity, the internal pressurized bag device 750 shown in these two figures is initially positioned in the patient's cavity. The device 750 has a port seal 752, an outer sleeve 754, and an inner sleeve 756. The outer sleeve 754 is releasably sealed at the distal end 758. That is, the outer sleeve 754 has a releasable seal that can be intentionally broken or released at a desired time during the procedure, as described below.

In use, the entire device 750 can be positioned through an incision port such that the inner and outer sleeves 754, 756 are positioned inside the patient's cavity with the port seal 752 coupled to the incision port (thereby creating a fluidic seal). Once the device 750 is positioned, the patient's cavity can be insufflated, and the outer sleeve 754 can be pressurized to a pressure that is greater than the pressure of the insufflated cavity, thereby expanding the outer sleeve 754 to its maximum expansion (and, in some cases, making the outer sleeve 754 substantially rigid). At this point, the surgical device can be inserted through the incision port and into the outer sleeve 754 and positioned as desired. At this point, the outer sleeve 754 can be removed by releasing the releasable seal at the distal end of the sleeve 754. That is, the releasable seal could be a chemical seal such as an adhesive that can be deactivated by applying a different composition to it. Alternatively, the releasable seal could be a mechanical release such as a pull cord or something of the like. In a further alternative, the releasable seal could be any known mechanism or method for being able to release the seal. Once the seal is released, the outer sleeve 754 can be pulled out of the cavity over the inner sleeve 756 and other components as best shown in FIG. 54B.

Figure 55:
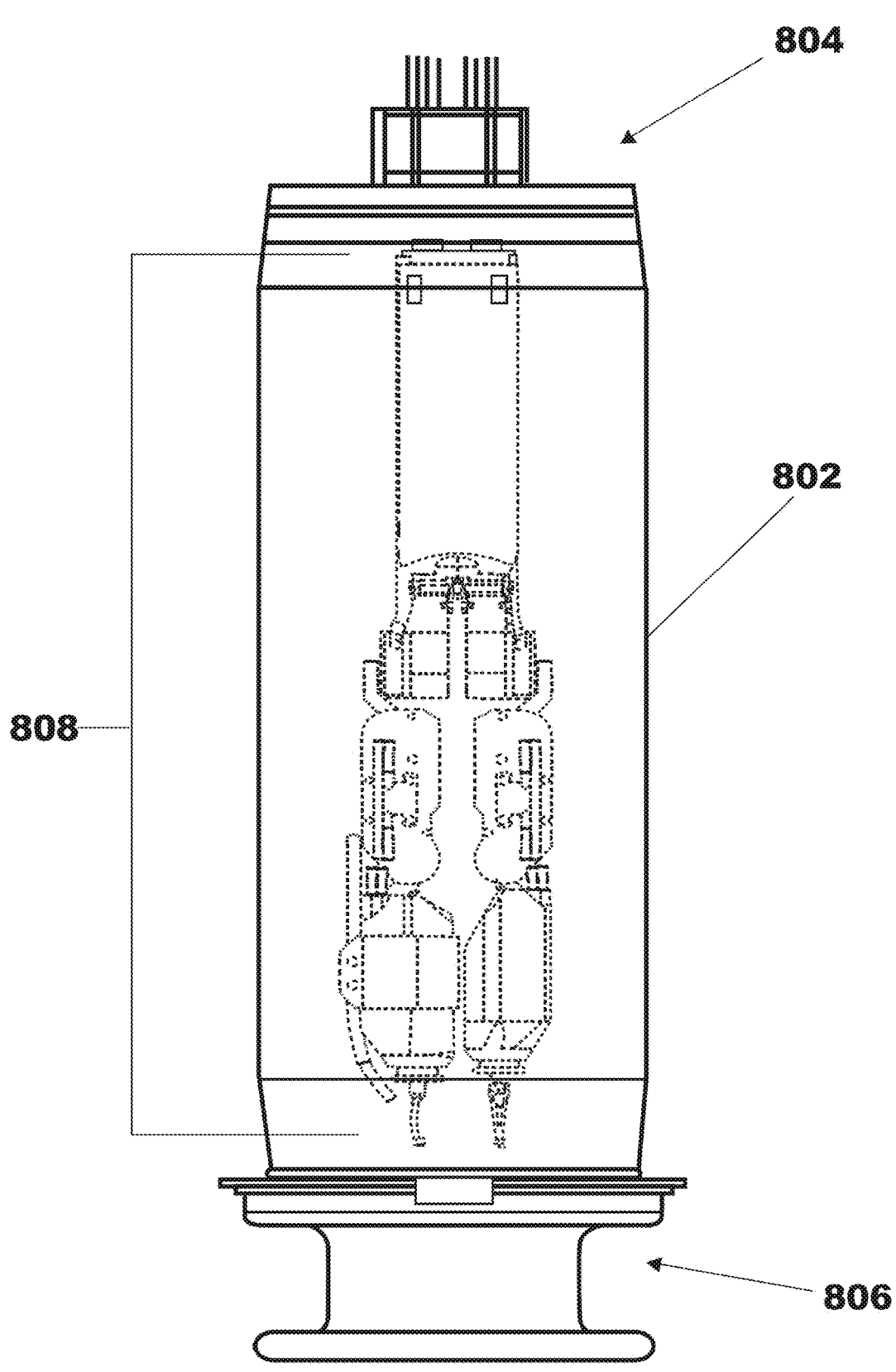
FIG. 55 is a side view of another external pressurized system or apparatus, according to one embodiment.

FIG. 55 depicts another implementation of an external pressurized system or apparatus 800. The apparatus 800 has a container 802 with a top cap 804 coupled to a top portion of the container 802. In this embodiment, the container 802 has a port 806 that is coupled to the container 802 at a base portion of the container 802. The port 806 is configured to be positionable in an incision in the skin of the patient, thereby providing access to a cavity of the patient. As shown in FIG. 55, the apparatus 800 is configured to receive a surgical device 808 such that the device 808 can be inserted into the patient cavity through the port 806 of the apparatus 800.

According to one embodiment, in contrast to the canister 12 described above and depicted in FIGS. 1A-10, the container 802 in this device 800 is made of a flexible material such as, for example, polyethylene plastic, latex, nylon, or silicone rubber. As such, the container 802 can be manipulated and configurable with respect to the shape of the container 802, and more specifically can be compressed longitudinally such that the height of the container 802 can be reduced during insertion of a robotic device into a patient's cavity. This will be described in further detail herein.

Figure 56A:
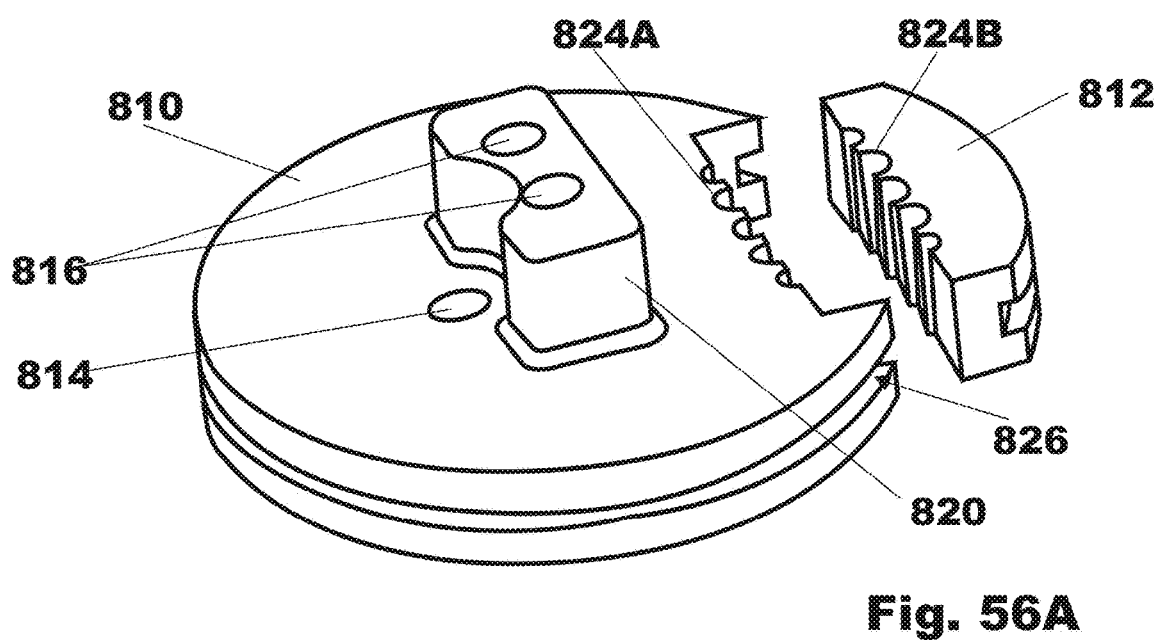
FIG. 56A is a perspective side view of a top cap, according to one embodiment.
Figure 56B:
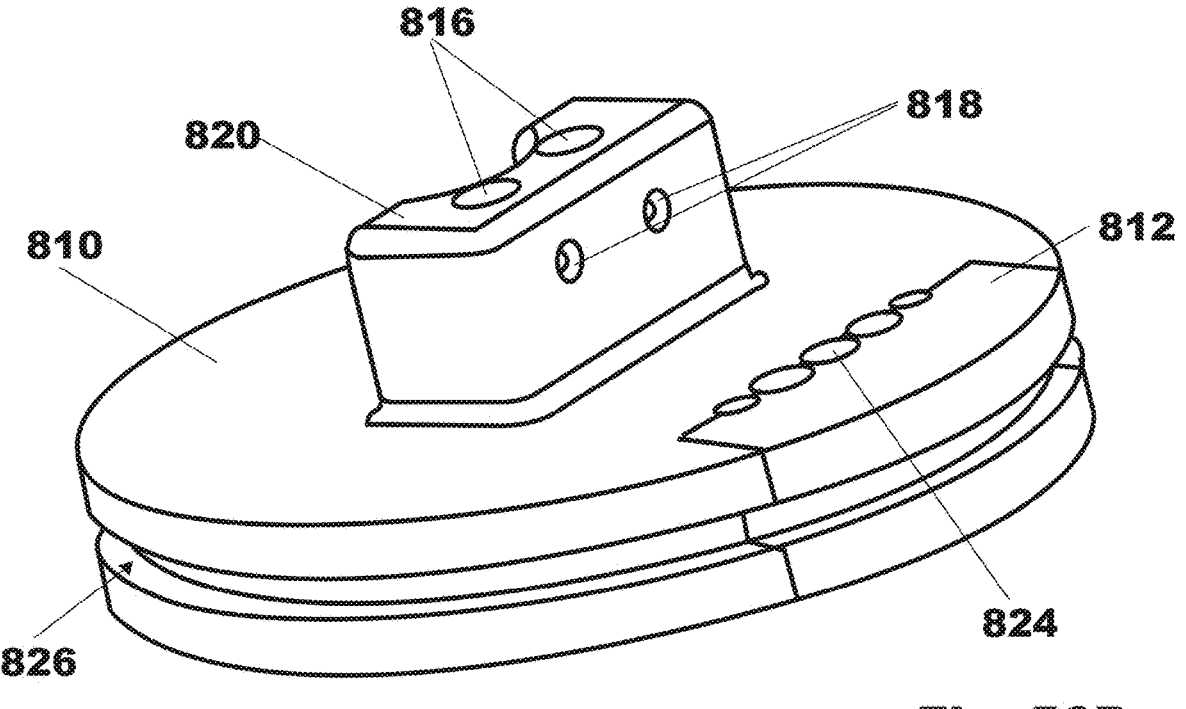
FIG. 56B is another perspective side view of the top cap of FIG. 56A.

The top cap 804 is depicted in further detail in FIGS. 56A-61B. As shown in FIGS. 56A and 56B, the top cap 804 has a cap body 810, a detachable cable harness 812, an access lumen 814, support rod lumens 816, threaded lumens 818, and a clamp projection 820. The cap 804 has a notch 822 defined in the cap 804 that is configured to receive the harness 812. In addition, the notch 822 has five channels 824A defined or formed in the notch 822. The channels 824A match with the channels 824B defined in the detachable harness 812 such that when the harness 812 is positioned in the notch 822 and thus coupled with the cap body 810, the channels 824A and the channels 824B match up to form lumens 824 as best shown in FIG. 56B. In one implementation, the lumens 824 can be formed in different sizes and configured to receive various cables and/or suction/irrigation tubes the extend from an external controller through the top cap 804 to the surgical device 808.

In addition, the cap body 810 has a groove 826 formed or defined around the outer edge of the body 810, including the outer edge of the harness 812, such that when the harness 812 is coupled to the body 810, an O-ring can be positioned around the outer edge of the body 810 in the groove 826.

Figure 57A:
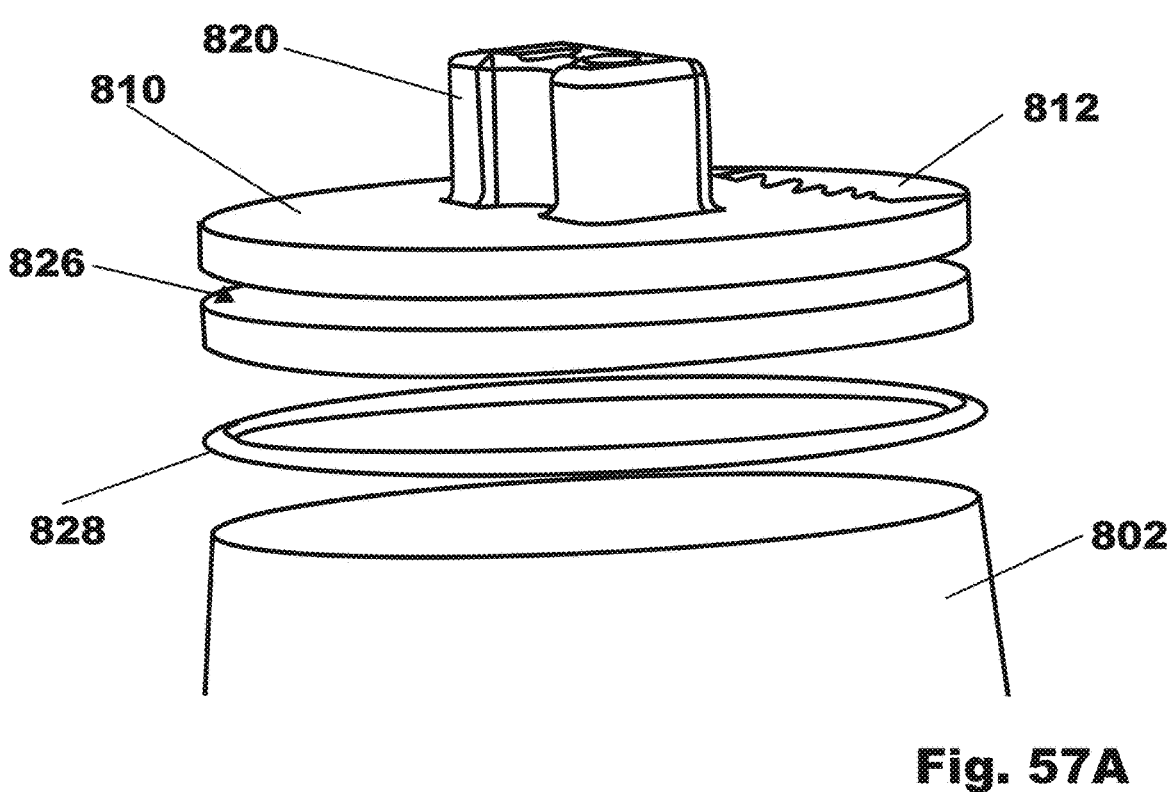
FIG. 57A is a perspective side view of a top cap and a canister, according to one embodiment.
Figure 57B:
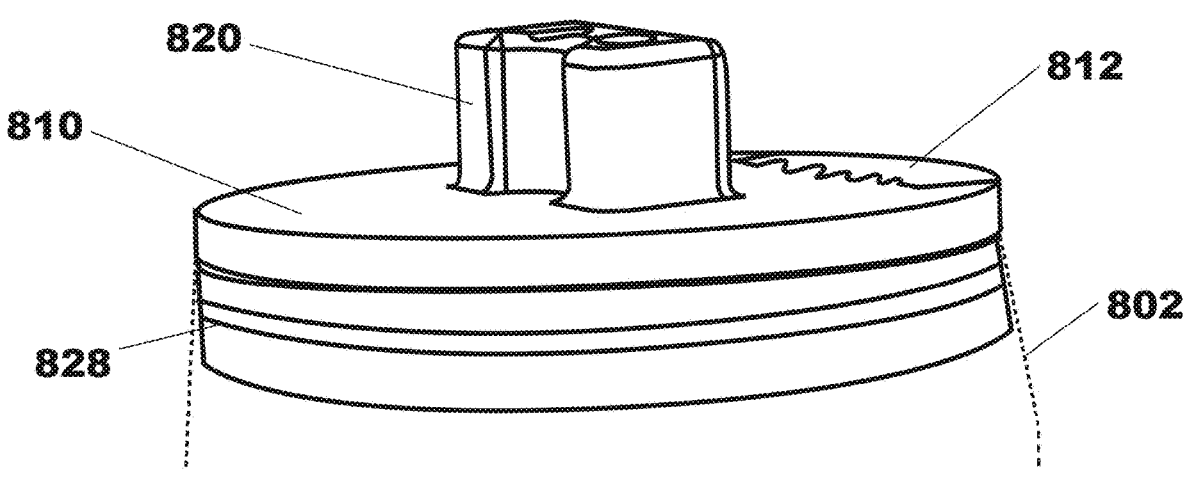
FIG. 57B is another perspective side view of the top cap and canister of FIG. 57A.

FIGS. 57A and 57B depict the top cap 804 being coupled to the canister 802. The flexible canister 802 is positioned over the peripheral edge of the body 810 as best shown in FIG. 57B and an elastic ring (also referred to as an "O-ring") 828 is positioned around the canister 802 at the groove 826 such that a portion of the canister 802 is positioned between the body 810 and the ring 828 in the groove 826 and the ring 828 urges the canister 802 into the groove 826, thereby creating a fluidic seal between the canister 802 and the top cap 804. Additionally, in one alternative embodiment, silicone sealant can be applied to the groove 826 to enhance the strength of the fluidic seal. In accordance with one implementation, the O-ring 828 can also help to secure the cap body 810 and the harness 812 together. In a further alternative, the O-ring 828 can be any elastic member that can be used to maintain a fluidically sealed coupling of the canister 802 and the top cap 804. In yet another alternative, any coupling mechanism can be used.

Figure 58A:
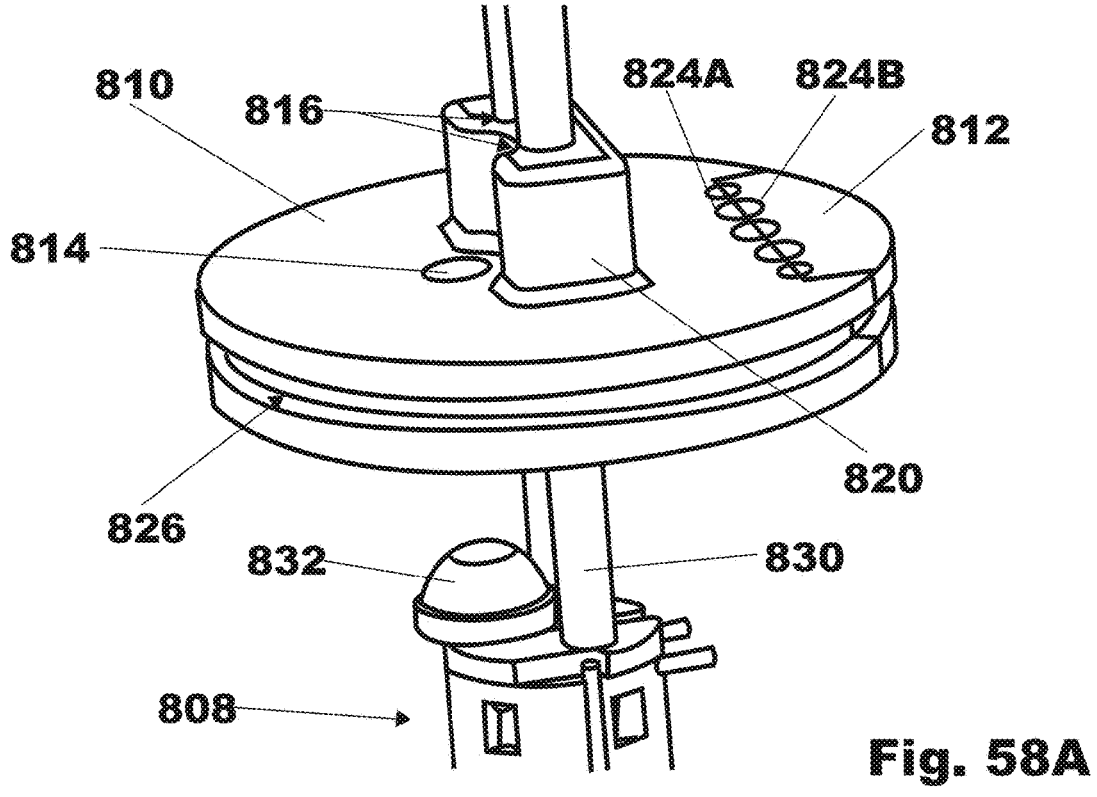
FIG. 58A is a perspective view of a top cap with a portion of a device assembly positioned therethrough, according to one embodiment.
Figure 58B:
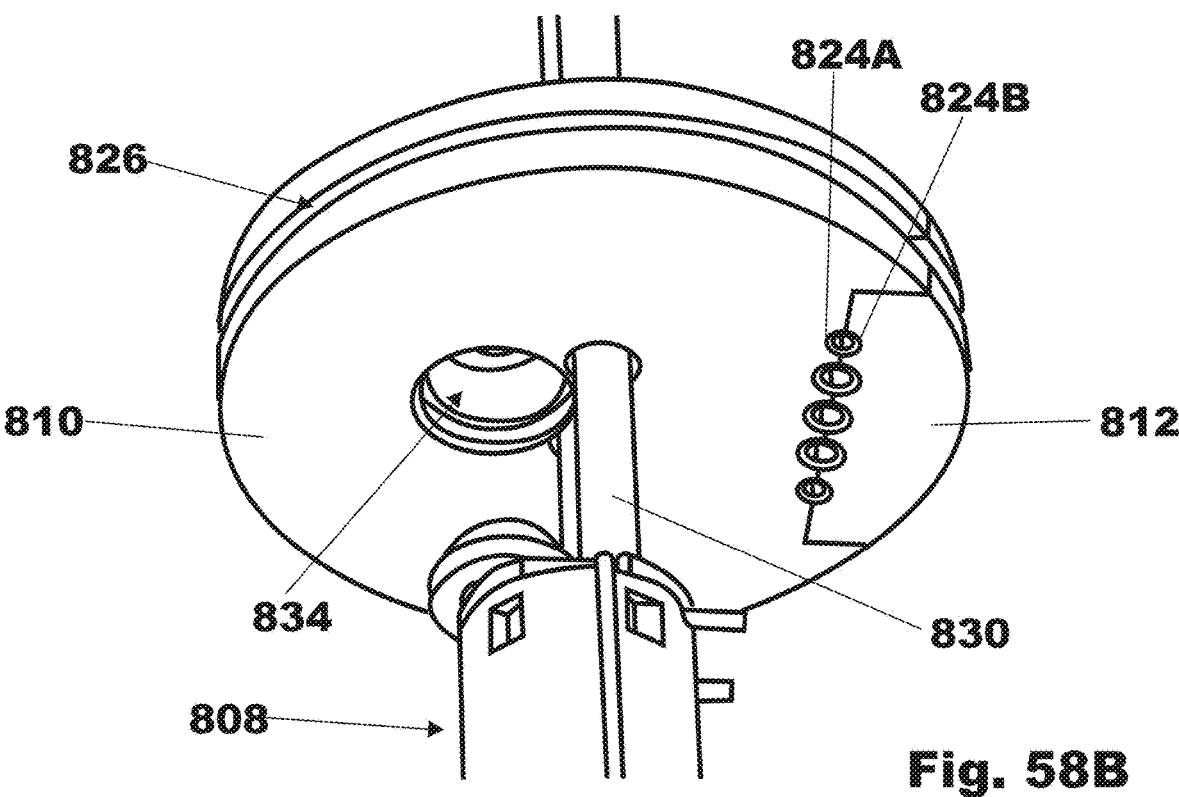
FIG. 58B is a perspective view of the underside of the top cap of FIG. 58A.

FIGS. 58A and 58B depict a portion of the device assembly 808 being positioned through the top cap 804. More specifically, the support rods 830 coupled to the device 808 are slidably positioned through the lumens 816 in the cap body 810. Further, according to one implementation, a portion of the device 808 also couples to or mates with the top cap 804. More specifically, a stabilization protrusion 832 on the device 808 is coupleable with a mating hole 834 defined or formed in an underside of the body 810 as best shown in FIG. 58B. The positioning of the stabilization protrusion 832 in the mating hole 834 creates a pathway from lumen 814 into and through the stabilization protrusion 832, thereby allowing for passage of additional tools or cameras through the device 800 without losing pressure.

Figure 59A:
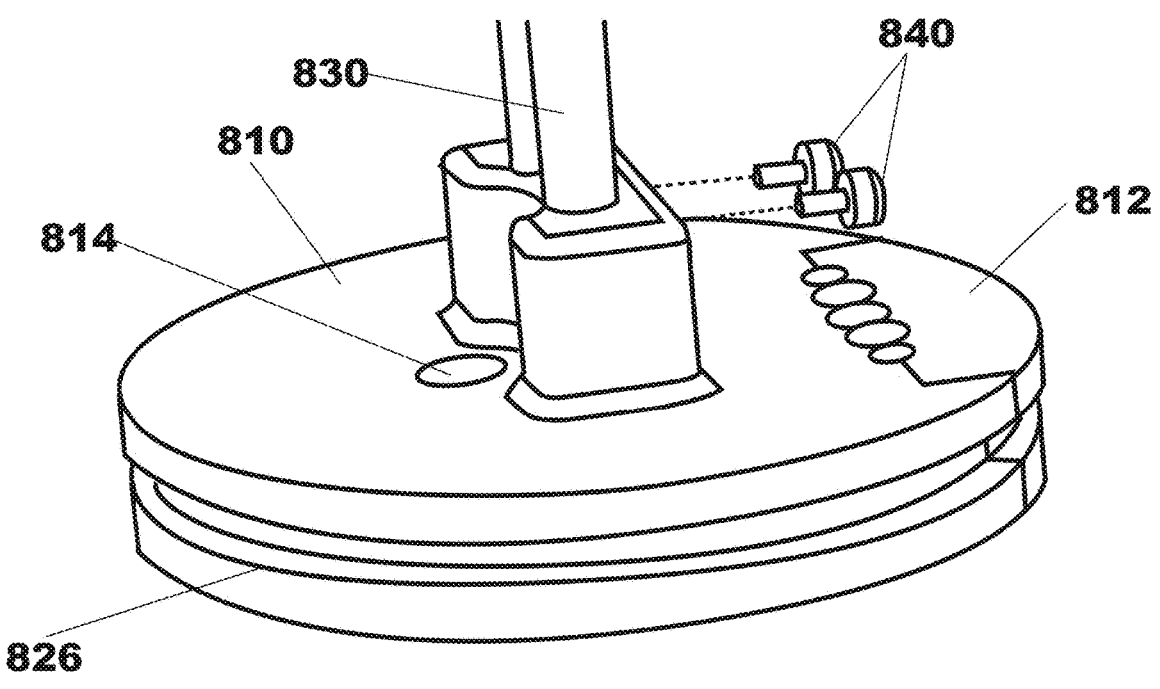
FIG. 59A is a perspective view of a top cap with a portion of a device assembly positioned therethrough, according to one embodiment.
Figure 59B:
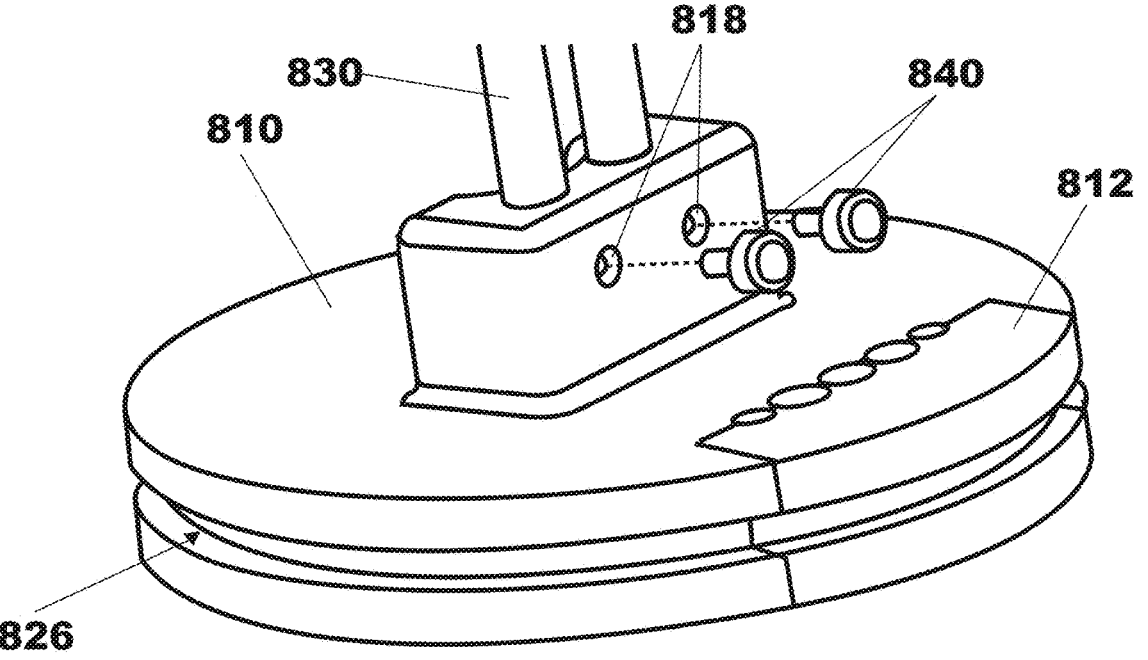
FIG. 59B is a another perspective view of the top cap of FIG. 59A.
Figure 60:
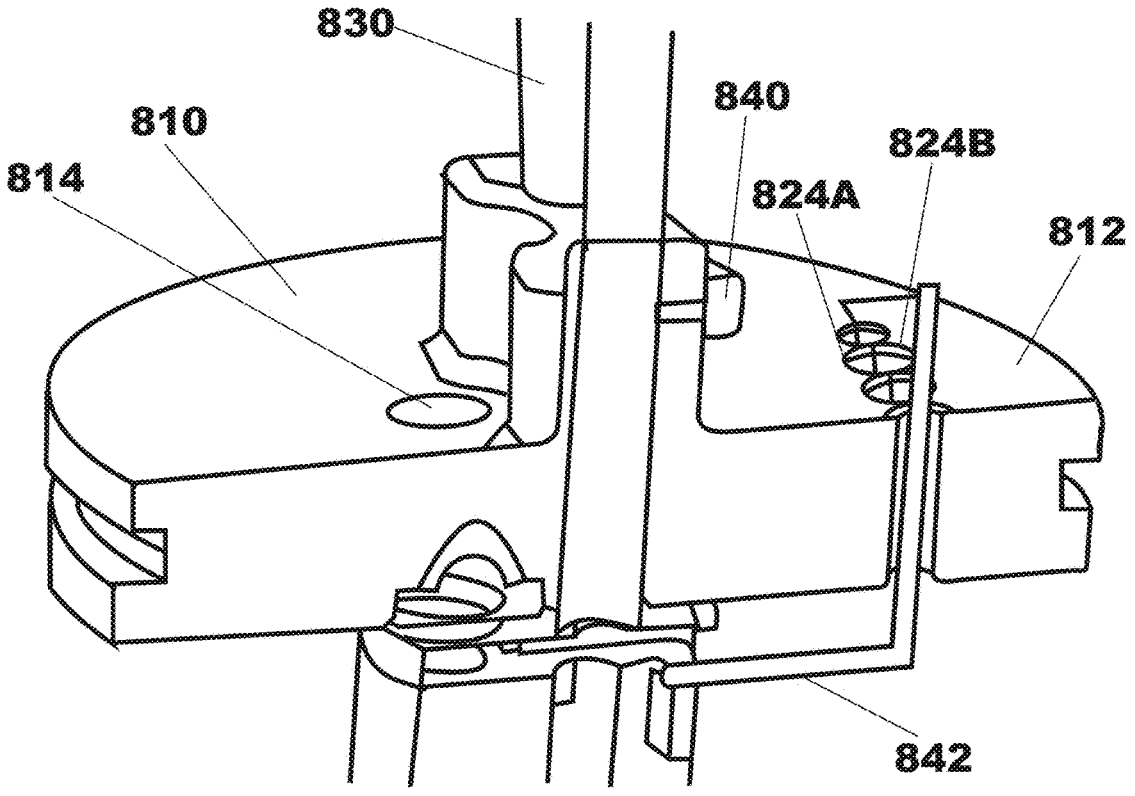
FIG. 60 is a cutaway perspective view of a top cap, according to one embodiment.

As shown in FIGS. 59A, 59B, and 60, the top cap 804 is coupled to the support rods 830 with two threaded set screws 840. The set screws 840 are threaded through lumens 818 as best shown in FIG. 59B. More specifically, the set screws 840 can be screwed into the threaded lumens 818 until the screws 840 contact the support rods 830. The set screws 840 are configured to exert pressure on the support rods 830, thereby creating frictional resistance that helps to secure the support rods 830 and thus the device 808 to the top cap 804.

As best shown in FIG. 60, a connection cable 842 that is coupled at its distal end to the robotic device 808 is positioned through one of the lumens 824. It is understood that other cables can be positioned through the additional lumens 824 as well. In accordance with one embodiment, the cables are positioned in the channels 824A or 824B prior to coupling the harness 812 to the body 810. Alternatively, one or more of the cables can be inserted through one of the lumens 824 after the body 810 and harness 812 are coupled together.

Figure 61A:
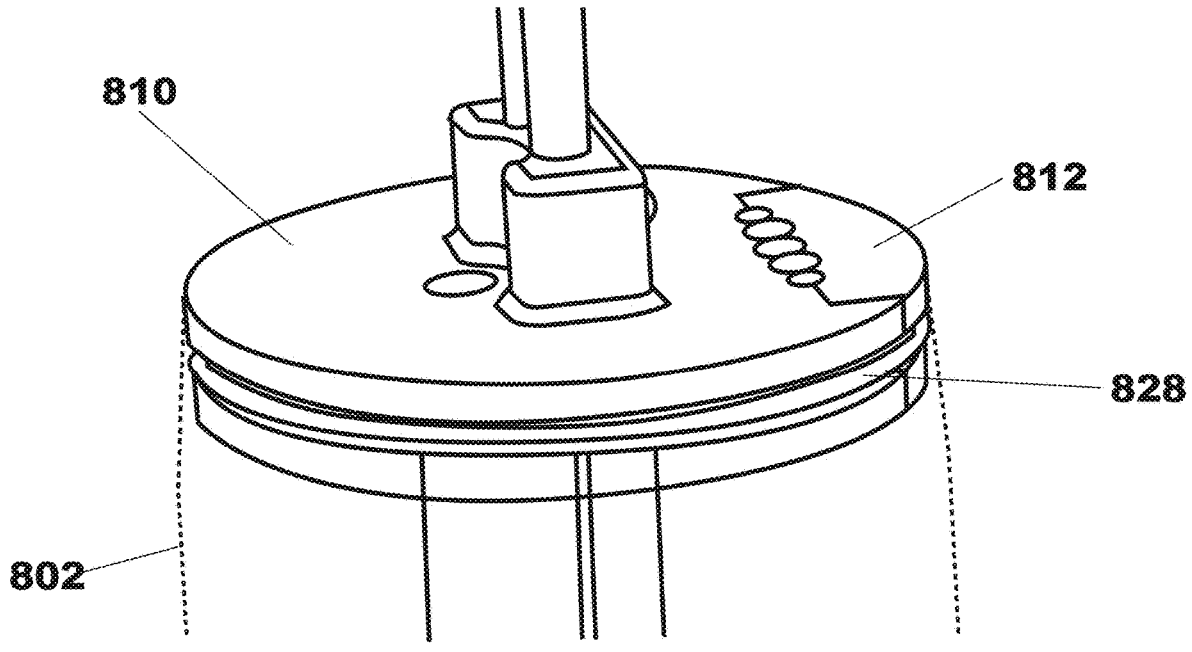
FIG. 61A is a perspective side view of a top cap coupled to a canister with a portion of a device assembly positioned therethrough, according to one embodiment.
Figure 61B:
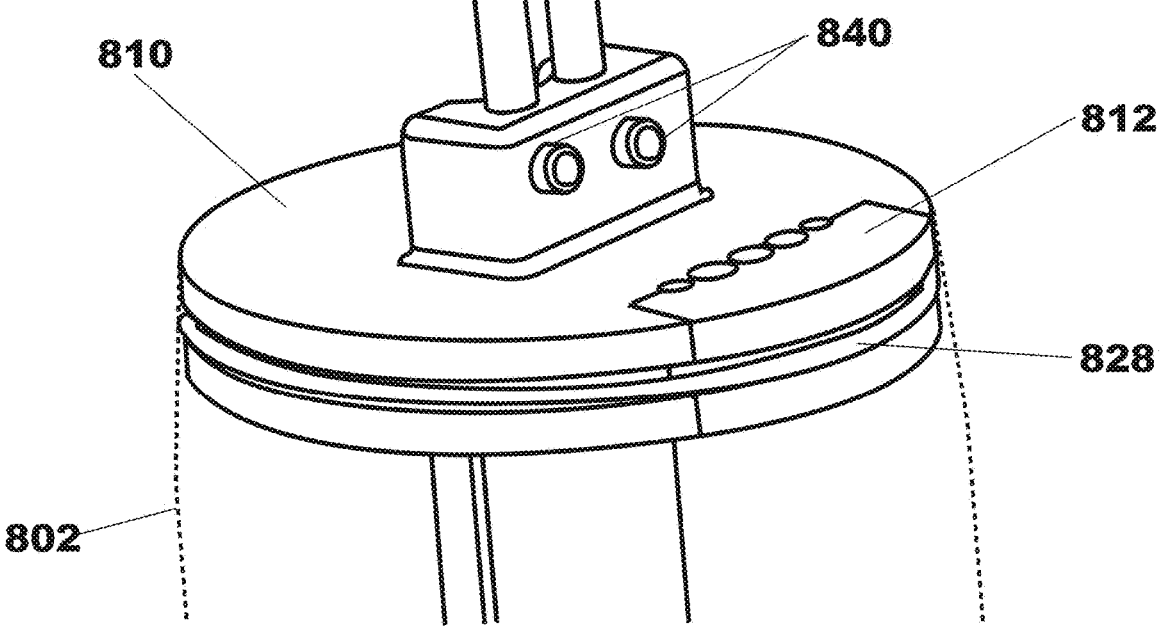
FIG. 61B is another perspective side view of the top cap of FIG. 61A.

FIGS. 61A and 61B show the container 802 coupled to the top cap 804.

Figure 62A:
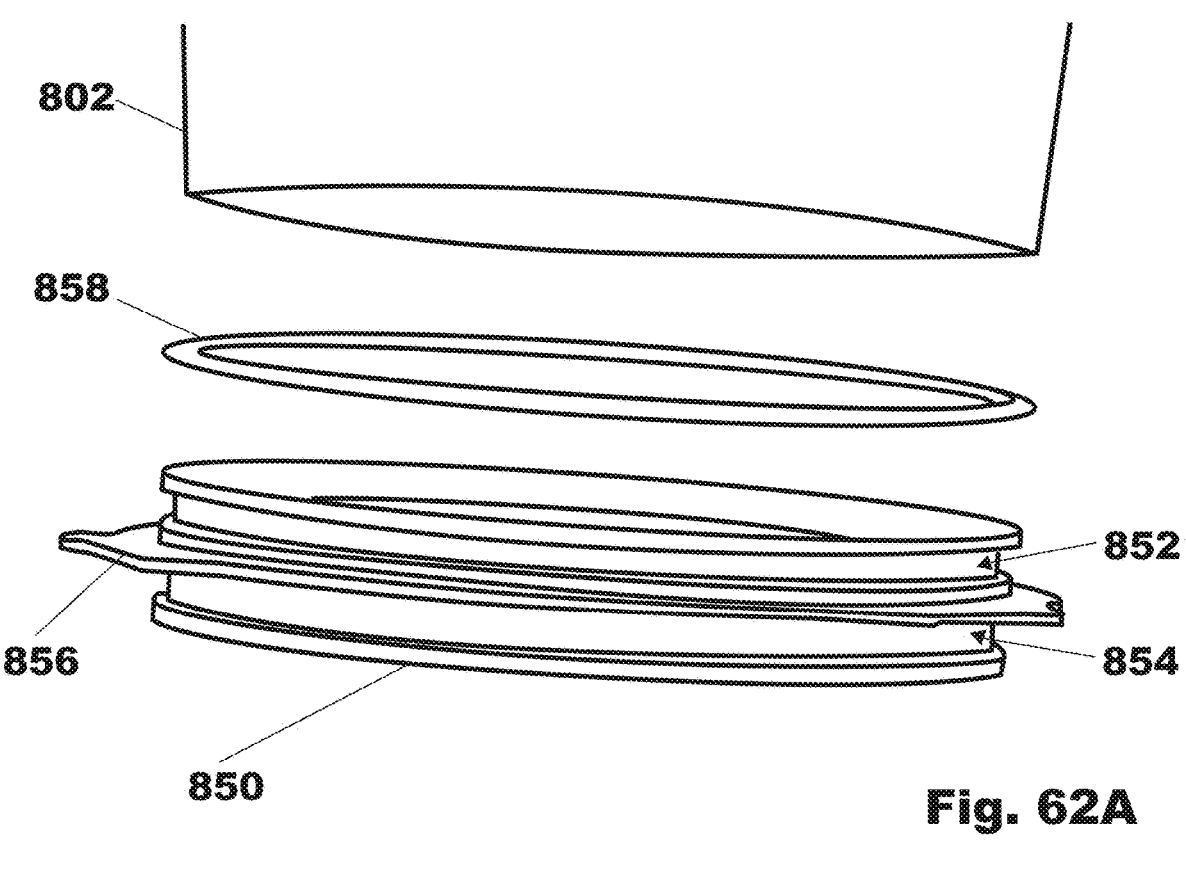
FIG. 62A is a perspective side view of a base coupling component, according to one embodiment.
Figure 62B:
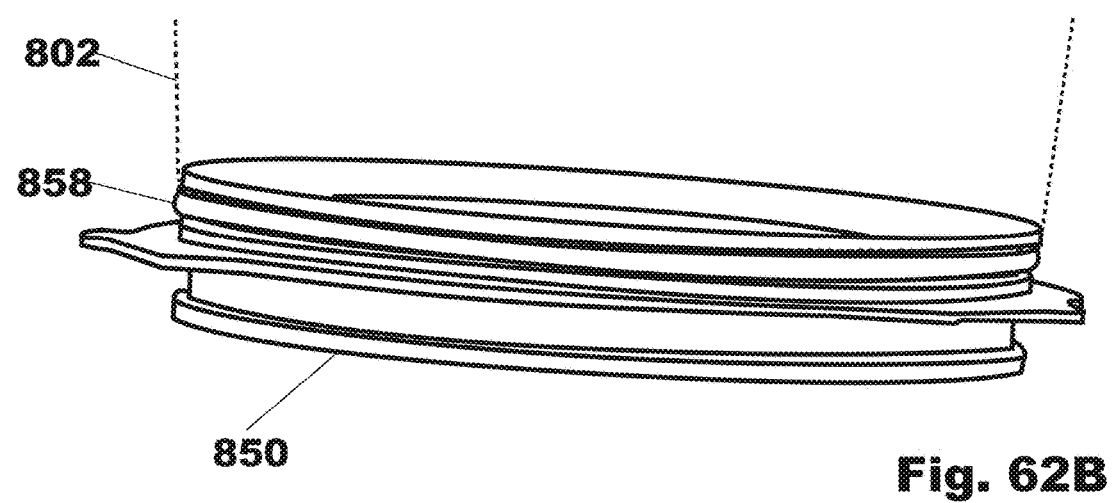
FIG. 62B is another perspective side view of the base coupling component of FIG. 62A.

FIGS. 62A and 62B depict the base coupling component (also referred to as the "base coupler") 850 that is coupled to a bottom portion of the container 802. The base coupler 850 has an upper groove 852, a lower groove 854, and three coupling protrusions (also referred to as "coupling notches") 856 that extend from a portion of the coupler 850 between the upper and lower grooves 852, 854.

Like with the top cap 804 described above, the container 802 is coupled to the base coupler 850 using an O-ring 858. More specifically, the container 802 is positioned over the upper portion of the coupler 850 such that the container 802 is positioned over the upper groove 852 and adjacent to or against the three protrusions 856. The O-ring 858 is positioned over the container 802 at the upper groove 852 such that the O-ring 858 urges a portion of the container 802 into the groove 852, thereby creating a fluidic seal between the container 802 and the base coupler 850.

FIGS. 63A, 63B, 63C, 63D, and 63E depict the coupling of the base coupler 850 to the access port 806. The access port 806 has a top portion (or "top ring") 860, a bottom portion (or "bottom ring") 862, and a middle portion (or "neck") 864. The top ring 860 has three coupling protrusions (also referred to as "coupling tabs") 866 that extend from a portion of the top ring 860 and are configured to mate with the coupling notches 856.

In one embodiment, the access port 806 is a known standard device used in hand-assisted laparoscopic surgery. As is understood in the art, the access port 806 provides a structured open pathway through the cavity wall, such as the abdominal wall. at the incision site. In one particular example, the access port 806 is a commercially available retractor port 806 called the DEXTRUS® Retractor, which is available from Ethicon Endo-Surgery.

Figure 63A:
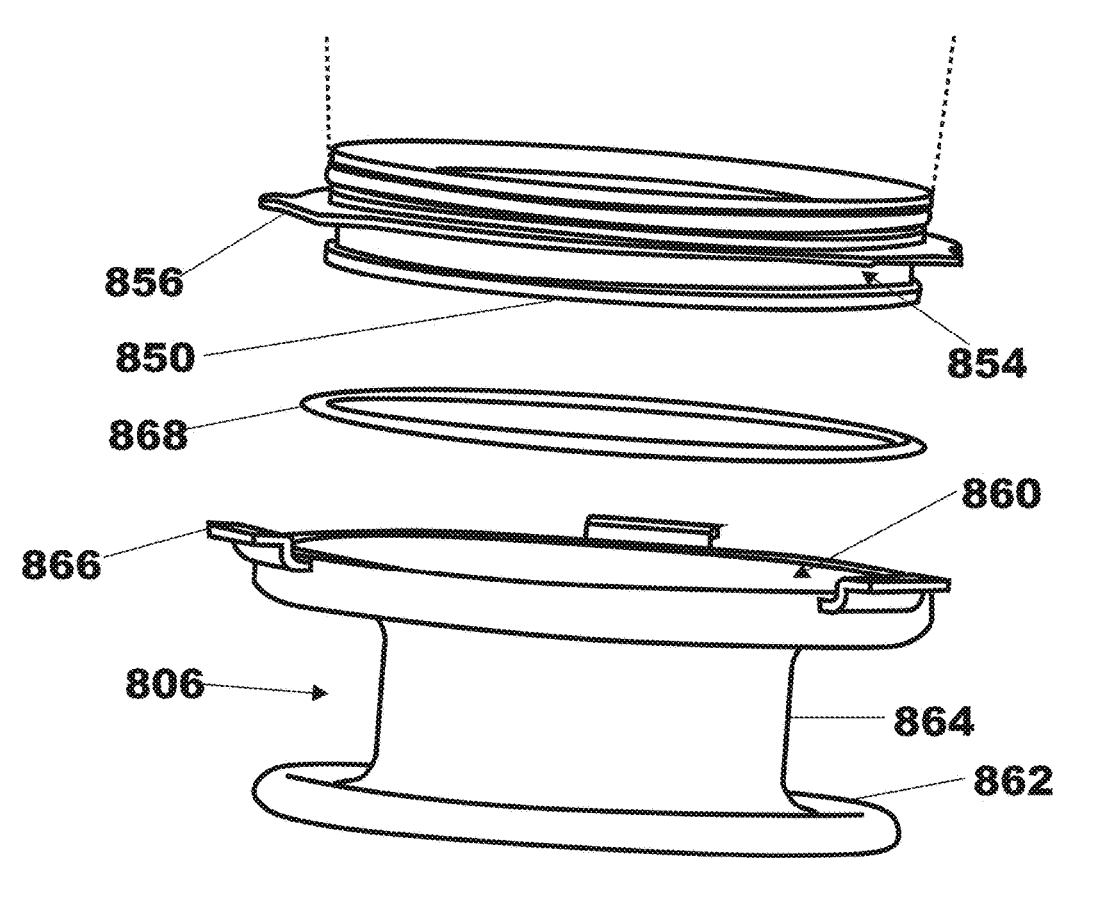
FIG. 63A is a perspective side view of a base coupling component and an access port, according to one embodiment.
Figure 63B:
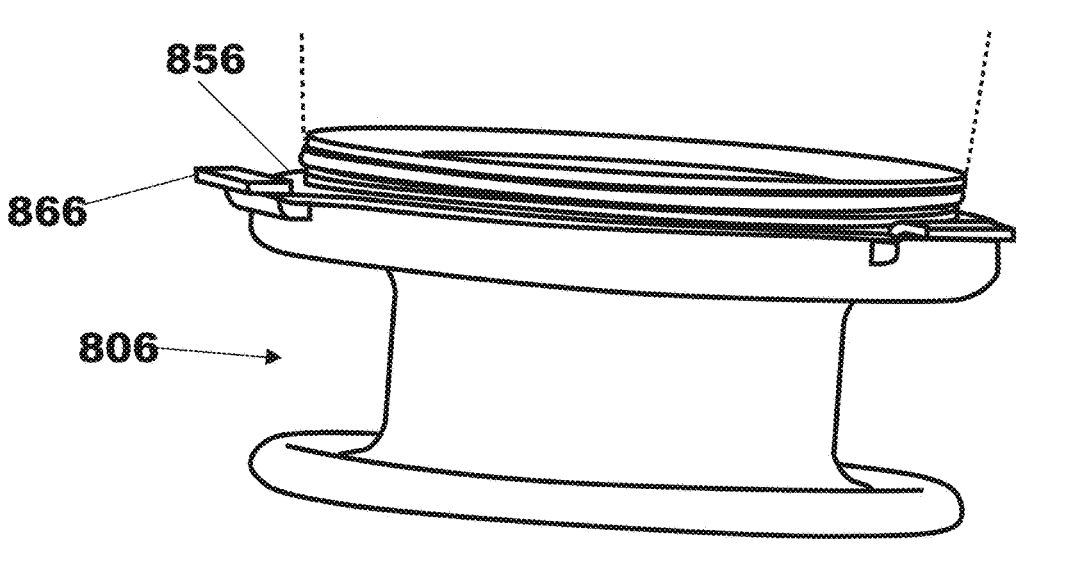
FIG. 63B is another perspective side view of the base coupling component and the access port of FIG. 63A.

As best shown in FIGS. 63A and 63B, the base coupler 850 is coupled to the access port 806 using an O-ring 868. More specifically, the O-ring 868 is positioned in the lower groove 854 of the coupler 850 and the top ring 860 is positioned over the lower portion of the coupler 850 and the O-ring 868 in the groove 854 such that the O-ring 868 is compressed between the coupler 850 and the top ring 860, thereby creating a fluidic seal between those two components.

Figure 63C:
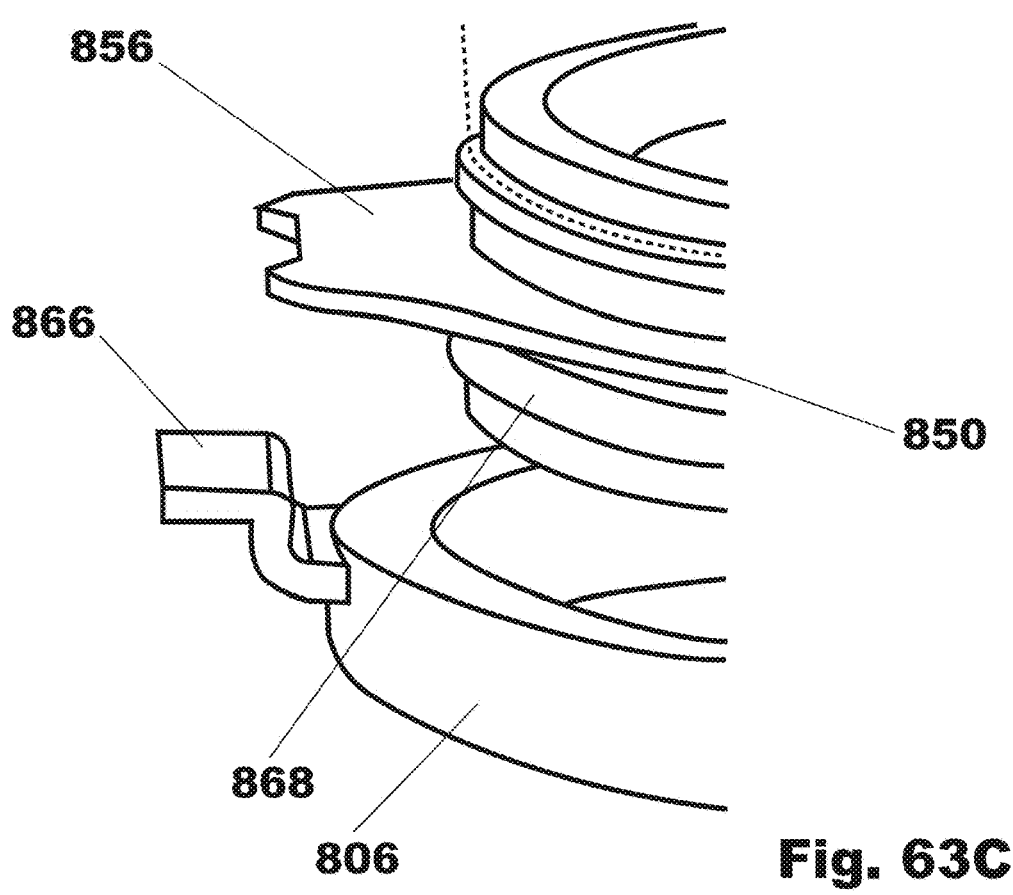
FIG. 63C is a perspective side view of a portion of the base coupling component and the access port of FIG. 63A.
Figure 63D:
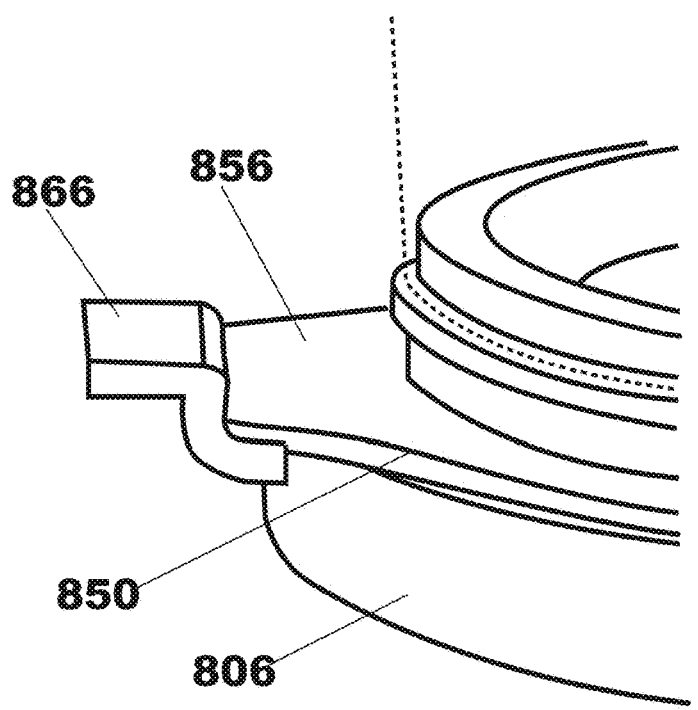
FIG. 63D is another perspective side view of a portion of the base coupling component and the access port of FIG. 63A.

As best shown in FIGS. 63C and 63D, as the top ring 860 is positioned over the lower portion of the coupler 850 and the O-ring 868 as described above, the coupling tabs 866 of the access port 806 are coupled with the coupling notches 856 of the base coupler 850, thereby enhancing the stability of the coupling of the coupler 850 and the access port 806.

Figure 63E:
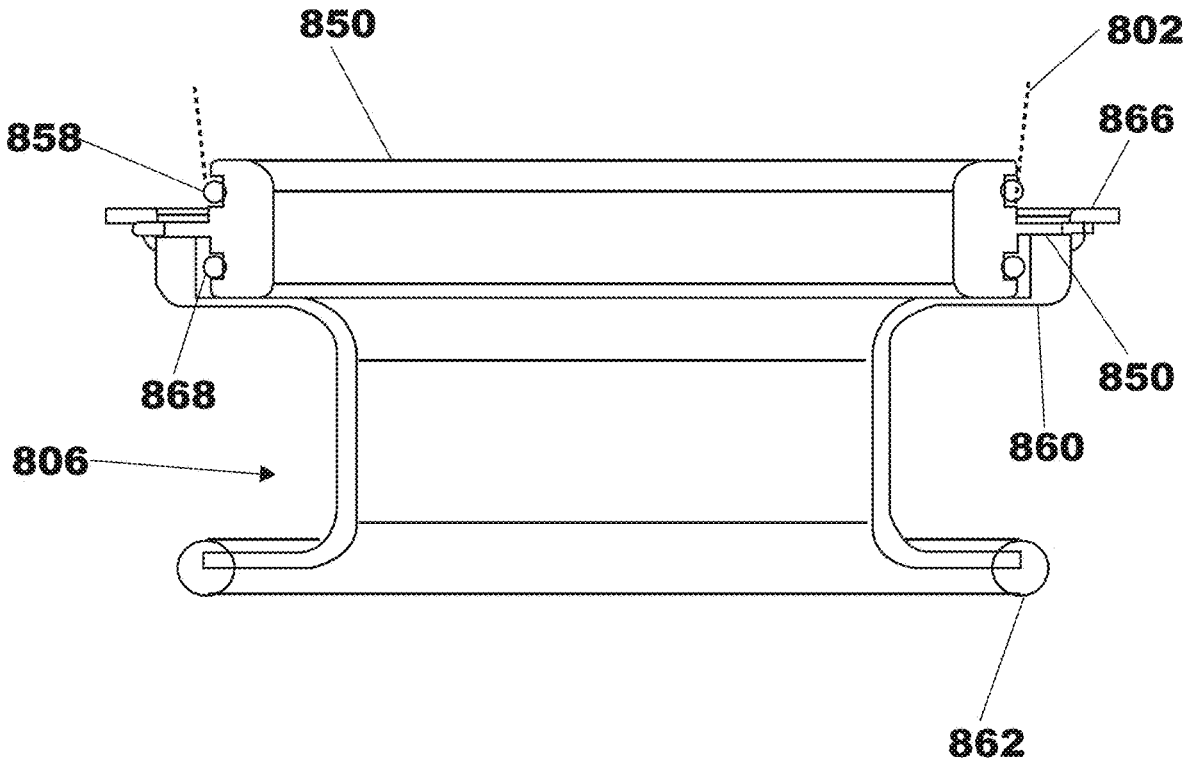
FIG. 63E is a cutaway side view of the base coupling component and the access port of FIG. 63A.
Figure 64A:
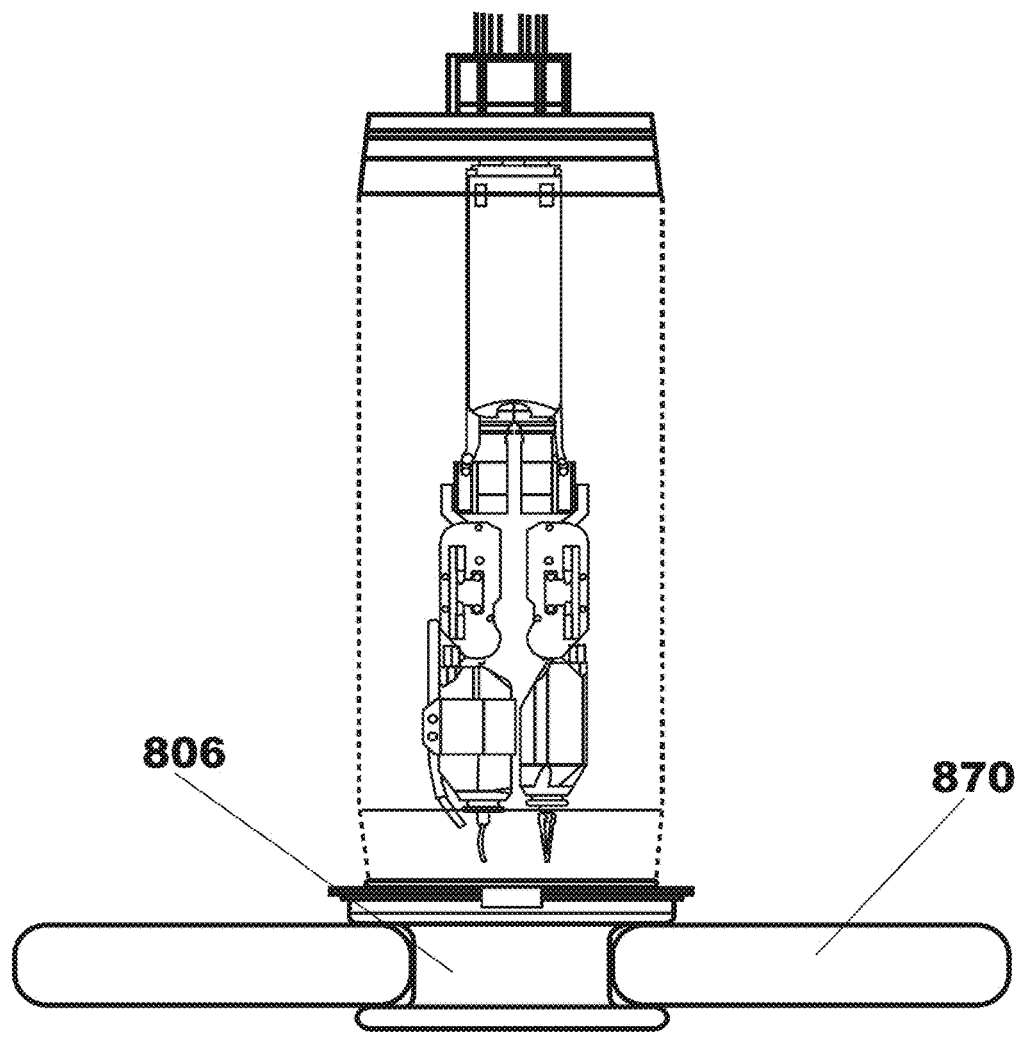
FIG. 64A is a side view of an external pressurized system or apparatus with a base coupling component and access port, according to one embodiment.
Figure 64B:
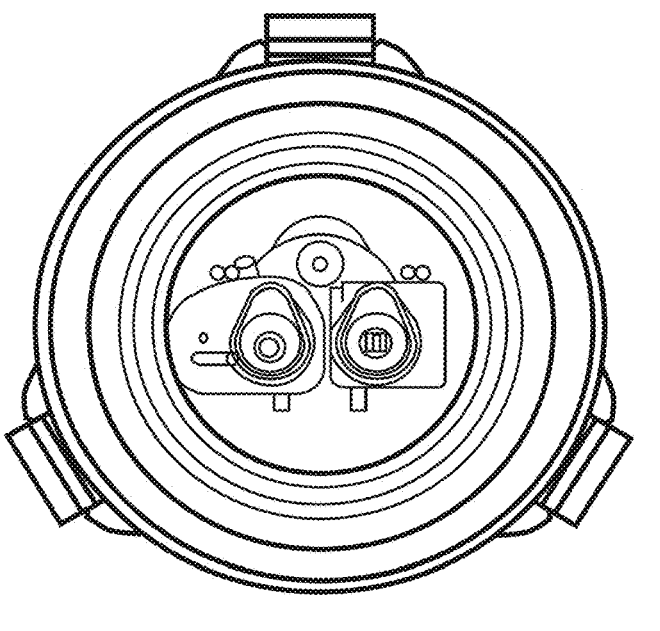
FIG. 64B is a top view of the external pressurized system of FIG. 64A.
Figure 66A:
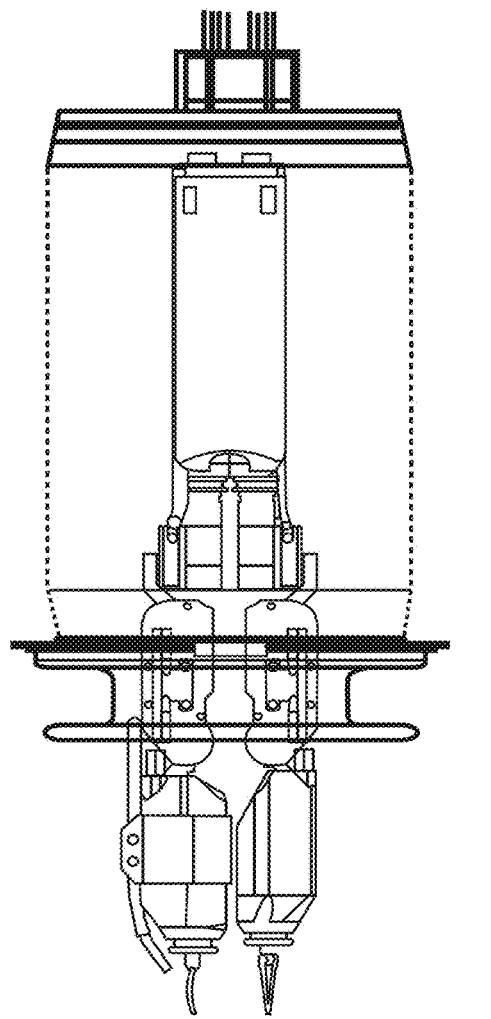
FIG. 66A is a side view of an external pressurized system or apparatus when the robotic device is lowered through an opening created by an access port, according to one embodiment.
Figure 66B:
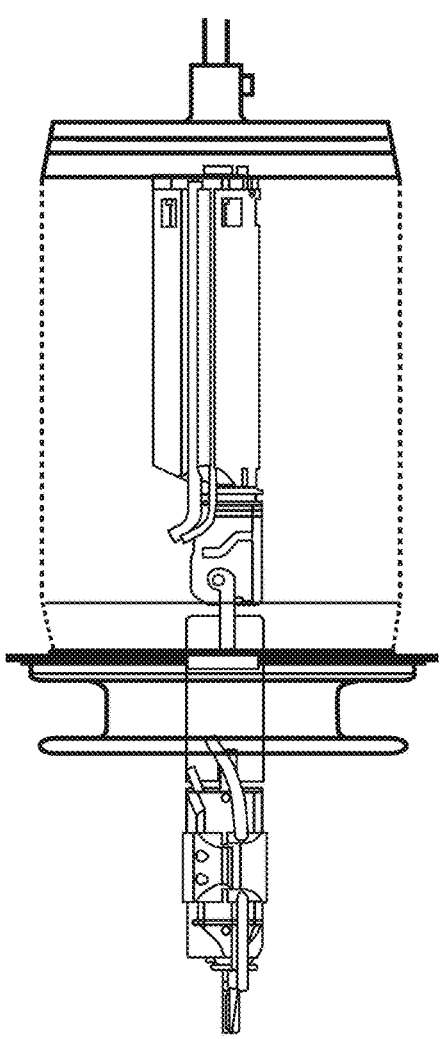
FIG. 66B is another side view of the external pressurized system or apparatus of FIG. 66A.

FIG. 63E depicts the entire coupling of the container 802 to the access port 806 via the coupler 850 as described above. Further, FIGS. 64A and 64B depict the external pressurized insertion device 800 in use, with the device 800 coupled to an access port 806 that is positioned in an incision in a patient's skin 870.

In use, according to one embodiment, the access port 806 and the external pressurized device 800 are positioned for a surgical procedure in the following manner. As an initial matter, according to one embodiment, the robotic device 808 is positioned inside the insertion device 800 prior to placing the port 806 and the device 800 in the appropriate surgical position. That is, the robotic device 808 is positioned inside the container 802, the support rods 830 coupled to the device 808 are secured to the top cap 804 with the set screws 840, any connection cables coupled to the device 808 are positioned through the lumens 824 in the top cap 804, and the flexible container 802 is coupled and fluidically sealed to the top cap 804 and the base coupler 850 via the O-rings 828, 858. Alternatively, the robotic device 808 is positioned inside the insertion device 800 after positioning the port 806 and device 800. Regardless, as far as positioning the port 806 and device 800, the port 806 is positioned first in certain implementations. That is, in one embodiment, the bottom ring 862 is first inserted through the incision previously made in the patient's cavity wall. Once the ring 862 is positioned through the incision and inside the cavity, the ring 862 can help constrain the entire port 806 within the incision by expanding to a diameter that is greater than the diameter of the incision, as best shown in FIG. 64A. In one embodiment, the container 802 and the coupler 850 are coupled to the access port 806 prior to positioning the port 806 in the incision. Alternatively, the port 806 is first positioned in the incision, and then the coupler 850 and the container are coupled to the port 806. Regardless, once the access port 806 and insertion device 800 are positioned, the patient's cavity can then be insufflated. Due to the fluidic communication between the cavity and the interior of the container 802 that is created by the access port 806, the entire interior of the insertion device 800 will be under the same pressure as the cavity.

In accordance with one implementation, once the access port 806 and insertion device 800 are positioned correctly, the process of inserting the robotic device 808 into the patient's insufflated cavity can take place in the following manner as best shown in FIGS. 65A-69B. Initially, the robotic device 808 begins with both arms parallel and vertical to the incision, as best shown in FIGS. 65A and 65B. Then, the robot 808 is lowered through the opening created by the access port 806 as shown in FIGS. 66A and 66B. In accordance with one embodiment, as best shown by comparing FIGS. 65A and 65B with FIGS. 66A and 66B, as the robot 808 is lowered, the flexible container 802 shrinks in height by allowing portions of the flexible material of the container 802 to "crumple" or begin forming folds such that the top cap 804 moves closer to the access port 806.

As best shown in FIGS. 67A and 67B, according to one embodiment, once the "elbow joints" of the arms of the robotic device 808 have cleared the cavity wall and access port 806, the forearms are rotated at the elbow joints until the forearms are positioned at an angle of or near 45° in relation to the upper arms (as best shown in FIG. 67A). Concurrently, the "upper arms" are rotated at the "shoulder joints" until the upper arms are positioned at an angle of or near 20°, as best shown in FIG. 67B. This rotation of the forearms and upper arms can help to ensure that the device 808 will fit within the patient's target cavity so that any contact of the robotic device 808 with any internal tissues or organs is minimized or eliminated. Alternatively, the forearms and upper arms can be rotated to any angle that minimizes the risk of contact with tissues or organs.

Figures 68A, 68B:
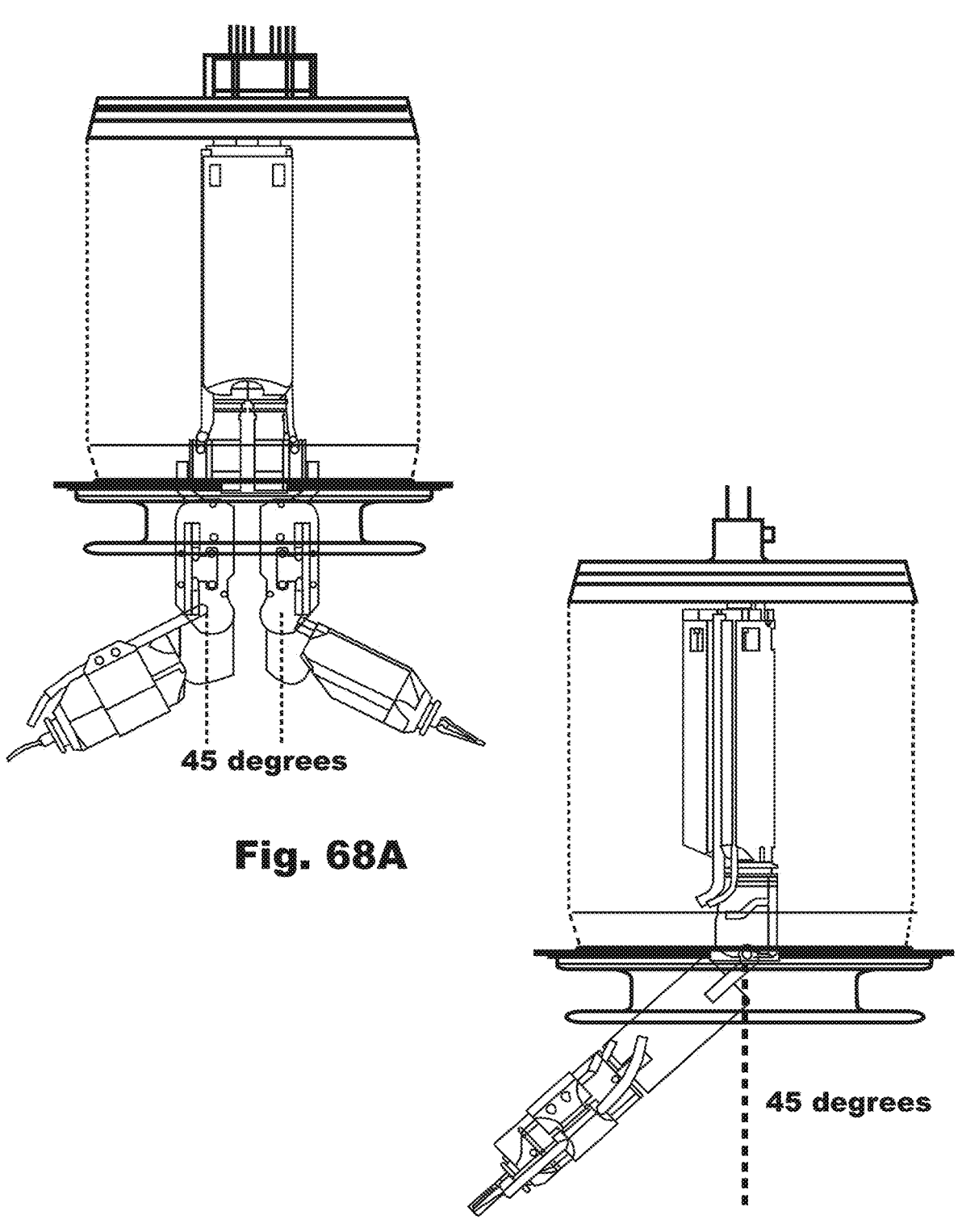

As best shown in FIGS. 68A and 68B, according to one embodiment, the device 808 can be inserted further into the patient's cavity by further positioning the arms of the device 808 while the container 802 continues to crumple, thereby resulting in further shrinkage of the insertion device 800. More specifically, the upper arms can be rotated further until they are positioned at an angle of or near 45°, as best shown in FIG. 68B. This process of moving the device 808 further into the cavity while positioning the arms to avoid contact with organs or tissues and causing the container 802 to crumple is continued until the shoulder joints of the device 808 have cleared the cavity wall and access port 806.

Figure 69A:
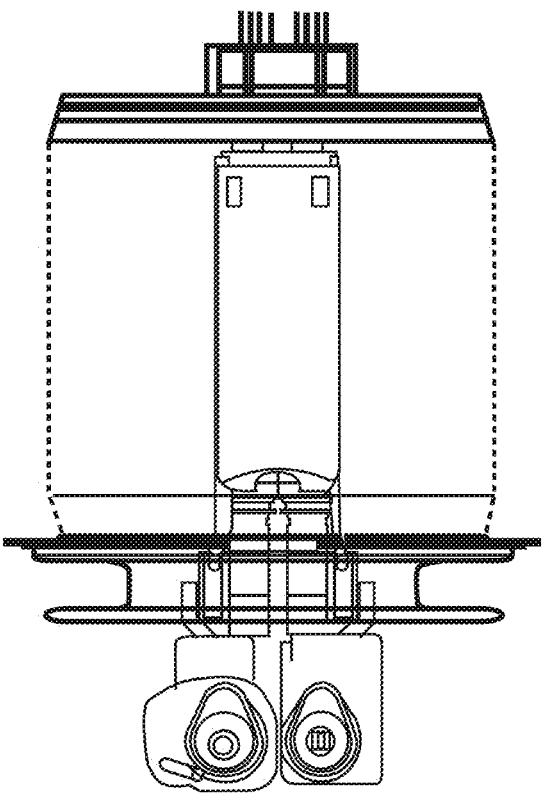
Figure 69B:
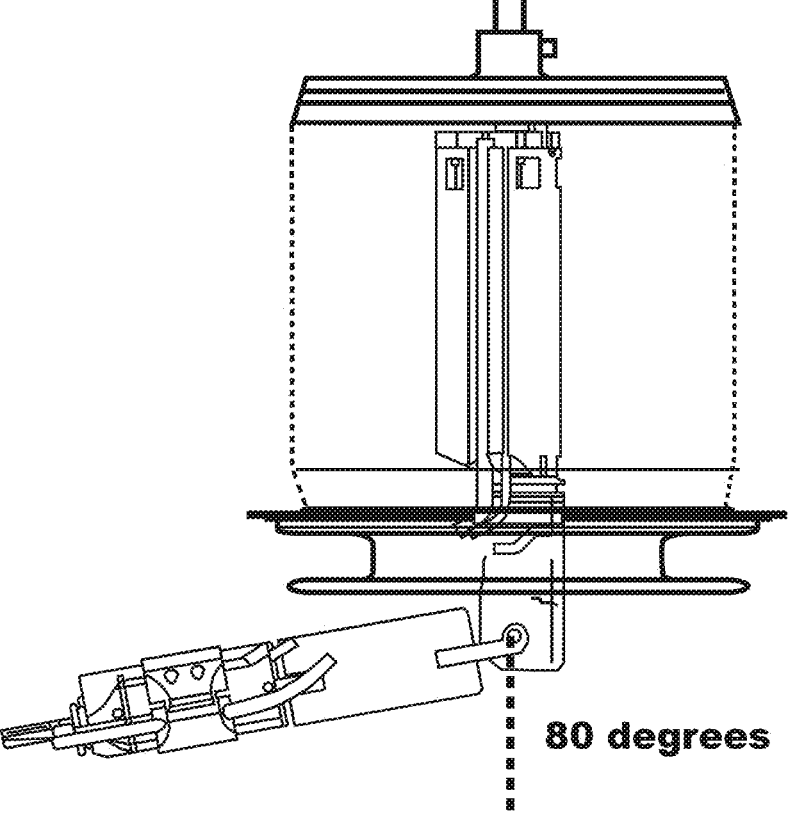

At this point, as best shown in FIGS. 69A and 69B, the forearms can be rotated back to center and the upper arms can be further rotated up, leaving the arms in an appropriate starting position for a surgical procedure. Once in the desired starting position, the device 808 can be locked or otherwise stabilized in place using a known external clamping mechanism such as, for example, an Iron Intern®, which is commercially available from Automated Medical Products Corp.

Figure 70:
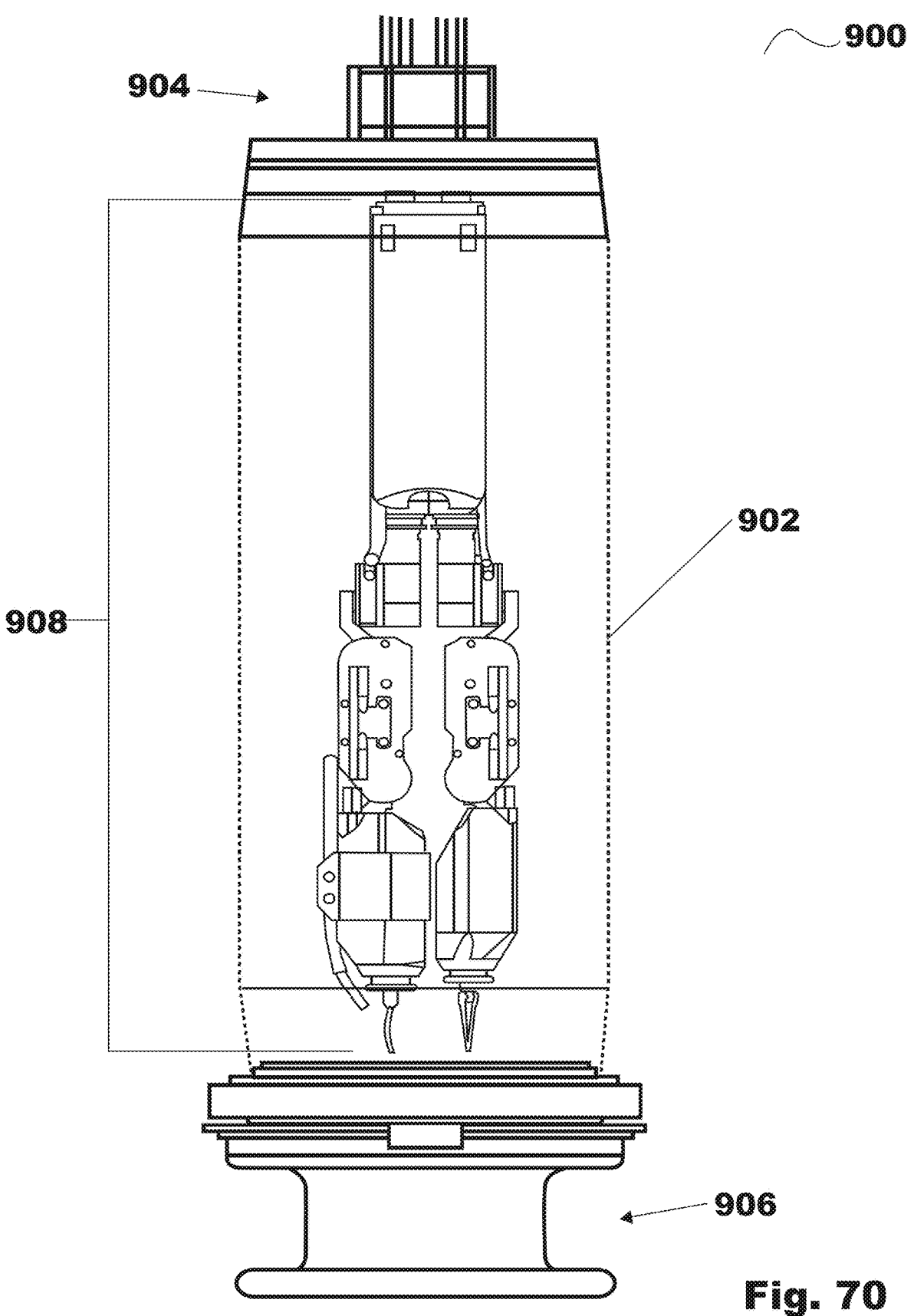

FIG. 70 depicts another implementation of an external pressurized system or apparatus 900. The apparatus 900 has a container 902 with a top cap 904 coupled to a top portion of the container 902. In this embodiment, the container 902 has a port 906 that is coupled to the container 902 at a base portion of the container 902. The port 906 is configured to be positionable in an incision in the skin of the patient, thereby providing access to a cavity of the patient. As shown in FIG. 70, the apparatus 900 is configured to receive a surgical device 908 such that the device 908 can be inserted into the patient cavity through the port 906 of the apparatus 900.

According to one embodiment, like the container 802 described above and depicted in FIGS. 55-69B, the container 902 in this device 900 is made of a flexible material such as, for example, polyethylene plastic, latex, nylon, or silicone rubber.

In this embodiment, the top cap 904, the container 902, and the robotic device 908 are substantially similar to the top cap 804 and container 802 depicted and described above. All the various features and components described above apply to these top cap 904, container 902, and device 908 embodiments as well.

Figure 71A:
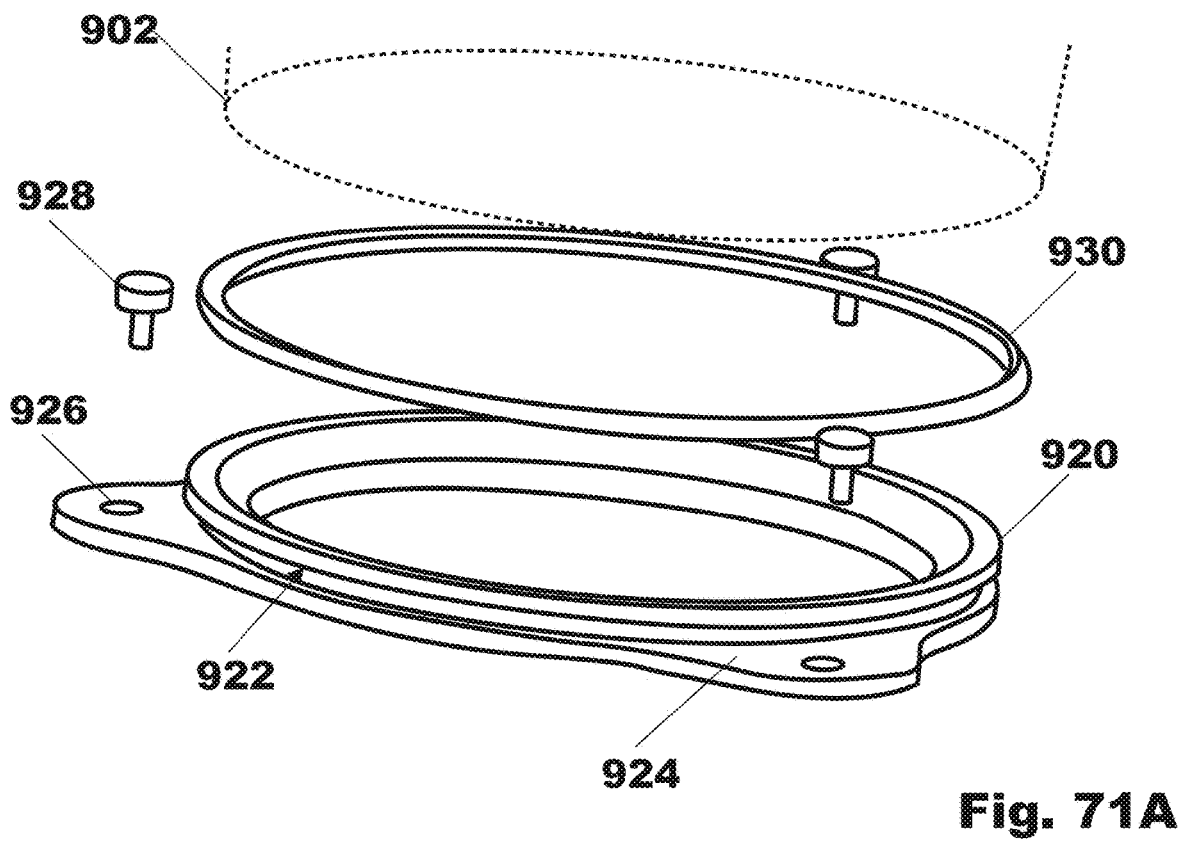
Figure 71B:
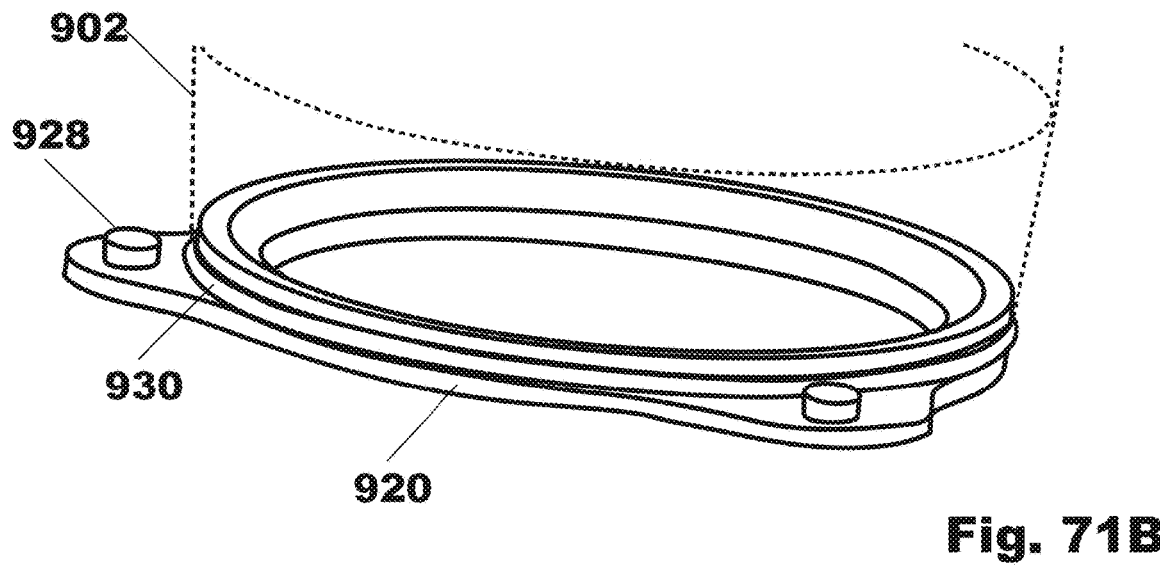

FIGS. 71A and 71B depict the base coupling component (also referred to as the "base coupler") 920 that is coupled to a bottom portion of the container 902. The base coupler 920 has a groove 922 and three coupling protrusions 924 that extend from the coupler 920. In accordance with one implementation, each of the coupling protrusions 924 has a lumen 926 configured to receive a thumb screw 928. The container 902 is coupled to the base coupler 920 using an O-ring 930. More specifically, the container 902 is positioned over the upper portion of the coupler 920 such that the container 902 is positioned over the groove 922 and adjacent to or against the three protrusions 924. The O-ring 930 is positioned over the container 902 at the groove 922 such that the O-ring 930 urges a portion of the container 902 into the groove 922, thereby creating a fluidic seal between the container 902 and the base coupler 920.

In this embodiment, the insertion device 900 has a port attachment 940 that is coupleable to the base coupler 920 and the access port 906 such that the port attachment 940 is positioned between the coupler 920 and the port 906. The port attachment 940 has a removable lid 944 that maintains a fluidic seal when the lid 944 is in place on the port attachment 940, thereby making it possible to maintain insufflation of the patient's cavity even when the insertion device 900 is not yet coupled to the access port 906.

Figure 72A:
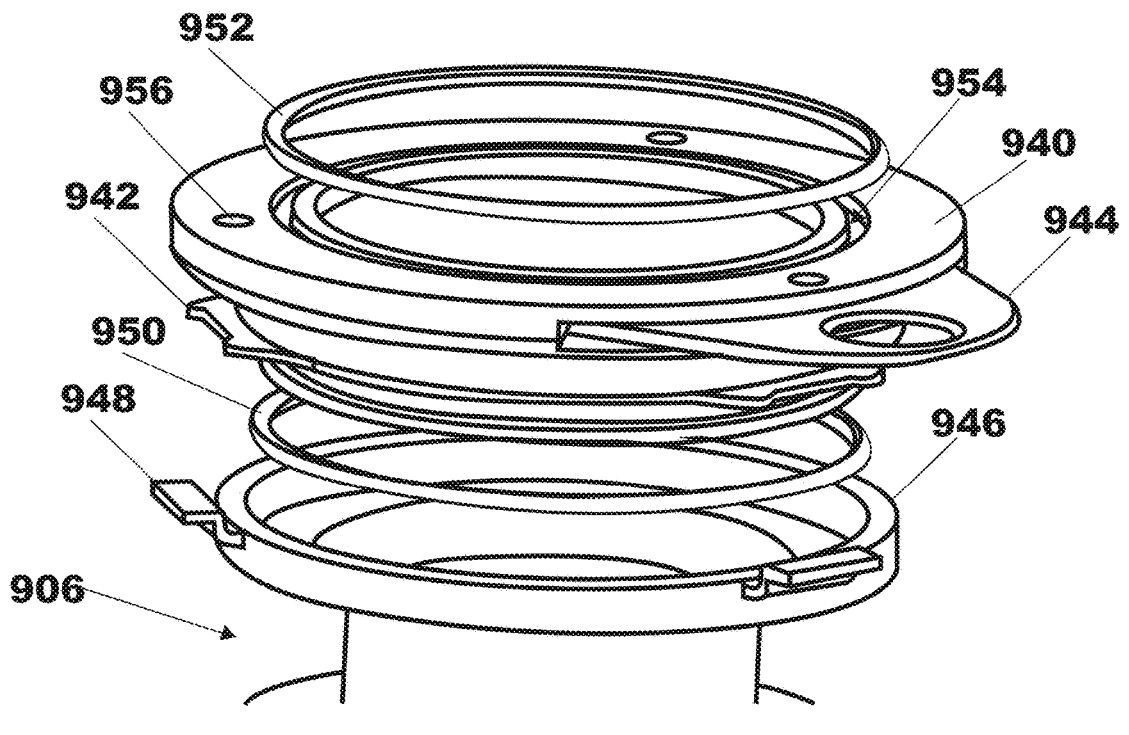
Figure 72B:
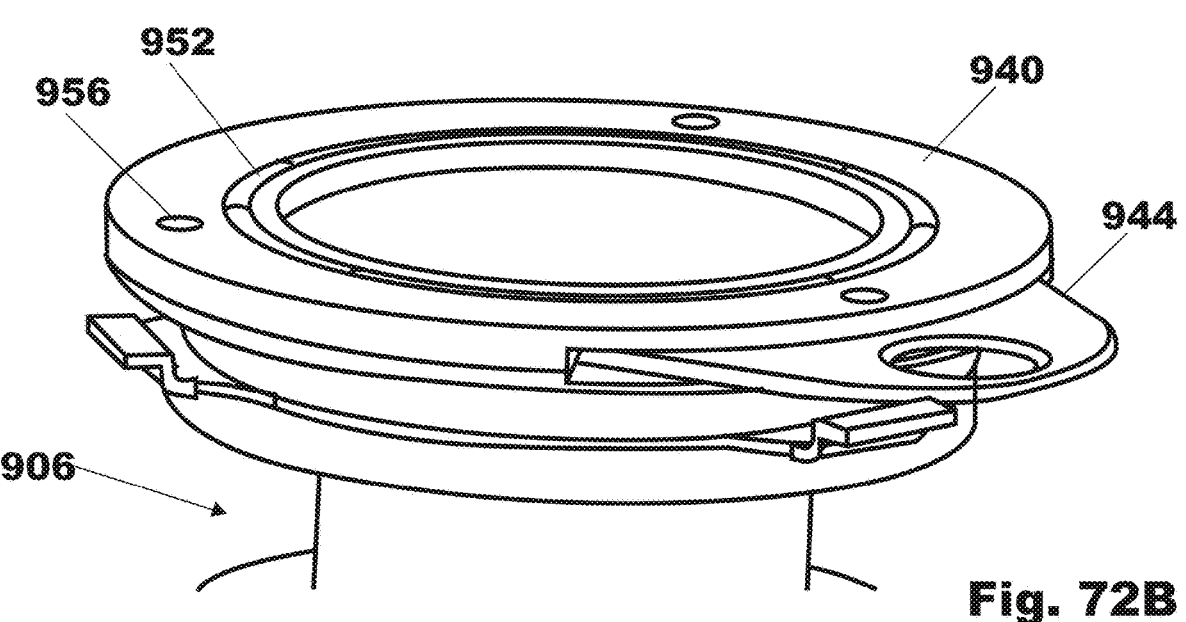

FIGS. 72A and 72B depict the coupling of the port attachment 940 to the access port 906. The port attachment 940 has three coupling notches 942 similar to the coupling notches 856 described and depicted above. In addition, the port attachment 940 has a removable lid 944 (also referred to as a "removable seal component," "removable lid seal component," or "removable seal component") that provides a fluidic seal when it is positioned in its closed position in relation to the port attachment 940. In the embodiment depicted in FIGS. 72A and 72B, the removable lid 944 is a slidable lid 944.

Like the access port 806 described and depicted above, this access port 906 (as best shown in FIG. 72A) has a top ring 946 that has three coupling protrusions (also referred to as "coupling tabs") 948 that extend from a portion of the top ring 946 and are configured to mate with the coupling notches 942 in the port attachment 940.

As best shown in FIG. 72A, the port attachment 940 has an O-ring 950 that can be positioned between the port attachment 940 and the access port 906 such that the O-ring 950 creates a fluidic seal when the two components are coupled together.

In use, the port attachment 940 can be coupled to the access port 906 by positioning the bottom portion of the port attachment 940 in the top portion of the top ring 946 with the O-ring 950 positioned between the two components, with the coupling notches 942 on the port attachment 940 mating with the coupling protrusions 948 on the top ring 946.

The port attachment 940 also has another O-ring 952 that is configured to be positioned in the groove 954 formed in the top of the port attachment 940. In one embodiment, the O-ring 952 can be placed in the groove 954 to help create an airtight seal when the port attachment 940 is coupled to the base coupler 920.

Further, the port attachment 940 also has three threaded lumens 956 in the top of the attachment 940. In one embodiment, these lumens 956 are configured to receive the thumb screws 928 that are positioned through the lumens 926 in the base coupler 920, thereby allowing for coupling the base coupler 920 to the port attachment 940 via the screws 928. Of course, it is understood that other coupling mechanisms besides thumb screws can be used. In various alternative embodiments, any known attachment or coupling mechanism or component can be used. Some non-limiting examples include magnets, quick clamps, quarter turn features, snap-in features, and the like.

Figure 73A:
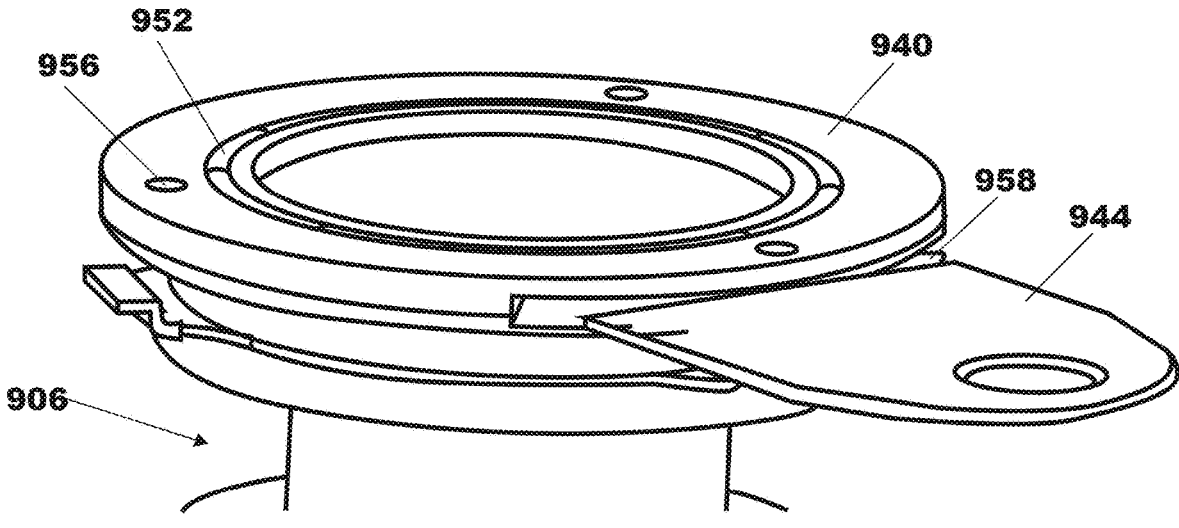
Figure 73B:
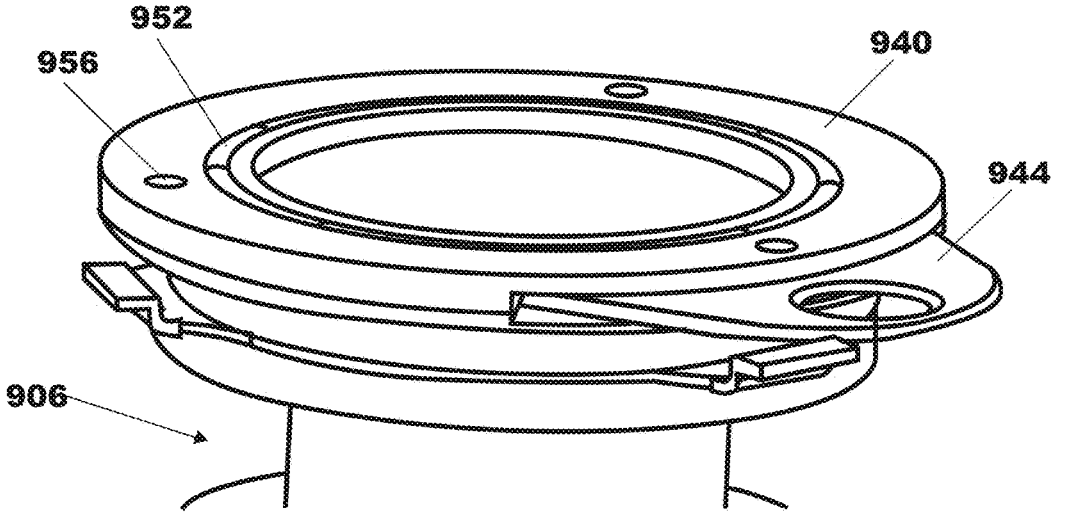

As best shown in FIGS. 73A and 73B, the slidable lid 944 can be moved between a closed position (as shown in FIG. 73B) and an open position (as shown in FIG. 73A). In this embodiment, the slidable lid 944 is positioned in the port attachment 940 via a lid slot 958 in the port attachment 940. In the open position, tools or robotic devices can be passed through the port attachment 940 and the access port 906. In the closed position, a fluid seal is established between the lid 944 and the port attachment 940, which makes it possible to insufflate the patient's cavity prior to attaching the insertion assembly 900. It is understood that while this embodiment of the removable lid 944 is a slidable lid 944, any other known method or device for establishing a fluidic seal could be used. Non-limiting examples include a mechanical iris, leaf shutter, or any other known method of providing a removable fluidic seal.

FIGS. 74A and 74B depict cross-sectional views of the entire lower subassembly as described above, including the base coupler 920, the port attachment 940, and the access port 906. More specifically, FIG. 74A shows the port attachment 940 coupled to the access port 906, with the slidable lid 944 fully inserted into the port attachment 940 in the closed position, thereby creating a fluidic seal. FIG. 74B shows all three components coupled together, including the base coupler 920, the port attachment 940, and the access port 906.

FIGS. 75A, 75B, and 75C depict the external pressurized insertion device 900 in use, according to one embodiment. Once the access port 906 is positioned in the incision as discussed above, the port attachment 940 can be coupled to the port 906, as best shown in FIG. 75A. With the slidable lid 944 in the closed position, a fluidic seal is established between the port attachment 940 and the port 906 such that the patient's cavity can be insufflated to the desired Insufflation pressure. The insertion device 900 can then be coupled to the port attachment 940 as best shown in FIG. 75B. Once the base coupler 920 is coupled to the port attachment 940 such that a fluidic seal is established between the two components, the slidable lid 944 can then be moved to its open position (or fully remove) as best shown in FIG. 75C, thereby providing fluidic communication between the patient's cavity and the interior of the insertion device 900, resulting in equalized pressure in the device 900 and the cavity. The robotic device 908 can be inserted via any of the same steps as described previously. If the device 908 completes the desired surgical procedure and a different robotic device or other type of tool needs to be used, the robotic device 908 can be removed from the cavity, the slidable lid 944 can be replaced in the closed position, and the base coupler 920 can be removed from port attachment 940. This allows pressure to be maintained within the cavity, even during tool changes.

FIG. 76 depicts an alternative embodiment having a top cap 960 that has a pressure relief valve 962. During the process of lowering either of the robotic devices 808, 908 out of the insertion device embodiments 800, 900 and into the cavity as described above with respect to insertion devices 800 and 900, there is a pressure increase in the patient's cavity due to the decreasing change in volume of the container 802, 902. The pressure relief valve 962 can be configured to release pressure if the internal insufflation pressure increases above a typical value, thereby aiding the process of inserting the robotic device 808, 908 such that the attendant will not need to wait for the pressure to equalize between the cavity and the insertion device 800, 900.

Another implementation of a top cap 1000 having a pressure relief valve 1002 is depicted in FIGS. 77A and 77B. This cap 1000 also has a dual port seal component 1004 that can be configured to receive one or more surgical instruments or devices such as a standard laparoscopic tool. Alternatively, it is contemplated that a top cap can have only one of the pressure relief valve 1002 or the dual seal component 1004.

As best shown in FIG. 77B, according to one implementation, the pressure relief valve 1002 has an adjustment component (also referred to as an adjustment "door," "wall," or "button," or "block") 1006 that is operably coupled to (or positioned against) one end of a tension spring 1008 and has two holes 1010A, 1010B that are configured to receive retention mechanisms such as bolts, screws, or other such standard devices or components configured to hold the adjustment component 1006 in place. The other end of the spring 1008 is coupled to a valve ball 1012 that is positioned against a rim 1016 of an opening 1014 on the underside of the top cap 1000. The spring 1008 is configured to urge the ball 1012 toward the opening 1014 such that the ball 1012 (which has a larger outer diameter than the inner diameter of the rim 1016) contacts the rim 1016 of the opening 1014 and thereby establishes a fluidic seal between the ball 1012 and the rim 1016. In this embodiment, the adjustment block 1006 is adjusted using the retention mechanisms to move the block 1006 toward or away from the ball 1012, thereby increasing or decreasing, respectively, the force applied by the spring 1008 against the ball 1012 (and thereby increasing or decreasing, respectively, the strength of the seal between the ball 1012 and the rim 1016 of the opening 1014). Thus, the adjustment block 1006 can be used to adjust the strength of the seal based on the target maximum pressure threshold such that when the target maximum pressure threshold is reached (such as while lowering either of the robotic devices 808, 908 out of the insertion device embodiments 800, 900 as described above), the ball 1012 is urged away from the rim 1016 and the seal between the rim 1016 and the ball 1012 is broken such that the pressure is reduced by the gas escaping through the valve 1002.

In an alternative embodiment, any known pressure relief valve for use in medical devices can be incorporated into the top cap 1000.

Continuing with FIG. 77B, the dual port seal component 1004 in this embodiment has two seal components: an elastic circular seal 1018 defining an opening 1020 and a flap seal 1022 in fluid communication with the circular seal 1018. The elastic circular seal 1018 is configured to form a strong seal around the smooth surfaces of a standard laparoscopic tool positioned through the opening 1020. In one implementation, the flap seal 1022 is a secondary seal that provides a fluid seal when no tool is positioned through the dual port seal component 1004. That is, when no tool is positioned therethrough, the two flaps 1024A, 1024B are urged into contact with each other by the pressure in the patient's insufflated cavity such that the two flaps 1024A, 1024B form a fluidic seal.

In an alternative embodiment, any known port seal component for use in establishing a fluidic seal with a laparoscopic tool positioned therethrough can be used.

According to various additional implementations, the insertion devices disclosed or contemplated herein can have one or more sensors or other types of measurement mechanisms for measuring the insertion depth of the surgical device being inserted into the patient's cavity.

As an example, FIGS. 78A, 78B, and 78C depict an automatic insertion device 1030 having a flexible container 1038 and an actuator and sensor package 1032. The actuator can be any known actuation device, including, for example, motor and gears, motor and timing belts, linear screw, pneumatics, hydraulics, or the like. The sensor could be any known sensing device, including, for example, a potentiometer, an encoder, optical sensors, or the like. When actuated, the actuator and sensor package 1032 lowers the surgical device 1034 through the incision. That is, as shown in FIG. 78B, the top portion of the device 1030 is urged toward the bottom portion of the device 1030 such that the overall height of the device 1030 is reduced and the surgical device 1034 is moved distally out of the bottom portion of the insertion device 1030. As the insertion occurs, the sensor in the package 1032 is configured to read the distance the surgical device 1034 has been inserted into the patient's cavity. Based on this distance, in one embodiment, the control program of the surgical device 1034 can actuate the motors of the surgical device 1034 to move the arms into desirable positions so as to avoid making contact with any organs or a cavity wall. The process can then be reversed to remove the surgical device 1034 from the incision. In another implementation, an additional actuator 1036 could be used to grossly position the surgical device 1034 during the insertion process or during the surgery in order to access multiple quadrants of the patient's cavity. This actuator 1034 rotates the upper portion of the insertion device 1030 relative to the access port. This rotation is possible because of the flexible nature of the container 1038.

FIG. 79 depicts another embodiment of an insertion device 1050 having one or more measurement mechanisms 1054 for measuring the insertion depth of the surgical device that is being inserted into the patient's cavity using the insertion device 1050. In this embodiment, the insertion depth of the surgical device is determined by measuring the relative distance between the top cap 1052 and the port 1056. Further, in this embodiment, the measurement mechanism 1054 is a sensor 1054 that is coupled to, integrated into, or otherwise associated with the top cap 1052. Alternatively, the top cap 1052 can have two or more sensors 1054. According to one embodiment, the sensor 1054 uses ultrasonic or infrared energy and transmits the energy toward the port 1056. The energy is reflected by the port 1056 back to the sensor 1054. In this embodiment, the sensor 1054 is a range finder that can utilize the energy reflected back from the port 1056 to determine the distance between the top cap 1052 and the port 1056. The distance between the top cap 1502 and the port 1056 can then be used to calculate the insertion depth of the surgical device.

In an alternative embodiment using a continuous sensor system, the insertion device 1050 has not only the sensor 1054 associated with the top cap 1052, but also a sensor (not shown) associated with the port 1056. In this implementation, the sensor 1054 emits energy that is received by the sensor associated with the port 1056, which triggers the sensor associated with the port 1056 to transmit energy back to the sensor 1054 associated with the top cap 1052. The sensor 1054 or a separate controller can then calculate the distance between the top cap 1052 and the port 1056, which can then be used to calculate the insertion depth of the surgical device.

In a further alternative, the measurement mechanism 1054 in the top cap 1052 is a camera 1054. The camera 1054 can utilize known image processing techniques on known features of the surgical device to determine the insertion depth of the device.

FIG. 80 depicts another embodiment relating to a port 1060 of an insertion device having one or more measurement mechanisms 1062 for measuring the insertion depth of a surgical device. In this implementation, as the surgical device (not shown) is urged through the port 1060 and into the patient's cavity, characteristics of the surgical device can be detected using the measurement mechanism(s) 1060 associated with the port 1060. And those characteristics can be used to estimate or determine the insertion depth of the surgical device. In one embodiment, the measurement mechanism 1062 is a camera 1062 that can use image processing to capture and recognize the portion of the surgical device that is passing through the opening 1064 in the port 1060. Alternatively, the surgical device can be marked with some type of markers that are easily recognized by the image processing technology. Upon recognition of the device portion or the marker, the camera 1062 or a separate processor or controller can calculate the insertion depth of the surgical device based on that information.

In a further implementation, the measurement mechanism 1062 is an RFID sensor 1062 that can sense one or more RFID markers (not shown) that are coupled to or implanted in the surgical device (not shown) passing through the port 1060. Alternatively, the RFID markers in this embodiment could also contain extra information that could be used in a two-way communication system. That is, one or more of the markers associated with the surgical device could be configured to transmit information through the same RF link to the sensor and/or a controller.

FIG. 81 depicts another embodiment of an insertion device having a measurement mechanism that measures the relative distance between the top cap and the port to determine the insertion depth of the surgical device. This embodiment relates to a top cap 1070 that has a string measurement system 1072, which, in some embodiments, is a string potentiometer system 1072. The string measurement system 1072 is a system in which a string is extended from the top cap 1070 to the port (not shown) at the bottom of the insertion device (not shown) and the amount of string that extends from a rotatable drum is measured. In this embodiment, the system 1072 has a rotatable sensor 1074, a rotatable drum 1076, a spring-loaded string dispenser 1078, and string (not shown) extending from the dispenser and around the drum 1076. According to one embodiment, the sensor 1074 is a potentiometer 1074, and in some specific embodiments, the sensor 1074 is a multiple-turn potentiometer 1074. The rotatable sensor 1074 is coupled to the rotatable drum 1076 such that the sensor 1074 rotates when the drum 1076 rotates. In one embodiment as shown, the drum 1076 is a dual drum 1076 having a measurement string drum half 1076A and a spring-loaded string drum half 1076B. More specifically, the string that extends down to the port (not shown) of the insertion device (not shown) wraps around the measurement string drum half 1076A, while a separate spring-loaded string (not shown) that is coupled at the other end to the spring-loaded string dispenser 1078 wraps around the spring-loaded string drum half 1076B.

Alternatively, the system 1072 can have a single string (not shown). For example, in one embodiment, a string (not shown) is coupled directly to the rotatable sensor 1074. In a further embodiment, the string measurement system 1072 can be used to measure the tilt of the insertion device (or the canister of the insertion device). According to one implementation, the string measurement system 1072 uses three strings to measure the tilt.

In use, the sensor 1074 can detect the distance between the top cap 1070 and the port (not shown) by sensing the number of turns of the drum 1076, as the number of turns is directly related to the length of the string extending down to the port (not shown) and thus directly related to the distance between the top cap 1070 and the port (not shown). This information can be used to calculate the insertion depth of the surgical device.

In an alternative embodiment, more than one measurement mechanism can be incorporated into an insertion device. That is, a first measurement mechanism can be incorporated into the insertion device to measure the insertion depth of the surgical device while a second measurement mechanism can be incorporated to measure the amount of "tilt" in the insertion device. It is understood that this could be any combination of the measurement devices that are capable of measuring depth and/or tilt. It is further understood that any known device for measuring tilt as described herein can be used within the insertion devices contemplated herein. In this context, "tilt" is intended to mean the angle of the longitudinal axis of the canister in relation to the plane parallel to the radius of the incision port. Several embodiments of the canisters and insertion devices herein are configured to allow for such tilt, which can be utilized to better position the surgical device in the cavity once it has exited the interior of the canister prior to or during a procedure.

FIGS. 82A, 82B, 82C, 82D, and 82E depict yet another implementation of an insertion device having a measurement mechanism that measures the relative distance between the top cap and the port to determine the insertion depth of the surgical device. This embodiment relates to a top cap 1090 that has a substantially rigid structure measurement system 1092. The measurement system 1092 is a system in which a substantially rigid structure 1094 extends from the top cap 1090 to the port 1096 at the bottom of the insertion device and the displacement of the structure 1094 is measured to determine the distance between the top cap 1090 and the port 1096, which can be used to calculate the insertion depth of the surgical device.

In this embodiment, as shown in FIG. 82A, the substantially rigid structure is a square bar 1094 that has a coupler 1098 at the top of the bar 1094. The bar 1094 extends through a seal 1100 in the top cap 1090 (as best shown in FIG. 82A), through a hole 1102 in the underside of the top cap 1090 (as best shown in FIG. 82B), and through a hole 1104 in the port 1096 (as best shown in FIG. 82E). In one embodiment, the hole 1102 in the top cap 1090 is square and thus the square bar 1094 cannot rotate in relation to the top cap 1090 (and thus can't rotate in relation to the insertion device). According to one implementation, the seal 1100 in the top cap 1090 is an elastomeric seal 1100. Alternatively, the seal 1100 is any seal that can maintain the pressure in the insertion device with the bar 1094 disposed therethough.

In one embodiment, the actual measurement of the displacement of the square bar 1094 is accomplished using a string measurement system such as the system described above with respect to FIG. 81. The coupler 1098 on the top end of the square bar 1094 is configured to be coupleable to a string (not shown) that is coupled in turn to the drum 1106 of the string measurement system 1108. In one embodiment the string measurement system 1108 operates in the same fashion as the similar system above.

As best shown in FIGS. 82C, 82D, and 82E, the bottom of the square bar 1094 is constrained in the port 1096 via a pegged ball 1110 having four pegs that is positioned in a cavity 1112 defined in the underside of the port 1096, wherein the cavity 1112 is in fluid communication with the hole 1104 in the top side of the port 1096. The cavity 1112 is configured to match the configuration of the pegged ball 1110 as shown (with the four slots in the cavity 1112 matching with the four pegs of the ball 1110) such that the ball 1110 can move within the cavity 1112 in a way that allows angular offset but not rotation about the longitudinal axis of the bar 1094. According to one embodiment, the combination of this constraint and the rotational constraint at the top cap 1090 allows the surgical device to be maneuvered into the body (that is, the insertion device can be tilted as described elsewhere herein and thereby maneuver and position the surgical device), but will maintain the centerline of the robot lined up with the insertion point.

In an alternative embodiment, the substantially rigid structure is another shape other than square. In a further implementation, the structure can have any shape that can match with a hole in the top cap such that the structure cannot rotate in relation to the top cap. Alternatively, the substantially rigid structure can be made up of more than one bar. For example, in one alternative embodiment, there can be two substantially rigid structures extending from the top cap to the port. In a further alternative, there are three or more structures.

Various other implementations of measurement mechanisms can be envisioned that fall within the scope and spirit of the embodiments disclosed herein. For example, while various embodiments discussed above relate to measurement of the relative distance between the top cap and the port, other alternative embodiments can measure the relative angular and linear displacement between the top and bottom of the insertion device. In addition, while various embodiments discuss above relate to sensors configured to emit and/or sense particular types of energy (such as infrared or ultrasonic energy), it is understood than any type of wireless technology that would work with a sensor can be used.

It is understood that any of these measurement technologies can be incorporated into any of the insertion device embodiments disclosed herein.

FIG. 83 depicts an alternative embodiment of an incision port 1120 that can be used with any of the insertion devices described above. In this implementation, the incision port 1120 has a slidable lid 1122 similar to the lid depicted in FIGS. 72A-75C. Further, the port 1120 also has an insufflation port 1124 that is in fluidic communication with the interior lumen or opening of the incision port 1120. In this embodiment, the insufflation port 1124 is a flow valve port 1124 that is positioned on the port 1120 such that it is below the slidable lid 1122. In one implementation, the insufflation port 1124 is used to insufflate the patient's cavity or to provide supplemental insufflation during a procedure. In use, the lid 1122 is positioned in the closed position to establish a fluid seal in the cavity (and in the insertion device, as described elsewhere above), and then gas is added to the patient's cavity via the insufflation port 1124.

FIGS. 84A and 84B depict alternative insertion device embodiments that, unlike the cylindrical canisters described above, have canisters with different shapes. More specifically, FIG. 84A is an insertion device 1130 with a flexible canister 1132 that is spherical in shape. Further, FIG. 84B is an insertion device 1140 with a flexible canister 1142 that is conical in shape. According to one embodiment, during compression, the spherical and conical canisters 1132, 1142 collapse or compress or otherwise allow the top cap to be moved toward the incision port such that the walls of the canisters 1132, 1142 expand or move outward. That is, the canisters 1132, 1142 do not bend inward and thereby interfere with the surgical device disposed within the canisters 1132, 1142 during collapse or compression of the canisters 1132, 1142.

FIGS. 85A, 85B, and 85C depict alternative insertion device embodiments that have canisters that are reinforced with rib structures. More specifically, FIG. 85A is an insertion device 1150 with a flexible canister 1152 having vertical rib structures 1154. FIG. 85B is an insertion device 1160 with a flexible canister 1162 having horizontal rib structures 1164. Further, FIG. 85C is an insertion device 1170 with a flexible canister 1172 having spiral-shaped rib structures 1174. In accordance with one embodiment, the rib structures in these exemplary embodiments create the structure of each canister while the flexible material in the canisters maintain the pressure therein. Alternatively, any combination of the rib structures can also be incorporated into a canister. In one implementation, the rib structures provide reinforcement for each canister such that the structures reduce the amount of undesired bending or collapsing of the canister during use.

FIGS. 86A, 86B, 86C, 86D depict an embodiment of a base coupler 1182 (of an incision port 1180) that is releasably coupled to the canister 1184 of the incision device. In this embodiment, the surgical device (not shown) can be positioned in the canister 1184 prior to the procedure and then releasably coupled to the incision port 1180. The coupler 1182 has at least one fixed support 1186 and at least one releasable latch 1188. According to one embodiment, there are two fixed supports 1186 (one is not visible). The canister 1184 has a lip 1190 on the bottom of the canister that can couple with the coupler 1182. In use, the canister 1184 is positioned against the top of the coupler 1182 in a tilted position as shown in FIGS. 86B and 86C such that the lip 1190 is positioned under the two fixed supports 1186. Then the entire bottom of the canister 1184 is placed into contact with the coupler 1182, thereby creating a seal between the lip 1190 and the coupler 1182. When the lip 1190 is positioned correctly, the latch 1188 is moved into the latched position such that the lip 1190 is retained in its position against the coupler 1182 via the two fixed supports 1186 and the latch 1188 as best shown in FIG. 86D.

FIGS. 87A, 87B, and 87C depict an embodiment of an insertion device having top cap 1200 that is coupled to an outer handle set 1202 such that the top cap 1200 and handle set 1202 can be moved relative to the flexible canister 1204. The outer handle set 1202 has an outer ring 1206 that is positioned around the outer circumference of the top cap 1200 such that there is a fluid seal established between the two components. In one embodiment, the fluidic seal is enhanced by a rubber seal 1210 disposed between the top cap 1200 and outer ring 1206. Further, the set 1202 also has two handles 1208 coupled to the ring 1206 such that a user or medical professional can easily grasp the set 1202. More specifically, as best shown in FIG. 87B, the top cap 1200 and outer handle set 1202 are moved down over the walls of the flexible canister 1204 such that the canister 1204 walls are disposed between the top cap 1200 and the handle set 1202. Thus, unlike certain embodiments above, the top cap 1200 is not fixed to the top of the canister 1204, but rather can be moved distally toward the bottom of the canister 1204 while pulling the walls of the canister 1204 through the seal of the top cap 1200 and outer handle set 1202 so as to reduce any bunching of the canister walls 1204 during compression of the device. In use, the top cap 1200 is free to slide within the flexible canister 1204 and is controlled via the outer handle set 1202, which has handles 1208 that provide direct control of the position and orientation of the top cap 1200.

FIGS. 88A, 88B, 88C, and 88D depict an alternative embodiment of an insertion device 1220 having top cap 1222 (as best shown in FIGS. 88A and 88B, a mobile seal 1224 (as best shown in FIG. 88C, an outer handle set 1226 (as best shown in FIGS. 88A and 88C) coupled to the mobile seal 1224, and an incision port 1228 (as best shown in FIGS. 88A and 88D). This embodiment differs from the previous embodiment in that the top cap 1222 in this device 1220 is not mobile and instead is coupled to the proximal end of the device 1220 as shown in FIG. 88A. Further, this embodiment has a mobile seal 1224 that is capable of moving along the length of the device 1220 in the same fashion as the top cap 1200 described above and depicted in FIGS. 87A-87C. Further, the outer handle set 1226 is coupled to the mobile seal 1224, instead of the top cap 1222.

According to one embodiment, the top cap 1222 in this device 1220 is the primary seal of the device 1220 such that it is not essential that the mobile seal 1224 maintains a fluidic seal as it is moved along the length of the device 1220. As such, the top cap 1222 can have all the sealing features and components of any of the top cap embodiments described above, including seals and access openings for wires, suction, irrigation, and auxiliary tools. In accordance with one implementation, the mobile seal 1224 is used primarily, along with the outer handle set 1226, to position the surgical device into the patient's cavity. The mobile seal 1224 and the outer handle set 1226 are coupled together, according to one embodiment, in a similar fashion and with similar components as the outer handle set 1202 and the top cap 1200 described above. When the outer handle set 1226 is moved, the mobile seal 1224 moves as well, and the handle set 1226 and seal 1224 can be moved relative to the canister walls in the same way as the top cap 1200 and handle set 1202 above.

According to one implementation, the external circumference of the mobile seal 1224 is non-circular such that coupling the seal 1224 to the outer handle set 1226 restrains the mobile seal 1224 from any axial movement in relation to the handle set 1226. As an example, the outer circumference of the seal 1224 can have the shape of a hexagon or an ellipse. Alternatively, any mechanism or component to restrain such axial movement can be used.

In one embodiment, the interface of the mobile seal 1224 and outer handle set 1226—where the canister is positioned and must pass through-need not provide a fluidic seal. Further, in certain implementations, the additional mechanisms or components such as ball bearings or surfaces conducive to movement can be incorporated into the interface, thereby enhancing the ability of the canister wall to pass through the interface easily. It is understood that these mechanisms or components can be incorporated into the seal 1224 or the handle set 1226 or both.

FIG. 89 depicts an alternative embodiment of an insertion device 1240 having a substantially non-flexible canister portion 1242 that is coupled to a flexible canister portion 1244, which in turn is coupled to the incision port 1246. In this embodiment, the top cap (not shown) can be coupled to an outer handle set similar to that described above such that the top cap can move along the non-flexible canister portion 1242 with ease. The flexible canister portion 1244 provides a flexible connection or interface (which could also be described as a "ball joint like" interface) that allows the movement of the surgical device as needed. That is, the flexible canister portion 1244 enhances the ability to tilt the insertion device 1240 as described above, thereby enhancing the ability to move the surgical device during insertion and during any procedure being performed. In one implementation, the coupling of the top cap and the outer handle set can be a magnetic connection so as to avoid the necessary sealing. Alternatively, different canister shapes and sizes can be envisioned. Further, the flexible canister portion can be located elsewhere on the device. In a further alternative, more than one flexible canister portion can be provided.

It is understood with respect to all of the various embodiments described herein that the medical devices being inserted into the patient are any known medical or surgical devices for performing procedures within a cavity of a patient. In certain embodiments, it is understood that the medical devices are robotic surgical devices having one or two arms. In various alternatives, the robotic surgical devices or systems can have or use three or more arms. In further alternatives, the devices (or additional devices) can be cameras or camera systems. Yet other alternatives, include the use of "helper" tools that can be inserted along with one or more medical devices or robotic devices.

Although the present invention has been described with reference to preferred embodiments, persons skilled in the art will recognize that changes may be made in form and detail without departing from the spirit and scope of the invention.

What is claimed is:

1. A surgical insertion device comprising:

(a) a canister comprising an elongate flexible body and a lumen, wherein the lumen is sized to receive a robotic surgical device therethrough, wherein the robotic surgical device comprises an elongate body and first and second arms operably coupled to the elongate body;

(b) a top cap coupled to a proximal end of the canister, the top cap comprising a pressure relief mechanism and at least one lumen defined in the top cap, wherein the at least one lumen is configured to receive a support rod, wherein the pressure relief mechanism is configured to release pressure if an internal insufflation pressure increases above a thresold value; and (c) an incision port removably coupled to a distal end of the canister, the incision port comprising a fluidic sealing component configured to maintain a fluidic seal.

2. The surgical insertion device of claim 1, wherein the lumen of the canister is fluidically sealed in relation to ambient air.

3. The surgical insertion device of claim 1, wherein the canister has a cylindrical shape, a spherical shape, or a conical shape.

4. The surgical insertion device of claim 1, wherein the canister comprises at least one rib structure.

5. The surgical insertion device of claim 1, wherein the fluidic sealing component comprises a sealable sleeve device, a flexible seal component, a removable lid seal component, or a flap seal component.

6. The surgical insertion device of claim 1, wherein the top cap comprises at least one of at least one threaded lumen, a detachable cable harness, and a clamp projection.

7. The surgical insertion device of claim 1, further comprising an outer handle set coupleable to the top cap.

8. The surgical insertion device of claim 1, further comprising at least one measurement mechanism coupled to the top cap or the incision port.

9. The surgical insertion device of claim 1, wherein the canister comprises at least one access port, wherein the at least one access port is a hand access port or a side access port.

10. A surgical insertion device comprising:

(a) a canister comprising an elongate flexible body and a lumen, wherein the lumen is sized to receive a robotic surgical device therethrough, wherein the robotic surgical device comprises an elongate body and first and second arms operably coupled to the elongate body;

(b) a top cap coupled to a proximal end of the canister, the top cap comprising:

(i) a pressure relief mechanism associated with the top cap, wherein the pressure relief mechanism is configured to release pressure if an internal insufflation pressure increases above a thresold value; and (ii) a first lumen defined in the top cap, wherein the first lumen is sized to receive the robotic surgical device; and (c) an incision port removably coupled to a distal end of the canister, the incision port comprising a fluidic sealing component configured to maintain a fluidic seal.

11. The surgical insertion device of claim 10, further comprising a first measurement mechanism coupled with the top cap or the incision port, the first measurement mechanism configured to measure the insertion depth of the surgical device.

12. The surgical insertion device of claim 11, wherein the first measurement mechanism comprises a sensor, a string measurement system, a substantially rigid structure system, or a camera.

13. The surgical insertion device of claim 12, further comprising a second measurement mechanism coupled to the top cap or the incision port, the second measurement mechanism configured to measure any tilt of the flexible canister.

14. The surgical insertion device of claim 10, wherein the fluidic sealing component comprises a sealable sleeve device, a flexible seal component, a removable lid seal component, or a flap seal component.

15. The surgical insertion device of claim 10, wherein the top cap further comprises a second lumen defined in the top cap, wherein the second lumen is configured to receive a support rod.

16. The surgical insertion device of claim 10, wherein the top cap further comprises at least one of at least one threaded lumen, a detachable cable harness, and a clamp projection.

17. A surgical insertion device comprising:

(a) a canister comprising an elongate flexible body and a lumen, wherein the lumen is sized to receive a robotic surgical device therethrough, wherein the robotic surgical device comprises an elongate body and first and second arms operably coupled to a distal end of the elongate body;

(b) a top cap coupled to a proximal end of the canister, the top cap comprising:

(i) a pressure relief mechanism associated with the top cap, wherein the pressure relief mechanism is configured to release pressure if an internal insufflation pressure increases above a thresold value; and (ii) a first lumen defined in the top cap, wherein the first lumen is sized to receive the robotic surgical device; and (c) an incision port removably coupled to a distal end of the canister, the incision port comprising a fluidic sealing component configured to maintain a fluidic seal.

18. The surgical insertion device of claim 17, wherein the fluidic sealing component comprises a sealable sleeve device, a flexible seal component, a removable lid seal component, or a flap seal component.

19. The surgical insertion device of claim 17, wherein the top cap comprises at least one of at least one threaded lumen, a detachable cable harness, and a clamp projection.

20. The surgical insertion device of claim 17, further comprising at least one measurement mechanism coupled to the top cap or the incision port.

\* \* \* \* \*